(12) United States Patent
Laurie

(10) Patent No.: US 7,939,708 B2
(45) Date of Patent: May 10, 2011

(54) MAIZE GENOMIC MARKER SET

(75) Inventor: Cathy C. Laurie, Saratoga, CA (US)

(73) Assignee: Monsanto Technology LLC, St. Louis, MO (US)

( * ) Notice: Subject to any disclaimer, the term of this patent is extended or adjusted under 35 U.S.C. 154(b) by 1474 days.

(21) Appl. No.: 10/898,546

(22) Filed: Jul. 22, 2004

(65) Prior Publication Data

US 2007/0039065 A1     Feb. 15, 2007

(51) Int. Cl.
*A01H 1/04* (2006.01)
*A01H 1/00* (2006.01)
*A01H 1/02* (2006.01)

(52) U.S. Cl. .......................... 800/267; 800/260; 800/266

(58) Field of Classification Search .................. 800/260, 800/264, 266, 267, 275, 320.1, 800
See application file for complete search history.

(56) References Cited

OTHER PUBLICATIONS

Berke et al. 1995. Crop Sci. 35: 1542-1549.*

* cited by examiner

*Primary Examiner* — Medina A. Ibrahim
*Assistant Examiner* — Keith O. Robinson
(74) *Attorney, Agent, or Firm* — Thomas P. McBride

(57) ABSTRACT

Maize markers useful for genotyping and association studies, e.g. association with oil content QTLs in populations derived from the Illinois High Oil and Illinois Low Oil maize lines. Primers and hybridization probes for Taqman™ assays are provided for 488 SNP markers in 484 loci.

1 Claim, No Drawings

MAIZE GENOMIC MARKER SET

REFERENCE TO RELATED APPLICATIONS

This application claims priority under 35 U.S.C. 120 to U.S. application Ser. No. 10/806,075, filed Mar. 22, 2004, now U.S. Pat. No. 7,194,205 application Ser. No. 10/613,520, filed Jul. 2, 2003, now abandoned application Ser. No. 10/389,566, filed Mar. 14, 2003 now abandoned which claims priority under 35 U.S.C. 119(e) to U.S. Provisional Application 60/365,301 filed Mar. 15, 2002, 60/391,786 filed Jun. 26, 2002 and 60/392,018 filed Jun. 26, 2002, all of which are incorporated herein by reference in their entireties.

INCORPORATION OF SEQUENCE LISTING

Two copies and a computer readable form of the sequence listing, i.e. labeled "Copy 1 of Sequence Listing", "Copy 2 of Sequence Listing" and "Computer Readable Form of Sequence Listing", each on a separate CD-ROM containing the file named "52900H.ST25.txt", which is 788 kb (measured in MS-Windows) and was created on Jul. 22, 2004, are herein incorporated by reference.

INCORPORATION OF TABLES

Two copies of Table 1, labeled as "Copy 1 of Table 1" and "Copy 2 of Table 1", each on a separate CD-ROM containing the file named "Table 1.txt", which is 145 kb (measured in MS-Windows) and was created on Jul. 22, 2004, are herein incorporated by reference.

all of which are incorporated herein by reference. The highly conserved nature of DNA combined with the rare occurrences of stable polymorphisms provide genetic markers that are both predictable and discerning of different genotypes. Among the classes of existing genetic markers are a variety of polymorphisms indicating genetic variation including restriction-fragment-length polymorphisms (RFLPs), amplified fragment-length polymorphisms (AFLPs), simple sequence repeats (SSRs), single nucleotide polymorphisms (SNPs), and insertion/deletion polymorphisms (Indels). Because the number of genetic markers for a plant species is limited, the discovery of additional genetic markers associated with a trait will facilitate genotyping applications including marker-trait association studies, gene mapping, gene discovery, marker-assisted selection, and marker-assisted breeding. Evolving technologies make certain genetic markers more amenable for rapid, large scale use. For instance, technologies for SNP detection indicate that SNPs may be preferred genetic markers.

SUMMARY OF THE INVENTION

This invention provides maize polymorphic markers, more specifically SNP and Indel markers located in 484 polymorphic maize genomic DNA loci having DNA sequence of SEQ ID NO:1 through SEQ ID NO:484. Such markers are useful for discovery and isolation of genes, marker trait association, discovery of QTLs and molecular breeding. This invention also provides primers and probes useful in genotyping with the 488 specific markers within the 484 polymorphic loci.

TABLES

The patent contains table(s) that have been included at the end of the specification.

FIELD OF THE INVENTION

Disclosed herein are inventions in the field of plant molecular biology, plant genetics and plant breeding. More specifically disclosed are maize genetic markers, i.e. polymorphic DNA, which are useful for discovery and isolation of genes, marker trait association, discovery of QTLs and molecular breeding.

BACKGROUND OF THE INVENTION

Maize, Zea mays L., is one of the major crops grown worldwide as a primary source for animal feed, human food and industrial purposes. Maize plants with improved agronomic traits and maize seed with improved quality traits are desirable for the farmer, processor and consumer of maize and maize derived products. The ability to breed or develop transgenic plants with improved traits depends in part on identification of genes or QTLs associated with a trait. The unique maize sequences disclosed herein are useful as mapping tools to assist in plant breeding, in gene and QTL discovery, as markers in marker trait association and molecular breeding.

Polymorphisms are useful as genetic markers for genotyping applications in the agriculture field, e.g., in plant genetic studies and commercial breeding. See for instance U.S. Pat. Nos. 5,385,835; 5,492,547 and 5,981,832, the disclosures of This invention also provides methods of using markers in the 484 polymorphic loci for genotyping maize, e.g. in identifying genes and QTLs, molecular breeding, mapping DNA clones, and the like.

DETAILED DESCRIPTION OF PREFERRED EMBODIMENTS

The following definitions are used to described the markers and their uses.

An "allele" means an alternative sequence at a particular locus; the length of an allele can be as small as 1 nucleotide base but is typically larger. Allelic sequence can be amino acid sequence or nucleic acid sequence.

A "locus" is a short sequence that is usually unique and usually found at one particular location by a point of reference, e.g., a short DNA sequence that is a gene, or part of a gene or intergenic region. A locus of this invention can be a unique PCR product. The loci of this invention are polymorphic between certain individuals.

"Genotype" means the specification of an allelic composition at one or more loci within an individual organism. In the case of diploid organisms, there are two alleles at each locus; a diploid genotype is said to be homozygous when the alleles are the same, and heterozygous when the alleles are different.

"Phenotype" means the detectable characteristics of a cell or organism that are a manifestation of gene expression.

"Marker" means a polymorphic sequence. A "polymorphism" is a variation among individuals in sequence, particularly in DNA sequence. Useful polymorphisms include a single nucleotide polymorphisms (SNPs) and insertions or deletions in DNA sequence (Indels).

"Marker assay" means a method for detecting a polymorphism at a particular locus using a particular method, e.g., phenotype (such as seed color, flower color, or other visually detectable trait), restriction fragment length polymorphism (RFLP), single base extension, electrophoresis, sequence alignment, allelic specific oligonucleotide hybridization (ASO), RAPID, etc. Preferred marker assays include single base extension as disclosed in U.S. Pat. No. 6,013,431 and allelic discrimination where endonuclease activity releases a reporter dye from a hybridization probe as disclosed in U.S. Pat. No. 5,538,848, the disclosures of both of which are incorporated herein by reference.

"Linkage" refers to relative frequency at which types of gametes are produced in a cross. For example, if locus A has alleles "A" or "a" and locus B has alleles "B" or "b," a cross between parent I with AABB and parent II with aabb will produce four possible gametes where the haploid genotypes are segregated into AB, Ab, aB and ab. The null expectation is that there will be independent and equal segregation into each of the four possible genotypes, i.e., with no linkage, ¼ of the gametes will be of each genotype. Segregation of gametes into a genotypes differing from ¼ are attributed to linkage. Two loci are said to be "genetically linked" when they show this deviation from the expected equal frequency of ¼.

"Linkage disequilibrium" is defined in the context of the relative frequency of gamete types in a population of many individuals in a single generation. If the frequency of allele A is p, a is p', B is q and b is q', then the expected frequency (with no linkage disequilibrium) of genotype AB is pq, Ab is pq', aB is p'q and ab is p'q'. Any deviation from the expected frequency is called linkage disequilibrium.

"Quantitative Trait Locus (QTL)" means a locus that controls to some degree numerically representable traits that are usually continuously distributed.

"Haplotype" means the genotype for multiple loci or genetic markers in a haploid gamete. Generally these loci or markers reside within a relatively small and defined region of a chromosome. A preferred haplotype comprises the 10 cM region or the 5 cM region or the 2 cM region surrounding an informative marker having a significant association with oil.

"Hybridizing" means the capacity of two nucleic acid molecules or fragments thereof to form anti-parallel, double-stranded nucleotide structure. The nucleic acid molecules of this invention are capable of hybridizing to other nucleic acid molecules under certain circumstances. A nucleic acid molecule is said to be the "complement" of another nucleic acid molecule if the molecules exhibit "complete complementarity," i.e., each nucleotide in one sequence is complementary to its base pairing partner nucleotide in another sequence. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Nucleic acid molecules that hybridize to other nucleic acid molecules, e.g., at least under low stringency conditions are said to be "hybridizable cognates" of the other nucleic acid molecules. Conventional stringency conditions are described by Sambrook et al., *Molecular Cloning, A Laboratory Manual*, 2nd Ed., Cold Spring Harbor Press, Cold Spring Harbor, N.Y. (1989) and by Haymes et al., *Nucleic Acid Hybridization, A Practical Approach*, IRL Press, Washington, D.C. (1985), each of which is incorporated herein by reference. Departures from complete complementarity are therefore permissible, as long as such departures do not completely preclude the capacity of the molecules to form a double-stranded structure. Thus, in order for a nucleic acid molecule to serve as a primer or probe, it need only be sufficiently complementary in sequence to be able to form a stable double-stranded structure under the particular solvent and salt concentrations employed. Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6, incorporated herein by reference. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

"Sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components that are shared by the two aligned sequences divided by the total number of components in reference sequence segment, i.e., the entire reference sequence or a smaller defined part of the reference sequence. "Percent identity" is the identity fraction times 100. Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc. Burlington, Mass.). Polynucleotides of the present invention that are variants of the polynucleotides provided herein will generally demonstrate significant identity with the polynucleotides provided herein. Of particular interest are polynucleotide homologs having at least about 70% sequence identity, at least about 80% sequence identity, at least about 90% sequence identity, and more preferably even greater, such as 98% or 99% sequence identity with polynucleotide sequences described herein.

"Purified" refers to a nucleic acid molecule or polypeptide separated from substantially all other molecules normally associated with it in its native state. More preferably, a substantially purified molecule is the predominant species present in a preparation. A substantially purified molecule may be greater than 60% free or 75% free or 90% free or 95% free from the other molecules (exclusive of solvent) present in the natural mixture. The terms "isolated and purified" and "substantially purified" are not intended to encompass molecules present in their native state.

Characteristics of Maize Markers

The maize loci of this invention comprise a DNA sequence that comprises at least 20 consecutive nucleotides and includes or is adjacent to one or more polymorphisms identified in Table 1. Such maize loci have a nucleic acid sequence having at least 90% sequence identity or at least 95% or for some alleles at least 98% and in many cases at least 99% sequence identity, to the sequence of the same number of nucleotides in either strand of a segment of maize DNA that includes or is adjacent to the polymorphism. The nucleotide sequence of one strand of such a segment of maize DNA may be found in a polymorphic locus with a sequence in the group consisting of SEQ ID NO:1 through SEQ ID NO:186. It is understood by the very nature of polymorphisms that for at least some alleles there will be no identity to the polymorphism, per se. Thus, sequence identity can be determined for sequence that is exclusive of the polymorphism sequence. The polymorphisms in each locus are identified more particularly in Table 1.

For many genotyping applications it is useful to employ as markers polymorphisms from more than one locus. Thus, aspects of the invention use a collection of different loci. The number of loci in such a collection can vary but will be a finite number, e.g., as few as 2 or 5 or 10 or 25 loci or more, for instance up to 40 or 75 or 100 or more loci.

Another aspect of the invention provides nucleic acid molecules that are capable of hybridizing to the polymorphic maize loci of this invention, e.g. PCR primers and hybridization probes. In certain embodiments of the invention, e.g., which provide PCR primers, such molecules comprise at least 15 nucleotide bases. Molecules useful as primers can hybridize under high stringency conditions to one of the strands of a segment of DNA in a polymorphic locus of this invention. Primers for amplifying DNA are provided in pairs, i.e., a forward primer and a reverse primer. One primer will be complementary to one strand of DNA in the locus and the other primer will be complementary to the other strand of DNA in the locus, i.e., the sequence of a primer is at least 90% or at least 95% identical to a sequence of the same number of nucleotides in one of the strands. It is understood that such primers can hybridize to a sequence in the locus that is distant from the polymorphism, e.g., at least 5, 10, 20, 50 or up to about 100 nucleotide bases away from the polymorphism. Design of a primer of this invention will depend on factors well known in the art, e.g., avoidance of repetitive sequence.

Another aspect of the nucleic acid molecules of this invention are hybridization probes for polymorphism assays. In one aspect of the invention such probes are oligonucleotides comprising at least 12 nucleotide bases and a detectable label. The purpose of such a molecule is to hybridize, e.g., under high stringency conditions, to one strand of DNA in a segment of nucleotide bases that includes or is adjacent to the polymorphism of interest in an amplified part of a polymorphic locus. Such oligonucleotides are at least 90% or at least 95% identical to the sequence of a segment of the same number of nucleotides in one strand of maize DNA in a polymorphic locus. The detectable label can be a radioactive element or a dye. In preferred aspects of the invention, the hybridization probe further comprises a fluorescent label and a quencher, e.g., for use in hybridization probe assays of the type known as Taqman assays, available from Applied Biosystems of Foster City, Calif.

For assays where the molecule is designed to hybridize adjacent to a polymorphism that is detected by single base extension, e.g., of a labeled dideoxynucleotide, such molecules can comprise at least 15 or at least 16 or 17 nucleotide bases in a sequence that is at least 90% or at least 95% identical to a sequence of the same number of consecutive nucleotides in either strand of a segment of polymorphic maize DNA. Oligonucleotides for single base extension assays are available from Orchid Biosystems.

Such primer and probe molecules are generally provided in groups of two primers and one or more probes for use in genotyping assays. Moreover, it is often desirable to conduct a plurality of genotyping assays for a plurality of polymorphisms. Thus, this invention also provides collections of nucleic acid molecules, e.g., in sets that characterize a plurality of polymorphisms.

Detecting Polymorphisms

Polymorphisms in DNA sequences can be detected by a variety of effective methods well known in the art including those methods disclosed in U.S. Pat. Nos. 5,468,613 and 5,217,863 by hybridization to allele-specific oligonucleotides; in U.S. Pat. Nos. 5,468,613 and 5,800,944 by probe ligation; in U.S. Pat. No. 5,616,464 by probe linking; and in U.S. Pat. Nos. 6,004,744; 6,013,431; 5,595,890; 5,762,876; and 5,945,283 by labeled base extension, all of which are incorporated herein by reference.

In another preferred method for detecting polymorphisms, SNPs and Indels can be detected by methods disclosed in U.S. Pat. Nos. 5,210,015; 5,876,930; and 6,030,787 in which an oligonucleotide probe having a 5'fluorescent reporter dye and a 3'quencher dye covalently linked to the 5' and 3' ends of the probe. When the probe is intact, the proximity of the reporter dye to the quencher dye results in the suppression of the reporter fluorescence, e.g., by Forster-type energy transfer. During PCR forward and reverse primers hybridize to a specific sequence of the target DNA flanking a polymorphism. The hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter. A useful assay is available from AB Biosystems as the Taqman® assay, which employs four synthetic oligonucleotides in a single reaction that concurrently amplifies the maize genomic DNA, discriminates between the alleles present, and directly provides a signal for discrimination and detection. Two of the four oligonucleotides serve as PCR primers and generate a PCR product encompassing the polymorphism to be detected. Two others are allele-specific fluorescence-resonance-energy-transfer (FRET) probes. FRET probes incorporate a fluorophore and a quencher molecule in close proximity so that the fluorescence of the fluorophore is quenched. The signal from a FRET probe is generated by degradation of the FRET oligonucleotide, so that the fluorophore is released from proximity to the quencher, and is thus able to emit light when excited at an appropriate wavelength. In the assay, two FRET probes bearing different fluorescent reporter dyes are used, where a unique dye is incorporated into an oligonucleotide that can anneal with high specificity to only one of the two alleles. Useful reporter dyes include 6-carboxy-4,7,2',7'-tetrachlorofluorecein (TET), VIC (a dye from Applied Biosystems Foster City, Calif.), and 6-carboxyfluorescein phosphoramidite (FAM). A useful quencher is 6-carboxy-N,N,N',N'-tetramethylrhodamine (TAMRA). Additionally, the 3'end of each FRET probe is chemically blocked so that it cannot act as a PCR primer. During the assay, maize genomic DNA is added to a buffer containing the two PCR primers and two FRET probes. Also present is a third fluorophore used as a passive reference, e.g., rhodamine X (ROX), to aid in later normalization of the relevant fluorescence values (correcting for volumetric errors in reaction assembly). Amplification of the genomic DNA is initiated. During each cycle of the PCR, the FRET probes anneal in an allele-specific manner to the template DNA molecules. Annealed (but not non-annealed) FRET probes are degraded by TAQ DNA polymerase as the enzyme encounters the 5' end of the annealed probe, thus releasing the fluorophore from proximity to its quencher. Following the PCR reaction, the fluorescence of each of the two fluorescers, as well as that of the passive reference, is determined fluorometrically. The normalized intensity of fluorescence for each of the two dyes will be proportional to the amounts of each allele initially present in the sample, and thus the genotype of the sample can be inferred.

To design primers and probes for the assay the locus sequence is first masked to prevent design of any of the three primers to sites that match known maize repetitive elements (e.g., transposons) or are of very low sequence complexity (di- or tri-nucleotide repeat sequences). Design of primers to such repetitive elements will result in assays of low specificity, through amplification of multiple loci or annealing of the FRET probes to multiple sites.

PCR primers are designed (a) to have a length in the size range of 18 to 25 bases and matching sequences in the polymorphic locus, (b) to have a calculated melting temperature in the range of 57° C. to 60° C., e.g., corresponding to an optimal PCR annealing temperature of 52° C. to 55° C., (c) to produce a product that includes the polymorphic site and has a length in the size range of 75 to 250 base pairs. The PCR primers are preferably located on the locus so that the polymorphic site is at least one base away from the 3' end of each PCR primer. The PCR primers must not contain regions that are extensively self- or inter-complementary.

FRET probes are designed to span the sequence of the polymorphic site, preferably with the polymorphism located in the 3' most ⅔ of the oligonucleotide. In the preferred embodiment, the FRET probes will have incorporated at their 3'end a chemical moiety that, when the probe is annealed to the template DNA, binds to the minor groove of the DNA, thus enhancing the stability of the probe-template complex. The probes should have a length in the range of 12 to 17 bases and, with the 3'MGB, have a calculated melting temperature of 5° C. to 7° C. above that of the PCR primers. Probe design is disclosed in U.S. Pat. Nos. 5,538,848; 6,084,102; and 6,127,121.

Use of Polymorphisms to Establish Marker/Trait Associations

The polymorphisms in the loci of this invention can be used in marker/trait associations that are inferred from statistical analysis of genotypes and phenotypes of the members of a population. These members may be individual organisms, e.g., maize, families of closely related individuals, inbred lines, dihaploids or other groups of closely related individuals. Such maize groups are referred to as "lines", indicating line of descent. The population may be descended from a single cross between two individuals or two lines (e.g., a mapping population) or it may consist of individuals with many lines of descent. Each individual or line is characterized by a single or average trait phenotype and by the genotypes at one or more marker loci.

Several types of statistical analysis can be used to infer marker/trait association from the phenotype/genotype data, but a basic idea is to detect markers, i.e., polymorphisms, for which alternative genotypes have significantly different average phenotypes. For example, if a given marker locus A has three alternative genotypes (AA, Aa and aa), and if those three classes of individuals have significantly different phenotypes, then one infers that locus A is associated with the trait. The significance of differences in phenotype may be tested by several types of standard statistical tests such as linear regression of marker genotypes on phenotype or analysis of variance (ANOVA). Commercially available, statistical software packages commonly used to do this type of analysis include SAS Enterprise Miner (SAS Institute Inc., Cary, N.C.) and Splus (Insightful Corporation. Cambridge, Mass.).

Often the goal of an association study is not simply to detect marker/trait associations, but to estimate the location of genes affecting the trait directly (i.e., QTLs) relative to the marker locations. In a simple approach to this goal, one makes a comparison among marker loci of the magnitude of difference among alternative genotypes or the level of significance of that difference. Trait genes are inferred to be located nearest the marker(s) that have the greatest associated genotypic difference. In a more complex analysis, such as interval mapping (Lander and Botstein, *Genetics* 121:185-199, 1989), each of many positions along the genetic map (say at 1 cM intervals) is tested for the likelihood that a QTL is located at that position. The genotype/phenotype data are used to calculate for each test position a LOD score (log of likelihood ratio). When the LOD score exceeds a critical threshold value, there is significant evidence for the location of a QTL at that position on the genetic map (which will fall between two particular marker loci).

1. Linkage Disequilibrium Mapping and Association Studies

Another approach to determining trait gene location is to analyze trait-marker associations in a population within which individuals differ at both trait and marker loci. Certain marker alleles may be associated with certain trait locus alleles in this population due to population genetic process such as the unique origin of mutations, founder events, random drift and population structure. This association is referred to as linkage disequilibrium. In linkage disequilibrium mapping, one compares the trait values of individuals with different genotypes at a marker locus. Typically, a significant trait difference indicates close proximity between marker locus and one or more trait loci. If the marker density is appropriately high and the linkage disequilibrium occurs only between very closely linked sites on a chromosome, the location of trait loci can be very precise.

A specific type of linkage disequilibrium mapping is known as association studies. This approach makes use of markers within candidate genes, which are genes that are thought to be functionally involved in development of the trait because of information such as biochemistry, physiology, transcriptional profiling and reverse genetic experiments in model organisms. In association studies, markers within candidate genes are tested for association with trait variation. If linkage disequilibrium in the study population is restricted to very closely linked sites (i.e., within a gene or between adjacent genes), a positive association provides nearly conclusive evidence that the candidate gene is a trait gene.

2. Positional Cloning and Transgenic Applications

Traditional linkage mapping typically localizes a trait gene to an interval between two genetic markers (referred to as flanking markers). When this interval is relatively small (say less than 1 Mb), it becomes feasible to precisely identify the trait gene by a positional cloning procedure. A high marker density is required to narrow down the interval length sufficiently. This procedure requires a library of large insert genomic clones (such as a BAC library), where the inserts are pieces (usually 100-150 kb in length) of genomic DNA from the species of interest. The library is screened by probe hybridization or PCR to identify clones that contain the flanking marker sequences. Then a series of partially overlapping clones that connects the two flanking clones (a "contig") is built up through physical mapping procedures. These procedures include fingerprinting, STS content mapping and sequence-tagged connector methodologies. Once the physical contig is constructed and sequenced, the sequence is searched for all transcriptional units. The transcriptional unit that corresponds to the trait gene can be determined by comparing sequences between mutant and wild type strains, by additional fine-scale genetic mapping, and/or by functional testing through plant transformation. Trait genes identified in this way become leads for transgenic product development. Similarly, trait genes identified by association studies with candidate genes become leads for transgenic product development.

3. Marker-Aided Breeding and Marker-Assisted Selection

When a trait gene has been localized in the vicinity of genetic markers, those markers can be used to select for improved values of the trait without the need for phenotypic analysis at each cycle of selection. In marker-aided breeding and marker-assisted selection, associations between trait genes and markers are established initially through genetic mapping analysis (as in M.1 or M.2). In the same process, one determines which marker alleles are linked to favorable trait gene alleles. Subsequently, marker alleles associated with favorable trait gene alleles are selected in the population. This procedure will improve the value of the trait provided that there is sufficiently close linkage between markers and trait genes. The degree of linkage required depends upon the number of generations of selection because, at each generation, there is opportunity for breakdown of the association through recombination.

4. Prediction of Crosses for New Inbred Line Development

The associations between specific marker alleles and favorable trait gene alleles also can be used to predict what types of progeny may segregate from a given cross. This prediction may allow selection of appropriate parents to generation populations from which new combinations of favorable trait gene alleles are assembled to produce a new inbred line. For example, if line A has marker alleles previously known to be associated with favorable trait alleles at loci 1, 20 and 31, while line B has marker alleles associated with favorable effects at loci 15, 27 and 29, then a new line could be developed by crossing A×B and selecting progeny that have favorable alleles at all 6 trait loci.

5. Hybrid Prediction

Commercial corn seed is produced by making hybrids between two elite inbred lines that belong to different "heterotic groups". These groups are sufficiently distinct genetically that hybrids between them show high levels of heterosis or hybrid vigor (i.e., increased performance relative to the parental lines). By analyzing the marker constitution of good hybrids, one can identify sets of alleles at different loci in both male and female lines that combine well to produce heterosis. Understanding these patterns, and knowing the marker constitution of different inbred lines, can allow prediction of the level of heterosis between different pairs of lines. These predictions can narrow down the possibilities of which line(s) of opposite heterotic group should be used to test the performance of a new inbred line.

6. Identity by Descent

One theory of heterosis predicts that regions of identity by descent (IBD) between the male and female lines used to produce a hybrid will reduce hybrid performance. Identity by descent can be inferred from patterns of marker alleles in different lines. An identical string of markers at a series of adjacent loci may be considered identical by descent if it is unlikely to occur independently by chance. Analysis of marker fingerprints in male and female lines can identify regions of IBD. Knowledge of these regions can inform the choice of hybrid parents, because avoiding IBD in hybrids is likely to improve performance. This knowledge may also inform breeding programs in that crosses could be designed to produce pairs of inbred lines (one male and one female) that show little or no IBD.

A fingerprint of an inbred line is the combination of alleles at a set of marker loci. High density fingerprints can be used to establish and trace the identity of germplasm, which has utility in germplasm ownership protection.

Genetic markers are used to accelerate introgression of transgenes into new genetic backgrounds (i.e., into a diverse range of germplasm). Simple introgression involves crossing a transgenic line to an elite inbred line and then backcrossing the hybrid repeatedly to the elite (recurrent) parent, while selecting for maintenance of the transgene. Over multiple backcross generations, the genetic background of the original transgenic line is replaced gradually by the genetic background of the elite inbred through recombination and segregation. This process can be accelerated by selection on marker alleles that derive from the recurrent parent.

Use of Polymorphism Assay for Mapping a Library of DNA Clones

The polymorphisms and loci of this invention are useful for identifying and mapping DNA sequence of QTLs and genes linked to the polymorphisms. For instance, BAC or YAC clone libraries can be queried using polymorphisms linked to a trait to find a clone containing specific QTLs and genes associated with the trait. For instance, QTLs and genes in a plurality, e.g., hundreds or thousands, of large, multi-gene sequences can be identified by hybridization with an oligonucleotide probe that hybridizes to a mapped and/or linked polymorphism. Such hybridization screening can be improved by providing clone sequence in a high density array. The screening method is more preferably enhanced by employing a pooling strategy to significantly reduce the number of hybridizations required to identify a clone containing the polymorphism. When the polymorphisms are mapped, the screening effectively maps the clones.

For instance, in a case where thousands of clones are arranged in a defined array, e.g., in 96-well plates, the plates can be arbitrarily arranged in three-dimensionally, arrayed stacks of wells each comprising a unique DNA clone. The wells in each stack can be represented as discrete elements in a three dimensional array of rows, columns and plates. In one aspect of the invention the number of stacks and plates in a stack are about equal to minimize the number of assays. The stacks of plates allow the construction of pools of cloned DNA.

For a three-dimensionally arrayed stack, pools of cloned DNA can be created for (a) all of the elements in each row, (b) all of the elements of each column, and (c) all of the elements of each plate. Hybridization screening of the pools with an oligonucleotide probe that hybridizes to a polymorphism unique to one of the clones will provide a positive indication for one column pool, one row pool and one plate pool, thereby indicating the well element containing the target clone.

In the case of multiple stacks, additional pools of all of the clone DNA in each stack allows indication of the stack having the row-column-plate coordinates of the target clone. For instance, a 4608 clone set can be disposed in 48 96-well plates. The 48 plates can be arranged in 8 sets of 6-plate stacks providing 6×12×8 three-dimensional arrays of elements, i.e., each stack comprises 6 stacks of 8 rows and 12 columns. For the entire clone set there are 36 pools, i.e., 6 stack pools, 8 row pools, 12 column pools and 8 stack pools. Thus, a maximum of 36 hybridization reactions is required to find the clone harboring QTLs or genes associated or linked to each mapped polymorphism.

Once a clone is identified, genes within that clone can be tested for whether they affect the trait by analysis of recombinants in a mapping population, further linkage disequilibrium analysis, and ultimately transgenic testing. Additional genes can be identified by finding additional clones overlapping the one containing the original polymorphism through contig building, as described above.

Breeding Plants of the Invention

In addition to direct transformation of a particular plant genotype with a construct prepared according to the current invention, transgenic plants may be made by crossing a plant having a construct of the invention to a second plant lacking the construct. For example, a selected coding region operably linked to a promoter can be introduced into a particular plant variety by crossing, without the need for ever directly transforming a plant of that given variety. Therefore, the current invention not only encompasses a plant directly regenerated from cells that have been transformed in accordance with the current invention, but also the progeny of such plants. As used herein the term "progeny" denotes the offspring of any generation of a parent plant prepared in accordance with the instant invention, wherein the progeny comprises a construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;
(b) grow the seeds of the first and second parent plants into plants that bear flowers;
(c) pollinate a flower from the first parent plant with pollen from the second parent plant; and
(d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;
(b) selecting one or more progeny plants containing the desired gene, DNA sequence or element;
(c) crossing the progeny plant to a plant of the second genotype; and
(d) repeating steps (b) and (c) for the purpose of transferring the desired gene, DNA sequence or element from a plant of a first genotype to a plant of a second genotype.

Plant Breeding

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

Backcrossing can be used to improve a starting plant. Backcrossing transfers a specific desirable trait from one source to an inbred or other plant that lacks that trait. This can be accomplished, for example, by first crossing a superior inbred (A) (recurrent parent) to a donor inbred (non-recurrent parent), which carries the appropriate gene(s) for the trait in question, for example, a construct prepared in accordance with the current invention. The progeny of this cross first are selected in the resultant progeny for the desired trait to be transferred from the non-recurrent parent, then the selected progeny are mated back to the superior recurrent parent (A). After five or more backcross generations with selection for the desired trait, the progeny are hemizygous for loci controlling the characteristic being transferred but are like the superior parent for most or almost all other genes. The last backcross generation would be selfed to give progeny that are pure breeding for the gene(s) being transferred, i.e., one or more transformation events.

Therefore, through a series a breeding manipulations, a selected transgene may be moved from one line into an entirely different line without the need for further recombinant manipulation. Transgenes are valuable in that they typically behave genetically as any other gene and can be manipulated by breeding techniques in a manner identical to any other corn gene. Therefore, one may produce inbred plants that are true breeding for one or more transgenes. By crossing different inbred plants, one may produce a large number of different hybrids with different combinations of transgenes. In this way, plants may be produced that have the desirable agronomic properties frequently associated with hybrids ("hybrid vigor"), as well as the desirable characteristics imparted by one or more transgene(s).

It is desirable to introgress the genes of the present invention into maize hybrids for characterization of the phenotype conferred by each gene in a transformed plant. The host genotype into which the transgene was introduced, preferably LH59, is an elite inbred and therefore only limited breeding is necessary in order to produce high yielding maize hybrids. The transformed plant, regenerated from callus is crossed, to the same genotype, e.g., LH59. The progeny are self-pollinated twice, and plants homozygous for the transgene are identified. Homozygous transgenic plants are crossed to a testcross parent in order to produce hybrids. The test cross parent is an inbred belonging to a heterotic group that is different from that of the transgenic parent and for which it is known that high yielding hybrids can be generated, for example hybrids are produced from crosses of LH59 to either LH195 or LH200.

The following examples illustrate the identification of polymorphic markers useful for mapping and isolating genes of this invention and as markers of QTLs and genes associated with an oil-related trait. Other examples illustrate the identification of oil-related genes and partial genes. Still other examples illustrate methods for inserting genes of this invention into a plant expression vector, i.e., operably linked to a promoter and other regulatory elements, to confer an oil-related trait to a transgenic plant.

Example 1

This example illustrates the identification of polymorphic maize markers of this invention.

A set of more than 800 candidate oil genes was identified (a) as homologs of plant genes that are believed to be in an oil-related metabolic pathway of a model plant such as *Arabidopsis thaliana*; (b) by comparing transcription profiling results for high oil and low oil maize lines; and (c) by subtractive hybridization between endosperm tissues of high oil and low oil lines. The sequences of the candidate oil genes were queried against a proprietary collection of maize genes and partial maize genes, e.g., genomic sequence or ESTs, to identify a set of DNA sequences for candidate maize markers.

Maize polymorphisms were identified by comparing alignments of DNA sequences from separate maize lines. Candidate polymorphisms were qualified by the following parameters:

The minimum length of sequence for a synthetic reference sequence is 200 bases.

The percentage identity of observed bases in a region of 15 bases on each side of a candidate SNP, is 75%.

The minimum BLAST quality in each of the various sequences at a polymorphism site is 35.

The minimum BLAST quality in a region of 15 bases on each side of the polymorphism site is 20.

The SNP and Indel polymorphisms in each locus were qualified for detection by development of an assay, e.g., Taqman® assay (Applied Biosystems, Foster City, Calif.). Assay qualified polymorphisms are evaluated for oil informativeness by comparing allelic frequencies in the two parental lines of an association study population. The parent lines were an oil rich maize line and an oil poor maize line, i.e., the University of Illinois High Oil and Low Oil maize lines as described by Dudley and Lambert (1992, Maydica 37: 81-87). Informativeness is reported as an allelic frequency difference between parental populations, i.e. the high oil line and the low oil line. When one of the parents, e.g., the high oil line, is fixed, its allelic frequency is 1. Markers were qualified if they had an allelic frequency difference of at least 0.6. If the marker was fixed on either parent with a frequency of 0 or 1, a marker could be selected at a lower allelic frequency difference of at least 0.4. The informative markers were viewed on a genetic map to identify marker-deficient regions of chromosomes. Markers with lower allelic frequency difference, e.g., as low as 0.15, were selected to fill in the marker-deficient regions of chromosomes.

DNA amplicons of 484 polymorphic maize genomic DNA loci of this invention are provided in the sequence listing as SEQ ID NO:1 through SEQ ID NO:484. Table 1 provides a description of polymorphisms in the 484 DNA amplicons. Particular aspects of the markers are identified in Table 1 by reference to:

SEQ_NUM, which refers to the sequence number of a nucleic acid sequence in the sequence listing, e.g. SEQ ID NO:1; and SEQ_ID, which refers to an arbitrary identifying name for an amplicon of a polymorphic locus, e.g. "Amplicon25";

MUTATION_ID, which refers to one or more arbitrary identifying names for each polymorphism, e.g. "91";

START_POS which refers to the position in the nucleotide sequence of the polymorphic maize DNA locus where the polymorphism begins, e.g. 110;

END_POS which refers to the position in the nucleotide sequence of the polymorphic maize DNA locus where the polymorphism ends; for SNPs the START_POS and END_POS are common;

TYPE which refers to the identification of the polymorphism as an SNP or IND (Indel);

ALLELEn and STRAINn which refer to the nucleotide sequence of a polymorphism in a specific allelic maize variety, e.g. "C", "T", and when strains are indicated "mo17" and "b73";

Taqman® assays for 488 markers in the 484 polymorphic loci (4 loci are represented by marker assays for 2 separate polymorphisms) are characterized by four separate DNA molecules, i.e. a forward PCR primer, a reverse PCR primer, a VIC-labeled hybridization probe and a FAM-labeled hybridization probe, identified by SEQ ID NO:485 through SEQ ID NO:2436. The primers and probes for each of the 488 markers are more particularly identified in Table 2 by reference to:

Chromosome which refers to one of ten maize chromosomes.

Position which refers to distance to the marker measured in cM from the 5' end of the chromosome.

Marker which corresponds to the MUTATION_ID in the amplicon of SEQ_NUM (1-484).

Forward designates the number in the Sequence Listing for the DNA sequence of the forward primer.

Reverse designates the number in the Sequence Listing for the DNA sequence of the reverse primer.

FAM designates the number in the Sequence Listing for the FAM-labeled hybridization probe.

VIC designates the number in the Sequence Listing for the VIC-labeled hybridization probe.

TABLE 2

| Chromosome | Position | Marker | SEQ_NUM | Forward | Reverse | FAM | VIC |
|---|---|---|---|---|---|---|---|
| 1 | 3.7 | 111829 | 406 | 2121 | 2122 | 2123 | 2124 |
| 1 | 5.6 | 147181 | 442 | 2265 | 2266 | 2267 | 2268 |
| 1 | 14.9 | 36199 | 222 | 1381 | 1382 | 1383 | 1384 |
| 1 | 17.3 | 25418 | 149 | 1081 | 1082 | 1083 | 1084 |
| 1 | 22.4 | 28164 | 155 | 1105 | 1106 | 1107 | 1108 |
| 1 | 25.1 | 43230 | 269 | 1573 | 1574 | 1575 | 1576 |
| 1 | 30.4 | 2847 | 11 | 525 | 526 | 527 | 528 |
| 1 | 30.4 | 144506 | 424 | 2193 | 2194 | 2195 | 2196 |
| 1 | 40.2 | 36685 | 228 | 1405 | 1406 | 1407 | 1408 |
| 1 | 44 | 104827 | 336 | 1841 | 1842 | 1843 | 1844 |
| 1 | 45 | 151360 | 459 | 2333 | 2334 | 2335 | 2336 |
| 1 | 46.8 | 35417 | 216 | 1353 | 1354 | 1355 | 1356 |
| 1 | 46.8 | 37716 | 236 | 1437 | 1438 | 1439 | 1440 |
| 1 | 47.1 | 4409 | 25 | 585 | 586 | 587 | 588 |
| 1 | 52.2 | 42173 | 266 | 1561 | 1562 | 1563 | 1564 |
| 1 | 58.4 | 116 | 2 | 489 | 490 | 491 | 492 |
| 1 | 58.4 | 9159 | 52 | 693 | 694 | 695 | 696 |
| 1 | 60.3 | 143100 | 412 | 2145 | 2146 | 2147 | 2148 |
| 1 | 60.5 | 16876 | 113 | 937 | 938 | 939 | 940 |
| 1 | 60.6 | 33819 | 206 | 1313 | 1314 | 1315 | 1316 |
| 1 | 60.6 | 40124 | 254 | 1513 | 1514 | 1515 | 1516 |
| 1 | 60.6 | 40189 | 255 | 1517 | 1518 | 1519 | 1520 |
| 1 | 62.5 | 9449 | 57 | 713 | 714 | 715 | 716 |
| 1 | 62.5 | 33372 | 203 | 1301 | 1302 | 1303 | 1304 |
| 1 | 68.8 | 148156 | 451 | 2301 | 2302 | 2303 | 2304 |
| 1 | 83.2 | 25863 | 147 | 1073 | 1074 | 1075 | 1076 |

TABLE 2-continued

| Chromosome | Position | Marker | SEQ_NUM | Forward | Reverse | FAM | VIC |
|---|---|---|---|---|---|---|---|
| 1 | 83.2 | 34205 | 207 | 1317 | 1318 | 1319 | 1320 |
| 1 | 83.2 | 43789 | 271 | 1581 | 1582 | 1583 | 1584 |
| 1 | 83.7 | 11522 | 74 | 781 | 782 | 783 | 784 |
| 1 | 83.7 | 106244 | 348 | 1889 | 1890 | 1891 | 1892 |
| 1 | 85.6 | 144090 | 423 | 2189 | 2190 | 2191 | 2192 |
| 1 | 85.9 | 5215 | 35 | 625 | 626 | 627 | 628 |
| 1 | 85.9 | 27375 | 152 | 1093 | 1094 | 1095 | 1096 |
| 1 | 85.9 | 69188 | 301 | 1701 | 1702 | 1703 | 1704 |
| 1 | 86.3 | 8984 | 49 | 681 | 682 | 683 | 684 |
| 1 | 86.3 | 36286 | 223 | 1385 | 1386 | 1387 | 1388 |
| 1 | 86.6 | 148194 | 452 | 2305 | 2306 | 2307 | 2308 |
| 1 | 88.8 | 29829 | 170 | 1165 | 1166 | 1167 | 1168 |
| 1 | 88.8 | 37068 | 231 | 1417 | 1418 | 1419 | 1420 |
| 1 | 88.8 | 68435 | 297 | 1685 | 1686 | 1687 | 1688 |
| 1 | 89.6 | 111365 | 399 | 2093 | 2094 | 2095 | 2096 |
| 1 | 90.5 | 60430 | 293 | 1669 | 1670 | 1671 | 1672 |
| 1 | 90.5 | 111828 | 405 | 2117 | 2118 | 2119 | 2120 |
| 1 | 91 | 113263 | 410 | 2137 | 2138 | 2139 | 2140 |
| 1 | 91.8 | 104474 | 333 | 1829 | 1830 | 1831 | 1832 |
| 1 | 92.3 | 145573 | 433 | 2229 | 2230 | 2231 | 2232 |
| 1 | 95 | 39351 | 247 | 1485 | 1486 | 1487 | 1488 |
| 1 | 96.4 | 107701 | 364 | 1953 | 1954 | 1955 | 1956 |
| 1 | 96.9 | 36448 | 225 | 1393 | 1394 | 1395 | 1396 |
| 1 | 99 | 40655 | 261 | 1541 | 1542 | 1543 | 1544 |
| 1 | 99 | 107077 | 357 | 1925 | 1926 | 1927 | 1928 |
| 1 | 103.3 | 8719 | 40 | 645 | 646 | 647 | 648 |
| 1 | 116.3 | 40338 | 257 | 1525 | 1526 | 1527 | 1528 |
| 1 | 116.3 | 54410 | 284 | 1633 | 1634 | 1635 | 1636 |
| 1 | 121.1 | 107621 | 362 | 1945 | 1946 | 1947 | 1948 |
| 1 | 121.5 | 16755 | 111 | 929 | 930 | 931 | 932 |
| 1 | 121.5 | 36863 | 230 | 1413 | 1414 | 1415 | 1416 |
| 1 | 122.1 | 41280 | 263 | 1549 | 1550 | 1551 | 1552 |
| 1 | 123.3 | 109328 | 379 | 2013 | 2014 | 2015 | 2016 |
| 1 | 124.6 | 33373 | 204 | 1305 | 1306 | 1307 | 1308 |
| 1 | 127.6 | 105648 | 346 | 1881 | 1882 | 1883 | 1884 |
| 1 | 129.5 | 4453 | 28 | 597 | 598 | 599 | 600 |
| 1 | 129.5 | 9626 | 64 | 741 | 742 | 743 | 744 |
| 1 | 129.5 | 37689 | 235 | 1433 | 1434 | 1435 | 1436 |
| 1 | 130.3 | 69565 | 302 | 1705 | 1706 | 1707 | 1708 |
| 1 | 132.1 | 34903 | 209 | 1325 | 1326 | 1327 | 1328 |
| 1 | 133.9 | 16724 | 102 | 893 | 894 | 895 | 896 |
| 1 | 138.5 | 12824 | 79 | 801 | 802 | 803 | 804 |
| 1 | 139.2 | 38701 | 241 | 1461 | 1462 | 1463 | 1464 |
| 1 | 140.8 | 5098 | 33 | 617 | 618 | 619 | 620 |
| 1 | 153.7 | 31993 | 191 | 1253 | 1254 | 1255 | 1256 |
| 1 | 156.7 | 8982 | 48 | 677 | 678 | 679 | 680 |
| 1 | 159.7 | 39502 | 248 | 1489 | 1490 | 1491 | 1492 |
| 1 | 160.4 | 148362 | 455 | 2317 | 2318 | 2319 | 2320 |
| 1 | 164.2 | 39896 | 252 | 1505 | 1506 | 1507 | 1508 |
| 1 | 165.6 | 108862 | 376 | 2001 | 2002 | 2003 | 2004 |
| 1 | 168.3 | 9701 | 67 | 753 | 754 | 755 | 756 |
| 1 | 178.6 | 151382 | 457 | 2325 | 2326 | 2327 | 2328 |
| 1 | 179.8 | 32253 | 198 | 1281 | 1282 | 1283 | 1284 |
| 1 | 194.2 | 13490 | 81 | 809 | 810 | 811 | 812 |
| 1 | 200.3 | 30840 | 181 | 1213 | 1214 | 1215 | 1216 |
| 1 | 207 | 16137 | 98 | 877 | 878 | 879 | 880 |
| 2 | 5.8 | 9867 | 71 | 769 | 770 | 771 | 772 |
| 2 | 5.8 | 31064 | 183 | 1221 | 1222 | 1223 | 1224 |
| 2 | 12.9 | 104447 | 332 | 1825 | 1826 | 1827 | 1828 |
| 2 | 14.1 | 39289 | 246 | 1481 | 1482 | 1483 | 1484 |
| 2 | 17.5 | 106678 | 351 | 1901 | 1902 | 1903 | 1904 |
| 2 | 19.5 | 82235 | 325 | 1797 | 1798 | 1799 | 1800 |
| 2 | 30.1 | 106842 | 353 | 1909 | 1910 | 1911 | 1912 |
| 2 | 32.8 | 2945 | 12 | 529 | 530 | 531 | 532 |
| 2 | 32.8 | 16074 | 97 | 873 | 874 | 875 | 876 |
| 2 | 33.9 | 80031 | 321 | 1781 | 1782 | 1783 | 1784 |
| 2 | 35.9 | 13691 | 89 | 841 | 842 | 843 | 844 |
| 2 | 35.9 | 50315 | 277 | 1605 | 1606 | 1607 | 1608 |
| 2 | 38.3 | 9706 | 68 | 757 | 758 | 759 | 760 |
| 2 | 42.4 | 32016 | 192 | 1257 | 1258 | 1259 | 1260 |
| 2 | 62.2 | 80704 | 323 | 1789 | 1790 | 1791 | 1792 |
| 2 | 70.4 | 9364 | 56 | 709 | 710 | 711 | 712 |
| 2 | 74.8 | 9623 | 63 | 737 | 738 | 739 | 740 |
| 2 | 75.6 | 40931 | 262 | 1545 | 1546 | 1547 | 1548 |
| 2 | 76.2 | 36323 | 224 | 1389 | 1390 | 1391 | 1392 |
| 2 | 76.2 | 104946 | 340 | 1857 | 1858 | 1859 | 1860 |
| 2 | 77.4 | 111617 | 403 | 2109 | 2110 | 2111 | 2112 |
| 2 | 78.2 | 11466 | 73 | 777 | 778 | 779 | 780 |

TABLE 2-continued

| Chromosome | Position | Marker | SEQ_NUM | Forward | Reverse | FAM | VIC |
|---|---|---|---|---|---|---|---|
| 2 | 78.2 | 79073 | 315 | 1757 | 1758 | 1759 | 1760 |
| 2 | 78.2 | 108493 | 374 | 1993 | 1994 | 1995 | 1996 |
| 2 | 87.3 | 23442 | 143 | 1057 | 1058 | 1059 | 1060 |
| 2 | 87.5 | 107911 | 368 | 1969 | 1970 | 1971 | 1972 |
| 2 | 92.5 | 551 | 4 | 497 | 498 | 499 | 500 |
| 2 | 92.5 | 3177 | 14 | 537 | 538 | 539 | 540 |
| 2 | 92.5 | 53097 | 282 | 1625 | 1626 | 1627 | 1628 |
| 2 | 92.9 | 366 | 3 | 493 | 494 | 495 | 496 |
| 2 | 92.9 | 84829 | 330 | 1817 | 1818 | 1819 | 1820 |
| 2 | 99.7 | 151288 | 458 | 2329 | 2330 | 2331 | 2332 |
| 2 | 104.8 | 82458 | 327 | 1805 | 1806 | 1807 | 1808 |
| 2 | 106 | 111475 | 402 | 2105 | 2106 | 2107 | 2108 |
| 2 | 106.2 | 108013 | 371 | 1981 | 1982 | 1983 | 1984 |
| 2 | 107.6 | 2307 | 8 | 513 | 514 | 515 | 516 |
| 2 | 114.9 | 22775 | 135 | 1025 | 1026 | 1027 | 1028 |
| 2 | 123.4 | 104954 | 341 | 1861 | 1862 | 1863 | 1864 |
| 2 | 127 | 41850 | 264 | 1553 | 1554 | 1555 | 1556 |
| 2 | 134.9 | 31474 | 187 | 1237 | 1238 | 1239 | 1240 |
| 2 | 139.8 | 109207 | 377 | 2005 | 2006 | 2007 | 2008 |
| 2 | 144.2 | 35297 | 212 | 1337 | 1338 | 1339 | 1340 |
| 2 | 152.4 | 43579 | 270 | 1577 | 1578 | 1579 | 1580 |
| 2 | 153.5 | 147548 | 448 | 2289 | 2290 | 2291 | 2292 |
| 2 | 156.6 | 14467 | 84 | 821 | 822 | 823 | 824 |
| 2 | 157.2 | 33320 | 202 | 1297 | 1298 | 1299 | 1300 |
| 2 | 164.2 | 735 | 7 | 509 | 510 | 511 | 512 |
| 2 | 164.2 | 76792 | 308 | 1729 | 1730 | 1731 | 1732 |
| 3 | 6 | 8911 | 45 | 665 | 666 | 667 | 668 |
| 3 | 6 | 51614 | 280 | 1617 | 1618 | 1619 | 1620 |
| 3 | 9.1 | 10667 | 72 | 773 | 774 | 775 | 776 |
| 3 | 19.7 | 19963 | 117 | 953 | 954 | 955 | 956 |
| 3 | 19.7 | 32137 | 196 | 1273 | 1274 | 1275 | 1276 |
| 3 | 46.2 | 49293 | 275 | 1597 | 1598 | 1599 | 1600 |
| 3 | 52.3 | 109315 | 378 | 2009 | 2010 | 2011 | 2012 |
| 3 | 53.5 | 25000 | 144 | 1061 | 1062 | 1063 | 1064 |
| 3 | 54.1 | 21154 | 125 | 985 | 986 | 987 | 988 |
| 3 | 54.1 | 109722 | 384 | 2033 | 2034 | 2035 | 2036 |
| 3 | 57.2 | 109509 | 382 | 2025 | 2026 | 2027 | 2028 |
| 3 | 57.2 | 146158 | 435 | 2237 | 2238 | 2239 | 2240 |
| 3 | 57.5 | 107784 | 365 | 1957 | 1958 | 1959 | 1960 |
| 3 | 58.6 | 29867 | 173 | 1177 | 1178 | 1179 | 1180 |
| 3 | 59.3 | 4599 | 30 | 605 | 606 | 607 | 608 |
| 3 | 59.3 | 21190 | 131 | 1009 | 1010 | 1011 | 1012 |
| 3 | 59.3 | 28923 | 159 | 1121 | 1122 | 1123 | 1124 |
| 3 | 59.3 | 83776 | 328 | 1809 | 1810 | 1811 | 1812 |
| 3 | 59.3 | 147511 | 447 | 2285 | 2286 | 2287 | 2288 |
| 3 | 59.3 | 147768 | 449 | 2293 | 2294 | 2295 | 2296 |
| 3 | 60.4 | 8685 | 39 | 641 | 642 | 643 | 644 |
| 3 | 60.4 | 9468 | 58 | 717 | 718 | 719 | 720 |
| 3 | 60.4 | 9470 | 59 | 721 | 722 | 723 | 724 |
| 3 | 60.5 | 145322 | 432 | 2225 | 2226 | 2227 | 2228 |
| 3 | 61 | 16729 | 103 | 897 | 898 | 899 | 900 |
| 3 | 61.7 | 32247 | 197 | 1277 | 1278 | 1279 | 1280 |
| 3 | 61.7 | 39785 | 251 | 1501 | 1502 | 1503 | 1504 |
| 3 | 62.7 | 9144 | 51 | 689 | 690 | 691 | 692 |
| 3 | 62.7 | 9739 | 69 | 761 | 762 | 763 | 764 |
| 3 | 68.5 | 153431 | 460 | 2337 | 2338 | 2339 | 2340 |
| 3 | 68.5 | 154505 | 474 | 2393 | 2394 | 2395 | 2396 |
| 3 | 68.5 | 154509 | 477 | 2405 | 2406 | 2407 | 2408 |
| 3 | 68.5 | 154511 | 475 | 2397 | 2398 | 2399 | 2400 |
| 3 | 68.5 | 154532 | 472 | 2385 | 2386 | 2387 | 2388 |
| 3 | 68.5 | 154536 | 469 | 2373 | 2374 | 2375 | 2376 |
| 3 | 68.5 | 154552 | 471 | 2381 | 2382 | 2383 | 2384 |
| 3 | 68.5 | 154616 | 473 | 2389 | 2390 | 2391 | 2392 |
| 3 | 68.5 | 155689 | 479 | 2413 | 2414 | 2415 | 2416 |
| 3 | 68.5 | 155708 | 480 | 2417 | 2418 | 2419 | 2420 |
| 3 | 71 | 4886 | 31 | 609 | 610 | 611 | 612 |
| 3 | 71.5 | 24395 | 141 | 1049 | 1050 | 1051 | 1052 |
| 3 | 71.8 | 79081 | 316 | 1761 | 1762 | 1763 | 1764 |
| 3 | 74.3 | 23890 | 145 | 1065 | 1066 | 1067 | 1068 |
| 3 | 79.2 | 9173 | 53 | 697 | 698 | 699 | 700 |
| 3 | 89.7 | 15954 | 93 | 857 | 858 | 859 | 860 |
| 3 | 89.7 | 15965 | 94 | 861 | 862 | 863 | 864 |
| 3 | 93.2 | 77118 | 309 | 1733 | 1734 | 1735 | 1736 |
| 3 | 96.1 | 21772 | 129 | 1001 | 1002 | 1003 | 1004 |
| 3 | 96.5 | 36694 | 229 | 1409 | 1410 | 1411 | 1412 |
| 3 | 98.2 | 111204 | 397 | 2085 | 2086 | 2087 | 2088 |
| 3 | 98.6 | 29390 | 165 | 1145 | 1146 | 1147 | 1148 |
| 3 | 101.3 | 108630 | 375 | 1997 | 1998 | 1999 | 2000 |

TABLE 2-continued

| Chromosome | Position | Marker | SEQ_NUM | Forward | Reverse | FAM | VIC |
|---|---|---|---|---|---|---|---|
| 3 | 105 | 35568 | 217 | 1357 | 1358 | 1359 | 1360 |
| 3 | 106.9 | 9473 | 60 | 725 | 726 | 727 | 728 |
| 3 | 109.4 | 21603 | 127 | 993 | 994 | 995 | 996 |
| 3 | 111.4 | 110780 | 392 | 2065 | 2066 | 2067 | 2068 |
| 3 | 118.4 | 146534 | 439 | 2253 | 2254 | 2255 | 2256 |
| 3 | 118.9 | 56939 | 287 | 1645 | 1646 | 1647 | 1648 |
| 3 | 123.8 | 143969 | 422 | 2185 | 2186 | 2187 | 2188 |
| 3 | 127.7 | 9079 | 50 | 685 | 686 | 687 | 688 |
| 3 | 139.1 | 3970 | 22 | 573 | 574 | 575 | 576 |
| 4 | 1 | 12340 | 77 | 793 | 794 | 795 | 796 |
| 4 | 23.6 | 2739 | 10 | 521 | 522 | 523 | 524 |
| 4 | 38.7 | 110069 | 386 | 2041 | 2042 | 2043 | 2044 |
| 4 | 38.7 | 111464 | 400 | 2097 | 2098 | 2099 | 2100 |
| 4 | 52.8 | 24647 | 146 | 1069 | 1070 | 1071 | 1072 |
| 4 | 53.2 | 40461 | 259 | 1533 | 1534 | 1535 | 1536 |
| 4 | 53.2 | 156243 | 484 | 2433 | 2434 | 2435 | 2436 |
| 4 | 58.6 | 1122 | 6 | 505 | 506 | 507 | 508 |
| 4 | 58.6 | 12012 | 75 | 785 | 786 | 787 | 788 |
| 4 | 62.1 | 10671 | 76 | 789 | 790 | 791 | 792 |
| 4 | 63.2 | 70730 | 305 | 1717 | 1718 | 1719 | 1720 |
| 4 | 64.9 | 38852 | 242 | 1465 | 1466 | 1467 | 1468 |
| 4 | 67.6 | 15096 | 90 | 845 | 846 | 847 | 848 |
| 4 | 67.6 | 154038 | 467 | 2365 | 2366 | 2367 | 2368 |
| 4 | 69.5 | 3351 | 19 | 561 | 562 | 563 | 564 |
| 4 | 69.5 | 5021 | 32 | 613 | 614 | 615 | 616 |
| 4 | 69.5 | 14666 | 88 | 837 | 838 | 839 | 840 |
| 4 | 69.5 | 15247 | 100 | 885 | 886 | 887 | 888 |
| 4 | 69.5 | 37503 | 232 | 1421 | 1422 | 1423 | 1424 |
| 4 | 69.5 | 80475 | 322 | 1785 | 1786 | 1787 | 1788 |
| 4 | 69.5 | 153424 | 464 | 2353 | 2354 | 2355 | 2356 |
| 4 | 69.9 | 107276 | 358 | 1929 | 1930 | 1931 | 1932 |
| 4 | 71.4 | 84527 | 329 | 1813 | 1814 | 1815 | 1816 |
| 4 | 73 | 35294 | 211 | 1333 | 1334 | 1335 | 1336 |
| 4 | 80 | 106845 | 354 | 1913 | 1914 | 1915 | 1916 |
| 4 | 86.5 | 3964 | 21 | 569 | 570 | 571 | 572 |
| 4 | 87.7 | 107840 | 366 | 1961 | 1962 | 1963 | 1964 |
| 4 | 92.1 | 9187 | 54 | 701 | 702 | 703 | 704 |
| 4 | 107.7 | 106491 | 350 | 1897 | 1898 | 1899 | 1900 |
| 4 | 108.2 | 39511 | 249 | 1493 | 1494 | 1495 | 1496 |
| 4 | 109.2 | 23289 | 138 | 1037 | 1038 | 1039 | 1040 |
| 4 | 109.7 | 26846 | 150 | 1085 | 1086 | 1087 | 1088 |
| 4 | 109.7 | 28933 | 161 | 1129 | 1130 | 1131 | 1132 |
| 4 | 110.3 | 8979 | 47 | 673 | 674 | 675 | 676 |
| 4 | 112.4 | 54460 | 285 | 1637 | 1638 | 1639 | 1640 |
| 4 | 115.1 | 71159 | 306 | 1721 | 1722 | 1723 | 1724 |
| 4 | 115.4 | 29435 | 166 | 1149 | 1150 | 1151 | 1152 |
| 4 | 117.6 | 30745 | 179 | 1205 | 1206 | 1207 | 1208 |
| 4 | 119.2 | 2435 | 9 | 517 | 518 | 519 | 520 |
| 4 | 119.2 | 12711 | 78 | 797 | 798 | 799 | 800 |
| 4 | 119.2 | 17828 | 108 | 917 | 918 | 919 | 920 |
| 4 | 119.2 | 18439 | 115 | 945 | 946 | 947 | 948 |
| 4 | 119.2 | 20933 | 121 | 969 | 970 | 971 | 972 |
| 4 | 119.2 | 20934 | 122 | 973 | 974 | 975 | 976 |
| 4 | 119.2 | 24422 | 142 | 1053 | 1054 | 1055 | 1056 |
| 4 | 120.9 | 29194 | 163 | 1137 | 1138 | 1139 | 1140 |
| 4 | 122.4 | 151472 | 456 | 2321 | 2322 | 2323 | 2324 |
| 4 | 128.1 | 32049 | 195 | 1269 | 1270 | 1271 | 1272 |
| 4 | 133.6 | 3224 | 16 | 545 | 546 | 547 | 548 |
| 4 | 133.6 | 3226 | 16 | 549 | 550 | 551 | 552 |
| 4 | 135.1 | 3152 | 13 | 533 | 534 | 535 | 536 |
| 4 | 135.1 | 4445 | 27 | 593 | 594 | 595 | 596 |
| 4 | 135.1 | 13833 | 82 | 813 | 814 | 815 | 816 |
| 4 | 135.8 | 17900 | 109 | 921 | 922 | 923 | 924 |
| 4 | 136.4 | 147219 | 443 | 2269 | 2270 | 2271 | 2272 |
| 4 | 142.1 | 147037 | 441 | 2261 | 2262 | 2263 | 2264 |
| 4 | 143.1 | 43121 | 268 | 1569 | 1570 | 1571 | 1572 |
| 4 | 144.8 | 35338 | 213 | 1341 | 1342 | 1343 | 1344 |
| 5 | 1.6 | 24265 | 140 | 1045 | 1046 | 1047 | 1048 |
| 5 | 1.6 | 31790 | 190 | 1249 | 1250 | 1251 | 1252 |
| 5 | 9.7 | 143251 | 414 | 2153 | 2154 | 2155 | 2156 |
| 5 | 13.8 | 69592 | 303 | 1709 | 1710 | 1711 | 1712 |
| 5 | 16.7 | 57137 | 288 | 1649 | 1650 | 1651 | 1652 |
| 5 | 16.7 | 105613 | 345 | 1877 | 1878 | 1879 | 1880 |
| 5 | 17.2 | 107858 | 367 | 1965 | 1966 | 1967 | 1968 |
| 5 | 27.4 | 91 | 1 | 485 | 486 | 487 | 488 |
| 5 | 31.3 | 5275 | 36 | 629 | 630 | 631 | 632 |
| 5 | 39.9 | 109403 | 381 | 2021 | 2022 | 2023 | 2024 |
| 5 | 41.7 | 16527 | 99 | 881 | 882 | 883 | 884 |

TABLE 2-continued

| Chromosome | Position | Marker | SEQ_NUM | Forward | Reverse | FAM | VIC |
|---|---|---|---|---|---|---|---|
| 5 | 50.9 | 109342 | 380 | 2017 | 2018 | 2019 | 2020 |
| 5 | 51.9 | 16762 | 104 | 901 | 902 | 903 | 904 |
| 5 | 51.9 | 16767 | 105 | 905 | 906 | 907 | 908 |
| 5 | 53.4 | 79519 | 318 | 1769 | 1770 | 1771 | 1772 |
| 5 | 56.5 | 9668 | 66 | 749 | 750 | 751 | 752 |
| 5 | 57.7 | 30270 | 177 | 1197 | 1198 | 1199 | 1200 |
| 5 | 57.7 | 52081 | 281 | 1621 | 1622 | 1623 | 1624 |
| 5 | 57.7 | 77545 | 311 | 1741 | 1742 | 1743 | 1744 |
| 5 | 62.3 | 51419 | 279 | 1613 | 1614 | 1615 | 1616 |
| 5 | 63 | 32272 | 199 | 1285 | 1286 | 1287 | 1288 |
| 5 | 66.9 | 30000 | 174 | 1181 | 1182 | 1183 | 1184 |
| 5 | 66.9 | 146415 | 437 | 2245 | 2246 | 2247 | 2248 |
| 5 | 69.3 | 106912 | 355 | 1917 | 1918 | 1919 | 1920 |
| 5 | 69.6 | 107061 | 356 | 1921 | 1922 | 1923 | 1924 |
| 5 | 69.6 | 144731 | 426 | 2201 | 2202 | 2203 | 2204 |
| 5 | 70.5 | 105854 | 347 | 1885 | 1886 | 1887 | 1888 |
| 5 | 70.8 | 22796 | 136 | 1029 | 1030 | 1031 | 1032 |
| 5 | 70.8 | 27874 | 158 | 1117 | 1118 | 1119 | 1120 |
| 5 | 71.7 | 143216 | 413 | 2149 | 2150 | 2151 | 2152 |
| 5 | 73.2 | 33249 | 201 | 1293 | 1294 | 1295 | 1296 |
| 5 | 76.4 | 29820 | 169 | 1161 | 1162 | 1163 | 1164 |
| 5 | 78.2 | 144687 | 425 | 2197 | 2198 | 2199 | 2200 |
| 5 | 80.2 | 36637 | 227 | 1401 | 1402 | 1403 | 1404 |
| 5 | 80.9 | 143418 | 419 | 2173 | 2174 | 2175 | 2176 |
| 5 | 81.2 | 38478 | 238 | 1449 | 1450 | 1451 | 1452 |
| 5 | 81.5 | 48616 | 274 | 1593 | 1594 | 1595 | 1596 |
| 5 | 83 | 104850 | 337 | 1845 | 1846 | 1847 | 1848 |
| 5 | 83.7 | 148026 | 450 | 2297 | 2298 | 2299 | 2300 |
| 5 | 86.2 | 9297 | 55 | 705 | 706 | 707 | 708 |
| 5 | 87.3 | 106300 | 349 | 1893 | 1894 | 1895 | 1896 |
| 5 | 90.6 | 5480 | 38 | 637 | 638 | 639 | 640 |
| 5 | 100.9 | 35377 | 214 | 1345 | 1346 | 1347 | 1348 |
| 5 | 104.5 | 58375 | 290 | 1657 | 1658 | 1659 | 1660 |
| 5 | 117.1 | 143380 | 416 | 2161 | 2162 | 2163 | 2164 |
| 5 | 136 | 105546 | 343 | 1869 | 1870 | 1871 | 1872 |
| 5 | 150.5 | 31084 | 184 | 1225 | 1226 | 1227 | 1228 |
| 6 | 16.4 | 27615 | 157 | 1113 | 1114 | 1115 | 1116 |
| 6 | 17.3 | 154854 | 476 | 2401 | 2402 | 2403 | 2404 |
| 6 | 19.4 | 105014 | 342 | 1865 | 1866 | 1867 | 1868 |
| 6 | 22.9 | 79529 | 319 | 1773 | 1774 | 1775 | 1776 |
| 6 | 30.5 | 3284 | 18 | 557 | 558 | 559 | 560 |
| 6 | 30.5 | 69630 | 304 | 1713 | 1714 | 1715 | 1716 |
| 6 | 32.8 | 29780 | 168 | 1157 | 1158 | 1159 | 1160 |
| 6 | 32.8 | 68941 | 298 | 1689 | 1690 | 1691 | 1692 |
| 6 | 32.8 | 146458 | 438 | 2249 | 2250 | 2251 | 2252 |
| 6 | 33.3 | 104510 | 334 | 1833 | 1834 | 1835 | 1836 |
| 6 | 33.3 | 107639 | 363 | 1949 | 1950 | 1951 | 1952 |
| 6 | 35.3 | 15304 | 101 | 889 | 890 | 891 | 892 |
| 6 | 35.3 | 16944 | 106 | 909 | 910 | 911 | 912 |
| 6 | 35.3 | 35574 | 218 | 1361 | 1362 | 1363 | 1364 |
| 6 | 35.3 | 77413 | 310 | 1737 | 1738 | 1739 | 1740 |
| 6 | 35.3 | 110607 | 389 | 2053 | 2054 | 2055 | 2056 |
| 6 | 37.3 | 36067 | 221 | 1373 | 1374 | 1375 | 1376 |
| 6 | 37.3 | 36073 | 221 | 1377 | 1378 | 1379 | 1380 |
| 6 | 41.2 | 34560 | 208 | 1321 | 1322 | 1323 | 1324 |
| 6 | 43.1 | 30176 | 176 | 1193 | 1194 | 1195 | 1196 |
| 6 | 52.8 | 4463 | 29 | 601 | 602 | 603 | 604 |
| 6 | 53.1 | 60751 | 294 | 1673 | 1674 | 1675 | 1676 |
| 6 | 53.5 | 32034 | 194 | 1265 | 1266 | 1267 | 1268 |
| 6 | 53.5 | 57758 | 289 | 1653 | 1654 | 1655 | 1656 |
| 6 | 53.5 | 108212 | 372 | 1985 | 1986 | 1987 | 1988 |
| 6 | 58.1 | 59008 | 292 | 1665 | 1666 | 1667 | 1668 |
| 6 | 58.1 | 146195 | 436 | 2241 | 2242 | 2243 | 2244 |
| 6 | 59.9 | 3277 | 17 | 553 | 554 | 555 | 556 |
| 6 | 59.9 | 105586 | 344 | 1873 | 1874 | 1875 | 1876 |
| 6 | 61.5 | 148039 | 453 | 2309 | 2310 | 2311 | 2312 |
| 6 | 61.5 | 155861 | 482 | 2425 | 2426 | 2427 | 2428 |
| 6 | 63.1 | 20410 | 128 | 997 | 998 | 999 | 1000 |
| 6 | 66.6 | 8838 | 43 | 657 | 658 | 659 | 660 |
| 6 | 67.5 | 14694 | 96 | 869 | 870 | 871 | 872 |
| 6 | 73.3 | 113381 | 411 | 2141 | 2142 | 2143 | 2144 |
| 6 | 86.9 | 110972 | 395 | 2077 | 2078 | 2079 | 2080 |
| 6 | 92.8 | 37947 | 237 | 1441 | 1442 | 1443 | 1444 |
| 6 | 92.8 | 37948 | 237 | 1445 | 1446 | 1447 | 1448 |
| 6 | 93.9 | 5319 | 37 | 633 | 634 | 635 | 636 |
| 6 | 95.8 | 30771 | 180 | 1209 | 1210 | 1211 | 1212 |
| 6 | 97.8 | 27295 | 151 | 1089 | 1090 | 1091 | 1092 |
| 6 | 99.1 | 108433 | 373 | 1989 | 1990 | 1991 | 1992 |

TABLE 2-continued

| Chromosome | Position | Marker | SEQ_NUM | Forward | Reverse | FAM | VIC |
|---|---|---|---|---|---|---|---|
| 6 | 110.4 | 31684 | 189 | 1245 | 1246 | 1247 | 1248 |
| 6 | 112.4 | 107449 | 361 | 1941 | 1942 | 1943 | 1944 |
| 6 | 117.4 | 16017 | 107 | 913 | 914 | 915 | 916 |
| 6 | 121 | 37634 | 234 | 1429 | 1430 | 1431 | 1432 |
| 6 | 128.7 | 9667 | 65 | 745 | 746 | 747 | 748 |
| 6 | 130.8 | 21433 | 126 | 989 | 990 | 991 | 992 |
| 6 | 132.7 | 37555 | 233 | 1425 | 1426 | 1427 | 1428 |
| 7 | 56.2 | 68954 | 299 | 1693 | 1694 | 1695 | 1696 |
| 7 | 62 | 31370 | 186 | 1233 | 1234 | 1235 | 1236 |
| 7 | 62 | 42164 | 265 | 1557 | 1558 | 1559 | 1560 |
| 7 | 67 | 30674 | 178 | 1201 | 1202 | 1203 | 1204 |
| 7 | 67.4 | 33769 | 205 | 1309 | 1310 | 1311 | 1312 |
| 7 | 67.9 | 39064 | 244 | 1473 | 1474 | 1475 | 1476 |
| 7 | 69.1 | 35633 | 219 | 1365 | 1366 | 1367 | 1368 |
| 7 | 72.8 | 42930 | 267 | 1565 | 1566 | 1567 | 1568 |
| 7 | 73.8 | 68426 | 296 | 1681 | 1682 | 1683 | 1684 |
| 7 | 73.9 | 29005 | 162 | 1133 | 1134 | 1135 | 1136 |
| 7 | 74 | 51405 | 278 | 1609 | 1610 | 1611 | 1612 |
| 7 | 83.6 | 29362 | 164 | 1141 | 1142 | 1143 | 1144 |
| 7 | 98.5 | 8799 | 42 | 653 | 654 | 655 | 656 |
| 7 | 98.8 | 48425 | 272 | 1585 | 1586 | 1587 | 1588 |
| 7 | 99.8 | 4415 | 26 | 589 | 590 | 591 | 592 |
| 7 | 99.8 | 35408 | 215 | 1349 | 1350 | 1351 | 1352 |
| 7 | 103.6 | 79695 | 320 | 1777 | 1778 | 1779 | 1780 |
| 7 | 107.5 | 38914 | 243 | 1469 | 1470 | 1471 | 1472 |
| 7 | 109.5 | 39978 | 253 | 1509 | 1510 | 1511 | 1512 |
| 7 | 113.3 | 155829 | 481 | 2421 | 2422 | 2423 | 2424 |
| 7 | 114.7 | 28932 | 160 | 1125 | 1126 | 1127 | 1128 |
| 7 | 114.7 | 31547 | 188 | 1241 | 1242 | 1243 | 1244 |
| 7 | 114.7 | 68149 | 295 | 1677 | 1678 | 1679 | 1680 |
| 7 | 115.8 | 4093 | 23 | 577 | 578 | 579 | 580 |
| 7 | 118.6 | 4302 | 24 | 581 | 582 | 583 | 584 |
| 7 | 118.6 | 38653 | 240 | 1457 | 1458 | 1459 | 1460 |
| 7 | 118.6 | 78828 | 314 | 1753 | 1754 | 1755 | 1756 |
| 7 | 118.6 | 81460 | 324 | 1793 | 1794 | 1795 | 1796 |
| 7 | 120.9 | 153856 | 463 | 2349 | 2350 | 2351 | 2352 |
| 7 | 122.2 | 145260 | 429 | 2213 | 2214 | 2215 | 2216 |
| 7 | 124.5 | 15184 | 92 | 853 | 854 | 855 | 856 |
| 7 | 124.5 | 39773 | 250 | 1497 | 1498 | 1499 | 1500 |
| 7 | 131.6 | 79307 | 317 | 1765 | 1766 | 1767 | 1768 |
| 7 | 132.8 | 30026 | 175 | 1185 | 1186 | 1187 | 1188 |
| 7 | 132.8 | 30029 | 175 | 1189 | 1190 | 1191 | 1192 |
| 7 | 144.6 | 30872 | 182 | 1217 | 1218 | 1219 | 1220 |
| 7 | 154.5 | 110771 | 391 | 2061 | 2062 | 2063 | 2064 |
| 7 | 164.7 | 155475 | 478 | 2409 | 2410 | 2411 | 2412 |
| 7 | 165.5 | 146593 | 440 | 2257 | 2258 | 2259 | 2260 |
| 7 | 167 | 143371 | 415 | 2157 | 2158 | 2159 | 2160 |
| 7 | 186.5 | 36490 | 226 | 1397 | 1398 | 1399 | 1400 |
| 7 | 189.3 | 18157 | 112 | 933 | 934 | 935 | 936 |
| 7 | 189.4 | 21038 | 124 | 981 | 982 | 983 | 984 |
| 7 | 189.4 | 69120 | 300 | 1697 | 1698 | 1699 | 1700 |
| 7 | 189.4 | 71624 | 307 | 1725 | 1726 | 1727 | 1728 |
| 7 | 193.9 | 19704 | 123 | 977 | 978 | 979 | 980 |
| 8 | 8.8 | 35173 | 210 | 1329 | 1330 | 1331 | 1332 |
| 8 | 16.4 | 40320 | 256 | 1521 | 1522 | 1523 | 1524 |
| 8 | 16.9 | 19198 | 116 | 949 | 950 | 951 | 952 |
| 8 | 34.3 | 29842 | 172 | 1173 | 1174 | 1175 | 1176 |
| 8 | 40.9 | 107937 | 369 | 1973 | 1974 | 1975 | 1976 |
| 8 | 43.1 | 111628 | 404 | 2113 | 2114 | 2115 | 2116 |
| 8 | 43.3 | 26720 | 154 | 1101 | 1102 | 1103 | 1104 |
| 8 | 45.5 | 32030 | 193 | 1261 | 1262 | 1263 | 1264 |
| 8 | 47.3 | 53899 | 283 | 1629 | 1630 | 1631 | 1632 |
| 8 | 47.9 | 104862 | 339 | 1853 | 1854 | 1855 | 1856 |
| 8 | 49.7 | 107396 | 360 | 1937 | 1938 | 1939 | 1940 |
| 8 | 53.9 | 27361 | 156 | 1109 | 1110 | 1111 | 1112 |
| 8 | 53.9 | 145200 | 428 | 2209 | 2210 | 2211 | 2212 |
| 8 | 55.7 | 23091 | 137 | 1033 | 1034 | 1035 | 1036 |
| 8 | 59.3 | 77568 | 312 | 1745 | 1746 | 1747 | 1748 |
| 8 | 64 | 110148 | 387 | 2045 | 2046 | 2047 | 2048 |
| 8 | 64.5 | 104858 | 338 | 1849 | 1850 | 1851 | 1852 |
| 8 | 65.8 | 104389 | 331 | 1821 | 1822 | 1823 | 1824 |
| 8 | 66.6 | 21895 | 130 | 1005 | 1006 | 1007 | 1008 |
| 8 | 67.4 | 48562 | 273 | 1589 | 1590 | 1591 | 1592 |
| 8 | 68.4 | 82295 | 326 | 1801 | 1802 | 1803 | 1804 |
| 8 | 76.8 | 111472 | 401 | 2101 | 2102 | 2103 | 2104 |
| 8 | 85.9 | 110684 | 390 | 2057 | 2058 | 2059 | 2060 |
| 8 | 87.5 | 9759 | 70 | 765 | 766 | 767 | 768 |
| 8 | 87.5 | 20537 | 120 | 965 | 966 | 967 | 968 |

TABLE 2-continued

| Chromosome | Position | Marker | SEQ_NUM | Forward | Reverse | FAM | VIC |
|---|---|---|---|---|---|---|---|
| 8 | 87.5 | 112497 | 408 | 2129 | 2130 | 2131 | 2132 |
| 8 | 105.5 | 107286 | 359 | 1933 | 1934 | 1935 | 1936 |
| 8 | 106.8 | 13100 | 80 | 805 | 806 | 807 | 808 |
| 8 | 117.3 | 145077 | 427 | 2205 | 2206 | 2207 | 2208 |
| 8 | 117.3 | 145298 | 430 | 2217 | 2218 | 2219 | 2220 |
| 8 | 132.8 | 14545 | 87 | 833 | 834 | 835 | 836 |
| 8 | 135.5 | 8757 | 41 | 649 | 650 | 651 | 652 |
| 8 | 137.4 | 561 | 5 | 501 | 502 | 503 | 504 |
| 9 | 0 | 14479 | 86 | 829 | 830 | 831 | 832 |
| 9 | 20.5 | 58904 | 291 | 1661 | 1662 | 1663 | 1664 |
| 9 | 38.1 | 49557 | 276 | 1601 | 1602 | 1603 | 1604 |
| 9 | 78.2 | 29745 | 167 | 1153 | 1154 | 1155 | 1156 |
| 9 | 87.7 | 12557 | 83 | 817 | 818 | 819 | 820 |
| 9 | 90.3 | 23779 | 139 | 1041 | 1042 | 1043 | 1044 |
| 9 | 93.4 | 29832 | 171 | 1169 | 1170 | 1171 | 1172 |
| 9 | 93.4 | 55370 | 286 | 1641 | 1642 | 1643 | 1644 |
| 9 | 93.8 | 110377 | 388 | 2049 | 2050 | 2051 | 2052 |
| 9 | 93.8 | 113113 | 409 | 2133 | 2134 | 2135 | 2136 |
| 9 | 93.9 | 155159 | 470 | 2377 | 2378 | 2379 | 2380 |
| 9 | 94 | 25961 | 148 | 1077 | 1078 | 1079 | 1080 |
| 9 | 94.5 | 148621 | 454 | 2313 | 2314 | 2315 | 2316 |
| 9 | 94.6 | 112139 | 407 | 2125 | 2126 | 2127 | 2128 |
| 9 | 94.7 | 31233 | 185 | 1229 | 1230 | 1231 | 1232 |
| 9 | 94.7 | 153885 | 465 | 2357 | 2358 | 2359 | 2360 |
| 9 | 100.6 | 20048 | 118 | 957 | 958 | 959 | 960 |
| 9 | 100.6 | 153427 | 461 | 2341 | 2342 | 2343 | 2344 |
| 9 | 108.3 | 109802 | 385 | 2037 | 2038 | 2039 | 2040 |
| 9 | 108.9 | 155793 | 483 | 2429 | 2430 | 2431 | 2432 |
| 9 | 110.3 | 8937 | 46 | 669 | 670 | 671 | 672 |
| 9 | 110.3 | 78438 | 313 | 1749 | 1750 | 1751 | 1752 |
| 9 | 111.2 | 147496 | 446 | 2281 | 2282 | 2283 | 2284 |
| 9 | 112.4 | 13086 | 85 | 825 | 826 | 827 | 828 |
| 9 | 115 | 145318 | 431 | 2221 | 2222 | 2223 | 2224 |
| 9 | 125.2 | 9555 | 62 | 733 | 734 | 735 | 736 |
| 9 | 137.2 | 36022 | 220 | 1369 | 1370 | 1371 | 1372 |
| 9 | 145.8 | 110800 | 393 | 2069 | 2070 | 2071 | 2072 |
| 9 | 165.8 | 110886 | 394 | 2073 | 2074 | 2075 | 2076 |
| 9 | 171.4 | 147417 | 445 | 2277 | 2278 | 2279 | 2280 |
| 10 | 23.9 | 153632 | 462 | 2345 | 2346 | 2347 | 2348 |
| 10 | 23.9 | 153987 | 466 | 2361 | 2362 | 2363 | 2364 |
| 10 | 23.9 | 154021 | 468 | 2369 | 2370 | 2371 | 2372 |
| 10 | 29.7 | 20502 | 119 | 961 | 962 | 963 | 964 |
| 10 | 31.7 | 104672 | 335 | 1837 | 1838 | 1839 | 1840 |
| 10 | 36.9 | 111004 | 396 | 2081 | 2082 | 2083 | 2084 |
| 10 | 43.4 | 16041 | 95 | 865 | 866 | 867 | 868 |
| 10 | 50.5 | 143408 | 418 | 2169 | 2170 | 2171 | 2172 |
| 10 | 51.1 | 147411 | 444 | 2273 | 2274 | 2275 | 2276 |
| 10 | 52.7 | 143754 | 421 | 2181 | 2182 | 2183 | 2184 |
| 10 | 54.7 | 5140 | 34 | 621 | 622 | 623 | 624 |
| 10 | 55.6 | 111212 | 398 | 2089 | 2090 | 2091 | 2092 |
| 10 | 55.8 | 8840 | 44 | 661 | 662 | 663 | 664 |
| 10 | 55.8 | 21292 | 132 | 1013 | 1014 | 1015 | 1016 |
| 10 | 55.8 | 22541 | 133 | 1017 | 1018 | 1019 | 1020 |
| 10 | 55.8 | 143388 | 417 | 2165 | 2166 | 2167 | 2168 |
| 10 | 56.1 | 39275 | 245 | 1477 | 1478 | 1479 | 1480 |
| 10 | 56.7 | 22717 | 134 | 1021 | 1022 | 1023 | 1024 |
| 10 | 57 | 3206 | 15 | 541 | 542 | 543 | 544 |
| 10 | 57 | 32428 | 200 | 1289 | 1290 | 1291 | 1292 |
| 10 | 65.5 | 3640 | 20 | 565 | 566 | 567 | 568 |
| 10 | 66.5 | 16730 | 110 | 925 | 926 | 927 | 928 |
| 10 | 68 | 107941 | 370 | 1977 | 1978 | 1979 | 1980 |
| 10 | 71.6 | 18392 | 114 | 941 | 942 | 943 | 944 |
| 10 | 73.6 | 27447 | 153 | 1097 | 1098 | 1099 | 1100 |
| 10 | 77.4 | 13745 | 91 | 849 | 850 | 851 | 852 |
| 10 | 83.9 | 38604 | 239 | 1453 | 1454 | 1455 | 1456 |
| 10 | 85.9 | 40431 | 258 | 1529 | 1530 | 1531 | 1532 |
| 10 | 85.9 | 40474 | 260 | 1537 | 1538 | 1539 | 1540 |
| 10 | 89.6 | 106742 | 352 | 1905 | 1906 | 1907 | 1908 |
| 10 | 93.2 | 143657 | 420 | 2177 | 2178 | 2179 | 2180 |
| 10 | 93.2 | 145800 | 434 | 2233 | 2234 | 2235 | 2236 |
| 10 | 96.4 | 9486 | 61 | 729 | 730 | 731 | 732 |
| 10 | 100.9 | 109666 | 383 | 2029 | 2030 | 2031 | 2032 |

Example 2

This example illustrates a labeled probe degradation assay for SNP detection and marker mapping.

A quantity of maize genomic template DNA (e.g., about 2-20 ng) is mixed in 5 μL1 total volume with four oligonucleotides, which can be designed by Applied Biosystems, i.e., a forward primer, a reverse primer, a hybridization probe having a VIC reporter attached to the 5' end, and a hybridization probe having a FAM reporter attached to the 5'end as well as PCR reaction buffer containing the passive reference dye ROX. The PCR reaction is conducted for 35 cycles using a 60° C. annealing-extension temperature. Following the reaction, the fluorescence of each fluorophore as well as that of the passive reference is determined in a fluorimeter. The fluorescence value for each fluorophore is normalized to the fluorescence value of the passive reference. The normalized values are plotted against each other for each sample, producing an allelogram as described above. As described above, the data points should fall into clearly separable clusters.

To confirm that an assay produces accurate results, each new assay is performed on a number of replicates of samples of known genotypic identity representing each of the three possible genotypes, i.e., two homozygous alleles and a heterozygous sample. To be a valid and useful assay, it must produce clearly separable clusters of data points, such that one of the three genotypes can be assigned for at least 90% of the data points, and the assignment is observed to be correct for at least 98% of the data points. Subsequent to this validation step, the assay is applied to progeny of a cross between two highly inbred individuals to obtain segregation data, which are then used to calculate a genetic map position for the polymorphic locus.

The maize markers were genetically mapped based on the genotypes of certain SNPs. The genotypes were combined with genotypes for public core SSR and RFLP markers scored on recombinant inbred lines. Before mapping, any loci showing distorted segregation (P<0.01 for a Chi-square test of a 1:1 segregation ratio) were removed. These loci could be added to the map later but without allowing them to change marker order. A map was constructed using the JoinMap version 2.0 software, which is described by Stam ("Construction of integrated genetic linkage maps by means of a new computer package: JoinMap, *The Plant Journal*, 3: 739-744 (1993); Stam, P. and van Ooijen, J. W. "JoinMap version 2.0: Software for the calculation of genetic linkage maps (1995) CPRO-DLO, Wageningen). JoinMap implements a weighted-least squares approach to multipoint mapping in which information from all pairs of linked loci (adjacent or not) is incorporated. Linkage groups were formed using a LOD threshold of 5.0. The SSR and RFLP public markers were used to assign linkage groups to chromosomes. Linkage groups were merged within chromosomes before map construction.

Haldane's mapping function was used to convert recombination fractions to map distances. Lenient criteria was applied for excluding pairwise linkage data; only data with a LOD not greater than 0.001 or a recombination fraction not less than 0.499 are excluded. Parameters for ordering loci were a jump threshold of 5.0, a triplet threshold of 7.0 and a ripple value of 3. About 38% of the loci were ordered in two rounds of map construction with a jump threshold of 5.0, which prevents the addition of a locus to the map if such addition results in a jump of more than 5.0 to a goodness-of-fit criterion. The remaining loci were added to the map without application of such a jump threshold. Addition of these loci had a negligible effect on the map order and distances for the initial loci. Mapped SNP polymorphisms are identified in Table 2.

Example 3

This example illustrates the utility of the markers in marker trait association

The 488 maize markers of this invention were used in an association study to identify which of the candidate genes were more significantly associated with oil level in corn (*Zea mays*).

The University of Illinois has corn lines differing in seed oil that have been developed by long-term selection. A high oil line (IHO) produces about 18% seed oil and a low oil line (ILO) produces about 1.5% seed oil. The IHO and ILO lines are available from the University of Illinois for research. A random mated population (RMn) was produced from random mating offspring of a cross between IHO and ILO by chain crossing for 10 generations to produce an RM10 population. From the RM10 population 504 S1-derived lines were developed by selfing and these lines constitute an association study population. This population along with 72 control samples were genotyped using oil informative SNPs.

Phenotypes were measured on 504 association population lines in replicated field trials with an alph(0,1) incomplete block design. The field trials comprised the 504 lines grown in each of two years at each of 3 locations with 2 replicates per location. The lines were blocked within each replicate. These field trials were performed on the 504 RM10:S1 lines, per se, and on hybrids made by crossing each line to a tester line, i.e., line (7051).

Association was analyzed between the SNP markers and oil level in the RM10:S1 lines, per se, and in the hybrids. A mixed model analysis of variance was performed with sources of variation: location, reps within location, blocks and lines. Line effects estimated from this model were regressed on single marker genotypes (i.e., number of A alleles in the genotypes AA, Aa and aa). The probability that the slope is significantly different from zero gives an indication of whether the marker has a significant effect on the trait. Through this analysis of percent oil in the kernel and oil per 200 kernels in both inbreds and hybrids, a total of 186 markers showed significance at the p<0.05 level. These 186 significant markers are very likely to either reside within an oil gene or to be closely linked to an oil gene and are more particularly described in Table 3 by:

"Map Position" which identifies the distance measured in cM from the 5' end of a maize chromosome for the SNP identified by "Mutation ID", which refers to an arbitrary identifying name for each polymorphism;

Pval % Oil Per se, which refers to probability of a test of significance of the regression of marker genotype on oil level as percent oil per kernel for inbred lines;

Pval % Oil Hybrid, which refers to probability of a test of significance of the regression of marker genotype on oil level as percent oil per kernel for hybrid lines.

Pval Oil/Kernel Per se, which refers to probability of a test of significance of the regression of marker genotype on oil level as oil weight per 200 kernels for inbred lines;

Pval Oil/Kernel Hybrid, which refers to probability of a test of significance of the regression of marker genotype on oil level as oil weight per 200 kernels for hybrid lines

TABLE 3

| Map Position | Mutation_ID | Pval % Oil Per se | Pval % Oil Hybrid | Pval Oil/Kernel Per se | Pval Oil/Kernel Hybrid |
|---|---|---|---|---|---|
| 1-3.7 | 111829 | 0.706 | 0.234 | 0.336 | 0.046 |
| 1-25.1 | 43230 | 0.030 | 0.228 | 0.042 | 0.037 |
| 1-44 | 104827 | 0.094 | 0.801 | 0.018 | 0.909 |
| 1-45 | 151360 | 0.025 | 0.811 | 0.005 | 0.395 |
| 1-46.8 | 37716 | 0.009 | 0.113 | 0.024 | 0.351 |
| 1-53.3 | 42173 | 0.020 | 0.050 | 0.024 | 0.907 |
| 1-58.4 | 116 | 0.059 | 0.018 | 0.018 | 0.395 |
| 1-60.3 | 143100 | 0.722 | 0.029 | 0.878 | 0.501 |
| 1-60.6 | 33819 | 0.200 | 0.039 | 0.043 | 0.640 |
| 1-60.6 | 40189 | 0.007 | 1.6E−4 | 0.062 | 0.172 |
| 1-83.2 | 34205 | 0.026 | 0.151 | 0.090 | 0.022 |
| 1-86.3 | 8984 | 0.405 | 8.0E−4 | 0.433 | 0.069 |
| 1-86.3 | 36286 | 0.261 | 7.3E−4 | 0.328 | 0.069 |
| 1-88.8 | 29829 | 0.063 | 0.164 | 0.597 | 0.029 |
| 1-88.8 | 37068 | 0.026 | 0.317 | 0.068 | 0.051 |
| 1-90.5 | 111828 | 0.052 | 0.198 | 0.018 | 0.014 |
| 1-91 | 113263 | 0.281 | 0.004 | 0.078 | 0.489 |
| 1-91.8 | 104474 | 0.047 | 0.346 | 0.776 | 0.069 |
| 1-96.9 | 36448 | 0.006 | 0.114 | 0.002 | 0.052 |
| 1-99 | 40655 | 0.029 | 0.272 | 0.052 | 0.080 |
| 1-99 | 107077 | 9.7E−6 | 0.014 | 9.1E−4 | 0.021 |
| 1-103.3 | 8719 | 0.167 | 0.728 | 0.008 | 0.271 |
| 1-124.6 | 33373 | 0.029 | 0.240 | 0.201 | 0.714 |
| 1-130.3 | 69565 | 0.032 | 0.201 | 0.568 | 0.962 |
| 1-165.6 | 108862 | 0.011 | 0.001 | 0.402 | 0.347 |
| 1-178.6 | 151382 | 0.027 | 0.480 | 0.116 | 0.509 |
| 1-200.3 | 30840 | 0.662 | 0.050 | 0.716 | 0.012 |
| 2-5.8 | 31064 | 0.091 | 0.002 | 0.143 | 0.064 |
| 2-12.9 | 104447 | 0.077 | 0.012 | 0.697 | 0.459 |
| 2-14.1 | 39289 | 0.095 | 0.016 | 0.778 | 0.571 |
| 2-17.5 | 106678 | 0.048 | 0.003 | 0.043 | 0.040 |
| 2-19.5 | 82235 | 0.018 | 0.002 | 0.045 | 0.009 |
| 2-33.9 | 80031 | 0.101 | 0.046 | 0.557 | 0.036 |
| 2-35.9 | 13691 | 0.225 | 0.469 | 0.040 | 0.419 |
| 2-78.2 | 11466 | 0.096 | 0.761 | 0.045 | 0.225 |
| 2-78.2 | 79073 | 0.020 | 0.825 | 0.015 | 0.413 |
| 2-78.2 | 108493 | 0.142 | 0.045 | 0.713 | 0.299 |
| 2-92.5 | 3177 | 0.082 | 0.334 | 0.038 | 0.224 |
| 2-92.9 | 84829 | 0.298 | 0.324 | 0.111 | 0.031 |
| 2-99.7 | 151288 | 0.549 | 0.036 | 0.245 | 0.846 |
| 2-106 | 111475 | 0.238 | 0.013 | 0.320 | 0.685 |
| 2-106.2 | 108013 | 0.574 | 0.033 | 0.441 | 0.591 |
| 2-107.6 | 2307 | 0.497 | 0.019 | 0.437 | 0.413 |
| 2-114.9 | 22775 | 0.036 | 0.064 | 0.424 | 0.160 |
| 2-123.4 | 104954 | 0.049 | 0.058 | 0.573 | 0.765 |
| 2-152.4 | 43579 | 0.064 | 0.123 | 0.037 | 0.659 |
| 2-164.2 | 735 | 0.497 | 0.920 | 0.048 | 0.729 |
| 2-164.2 | 76792 | 0.939 | 0.524 | 0.044 | 0.345 |
| 3-6 | 8911 | 0.067 | 0.561 | 0.045 | 0.979 |
| 3-6 | 51614 | 0.071 | 0.551 | 0.030 | 0.980 |
| 3-9.1 | 10667 | 0.009 | 0.193 | 0.068 | 0.262 |
| 3-19.7 | 19963 | 0.115 | 0.084 | 0.029 | 0.373 |
| 3-19.7 | 32137 | 2.4E−4 | 1.1E−4 | 2.3E−4 | 0.037 |
| 3-46.2 | 49293 | 0.036 | 0.003 | 0.167 | 0.030 |
| 3-52.3 | 109315 | 0.175 | 0.7E−4 | 0.527 | 0.040 |
| 3-53.5 | 25000 | 0.098 | 4.5E−4 | 0.350 | 0.157 |
| 3-54.1 | 21154 | 0.060 | 7.7E−4 | 0.543 | 0.542 |
| 3-54.1 | 109722 | 0.482 | 0.022 | 0.526 | 0.284 |
| 3-57.2 | 109509 | 0.394 | 0.006 | 0.464 | 0.213 |
| 3-58.6 | 29867 | 0.036 | 1.8E−8 | 0.696 | 0.169 |
| 3-59.3 | 4599 | 0.093 | 7.9E−4 | 0.562 | 0.571 |
| 3-59.3 | 21190 | 0.020 | 0.006 | 0.637 | 0.215 |
| 3-59.3 | 28923 | 0.150 | 9.6E−4 | 0.703 | 0.351 |
| 3-59.3 | 147511 | 0.116 | 0.001 | 0.588 | 0.571 |
| 3-59.3 | 147768 | 0.066 | 7.6E−4 | 0.627 | 0.524 |
| 3-60.4 | 8685 | 0.592 | 0.001 | 0.913 | 0.681 |
| 3-61 | 16729 | 0.229 | 0.112 | 0.198 | 0.005 |
| 3-61.7 | 32247 | 0.115 | 3.5E−4 | 0.891 | 0.113 |
| 3-62.7 | 9144 | 0.066 | 0.003 | 0.277 | 0.014 |
| 3-62.7 | 9739 | 0.031 | 0.003 | 0.439 | 0.130 |
| 3-111.4 | 110780 | 0.246 | 0.040 | 0.572 | 0.207 |
| 3-123.8 | 143969 | 0.015 | 0.158 | 0.081 | 0.438 |
| 3-127.7 | 9079 | 0.040 | 0.071 | 0.296 | 0.134 |
| 4-38.7 | 110069 | 0.026 | 0.048 | 0.188 | 0.108 |
| 4-38.7 | 111464 | 0.029 | 0.053 | 0.129 | 0.096 |
| 4-52.8 | 24647 | 0.013 | 0.084 | 0.382 | 0.827 |

TABLE 3-continued

| Map Position | Mutation_ID | Pval % Oil Per se | Pval % Oil Hybrid | Pval Oil/Kernel Per se | Pval Oil/Kernel Hybrid |
|---|---|---|---|---|---|
| 4-53.2 | 156243 | 0.004 | 0.007 | 0.096 | 0.368 |
| 4-62.1 | 10671 | 0.156 | 0.040 | 0.337 | 0.099 |
| 4-64.9 | 38852 | 0.285 | 0.072 | 0.342 | 0.007 |
| 4-69.5 | 5021 | 0.341 | 0.499 | 0.098 | 0.004 |
| 4-69.5 | 37503 | 0.262 | 0.126 | 0.303 | 0.002 |
| 4-69.9 | 107276 | 0.006 | 0.331 | 0.017 | 0.016 |
| 4-71.4 | 84527 | 0.346 | 0.014 | 0.363 | 0.040 |
| 4-80 | 106845 | 0.112 | 0.042 | 0.393 | 0.434 |
| 4-107.7 | 106491 | 0.020 | 0.040 | 0.409 | 0.521 |
| 4-112.4 | 54460 | 0.037 | 0.146 | 0.124 | 0.150 |
| 4-122.4 | 151472 | 0.186 | 0.994 | 0.011 | 0.967 |
| 4-128.1 | 32049 | 0.195 | 0.620 | 0.756 | 0.011 |
| 4-135.8 | 17900 | 4.2E−4 | 0.037 | 3.7E−4 | 0.019 |
| 4-136.4 | 147219 | 0.038 | 0.214 | 0.104 | 0.029 |
| 5-1.6 | 24265 | 0.082 | 0.035 | 0.472 | 0.010 |
| 5-39.9 | 109403 | 2.0E−6 | 9.1E−5 | 0.135 | 0.006 |
| 5-41.7 | 16527 | 0.028 | 0.161 | 0.333 | 0.791 |
| 5-50.9 | 109342 | 0.005 | 0.167 | 0.015 | 0.024 |
| 5-51.9 | 16762 | 7.6E−5 | 0.018 | 4.9E−4 | 0.029 |
| 5-51.9 | 16767 | 1.2E−4 | 0.017 | 5.1E−4 | 0.033 |
| 5-62.3 | 51419 | 0.046 | 0.002 | 0.163 | 0.031 |
| 5-63 | 32272 | 5.7E−5 | 0.001 | 0.008 | 0.100 |
| 5-66.9 | 30000 | 0.004 | 6.5E−4 | 0.035 | 0.002 |
| 5-66.9 | 146415 | 1.1E−4 | 1.9E−5 | 0.163 | 0.037 |
| 5-69.6 | 144731 | 8.5E−4 | 2.8E−4 | 0.162 | 0.042 |
| 5-70.5 | 105854 | 0.205 | 0.011 | 0.976 | 0.063 |
| 5-71.7 | 143216 | 0.023 | 0.014 | 0.065 | 0.098 |
| 5-76.4 | 29820 | 0.010 | 5.8E−4 | 0.128 | 0.140 |
| 5-80.2 | 36637 | 0.020 | 0.052 | 0.087 | 0.365 |
| 5-104.5 | 58375 | 0.028 | 0.097 | 0.024 | 0.003 |
| 5-150.5 | 31084 | 0.025 | 0.210 | 0.350 | 0.763 |
| 6-17.3 | 154854 | 0.010 | 0.222 | 0.049 | 0.688 |
| 6-30.8 | 69630 | 0.484 | 0.678 | 0.094 | 0.047 |
| 6-37.3 | 36067 | 0.018 | 0.290 | 0.215 | 0.874 |
| 6-37.3 | 36073 | 0.014 | 0.165 | 0.234 | 0.945 |
| 6-43.1 | 30176 | 0.827 | 0.323 | 0.969 | 0.015 |
| 6-52.8 | 4463 | 3.9E−9 | 1.8E−12 | 2.3E−6 | 3.7E−9 |
| 6-53.1 | 60751 | 3.9E−9 | 1.6E−6 | 5.4E−7 | 2.2E−4 |
| 6-53.5 | 32034 | 5.0E−7 | 3.7E−4 | 5.3E−5 | 0.048 |
| 6-53.5 | 57758 | 6.3E−5 | 0.008 | 0.002 | 0.566 |
| 6-53.5 | 108212 | 8.6E−7 | 6.0E−4 | 4.0E−5 | 0.043 |
| 6-58.1 | 59008 | 9.7E−5 | 3.9E−4 | 8.2E−5 | 0.002 |
| 6-58.1 | 146195 | 5.3E−4 | 8.5E−4 | 1.8E−5 | 0.004 |
| 6-59.9 | 3277 | 0.004 | 0.215 | 0.087 | 0.515 |
| 6-59.9 | 105586 | 0.003 | 4.9E−4 | 0.002 | 0.001 |
| 6-61.5 | 148039 | 0.120 | 7.6E−4 | 0.565 | 0.006 |
| 6-61.5 | 155861 | 0.082 | 7.2E−4 | 0.490 | 0.003 |
| 6-63.1 | 20410 | 0.028 | 0.012 | 0.055 | 0.138 |
| 6-66.6 | 8838 | 0.050 | 0.009 | 0.031 | 0.025 |
| 6-67.5 | 14694 | 0.226 | 8.2E−4 | 0.496 | 0.151 |
| 6-86.9 | 110972 | 0.023 | 0.050 | 0.072 | 0.482 |
| 6-110.4 | 31684 | 0.012 | 9.6E−4 | 0.162 | 0.240 |
| 6-121 | 37634 | 0.002 | 0.052 | 0.052 | 0.008 |
| 6-132.7 | 37555 | 0.089 | 0.364 | 0.665 | 0.025 |
| 7-62 | 42164 | 0.075 | 0.424 | 0.045 | 0.235 |
| 7-67 | 30674 | 0.424 | 0.048 | 0.187 | 0.015 |
| 7-68.7 | 39064 | 0.321 | 0.558 | 0.028 | 0.357 |
| 7-72.8 | 42930 | 0.111 | 0.076 | 0.006 | 0.002 |
| 7-74.2 | 68426 | 0.013 | 0.662 | 0.047 | 0.088 |
| 7-98.5 | 8799 | 0.031 | 0.429 | 0.009 | 0.160 |
| 7-98.8 | 48425 | 7.4E−4 | 0.063 | 2.6E−4 | 0.034 |
| 7-99.8 | 4415 | 6.9E−4 | 0.057 | 1.5E−4 | 0.032 |
| 7-99.8 | 35408 | 0.003 | 0.055 | 0.002 | 0.069 |
| 7-107.5 | 38914 | 0.024 | 0.002 | 0.682 | 0.747 |
| 7-115.8 | 4093 | 0.185 | 0.007 | 0.512 | 0.050 |
| 7-118.6 | 4302 | 0.032 | 6.5E−4 | 0.522 | 0.120 |
| 7-118.6 | 38653 | 0.199 | 0.011 | 0.471 | 0.035 |
| 7-118.6 | 81460 | 0.061 | 0.002 | 0.578 | 0.257 |
| 7-122.2 | 145260 | 0.062 | 0.003 | 0.108 | 0.003 |
| 7-124.5 | 15184 | 0.044 | 0.009 | 0.079 | 0.008 |
| 7-124.5 | 39773 | 0.065 | 0.022 | 0.814 | 0.608 |
| 7-132.8 | 30029 | 0.330 | 0.046 | 0.577 | 0.552 |
| 8-16.4 | 40320 | 0.657 | 0.063 | 0.405 | 0.006 |
| 8-40.9 | 107937 | 0.048 | 0.046 | 0.221 | 0.077 |
| 8-43.1 | 111628 | 0.105 | 0.011 | 0.401 | 0.144 |
| 8-45.5 | 26720 | 0.109 | 0.043 | 0.459 | 0.282 |

TABLE 3-continued

| Map Position | Mutation_ID | Pval % Oil Per se | Pval % Oil Hybrid | Pval Oil/Kernel Per se | Pval Oil/Kernel Hybrid |
|---|---|---|---|---|---|
| 8-47.9 | 104862 | 0.152 | 0.143 | 0.011 | 0.276 |
| 8-53.9 | 27361 | 0.798 | 0.947 | 0.378 | 0.048 |
| 8-53.9 | 145200 | 0.260 | 0.129 | 0.033 | 0.016 |
| 8-55.7 | 23091 | 0.040 | 0.183 | 0.069 | 0.872 |
| 8-59.3 | 77568 | 0.003 | 0.258 | 4.4E−5 | 0.249 |
| 8-64 | 110148 | 0.005 | 0.085 | 0.005 | 0.528 |
| 8-65.8 | 104389 | 0.003 | 0.117 | 0.004 | 0.415 |
| 8-66.6 | 21895 | 0.003 | 0.143 | 0.002 | 0.417 |
| 8-67.4 | 48562 | 0.006 | 0.081 | 0.005 | 0.416 |
| 8-68.4 | 82295 | 0.003 | 0.311 | 4.9E−4 | 0.067 |
| 8-85.9 | 110684 | 0.039 | 0.588 | 0.030 | 0.082 |
| 8-87.5 | 9759 | 0.473 | 0.574 | 0.010 | 0.353 |
| 8-105.5 | 107286 | 0.028 | 0.063 | 0.104 | 0.076 |
| 8-106.8 | 13100 | 0.030 | 0.068 | 0.107 | 0.043 |
| 8-117.3 | 145077 | 0.006 | 0.009 | 0.055 | 0.192 |
| 8-117.3 | 145298 | 0.005 | 0.004 | 0.076 | 0.210 |
| 9-20.5 | 58904 | 0.578 | 0.351 | 0.078 | 0.041 |
| 9-80 | 29745 | 0.182 | 0.025 | 0.538 | 0.116 |
| 9-93.8 | 110377 | 0.021 | 0.097 | 0.019 | 0.134 |
| 9-93.8 | 113113 | 0.022 | 0.098 | 0.026 | 0.290 |
| 9-94 | 25961 | 0.058 | 0.047 | 0.039 | 0.177 |
| 9-94.5 | 148621 | 0.060 | 0.300 | 0.030 | 0.066 |
| 9-100.6 | 20048 | 0.034 | 0.137 | 0.155 | 0.156 |
| 9-100.6 | 153427 | 0.022 | 0.154 | 0.092 | 0.101 |
| 9-110.3 | 8937 | 0.014 | 0.652 | 0.035 | 0.233 |
| 9-125.2 | 9555 | 0.419 | 0.270 | 0.307 | 0.049 |
| 9-137.2 | 36022 | 0.136 | 0.014 | 0.290 | 0.096 |
| 10-52.7 | 143754 | 0.608 | 0.127 | 0.648 | 0.044 |
| 10-56.1 | 39275 | 0.061 | 0.019 | 0.054 | 0.085 |
| 10-89.6 | 106742 | 0.064 | 0.105 | 0.035 | 0.088 |
| 10-93.2 | 143657 | 0.560 | 0.046 | 0.790 | 0.186 |
| 10-93.2 | 145800 | 0.551 | 0.030 | 0.793 | 0.190 |
| 10-100.9 | 109666 | 0.083 | 0.007 | 0.144 | 0.148 |
| unmapped | 152577 | 0.315 | 0.001 | 0.627 | 0.914 |
| unmapped | 20742 | 0.425 | 0.141 | 0.435 | 0.041 |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 1 | Amplicon25 | 90 | 106 | 106 | SNP | A | T | | | | | | |
| 1 | Amplicon25 | 91 | 110 | 110 | SNP | C | T | | | | | | |
| 1 | Amplicon25 | 92 | 130 | 130 | SNP | A | T | | | | | | |
| 1 | Amplicon25 | 93 | 175 | 175 | SNP | C | T | | | | | | |
| 1 | Amplicon25 | 94 | 185 | 185 | SNP | A | G | | | | | | |
| 1 | Amplicon25 | 95 | 189 | 189 | SNP | A | G | | | | | | |
| 1 | Amplicon25 | 96 | 279 | 279 | SNP | A | C | | | | | | |
| 1 | Amplicon25 | 97 | 300 | 300 | SNP | C | G | | | | | | |
| 2 | Amplicon29 | 114 | 68 | 68 | SNP | A | C | | | | | | |
| 2 | Amplicon29 | 115 | 101 | 101 | SNP | G | T | | | | | | |
| 2 | Amplicon29 | 116 | 283 | 283 | SNP | A | G | | | | | | |
| 3 | Amplicon78 | 366 | 145 | 145 | SNP | A | G | | | | | | |
| 4 | Amplicon150 | 548 | 84 | 84 | SNP | A | C | | | | | | |
| 4 | Amplicon150 | 549 | 107 | 107 | SNP | C | T | | | | | | |
| 4 | Amplicon150 | 550 | 157 | 157 | SNP | A | T | | | | | | |
| 4 | Amplicon150 | 551 | 174 | 174 | SNP | G | T | | | | | | |
| 5 | Amplicon155 | 561 | 70 | 70 | SNP | A | C | | | | | | |
| 6 | Amplicon161 | 1122 | 215 | 215 | SNP | C | T | | | | | | |
| 6 | Amplicon161 | 1123 | 233 | 233 | SNP | C | T | | | | | | |
| 7 | Amplicon213 | 734 | 11 | 11 | SNP | C | T | | | | | | |
| 7 | Amplicon213 | 735 | 93 | 93 | SNP | A | G | | | | | | |
| 7 | Amplicon213 | 736 | 210 | 210 | SNP | A | G | | | | | | |
| 7 | Amplicon213 | 737 | 216 | 216 | SNP | G | T | | | | | | |
| 7 | Amplicon213 | 738 | 233 | 238 | IND | ****** | ttgagt | | | | | | |
| 8 | Amplicon49714 | 2300 | 59 | 59 | SNP | A | b73 | G | mo17 | | | | |
| 8 | Amplicon49714 | 2301 | 172 | 172 | SNP | G | mo17 | T | b73 | | | | |
| 8 | Amplicon49714 | 2302 | 182 | 182 | SNP | C | mo17 | T | b73 | | | | |
| 8 | Amplicon49714 | 2303 | 221 | 221 | SNP | C | mo17 | T | b73 | | | | |
| 8 | Amplicon49714 | 2304 | 230 | 230 | SNP | C | b73 | T | mo17 | | | | |
| 8 | Amplicon49714 | 2305 | 308 | 308 | SNP | C | mo17 | G | b73 | | | | |
| 8 | Amplicon49714 | 2306 | 344 | 344 | SNP | A | b73 | G | mo17 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 8 | Ampli-con49714 | 2307 | 378 | 378 | SNP | A | b73 | G | mo17 | | | | |
| 8 | Ampli-con49714 | 2308 | 389 | 389 | SNP | C | b73 | G | mo17 | | | | |
| 8 | Ampli-con49714 | 2309 | 424 | 424 | SNP | C | b73 | T | mo17 | | | | |
| 8 | Ampli-con49714 | 2310 | 446 | 446 | SNP | C | mo17 | T | b73 | | | | |
| 9 | Ampli-con49778 | 2435 | 355 | 355 | SNP | C | mo17 | T | b73 | | | | |
| 10 | Ampli-con49935 | 2739 | 133 | 133 | IND | * | b73 | C | mo17 | | | | |
| 11 | Ampli-con49980 | 2841 | 158 | 158 | SNP | C | b73 | T | mo17 | | | | |
| 11 | Ampli-con49980 | 2842 | 215 | 215 | SNP | C | mo17 | T | b73 | | | | |
| 11 | Ampli-con49980 | 2843 | 303 | 303 | SNP | A | mo17 | C | b73 | | | | |
| 11 | Ampli-con49980 | 2844 | 304 | 304 | SNP | C | mo17 | T | b73 | | | | |
| 11 | Ampli-con49980 | 2845 | 380 | 380 | SNP | G | mo17 | T | b73 | | | | |
| 11 | Ampli-con49980 | 2846 | 434 | 434 | SNP | C | mo17 | T | b73 | | | | |
| 11 | Ampli-con49980 | 2847 | 445 | 445 | SNP | G | mo17 | T | b73 | | | | |
| 11 | Ampli-con49980 | 2848 | 466 | 466 | SNP | A | mo17 | G | b73 | | | | |
| 12 | Ampli-con50024 | 2941 | 99 | 99 | SNP | C | b73 | T | mo17 | | | | |
| 12 | Ampli-con50024 | 2942 | 127 | 127 | SNP | A | b73 | T | mo17 | | | | |
| 12 | Ampli-con50024 | 2943 | 169 | 169 | SNP | A | b73 | G | mo17 | | | | |
| 12 | Ampli-con50024 | 2944 | 234 | 240 | IND | ******** | mo17 | GGCTACA | b73 | | | | |
| 12 | Ampli-con50024 | 2945 | 255 | 255 | SNP | A | mo17 | G | b73 | | | | |
| 12 | Ampli-con50024 | 2946 | 270 | 270 | SNP | A | mo17 | T | b73 | | | | |
| 12 | Ampli-con50024 | 2947 | 304 | 304 | SNP | C | b73 | T | mo17 | | | | |
| 12 | Ampli-con50024 | 2948 | 351 | 351 | SNP | A | mo17 | G | b73 | | | | |
| 12 | Ampli-con50024 | 2949 | 361 | 361 | SNP | G | b73 | T | mo17 | | | | |
| 12 | Ampli-con50024 | 2950 | 363 | 363 | SNP | G | b73 | T | mo17 | | | | |
| 12 | Ampli-con50024 | 2951 | 378 | 378 | SNP | C | b73 | T | mo17 | | | | |
| 12 | Ampli-con50024 | 2952 | 398 | 398 | SNP | A | b73 | C | mo17 | | | | |
| 12 | Ampli-con50024 | 2953 | 401 | 401 | SNP | C | mo17 | T | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 12 | Ampli-con50024 | 2954 | 406 | 406 | SNP | C | mo17 | G | b73 | | | | |
| 12 | Ampli-con50024 | 2955 | 417 | 417 | SNP | C | mo17 | G | b73 | | | | |
| 12 | Ampli-con50024 | 2956 | 442 | 442 | SNP | A | mo17 | G | b73 | | | | |
| 12 | Ampli-con50024 | 2957 | 477 | 477 | SNP | G | b73 | T | mo17 | | | | |
| 12 | Ampli-con50024 | 2958 | 503 | 503 | SNP | C | b73 | T | mo17 | | | | |
| 12 | Ampli-con50024 | 2959 | 514 | 514 | IND | * | mo17 | T | b73 | | | | |
| 12 | Ampli-con50024 | 2960 | 556 | 556 | SNP | C | b73 | G | mo17 | | | | |
| 12 | Ampli-con50024 | 2961 | 557 | 557 | IND | * | b73 | G | mo17 | | | | |
| 12 | Ampli-con50024 | 2962 | 559 | 559 | IND | * | b73 | C | mo17 | | | | |
| 13 | Ampli-con50099 | 3152 | 290 | 290 | SNP | C | b73 | G | mo17 | | | | |
| 14 | Ampli-con50106 | 3172 | 94 | 94 | SNP | A | b73 | C | mo17 | | | | |
| 14 | Ampli-con50106 | 3173 | 187 | 187 | SNP | A | b73 | G | mo17 | | | | |
| 14 | Ampli-con50106 | 3174 | 243 | 243 | IND | * | b73 | A | mo17 | | | | |
| 14 | Ampli-con50106 | 3175 | 243 | 244 | IND | ** | b73 | AT | mo17 | | | | |
| 14 | Ampli-con50106 | 3176 | 283 | 283 | SNP | A | b73 | G | mo17 | | | | |
| 14 | Ampli-con50106 | 3177 | 415 | 416 | IND | ** | mo17 | TC | b73 | | | | |
| 14 | Ampli-con50106 | 3178 | 438 | 438 | SNP | C | mo17 | T | b73 | | | | |
| 14 | Ampli-con50106 | 3179 | 442 | 442 | SNP | C | b73 | T | mo17 | | | | |
| 15 | Ampli-con50125 | 3180 | 443 | 443 | SNP | A | b73 | G | mo17 | | | | |
| 15 | Ampli-con50125 | 3205 | 215 | 215 | SNP | C | mo17 | G | b73 | | | | |
| 16 | Ampli-con50142 | 3206 | 256 | 256 | SNP | C | mo17 | T | b73 | | | | |
| 16 | Ampli-con50142 | 3222 | 104 | 104 | SNP | C | b73 | T | mo17 | | | | |
| 16 | Ampli-con50142 | 3223 | 110 | 110 | SNP | C | b73 | T | mo17 | | | | |
| 16 | Ampli-con50142 | 3224 | 171 | 171 | SNP | C | mo17 | G | b73 | | | | |
| 16 | Ampli-con50142 | 3225 | 372 | 374 | IND | *** | b73 | CGG | mo17 | | | | |
| 16 | Ampli-con50142 | 3226 | 401 | 401 | SNP | C | mo17 | T | b73 | | | | |
| 17 | Ampli-con50179 | 3277 | 83 | 83 | SNP | C | mo17 | T | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 17 | Amplicon50179 | 3278 | 265 | 271 | IND | ******** | mo17 | AAGTACC | b73 | | | | |
| 17 | Amplicon50179 | 3279 | 265 | 272 | IND | ********* | mo17 | AAGTACCT | b73 | | | | |
| 17 | Amplicon50179 | 3280 | 338 | 338 | SNP | C | mo17 | T | b73 | | | | |
| 18 | Amplicon50182 | 3282 | 52 | 52 | SNP | G | b73 | T | mo17 | | | | |
| 18 | Amplicon50182 | 3283 | 93 | 93 | SNP | C | mo17 | G | b73 | | | | |
| 18 | Amplicon50182 | 3284 | 438 | 438 | SNP | C | b73 | G | mo17 | | | | |
| 18 | Amplicon50182 | 3285 | 480 | 480 | IND | * | mo17 | G | b73 | | | | |
| 18 | Amplicon50182 | 3286 | 537 | 539 | IND | *** | b73 | CGA | mo17 | | | | |
| 18 | Amplicon50182 | 3287 | 537 | 540 | IND | **** | b73 | CGAT | mo17 | | | | |
| 19 | Amplicon50190 | 3341 | 54 | 54 | SNP | A | mo17 | G | b73 | | | | |
| 19 | Amplicon50190 | 3342 | 91 | 91 | SNP | A | mo17 | G | b73 | | | | |
| 19 | Amplicon50190 | 3343 | 100 | 100 | SNP | A | b73 | G | mo17 | | | | |
| 19 | Amplicon50190 | 3344 | 104 | 104 | SNP | A | mo17 | C | b73 | | | | |
| 19 | Amplicon50190 | 3345 | 146 | 146 | SNP | C | b73 | T | mo17 | | | | |
| 19 | Amplicon50190 | 3346 | 197 | 197 | SNP | C | b73 | G | mo17 | | | | |
| 19 | Amplicon50190 | 3347 | 208 | 208 | SNP | A | mo17 | G | b73 | | | | |
| 19 | Amplicon50190 | 3348 | 266 | 266 | SNP | A | mo17 | C | b73 | | | | |
| 19 | Amplicon50190 | 3349 | 290 | 290 | SNP | A | b73 | G | mo17 | | | | |
| 19 | Amplicon50190 | 3350 | 314 | 314 | SNP | C | b73 | T | mo17 | | | | |
| 19 | Amplicon50190 | 3351 | 431 | 431 | SNP | A | mo17 | C | b73 | | | | |
| 19 | Amplicon50190 | 3352 | 438 | 438 | SNP | A | mo17 | C | b73 | | | | |
| 19 | Amplicon50190 | 3353 | 468 | 468 | SNP | C | b73 | T | mo17 | | | | |
| 19 | Amplicon50190 | 3354 | 552 | 553 | IND | ** | b73 | AA | mo17 | | | | |
| 20 | Amplicon50302 | 3640 | 444 | 444 | SNP | C | b73 | G | mo17 | | | | |
| 21 | Amplicon50453 | 3964 | 170 | 170 | SNP | G | mo17 | T | b73 | | | | |
| 21 | Amplicon50453 | 3965 | 209 | 209 | SNP | G | b73 | T | mo17 | | | | |
| 21 | Amplicon50453 | 3966 | 286 | 286 | SNP | C | b73 | T | mo17 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 21 | Ampli-con50453 | 3967 | 359 | 359 | SNP | G | mo17 | T | b73 | | | | |
| 22 | Ampli-con50455 | 3970 | 354 | 354 | SNP | A | mo17 | G | b73 | | | | |
| 23 | Ampli-con50517 | 4091 | 47 | 47 | IND | * | b73 | G | mo17 | | | | |
| 23 | Ampli-con50517 | 4092 | 51 | 51 | SNP | C | b73 | T | mo17 | | | | |
| 23 | Ampli-con50517 | 4093 | 67 | 67 | SNP | A | b73 | T | mo17 | | | | |
| 23 | Ampli-con50517 | 4094 | 74 | 74 | IND | * | mo17 | T | b73 | | | | |
| 23 | Ampli-con50517 | 4095 | 88 | 88 | SNP | A | mo17 | C | b73 | | | | |
| 23 | Ampli-con50517 | 4096 | 91 | 91 | SNP | A | mo17 | C | b73 | | | | |
| 23 | Ampli-con50517 | 4097 | 92 | 92 | IND | * | b73 | G | mo17 | | | | |
| 23 | Ampli-con50517 | 4098 | 146 | 146 | SNP | A | b73 | G | mo17 | | | | |
| 23 | Ampli-con50517 | 4099 | 181 | 185 | IND | ***** | b73 | CCAGG | mo17 | | | | |
| 23 | Ampli-con50517 | 4100 | 231 | 231 | SNP | A | mo17 | G | b73 | | | | |
| 23 | Ampli-con50517 | 4101 | 290 | 293 | IND | **** | mo17 | GATC | b73 | | | | |
| 23 | Ampli-con50517 | 4102 | 360 | 360 | SNP | G | mo17 | T | b73 | | | | |
| 23 | Ampli-con50517 | 4103 | 361 | 361 | SNP | A | mo17 | C | b73 | | | | |
| 23 | Ampli-con50517 | 4104 | 364 | 364 | SNP | G | b73 | T | mo17 | | | | |
| 23 | Ampli-con50517 | 4105 | 365 | 365 | SNP | C | b73 | G | mo17 | | | | |
| 23 | Ampli-con50517 | 4106 | 415 | 415 | SNP | G | mo17 | T | b73 | | | | |
| 23 | Ampli-con50517 | 4107 | 432 | 432 | SNP | A | b73 | C | mo17 | | | | |
| 24 | Ampli-con50606 | 4300 | 77 | 77 | SNP | G | b73 | T | mo17 | | | | |
| 24 | Ampli-con50606 | 4301 | 232 | 232 | SNP | C | mo17 | T | b73 | | | | |
| 24 | Ampli-con50606 | 4302 | 357 | 357 | SNP | C | b73 | T | mo17 | | | | |
| 25 | Ampli-con50664 | 4408 | 61 | 61 | SNP | A | b73 | G | mo17 | | | | |
| 25 | Ampli-con50664 | 4409 | 124 | 124 | IND | * | mo17 | A | b73 | | | | |
| 25 | Ampli-con50664 | 4410 | 203 | 203 | SNP | C | mo17 | T | b73 | | | | |
| 25 | Ampli-con50664 | 4411 | 207 | 207 | SNP | A | mo17 | G | b73 | | | | |
| 26 | Ampli-con50676 | 4415 | 291 | 291 | SNP | A | mo17 | C | b73 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 27 | Ampli-con50691 | 4444 | 26 | 26 | SNP | A | b73 | T | mo17 | | | | |
| 27 | Ampli-con50691 | 4445 | 273 | 273 | SNP | C | mo17 | T | b73 | | | | |
| 28 | Ampli-con50693 | 4446 | 33 | 33 | SNP | C | b73 | T | mo17 | | | | |
| 28 | Ampli-con50693 | 4447 | 41 | 41 | SNP | A | mo17 | G | b73 | | | | |
| 28 | Ampli-con50693 | 4448 | 68 | 68 | SNP | C | mo17 | G | b73 | | | | |
| 28 | Ampli-con50693 | 4449 | 111 | 111 | SNP | C | mo17 | G | b73 | | | | |
| 28 | Ampli-con50693 | 4450 | 124 | 124 | SNP | A | b73 | G | mo17 | | | | |
| 28 | Ampli-con50693 | 4451 | 328 | 328 | SNP | A | b73 | G | mo17 | | | | |
| 28 | Ampli-con50693 | 4452 | 340 | 340 | SNP | A | mo17 | T | b73 | | | | |
| 28 | Ampli-con50693 | 4453 | 377 | 377 | SNP | C | b73 | T | mo17 | | | | |
| 28 | Ampli-con50693 | 4454 | 412 | 412 | SNP | A | b73 | G | mo17 | | | | |
| 29 | Ampli-con50693 | 4463 | 281 | 281 | SNP | C | b73 | T | mo17 | | | | |
| 30 | Ampli-con50699 | 4598 | 100 | 100 | SNP | A | mo17 | C | b73 | | | | |
| 30 | Ampli-con50748 | 4599 | 104 | 104 | SNP | C | mo17 | T | b73 | | | | |
| 31 | Ampli-con50748 | 4886 | 548 | 548 | SNP | C | b73 | T | mo17 | | | | |
| 32 | Ampli-con50852 | 5021 | 371 | 371 | SNP | C | mo17 | T | b73 | | | | |
| 33 | Ampli-con50932 | 5097 | 109 | 109 | IND | * | mo17 | T | b73 | | | | |
| 33 | Ampli-con50995 | 5098 | 138 | 138 | SNP | A | b73 | G | mo17 | | | | |
| 33 | Ampli-con50995 | 5099 | 230 | 230 | SNP | G | mo17 | T | b73 | | | | |
| 33 | Ampli-con50995 | 5100 | 321 | 321 | SNP | A | mo17 | C | b73 | | | | |
| 33 | Ampli-con50995 | 5101 | 331 | 331 | IND | * | b73 | G | mo17 | | | | |
| 33 | Ampli-con50995 | 5102 | 351 | 351 | SNP | A | b73 | C | mo17 | | | | |
| 33 | Ampli-con50995 | 5103 | 366 | 366 | SNP | A | mo17 | G | b73 | | | | |
| 33 | Ampli-con50995 | 5104 | 417 | 417 | SNP | A | b73 | G | mo17 | | | | |
| 33 | Ampli-con50995 | 5105 | 436 | 436 | SNP | A | b73 | T | mo17 | | | | |
| 33 | Ampli-con50995 | 5106 | 519 | 519 | SNP | C | b73 | T | mo17 | | | | |
| 33 | Ampli-con50995 | 5107 | 576 | 576 | SNP | A | b73 | G | mo17 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 34 | Ampli-con51024 | 5139 | 189 | 189 | SNP | C | mo17 | T | b73 | | | | |
| 34 | Ampli-con51024 | 5140 | 347 | 347 | SNP | C | mo17 | T | b73 | | | | |
| 35 | Ampli-con51063 | 5215 | 494 | 494 | SNP | A | mo17 | T | b73 | | | | |
| 36 | Ampli-con51114 | 5274 | 185 | 185 | IND | * | mo17 | G | b73 | | | | |
| 36 | Ampli-con51114 | 5275 | 222 | 222 | SNP | A | mo17 | G | b73 | | | | |
| 36 | Ampli-con51114 | 5276 | 358 | 358 | SNP | A | mo17 | T | b73 | | | | |
| 36 | Ampli-con51114 | 5277 | 451 | 451 | SNP | C | b73 | T | mo17 | | | | |
| 37 | Ampli-con51134 | 5314 | 279 | 279 | SNP | C | mo17 | G | b73 | | | | |
| 37 | Ampli-con51134 | 5315 | 340 | 340 | SNP | A | mo17 | G | b73 | | | | |
| 37 | Ampli-con51134 | 5316 | 442 | 442 | SNP | A | b73 | G | mo17 | | | | |
| 37 | Ampli-con51134 | 5317 | 443 | 443 | SNP | A | b73 | C | mo17 | | | | |
| 37 | Ampli-con51134 | 5318 | 467 | 467 | SNP | A | b73 | T | mo17 | | | | |
| 37 | Ampli-con51134 | 5319 | 479 | 479 | SNP | A | b73 | G | mo17 | | | | |
| 38 | Ampli-con51241 | 5480 | 173 | 173 | SNP | A | b73 | G | mo17 | | | | |
| 38 | Ampli-con51241 | 5481 | 325 | 325 | SNP | A | mo17 | G | b73 | | | | |
| 38 | Ampli-con51241 | 5482 | 405 | 405 | SNP | C | b73 | T | mo17 | | | | |
| 39 | Ampli-con51241 | 8685 | 112 | 112 | SNP | A | mo17 | G | b73 | | | | |
| 40 | Ampli-con173892 | 8716 | 118 | 118 | IND | * | b73 | A | mo17 | | | | |
| 40 | Ampli-con173943 | 8717 | 129 | 129 | SNP | C | mo17 | G | b73 | | | | |
| 40 | Ampli-con173943 | 8718 | 197 | 197 | SNP | A | mo17 | G | b73 | | | | |
| 40 | Ampli-con173943 | 8719 | 257 | 257 | SNP | A | b73 | G | mo17 | | | | |
| 40 | Ampli-con173943 | 8720 | 286 | 286 | SNP | A | b73 | C | mo17 | | | | |
| 41 | Ampli-con173943 | 8757 | 285 | 285 | SNP | C | mo17 | T | b73 | | | | |
| 41 | Ampli-con173990 | 8758 | 323 | 323 | SNP | A | b73 | C | mo17 | | | | |
| 41 | Ampli-con173990 | 8759 | 379 | 379 | SNP | A | b73 | G | mo17 | | | | |
| 41 | Ampli-con173990 | 8760 | 412 | 412 | SNP | A | b73 | T | mo17 | | | | |
| 41 | Ampli-con173990 | 8761 | 413 | 413 | IND | * | mo17 | C | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 41 | Ampli-con173990 | 8762 | 427 | 427 | SNP | A | mo17 | T | b73 | | | | |
| 42 | Ampli-con174021 | 8799 | 352 | 352 | SNP | A | mo17 | G | b73 | | | | |
| 42 | Ampli-con174021 | 8800 | 445 | 445 | SNP | A | mo17 | G | b73 | | | | |
| 43 | Ampli-con174108 | 8838 | 294 | 294 | SNP | A | b73 | G | mo17 | | | | |
| 44 | Ampli-con174113 | 8840 | 108 | 108 | SNP | A | b73 | G | mo17 | | | | |
| 45 | Ampli-con174252 | 8911 | 211 | 211 | SNP | A | b73 | G | mo17 | | | | |
| 46 | Ampli-con174322 | 8937 | 151 | 151 | SNP | A | mo17 | T | b73 | | | | |
| 47 | Ampli-con174423 | 8979 | 196 | 196 | SNP | A | mo17 | T | b73 | | | | |
| 48 | Ampli-con174434 | 8981 | 58 | 58 | SNP | A | b73 | G | mo17 | | | | |
| 48 | Ampli-con174434 | 8982 | 358 | 358 | SNP | A | b73 | G | mo17 | | | | |
| 49 | Ampli-con174442 | 8984 | 402 | 402 | SNP | C | mo17 | T | b73 | | | | |
| 50 | Ampli-con174632 | 9079 | 126 | 126 | SNP | C | b73 | T | mo17 | | | | |
| 51 | Ampli-con174763 | 9142 | 86 | 86 | IND | * | mo17 | C | b73 | | | | |
| 51 | Ampli-con174763 | 9143 | 96 | 96 | IND | * | mo17 | C | b73 | | | | |
| 52 | Ampli-con174793 | 9144 | 233 | 233 | SNP | A | mo17 | T | b73 | | | | |
| 52 | Ampli-con174793 | 9157 | 167 | 167 | SNP | C | b73 | G | mo17 | | | | |
| 52 | Ampli-con174793 | 9158 | 318 | 318 | SNP | A | b73 | G | mo17 | | | | |
| 52 | Ampli-con174793 | 9159 | 359 | 359 | SNP | C | mo17 | T | b73 | | | | |
| 52 | Ampli-con174793 | 9160 | 396 | 396 | SNP | C | b73 | G | mo17 | | | | |
| 52 | Ampli-con174793 | 9161 | 399 | 399 | SNP | A | b73 | C | mo17 | | | | |
| 52 | Ampli-con174793 | 9162 | 412 | 412 | SNP | A | b73 | C | mo17 | | | | |
| 53 | Ampli-con174811 | 9173 | 133 | 133 | SNP | A | mo17 | C | b73 | | | | |
| 53 | Ampli-con174811 | 9174 | 163 | 166 | IND | **** | mo17 | GTAT | b73 | | | | |
| 53 | Ampli-con174811 | 9175 | 173 | 173 | SNP | A | b73 | G | mo17 | | | | |
| 53 | Ampli-con174811 | 9176 | 174 | 174 | SNP | C | mo17 | T | b73 | | | | |
| 54 | Ampli-con174832 | 9187 | 146 | 146 | SNP | C | b73 | T | mo17 | | | | |
| 54 | Ampli-con174832 | 9188 | 244 | 245 | IND | ** | b73 | TT | mo17 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 54 | Ampli-con174832 | 9189 | 248 | 249 | IND | ** | b73 | CC | mo17 | | | | |
| 54 | Ampli-con174832 | 9190 | 268 | 268 | SNP | C | mo17 | T | b73 | | | | |
| 54 | Ampli-con174832 | 9191 | 275 | 275 | IND | * | b73 | T | mo17 | | | | |
| 54 | Ampli-con174832 | 9192 | 285 | 285 | SNP | A | mo17 | G | b73 | | | | |
| 54 | Ampli-con174832 | 9193 | 367 | 367 | SNP | C | mo17 | G | b73 | | | | |
| 55 | Ampli-con175020 | 9297 | 118 | 118 | SNP | A | mo17 | G | b73 | | | | |
| 55 | Ampli-con175020 | 9298 | 189 | 189 | SNP | A | b73 | T | mo17 | | | | |
| 55 | Ampli-con175020 | 9299 | 195 | 195 | SNP | A | mo17 | G | b73 | | | | |
| 56 | Ampli-con175137 | 9364 | 409 | 409 | SNP | C | mo17 | T | b73 | | | | |
| 57 | Ampli-con175303 | 9449 | 209 | 209 | SNP | A | mo17 | G | b73 | | | | |
| 57 | Ampli-con175303 | 9450 | 262 | 266 | IND | ***** | mo17 | CCTTG | b73 | | | | |
| 57 | Ampli-con175303 | 9451 | 426 | 426 | SNP | A | mo17 | T | b73 | | | | |
| 58 | Ampli-con175327 | 9467 | 57 | 57 | IND | * | mo17 | T | b73 | | | | |
| 58 | Ampli-con175327 | 9468 | 126 | 126 | SNP | A | b73 | G | mo17 | | | | |
| 58 | Ampli-con175327 | 9469 | 333 | 333 | SNP | A | mo17 | G | b73 | | | | |
| 59 | Ampli-con175328 | 9470 | 154 | 154 | SNP | C | mo17 | G | b73 | | | | |
| 59 | Ampli-con175328 | 9471 | 213 | 215 | IND | *** | b73 | TAG | mo17 | | | | |
| 60 | Ampli-con175332 | 9472 | 146 | 146 | IND | * | b73 | A | mo17 | | | | |
| 60 | Ampli-con175332 | 9473 | 335 | 335 | SNP | C | mo17 | T | mo17 | | | | |
| 61 | Ampli-con175347 | 9485 | 153 | 153 | SNP | A | b73 | C | mo17 | | | | |
| 61 | Ampli-con175347 | 9486 | 242 | 242 | SNP | A | b73 | T | mo17 | | | | |
| 62 | Ampli-con175497 | 9553 | 73 | 73 | SNP | A | b73 | T | mo17 | | | | |
| 62 | Ampli-con175497 | 9554 | 263 | 263 | SNP | A | mo17 | G | b73 | | | | |
| 62 | Ampli-con175497 | 9555 | 284 | 284 | SNP | A | mo17 | C | b73 | | | | |
| 62 | Ampli-con175497 | 9556 | 289 | 289 | SNP | A | mo17 | C | b73 | | | | |
| 62 | Ampli-con175497 | 9557 | 374 | 374 | SNP | A | mo17 | C | b73 | | | | |
| 63 | Ampli-con175582 | 9622 | 37 | 37 | SNP | C | mo17 | T | b73 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 63 | Ampli-con175582 | 9623 | 198 | 198 | SNP | C | b73 | T | mo17 | | | | |
| 63 | Ampli-con175582 | 9624 | 258 | 258 | SNP | A | b73 | G | mo17 | | | | |
| 63 | Ampli-con175582 | 9625 | 354 | 354 | SNP | C | mo17 | T | b73 | | | | |
| 64 | Ampli-con175589 | 9626 | 238 | 238 | SNP | C | mo17 | G | b73 | | | | |
| 64 | Ampli-con175589 | 9627 | 260 | 260 | SNP | A | b73 | C | mo17 | | | | |
| 65 | Ampli-con175642 | 9667 | 240 | 240 | SNP | C | b73 | G | mo17 | | | | |
| 66 | Ampli-con175645 | 9668 | 108 | 108 | SNP | A | b73 | G | mo17 | | | | |
| 66 | Ampli-con175645 | 9669 | 388 | 388 | SNP | A | mo17 | T | b73 | | | | |
| 67 | Ampli-con175693 | 9698 | 330 | 330 | SNP | C | b73 | G | mo17 | | | | |
| 67 | Ampli-con175693 | 9699 | 347 | 350 | IND | **** | b73 | GTTG | mo17 | | | | |
| 67 | Ampli-con175693 | 9700 | 352 | 354 | IND | *** | b73 | TTT | mo17 | | | | |
| 67 | Ampli-con175693 | 9701 | 448 | 448 | SNP | A | b73 | G | mo17 | | | | |
| 68 | Ampli-con175701 | 9703 | 21 | 21 | SNP | G | b73 | T | mo17 | | | | |
| 68 | Ampli-con175701 | 9704 | 61 | 61 | SNP | C | mo17 | T | b73 | | | | |
| 68 | Ampli-con175701 | 9705 | 213 | 213 | SNP | C | mo17 | T | b73 | | | | |
| 68 | Ampli-con175701 | 9706 | 284 | 284 | SNP | A | b73 | G | mo17 | | | | |
| 68 | Ampli-con175701 | 9707 | 381 | 381 | SNP | A | mo17 | G | b73 | | | | |
| 68 | Ampli-con175701 | 9708 | 402 | 402 | SNP | G | b73 | T | mo17 | | | | |
| 68 | Ampli-con175701 | 9709 | 418 | 418 | SNP | C | b73 | T | mo17 | | | | |
| 68 | Ampli-con175701 | 9710 | 419 | 419 | SNP | A | mo17 | C | b73 | | | | |
| 68 | Ampli-con175701 | 9711 | 435 | 435 | SNP | A | mo17 | G | b73 | | | | |
| 69 | Ampli-con175758 | 9739 | 290 | 290 | SNP | A | b73 | G | mo17 | | | | |
| 70 | Ampli-con175783 | 9759 | 167 | 167 | SNP | A | mo17 | G | b73 | | | | |
| 70 | Ampli-con175783 | 9760 | 220 | 220 | SNP | A | b73 | G | mo17 | | | | |
| 70 | Ampli-con175783 | 9761 | 275 | 275 | SNP | A | mo17 | G | b73 | | | | |
| 70 | Ampli-con175783 | 9762 | 282 | 282 | SNP | A | b73 | T | mo17 | | | | |
| 70 | Ampli-con175783 | 9763 | 327 | 330 | IND | **** | mo17 | ACGA | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 70 | Ampli-con175783 | 9764 | 476 | 476 | SNP | A | mo17 | G | b73 | | | | |
| 70 | Ampli-con175783 | 9765 | 483 | 483 | IND | * | mo17 | C | b73 | | | | |
| 71 | Ampli-con176287 | 9864 | 36 | 36 | SNP | C | mo17 | T | b73 | | | | |
| 71 | Ampli-con176287 | 9865 | 155 | 155 | SNP | A | b73 | C | mo17 | | | | |
| 71 | Ampli-con176287 | 9866 | 159 | 159 | SNP | A | mo17 | T | b73 | | | | |
| 71 | Ampli-con176287 | 9867 | 247 | 247 | SNP | A | b73 | T | mo17 | | | | |
| 72 | Ampli-con176352 | 9927 | 40 | 40 | SNP | A | mo17 | T | b73 | | | | |
| 72 | Ampli-con176352 | 10667 | 308 | 308 | SNP | A | mo17 | G | b73 | | | | |
| 73 | Ampli-con176515 | 10323 | 100 | 100 | SNP | A | b73 | G | mo17 | | | | |
| 73 | Ampli-con176515 | 10324 | 105 | 105 | SNP | A | b73 | G | mo17 | | | | |
| 73 | Ampli-con176515 | 10325 | 111 | 111 | SNP | C | b73 | G | mo17 | | | | |
| 73 | Ampli-con176515 | 10326 | 112 | 112 | SNP | C | mo17 | T | b73 | | | | |
| 73 | Ampli-con176515 | 10327 | 117 | 117 | IND | * | mo17 | C | b73 | | | | |
| 73 | Ampli-con176515 | 10328 | 119 | 120 | IND | ** | mo17 | TC | b73 | | | | |
| 73 | Ampli-con176515 | 10329 | 143 | 143 | SNP | C | mo17 | T | b73 | | | | |
| 73 | Ampli-con176515 | 10330 | 157 | 157 | SNP | C | b73 | G | mo17 | | | | |
| 73 | Ampli-con176515 | 10331 | 160 | 160 | IND | * | b73 | C | mo17 | | | | |
| 73 | Ampli-con176515 | 10332 | 174 | 175 | IND | ** | mo17 | TA | b73 | | | | |
| 73 | Ampli-con176515 | 10334 | 252 | 252 | IND | * | mo17 | C | b73 | | | | |
| 73 | Ampli-con176515 | 10335 | 269 | 269 | IND | * | b73 | C | mo17 | | | | |
| 73 | Ampli-con176515 | 10336 | 269 | 270 | IND | ** | b73 | CA | mo17 | | | | |
| 73 | Ampli-con176515 | 10337 | 417 | 422 | IND | ****** | mo17 | CAGAGA | b73 | | | | |
| 73 | Ampli-con176515 | 10338 | 462 | 462 | SNP | A | b73 | G | mo17 | | | | |
| 73 | Ampli-con176515 | 11466 | 213 | 213 | SNP | G | b73 | T | mo17 | | | | |
| 73 | Ampli-con176515 | 11472 | 320 | 320 | SNP | A | b73 | G | mo17 | | | | |
| 74 | Ampli-con176522 | 11522 | 249 | 249 | SNP | A | b73 | C | mo17 | | | | |
| 75 | Ampli-con176583 | 10618 | 162 | 162 | SNP | C | mo17 | T | b73 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 75 | Ampli-con176583 | 12012 | 128 | 128 | SNP | C | b73 | T | mo17 | | | | |
| 76 | Ampli-con176608 | 10668 | 27 | 27 | SNP | A | b73 | C | mo17 | | | | |
| 76 | Ampli-con176608 | 10669 | 46 | 46 | SNP | A | b73 | G | mo17 | | | | |
| 76 | Ampli-con176608 | 10671 | 71 | 71 | SNP | A | mo17 | C | b73 | | | | |
| 76 | Ampli-con176608 | 10673 | 227 | 227 | SNP | A | mo17 | C | b73 | | | | |
| 76 | Ampli-con176608 | 10674 | 246 | 246 | SNP | C | b73 | T | mo17 | | | | |
| 76 | Ampli-con176608 | 10675 | 283 | 283 | IND | * | b73 | T | mo17 | | | | |
| 76 | Ampli-con176608 | 10677 | 340 | 340 | SNP | A | b73 | G | mo17 | | | | |
| 77 | Ampli-con176683 | 12340 | 401 | 401 | SNP | A | mo17 | T | b73 | | | | |
| 78 | Ampli-con176749 | 11302 | 77 | 77 | SNP | A | b73 | C | mo17 | | | | |
| 78 | Ampli-con176749 | 11304 | 227 | 227 | SNP | C | b73 | G | mo17 | | | | |
| 78 | Ampli-con176749 | 11306 | 284 | 284 | SNP | A | mo17 | G | b73 | | | | |
| 78 | Ampli-con176749 | 11308 | 286 | 286 | SNP | C | mo17 | T | b73 | | | | |
| 78 | Ampli-con176749 | 11310 | 373 | 373 | SNP | A | mo17 | C | b73 | | | | |
| 78 | Ampli-con176749 | 11311 | 374 | 374 | IND | * | mo17 | C | b73 | | | | |
| 78 | Ampli-con176749 | 11313 | 393 | 393 | SNP | A | mo17 | G | b73 | | | | |
| 78 | Ampli-con176749 | 11316 | 538 | 538 | SNP | A | b73 | G | mo17 | | | | |
| 78 | Ampli-con176749 | 11318 | 609 | 609 | SNP | A | mo17 | G | b73 | | | | |
| 78 | Ampli-con176749 | 12711 | 512 | 512 | SNP | A | mo17 | G | b73 | | | | |
| 79 | Ampli-con176767 | 12824 | 411 | 411 | SNP | C | b73 | T | mo17 | | | | |
| 80 | Ampli-con176822 | 11713 | 300 | 300 | SNP | C | mo17 | G | b73 | | | | |
| 80 | Ampli-con176822 | 13100 | 286 | 286 | SNP | A | b73 | C | mo17 | | | | |
| 81 | Ampli-con176863 | 12092 | 241 | 241 | SNP | C | mo17 | T | b73 | | | | |
| 81 | Ampli-con176863 | 12093 | 297 | 298 | IND | ** | mo17 | TT | b73 | | | | |
| 81 | Ampli-con176863 | 12094 | 322 | 322 | SNP | A | b73 | G | mo17 | | | | |
| 81 | Ampli-con176863 | 12096 | 345 | 345 | SNP | A | b73 | G | mo17 | | | | |
| 81 | Ampli-con176863 | 12098 | 422 | 422 | SNP | C | b73 | T | mo17 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 81 | Ampli-con176863 | 13490 | 481 | 481 | SNP | C | b73 | T | mo17 | | | | |
| 82 | Ampli-con176899 | 12427 | 28 | 28 | SNP | C | mo17 | T | b73 | | | | |
| 82 | Ampli-con176899 | 12428 | 136 | 136 | SNP | G | b73 | T | mo17 | | | | |
| 82 | Ampli-con176899 | 12430 | 205 | 205 | SNP | A | mo17 | C | b73 | | | | |
| 82 | Ampli-con176899 | 12432 | 237 | 237 | SNP | C | mo17 | T | b73 | | | | |
| 82 | Ampli-con176899 | 12434 | 405 | 405 | SNP | A | b73 | G | mo17 | | | | |
| 82 | Ampli-con176899 | 13833 | 440 | 440 | SNP | A | mo17 | G | b73 | | | | |
| 83 | Ampli-con176937 | 12557 | 134 | 134 | SNP | A | b73 | G | mo17 | | | | |
| 83 | Ampli-con176937 | 12559 | 305 | 305 | SNP | A | mo17 | G | b73 | | | | |
| 83 | Ampli-con176937 | 12561 | 368 | 368 | SNP | A | b73 | G | mo17 | | | | |
| 83 | Ampli-con176937 | 12563 | 382 | 382 | IND | * | mo17 | C | b73 | | | | |
| 83 | Ampli-con176937 | 12565 | 384 | 384 | IND | * | b73 | C | mo17 | | | | |
| 83 | Ampli-con176937 | 12567 | 386 | 386 | IND | * | b73 | C | mo17 | | | | |
| 83 | Ampli-con176937 | 12569 | 388 | 388 | IND | * | b73 | C | mo17 | | | | |
| 83 | Ampli-con176937 | 12571 | 391 | 391 | SNP | A | mo17 | G | b73 | | | | |
| 83 | Ampli-con176937 | 12573 | 392 | 392 | SNP | A | mo17 | T | b73 | | | | |
| 83 | Ampli-con176937 | 12575 | 393 | 393 | SNP | G | mo17 | T | b73 | | | | |
| 84 | Ampli-con176937 | 13082 | 460 | 461 | IND | ** | b73 | TA | mo17 | | | | |
| 84 | Ampli-con177031 | 14467 | 370 | 371 | IND | ** | b73 | AT | mo17 | | | | |
| 85 | Ampli-con177031 | 13083 | 118 | 118 | SNP | A | mo17 | G | b73 | | | | |
| 85 | Ampli-con177035 | 13086 | 364 | 364 | SNP | A | mo17 | G | b73 | | | | |
| 85 | Ampli-con177035 | 13088 | 384 | 384 | SNP | A | b73 | G | mo17 | | | | |
| 86 | Ampli-con177035 | 14479 | 308 | 308 | SNP | G | mo17 | T | b73 | | | | |
| 87 | Ampli-con177038 | 13160 | 585 | 585 | SNP | C | b73 | T | mo17 | | | | |
| 87 | Ampli-con177055 | 14545 | 513 | 513 | SNP | G | b73 | T | mo17 | | | | |
| 88 | Ampli-con177055 | 13283 | 139 | 139 | SNP | A | b73 | T | mo17 | | | | |
| 88 | Ampli-con177093 | 14666 | 125 | 125 | SNP | C | mo17 | G | b73 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 89 | Ampli-con177147 | 13685 | 230 | 230 | SNP | A | b73 | G | mo17 | | | | |
| 89 | Ampli-con177147 | 13687 | 245 | 245 | SNP | C | b73 | T | mo17 | | | | |
| 89 | Ampli-con177147 | 13688 | 300 | 300 | SNP | A | b73 | C | mo17 | | | | |
| 89 | Ampli-con177147 | 13689 | 392 | 392 | SNP | A | b73 | C | mo17 | | | | |
| 89 | Ampli-con177147 | 13691 | 489 | 489 | SNP | C | mo17 | T | b73 | | | | |
| 90 | Ampli-con177150 | 13714 | 204 | 204 | SNP | A | mo17 | G | b73 | | | | |
| 90 | Ampli-con177150 | 13716 | 224 | 224 | SNP | C | b73 | G | mo17 | | | | |
| 90 | Ampli-con177150 | 13718 | 283 | 283 | SNP | C | b73 | T | mo17 | | | | |
| 90 | Ampli-con177150 | 13720 | 424 | 424 | SNP | C | mo17 | T | b73 | | | | |
| 90 | Ampli-con177150 | 13722 | 450 | 450 | SNP | A | b73 | G | mo17 | | | | |
| 90 | Ampli-con177150 | 15096 | 397 | 397 | SNP | A | b73 | G | mo17 | | | | |
| 91 | Ampli-con177154 | 13745 | 51 | 51 | SNP | A | b73 | G | mo17 | | | | |
| 91 | Ampli-con177154 | 13747 | 71 | 71 | SNP | C | b73 | T | mo17 | | | | |
| 91 | Ampli-con177154 | 13748 | 114 | 114 | SNP | C | mo17 | T | b73 | | | | |
| 91 | Ampli-con177154 | 13750 | 152 | 152 | SNP | A | b73 | T | mo17 | | | | |
| 91 | Ampli-con177154 | 13752 | 312 | 312 | SNP | A | mo17 | G | b73 | | | | |
| 91 | Ampli-con177154 | 13754 | 449 | 449 | SNP | C | b73 | T | mo17 | | | | |
| 91 | Ampli-con177154 | 13756 | 498 | 498 | SNP | A | b73 | G | mo17 | | | | |
| 92 | Ampli-con177165 | 13783 | 66 | 66 | SNP | C | mo17 | T | b73 | | | | |
| 92 | Ampli-con177165 | 13785 | 101 | 101 | SNP | * | mo17 | | b73 | | | | |
| 92 | Ampli-con177165 | 13787 | 111 | 111 | IND | C | mo17 | T | b73 | | | | |
| 92 | Ampli-con177165 | 13791 | 143 | 143 | SNP | A | mo17 | T | b73 | | | | |
| 92 | Ampli-con177165 | 13793 | 144 | 144 | SNP | A | mo17 | T | b73 | | | | |
| 92 | Ampli-con177165 | 13795 | 190 | 190 | SNP | C | b73 | T | mo17 | | | | |
| 92 | Ampli-con177165 | 13797 | 191 | 191 | SNP | C | mo17 | G | b73 | | | | |
| 92 | Ampli-con177165 | 13799 | 193 | 193 | SNP | A | b73 | G | mo17 | | | | |
| 92 | Ampli-con177165 | 13801 | 229 | 229 | SNP | A | b73 | G | mo17 | | | | |

-continued

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 92 | Ampli-con171165 | 13803 | 241 | 243 | IND | *** | b73 | TAC | mo17 | | | | |
| 92 | Ampli-con171165 | 13805 | 274 | 274 | SNP | A | b73 | G | mo17 | | | | |
| 92 | Ampli-con171165 | 13807 | 334 | 334 | SNP | A | mo17 | C | b73 | | | | |
| 92 | Ampli-con171165 | 13811 | 567 | 567 | SNP | C | b73 | T | mo17 | | | | |
| 92 | Ampli-con171165 | 15184 | 390 | 390 | SNP | C | b73 | T | mo17 | | | | |
| 93 | Ampli-con171340 | 14596 | 216 | 216 | SNP | C | mo17 | C | b73 | | | | |
| 93 | Ampli-con171340 | 14599 | 502 | 502 | SNP | A | b73 | T | mo17 | | | | |
| 93 | Ampli-con171340 | 15954 | 253 | 253 | SNP | A | b73 | T | mo17 | | | | |
| 94 | Ampli-con171341 | 14602 | 67 | 67 | SNP | A | b73 | G | mo17 | | | | |
| 94 | Ampli-con171341 | 14604 | 102 | 102 | SNP | A | b73 | T | mo17 | | | | |
| 94 | Ampli-con171341 | 14606 | 187 | 187 | SNP | C | b73 | T | mo17 | | | | |
| 94 | Ampli-con171341 | 15965 | 389 | 389 | SNP | A | b73 | T | mo17 | | | | |
| 95 | Ampli-con171359 | 16041 | 189 | 189 | SNP | A | mo17 | C | b73 | | | | |
| 96 | Ampli-con171361 | 14692 | 74 | 74 | SNP | C | b73 | G | mo17 | | | | |
| 96 | Ampli-con171361 | 14694 | 104 | 104 | SNP | A | mo17 | C | b73 | | | | |
| 96 | Ampli-con171361 | 14697 | 528 | 528 | SNP | C | b73 | T | mo17 | | | | |
| 96 | Ampli-con171361 | 14698 | 556 | 556 | SNP | C | mo17 | T | b73 | | | | |
| 96 | Ampli-con171361 | 14700 | 560 | 560 | SNP | G | mo17 | T | b73 | | | | |
| 97 | Ampli-con171370 | 16074 | 384 | 384 | SNP | A | b73 | G | mo17 | | | | |
| 98 | Ampli-con171382 | 16137 | 481 | 481 | SNP | C | b73 | T | mo17 | | | | |
| 99 | Ampli-con171440 | 15165 | 229 | 229 | SNP | A | mo17 | G | b73 | | | | |
| 99 | Ampli-con171440 | 15167 | 241 | 241 | SNP | C | b73 | T | mo17 | | | | |
| 99 | Ampli-con171440 | 15171 | 411 | 411 | SNP | A | mo17 | T | b73 | | | | |
| 99 | Ampli-con171440 | 15173 | 412 | 412 | IND | * | b73 | A | mo17 | | | | |
| 99 | Ampli-con171440 | 15175 | 433 | 433 | SNP | A | b73 | G | mo17 | | | | |
| 99 | Ampli-con171440 | 15177 | 501 | 501 | SNP | A | b73 | G | mo17 | | | | |
| 99 | Ampli-con171440 | 16527 | 353 | 353 | SNP | A | b73 | T | mo17 | | | | |

-continued

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 100 | Ampli-con177450 | 15244 | 344 | 345 | IND | ** | b73 | AT | mo17 | | | | |
| 100 | Ampli-con177450 | 15245 | 475 | 475 | IND | * | b73 | T | mo17 | | | | |
| 100 | Ampli-con177450 | 15247 | 482 | 482 | SNP | C | mo17 | T | b73 | | | | |
| 101 | Ampli-con177463 | 15304 | 79 | 79 | SNP | A | mo17 | G | b73 | | | | |
| 101 | Ampli-con177463 | 15305 | 326 | 326 | SNP | A | mo17 | G | b73 | | | | |
| 102 | Ampli-con177482 | 15369 | 21 | 21 | SNP | G | b73 | T | mo17 | | | | |
| 102 | Ampli-con177482 | 15373 | 256 | 256 | SNP | A | mo17 | G | b73 | | | | |
| 102 | Ampli-con177482 | 16724 | 87 | 87 | SNP | C | mo17 | T | b73 | | | | |
| 103 | Ampli-con177485 | 15378 | 447 | 447 | IND | * | b73 | T | mo17 | | | | |
| 103 | Ampli-con177485 | 15379 | 455 | 455 | SNP | G | mo17 | T | b73 | | | | |
| 103 | Ampli-con177485 | 15381 | 465 | 465 | SNP | C | b73 | G | mo17 | | | | |
| 103 | Ampli-con177485 | 15383 | 503 | 503 | SNP | A | b73 | C | mo17 | | | | |
| 103 | Ampli-con177485 | 16729 | 103 | 103 | SNP | C | b73 | T | mo17 | | | | |
| 104 | Ampli-con177492 | 15405 | 81 | 84 | IND | **** | mo17 | CATG | b73 | | | | |
| 104 | Ampli-con177492 | 15407 | 136 | 136 | SNP | C | b73 | G | mo17 | | | | |
| 104 | Ampli-con177492 | 15409 | 194 | 194 | SNP | A | b73 | G | mo17 | | | | |
| 104 | Ampli-con177492 | 15411 | 275 | 275 | SNP | C | b73 | G | mo17 | | | | |
| 104 | Ampli-con177492 | 15415 | 404 | 404 | SNP | C | mo17 | T | b73 | | | | |
| 104 | Ampli-con177492 | 15417 | 532 | 532 | SNP | A | mo17 | G | b73 | | | | |
| 105 | Ampli-con177492 | 16762 | 379 | 379 | SNP | A | mo17 | C | b73 | | | | |
| 105 | Ampli-con177493 | 16767 | 61 | 61 | SNP | A | mo17 | C | b73 | | | | |
| 106 | Ampli-con177524 | 15604 | 141 | 141 | SNP | A | mo17 | G | b73 | | | | |
| 106 | Ampli-con177524 | 16944 | 231 | 231 | SNP | A | b73 | T | mo17 | | | | |
| 107 | Ampli-con177615 | 16016 | 112 | 112 | SNP | C | b73 | T | mo17 | | | | |
| 107 | Ampli-con177615 | 16017 | 158 | 158 | SNP | A | mo17 | T | b73 | | | | |
| 107 | Ampli-con177615 | 16019 | 286 | 286 | SNP | A | b73 | G | mo17 | | | | |
| 107 | Ampli-con177615 | 16021 | 288 | 288 | SNP | A | mo17 | G | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 107 | Ampli-con177615 | 16023 | 295 | 295 | SNP | A | b73 | G | mo17 | | | | |
| 107 | Ampli-con177615 | 16024 | 334 | 334 | SNP | C | b73 | T | mo17 | | | | |
| 107 | Ampli-con177615 | 16026 | 381 | 381 | SNP | A | b73 | G | mo17 | | | | |
| 108 | Ampli-con177707 | 16497 | 125 | 125 | SNP | A | b73 | G | mo17 | | | | |
| 108 | Ampli-con177707 | 17828 | 340 | 340 | SNP | A | mo17 | G | b73 | | | | |
| 109 | Ampli-con177729 | 16576 | 63 | 63 | SNP | C | mo17 | T | b73 | | | | |
| 109 | Ampli-con177729 | 16578 | 83 | 83 | SNP | A | mo17 | T | b73 | | | | |
| 109 | Ampli-con177729 | 16582 | 208 | 208 | SNP | G | mo17 | T | b73 | | | | |
| 109 | Ampli-con177729 | 16584 | 248 | 248 | SNP | C | mo17 | T | b73 | | | | |
| 109 | Ampli-con177729 | 16585 | 250 | 253 | IND | **** | b73 | GGAC | mo17 | | | | |
| 109 | Ampli-con177729 | 16588 | 331 | 331 | SNP | G | mo17 | T | b73 | | | | |
| 109 | Ampli-con177729 | 16589 | 377 | 377 | SNP | G | mo17 | T | b73 | | | | |
| 109 | Ampli-con177729 | 16591 | 391 | 391 | SNP | A | b73 | T | mo17 | | | | |
| 109 | Ampli-con177729 | 16593 | 397 | 397 | SNP | C | b73 | T | mo17 | | | | |
| 109 | Ampli-con177729 | 16595 | 398 | 398 | IND | * | mo17 | T | b73 | | | | |
| 109 | Ampli-con177729 | 17900 | 155 | 155 | SNP | A | mo17 | G | b73 | | | | |
| 109 | Ampli-con177729 | 17908 | 256 | 259 | IND | **** | b73 | CTGG | mo17 | | | | |
| 110 | Ampli-con177761 | 16726 | 150 | 150 | SNP | A | b73 | G | mo17 | | | | |
| 110 | Ampli-con177761 | 16727 | 152 | 152 | SNP | A | mo17 | G | b73 | | | | |
| 110 | Ampli-con177761 | 16728 | 184 | 184 | SNP | C | b73 | T | mo17 | | | | |
| 110 | Ampli-con177761 | 16730 | 302 | 302 | SNP | A | mo17 | G | b73 | | | | |
| 111 | Ampli-con177766 | 16752 | 26 | 26 | SNP | C | mo17 | T | b73 | | | | |
| 111 | Ampli-con177766 | 16753 | 59 | 59 | SNP | C | mo17 | G | b73 | | | | |
| 111 | Ampli-con177766 | 16755 | 140 | 140 | SNP | C | mo17 | T | b73 | | | | |
| 111 | Ampli-con177766 | 16757 | 229 | 229 | SNP | C | b73 | T | mo17 | | | | |
| 111 | Ampli-con177766 | 16759 | 239 | 239 | SNP | C | mo17 | G | b73 | | | | |
| 111 | Ampli-con177766 | 16761 | 242 | 242 | SNP | A | mo17 | G | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 111 | Ampli-con177766 | 16763 | 265 | 265 | SNP | G | b73 | T | mo17 | | | | |
| 112 | Ampli-con177785 | 16839 | 146 | 146 | SNP | A | mo17 | C | b73 | | | | |
| 112 | Ampli-con177785 | 18157 | 576 | 576 | SNP | C | b73 | T | mo17 | | | | |
| 113 | Ampli-con177791 | 16876 | 90 | 90 | SNP | A | mo17 | G | b73 | | | | |
| 113 | Ampli-con177791 | 16877 | 108 | 112 | IND | ***** | mo17 | AGTAC | b73 | | | | |
| 113 | Ampli-con177791 | 16878 | 197 | 197 | SNP | C | b73 | G | mo17 | | | | |
| 113 | Ampli-con177791 | 16880 | 199 | 200 | IND | ** | b73 | CA | mo17 | | | | |
| 113 | Ampli-con177791 | 16882 | 202 | 202 | SNP | G | mo17 | T | b73 | | | | |
| 113 | Ampli-con177791 | 16883 | 205 | 205 | SNP | A | b73 | G | mo17 | | | | |
| 113 | Ampli-con177791 | 16885 | 206 | 206 | SNP | C | b73 | G | mo17 | | | | |
| 113 | Ampli-con177791 | 16887 | 209 | 210 | IND | ** | b73 | CG | mo17 | | | | |
| 113 | Ampli-con177791 | 16889 | 214 | 215 | IND | ** | b73 | AA | mo17 | | | | |
| 113 | Ampli-con177791 | 16891 | 218 | 218 | IND | * | b73 | A | mo17 | | | | |
| 113 | Ampli-con177791 | 16893 | 220 | 220 | IND | * | b73 | T | mo17 | | | | |
| 113 | Ampli-con177791 | 16895 | 259 | 259 | SNP | A | mo17 | C | b73 | | | | |
| 114 | Ampli-con177843 | 17079 | 516 | 516 | SNP | C | b73 | G | mo17 | | | | |
| 114 | Ampli-con177843 | 18392 | 356 | 356 | SNP | A | b73 | T | mo17 | | | | |
| 115 | Ampli-con177848 | 17120 | 150 | 150 | SNP | A | mo17 | G | b73 | | | | |
| 115 | Ampli-con177848 | 18439 | 171 | 171 | SNP | A | b73 | G | mo17 | | | | |
| 116 | Ampli-con178002 | 17897 | 336 | 336 | SNP | A | b73 | G | mo17 | | | | |
| 116 | Ampli-con178002 | 19198 | 322 | 322 | SNP | C | mo17 | T | b73 | | | | |
| 117 | Ampli-con178141 | 18677 | 919 | 919 | SNP | C | b73 | T | mo17 | | | | |
| 117 | Ampli-con178141 | 18679 | 921 | 921 | SNP | C | mo17 | T | b73 | | | | |
| 117 | Ampli-con178141 | 18681 | 1033 | 1033 | SNP | C | mo17 | T | b73 | | | | |
| 117 | Ampli-con178141 | 18683 | 1087 | 1087 | SNP | A | b73 | G | mo17 | | | | |
| 117 | Ampli-con178141 | 18685 | 1099 | 1099 | SNP | A | mo17 | T | b73 | | | | |
| 117 | Ampli-con178141 | 18689 | 1223 | 1223 | SNP | C | b73 | T | mo17 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 117 | Ampli-con178141 | 19963 | 1174 | 1174 | SNP | A | b73 | C | mo17 | | | | |
| 118 | Ampli-con178159 | 20048 | 415 | 415 | SNP | A | b73 | G | mo17 | | | | |
| 119 | Ampli-con178261 | 19236 | 152 | 152 | SNP | A | mo17 | G | b73 | | | | |
| 119 | Ampli-con178261 | 19240 | 243 | 243 | SNP | A | mo17 | G | b73 | | | | |
| 119 | Ampli-con178261 | 19241 | 245 | 245 | SNP | G | mo17 | T | b73 | | | | |
| 119 | Ampli-con178261 | 19242 | 406 | 406 | SNP | C | b73 | T | mo17 | | | | |
| 120 | Ampli-con178261 | 20502 | 171 | 171 | SNP | A | b73 | G | mo17 | | | | |
| 120 | Ampli-con178278 | 19266 | 113 | 113 | SNP | G | b73 | T | b73 | | | | |
| 120 | Ampli-con178278 | 19268 | 114 | 116 | IND | *** | mo17 | GAG | b73 | | | | |
| 120 | Ampli-con178278 | 19271 | 158 | 158 | SNP | A | mo17 | G | mo17 | | | | |
| 120 | Ampli-con178278 | 20537 | 139 | 139 | SNP | C | b73 | T | b73 | | | | |
| 121 | Ampli-con178389 | 19661 | 48 | 48 | SNP | G | mo17 | T | mo17 | | | | |
| 121 | Ampli-con178389 | 19663 | 338 | 338 | SNP | C | mo17 | T | b73 | | | | |
| 121 | Ampli-con178389 | 20933 | 372 | 372 | SNP | C | mo17 | T | b73 | | | | |
| 122 | Ampli-con178389 | 19669 | 299 | 299 | SNP | A | b73 | C | mo17 | | | | |
| 122 | Ampli-con178390 | 20934 | 172 | 172 | SNP | A | mo17 | G | b73 | | | | |
| 123 | Ampli-con178390 | 19702 | 81 | 81 | SNP | G | mo17 | T | mo17 | | | | |
| 123 | Ampli-con178392 | 19704 | 182 | 182 | SNP | A | b73 | T | mo17 | | | | |
| 123 | Ampli-con178392 | 19705 | 402 | 402 | IND | * | b73 | A | mo17 | | | | |
| 124 | Ampli-con178392 | 19767 | 38 | 38 | SNP | G | mo17 | T | b73 | | | | |
| 124 | Ampli-con178401 | 19771 | 178 | 178 | SNP | G | mo17 | T | b73 | | | | |
| 124 | Ampli-con178401 | 19773 | 193 | 193 | SNP | A | mo17 | C | b73 | | | | |
| 124 | Ampli-con178401 | 19775 | 205 | 210 | IND | ****** | b73 | GGAGAG | mo17 | | | | |
| 124 | Ampli-con178401 | 19777 | 219 | 223 | IND | ***** | b73 | AAAAA | mo17 | | | | |
| 124 | Ampli-con178401 | 19782 | 420 | 420 | SNP | C | mo17 | T | b73 | | | | |
| 124 | Ampli-con178401 | 19784 | 428 | 428 | SNP | A | b73 | G | mo17 | | | | |
| 124 | Ampli-con178401 | 21038 | 125 | 125 | SNP | A | mo17 | T | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 124 | Ampli-con178401 | 21045 | 307 | 307 | SNP | C | b73 | T | mo17 | | | | |
| 125 | Ampli-con178430 | 19893 | 113 | 113 | SNP | G | mo17 | T | b73 | | | | |
| 125 | Ampli-con178430 | 19896 | 239 | 239 | SNP | A | mo17 | C | b73 | | | | |
| 125 | Ampli-con178430 | 19897 | 465 | 465 | SNP | C | b73 | T | mo17 | | | | |
| 126 | Ampli-con178454 | 21154 | 54 | 54 | SNP | C | b73 | T | mo17 | | | | |
| 126 | Ampli-con178454 | 20172 | 157 | 157 | SNP | C | mo17 | T | b73 | | | | |
| 126 | Ampli-con178454 | 20173 | 172 | 172 | SNP | C | b73 | G | mo17 | | | | |
| 126 | Ampli-con178454 | 20175 | 194 | 194 | SNP | G | b73 | T | mo17 | | | | |
| 126 | Ampli-con178454 | 20177 | 203 | 203 | SNP | A | mo17 | C | b73 | | | | |
| 126 | Ampli-con178454 | 20180 | 296 | 296 | SNP | A | b73 | C | mo17 | | | | |
| 126 | Ampli-con178454 | 20182 | 297 | 297 | SNP | C | b73 | T | mo17 | | | | |
| 126 | Ampli-con178454 | 20184 | 335 | 335 | SNP | A | b73 | C | mo17 | | | | |
| 126 | Ampli-con178454 | 20187 | 367 | 367 | SNP | G | b73 | T | mo17 | | | | |
| 126 | Ampli-con178454 | 20189 | 371 | 371 | SNP | A | mo17 | G | b73 | | | | |
| 126 | Ampli-con178454 | 20191 | 402 | 402 | SNP | A | mo17 | C | b73 | | | | |
| 126 | Ampli-con178454 | 21433 | 59 | 59 | SNP | C | mo17 | G | b73 | | | | |
| 126 | Ampli-con178454 | 21443 | 223 | 223 | SNP | A | b73 | G | mo17 | | | | |
| 127 | Ampli-con178494 | 20348 | 303 | 303 | SNP | C | b73 | T | b73 | | | | |
| 127 | Ampli-con178494 | 20350 | 391 | 391 | SNP | A | b73 | T | mo17 | | | | |
| 127 | Ampli-con178494 | 21603 | 180 | 180 | SNP | G | b73 | T | mo17 | | | | |
| 128 | Ampli-con178507 | 20406 | 52 | 52 | SNP | C | mo17 | G | b73 | | | | |
| 128 | Ampli-con178507 | 20408 | 219 | 219 | SNP | G | mo17 | T | b73 | | | | |
| 128 | Ampli-con178507 | 20410 | 283 | 283 | SNP | A | b73 | T | mo17 | | | | |
| 128 | Ampli-con178507 | 20412 | 294 | 294 | SNP | G | mo17 | T | b73 | | | | |
| 128 | Ampli-con178507 | 20414 | 359 | 359 | SNP | A | mo17 | G | b73 | | | | |
| 128 | Ampli-con178507 | 20416 | 396 | 396 | SNP | A | mo17 | G | b73 | | | | |
| 128 | Ampli-con178507 | 20418 | 397 | 397 | SNP | G | mo17 | T | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 128 | Ampli-con178507 | 20420 | 429 | 429 | SNP | C | b73 | T | mo17 | | | | |
| 128 | Ampli-con178507 | 20422 | 432 | 432 | SNP | C | b73 | G | mo17 | | | | |
| 128 | Ampli-con178507 | 20424 | 457 | 457 | SNP | C | b73 | T | mo17 | | | | |
| 128 | Ampli-con178507 | 20426 | 462 | 462 | SNP | G | mo17 | T | b73 | | | | |
| 129 | Ampli-con178546 | 20513 | 147 | 147 | SNP | A | b73 | C | mo17 | | | | |
| 129 | Ampli-con178546 | 20515 | 180 | 180 | SNP | C | b73 | T | mo17 | | | | |
| 129 | Ampli-con178546 | 20517 | 312 | 312 | SNP | C | mo17 | T | b73 | | | | |
| 129 | Ampli-con178546 | 20519 | 336 | 336 | SNP | A | b73 | C | mo17 | | | | |
| 129 | Ampli-con178546 | 20521 | 342 | 342 | SNP | C | b73 | T | mo17 | | | | |
| 129 | Ampli-con178546 | 20523 | 396 | 396 | SNP | C | b73 | T | mo17 | | | | |
| 129 | Ampli-con178546 | 20525 | 435 | 435 | SNP | C | mo17 | T | b73 | | | | |
| 129 | Ampli-con178546 | 21772 | 258 | 258 | SNP | C | b73 | T | mo17 | | | | |
| 130 | Ampli-con178546 | 21895 | 37 | 37 | SNP | C | b73 | T | mo17 | | | | |
| 131 | Ampli-con178569 | 21190 | 285 | 285 | SNP | A | b73 | G | mo17 | | | | |
| 131 | Ampli-con178666 | 21192 | 498 | 498 | SNP | C | mo17 | T | b73 | | | | |
| 132 | Ampli-con178666 | 21292 | 130 | 130 | SNP | C | mo17 | T | b73 | | | | |
| 133 | Ampli-con178673 | 22541 | 130 | 130 | SNP | C | mo17 | T | b73 | | | | |
| 134 | Ampli-con178674 | 22717 | 63 | 63 | SNP | A | mo17 | T | b73 | | | | |
| 135 | Ampli-con178700 | 21524 | 115 | 115 | IND | * | mo17 | T | b73 | | | | |
| 135 | Ampli-con178723 | 21526 | 117 | 117 | IND | * | mo17 | A | b73 | | | | |
| 135 | Ampli-con178723 | 21528 | 209 | 215 | IND | ******* | b73 | AGCTAGC | mo17 | | | | |
| 135 | Ampli-con178723 | 21530 | 217 | 217 | IND | * | b73 | T | mo17 | | | | |
| 135 | Ampli-con178723 | 21532 | 481 | 481 | SNP | C | mo17 | T | b73 | | | | |
| 135 | Ampli-con178723 | 21533 | 485 | 485 | SNP | C | mo17 | G | b73 | | | | |
| 135 | Ampli-con178723 | 21535 | 487 | 487 | SNP | C | b73 | G | mo17 | | | | |
| 135 | Ampli-con178723 | 21536 | 488 | 488 | IND | * | mo17 | T | b73 | | | | |
| 135 | Ampli-con178723 | 21539 | 490 | 490 | SNP | C | b73 | T | mo17 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 135 | Ampli-con178723 | 21541 | 496 | 496 | SNP | A | mo17 | T | b73 | | | | |
| 135 | Ampli-con178723 | 21543 | 500 | 501 | IND | ** | mo17 | GC | b73 | | | | |
| 135 | Ampli-con178723 | 21545 | 503 | 503 | SNP | A | b73 | G | mo17 | | | | |
| 135 | Ampli-con178723 | 22775 | 526 | 526 | SNP | A | mo17 | G | b73 | | | | |
| 136 | Ampli-con178723 | 21564 | 163 | 163 | SNP | C | mo17 | T | b73 | | | | |
| 136 | Ampli-con178726 | 22796 | 198 | 198 | SNP | A | mo17 | G | b73 | | | | |
| 137 | Ampli-con178726 | 23091 | 169 | 169 | SNP | G | b73 | T | mo17 | | | | |
| 138 | Ampli-con178785 | 23289 | 250 | 250 | SNP | A | b73 | G | mo17 | | | | |
| 139 | Ampli-con178833 | 23779 | 342 | 342 | SNP | A | mo17 | G | b73 | | | | |
| 140 | Ampli-con178895 | 23075 | 54 | 54 | SNP | A | mo17 | T | b73 | | | | |
| 140 | Ampli-con179006 | 23078 | 224 | 224 | SNP | A | mo17 | G | b73 | | | | |
| 140 | Ampli-con179006 | 23080 | 306 | 306 | SNP | A | b73 | G | mo17 | | | | |
| 140 | Ampli-con179006 | 23082 | 329 | 329 | IND | * | mo17 | C | b73 | | | | |
| 140 | Ampli-con179006 | 23085 | 342 | 342 | SNP | A | b73 | G | mo17 | | | | |
| 140 | Ampli-con179006 | 23086 | 363 | 363 | SNP | C | mo17 | T | b73 | | | | |
| 140 | Ampli-con179006 | 23087 | 390 | 390 | SNP | A | b73 | C | mo17 | | | | |
| 140 | Ampli-con179006 | 23089 | 503 | 503 | SNP | A | b73 | T | mo17 | | | | |
| 140 | Ampli-con179006 | 24265 | 136 | 136 | SNP | A | mo17 | G | b73 | | | | |
| 141 | Ampli-con179006 | 23203 | 38 | 40 | IND | *** | mo17 | TCA | b73 | | | | |
| 141 | Ampli-con179027 | 23207 | 282 | 282 | SNP | C | b73 | G | mo17 | | | | |
| 141 | Ampli-con179027 | 24395 | 76 | 76 | SNP | C | b73 | T | mo17 | | | | |
| 142 | Ampli-con179027 | 24422 | 45 | 45 | SNP | C | mo17 | T | b73 | | | | |
| 143 | Ampli-con179035 | 23438 | 32 | 32 | SNP | A | mo17 | C | b73 | | | | |
| 143 | Ampli-con179070 | 23440 | 71 | 71 | SNP | A | b73 | T | mo17 | | | | |
| 143 | Ampli-con179070 | 23442 | 353 | 353 | SNP | C | mo17 | G | b73 | | | | |
| 144 | Ampli-con179140 | 23820 | 41 | 41 | SNP | C | mo17 | G | b73 | | | | |
| 144 | Ampli-con179140 | 23822 | 50 | 50 | IND | * | b73 | G | mo17 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 144 | Ampli-con179140 | 25000 | 72 | 72 | SNP | A | mo17 | G | b73 | | | | |
| 145 | Ampli-con179151 | 23890 | 120 | 120 | SNP | C | b73 | T | mo17 | | | | |
| 145 | Ampli-con179151 | 23892 | 476 | 476 | SNP | C | mo17 | T | b73 | | | | |
| 146 | Ampli-con179283 | 24647 | 190 | 190 | SNP | A | b73 | G | mo17 | | | | |
| 146 | Ampli-con179283 | 24649 | 265 | 265 | SNP | A | mo17 | G | b73 | | | | |
| 146 | Ampli-con179283 | 24651 | 375 | 375 | SNP | C | b73 | T | mo17 | | | | |
| 146 | Ampli-con179283 | 24653 | 431 | 431 | SNP | A | b73 | G | mo17 | | | | |
| 147 | Ampli-con179301 | 24693 | 92 | 92 | SNP | A | b73 | G | mo17 | | | | |
| 147 | Ampli-con179301 | 24697 | 201 | 201 | SNP | C | b73 | T | mo17 | | | | |
| 147 | Ampli-con179301 | 24699 | 245 | 245 | SNP | C | b73 | T | mo17 | | | | |
| 147 | Ampli-con179301 | 24701 | 272 | 272 | SNP | C | b73 | T | mo17 | | | | |
| 147 | Ampli-con179301 | 24703 | 395 | 395 | SNP | A | b73 | G | mo17 | | | | |
| 147 | Ampli-con179301 | 24704 | 418 | 418 | SNP | C | mo17 | T | b73 | | | | |
| 147 | Ampli-con179301 | 24705 | 505 | 505 | SNP | C | mo17 | T | b73 | | | | |
| 148 | Ampli-con179301 | 25863 | 128 | 128 | SNP | A | mo17 | G | b73 | | | | |
| 149 | Ampli-con179301 | 25961 | 399 | 399 | SNP | A | b73 | G | mo17 | | | | |
| 149 | Ampli-con179323 | 25414 | 23 | 23 | SNP | A | mo17 | G | b73 | | | | |
| 149 | Ampli-con179392 | 25416 | 212 | 212 | SNP | A | mo17 | G | b73 | | | | |
| 149 | Ampli-con179392 | 25418 | 224 | 226 | IND | *** | mo17 | ATC | b73 | | | | |
| 150 | Ampli-con179392 | 26846 | 467 | 467 | SNP | A | b73 | C | mo17 | | | | |
| 151 | Ampli-con179414 | 26151 | 183 | 183 | SNP | C | mo17 | T | b73 | | | | |
| 151 | Ampli-con179487 | 26153 | 207 | 209 | IND | *** | mo17 | CGG | b73 | | | | |
| 151 | Ampli-con179487 | 26155 | 212 | 213 | IND | ** | mo17 | AC | b73 | | | | |
| 151 | Ampli-con179487 | 26157 | 215 | 216 | IND | ** | mo17 | CC | b73 | | | | |
| 151 | Ampli-con179487 | 26159 | 236 | 236 | IND | * | mo17 | G | b73 | | | | |
| 151 | Ampli-con179487 | 26163 | 306 | 306 | SNP | C | b73 | T | mo17 | | | | |
| 151 | Ampli-con179487 | 26165 | 339 | 339 | SNP | A | b73 | T | mo17 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 151 | Ampli-con179487 | 26167 | 407 | 407 | SNP | A | mo17 | C | b73 | | | | |
| 151 | Ampli-con179487 | 26169 | 408 | 408 | SNP | A | mo17 | C | b73 | | | | |
| 151 | Ampli-con179487 | 26171 | 409 | 409 | SNP | A | b73 | G | mo17 | | | | |
| 151 | Ampli-con179487 | 27295 | 279 | 279 | SNP | A | mo17 | G | b73 | | | | |
| 152 | Ampli-con179497 | 26233 | 118 | 118 | SNP | C | b73 | G | mo17 | | | | |
| 152 | Ampli-con179497 | 26235 | 167 | 167 | SNP | A | mo17 | G | b73 | | | | |
| 152 | Ampli-con179497 | 26237 | 178 | 178 | SNP | A | b73 | G | mo17 | | | | |
| 152 | Ampli-con179497 | 26239 | 287 | 287 | SNP | A | b73 | G | mo17 | | | | |
| 152 | Ampli-con179497 | 26241 | 370 | 370 | SNP | G | b73 | T | mo17 | | | | |
| 152 | Ampli-con179497 | 26243 | 423 | 423 | SNP | G | mo17 | T | b73 | | | | |
| 152 | Ampli-con179497 | 26245 | 433 | 433 | SNP | A | mo17 | G | b73 | | | | |
| 152 | Ampli-con179497 | 26247 | 462 | 462 | SNP | C | mo17 | T | b73 | | | | |
| 152 | Ampli-con179497 | 27375 | 478 | 478 | SNP | A | b73 | C | mo17 | | | | |
| 153 | Ampli-con179515 | 26314 | 16 | 16 | SNP | A | b73 | G | mo17 | | | | |
| 153 | Ampli-con179515 | 26316 | 33 | 33 | IND | * | b73 | A | mo17 | | | | |
| 153 | Ampli-con179515 | 26318 | 95 | 95 | SNP | A | mo17 | G | b73 | | | | |
| 153 | Ampli-con179515 | 26319 | 132 | 132 | SNP | A | b73 | G | mo17 | | | | |
| 153 | Ampli-con179515 | 26321 | 161 | 161 | SNP | C | mo17 | G | b73 | | | | |
| 153 | Ampli-con179515 | 26322 | 281 | 283 | IND | *** | b73 | CTG | mo17 | | | | |
| 153 | Ampli-con179515 | 26326 | 351 | 351 | SNP | A | mo17 | C | b73 | | | | |
| 153 | Ampli-con179515 | 27447 | 310 | 310 | SNP | C | mo17 | G | b73 | | | | |
| 154 | Ampli-con179595 | 26711 | 30 | 30 | SNP | C | mo17 | T | b73 | | | | |
| 154 | Ampli-con179595 | 26713 | 51 | 51 | SNP | A | b73 | C | mo17 | | | | |
| 154 | Ampli-con179595 | 26715 | 155 | 155 | IND | * | mo17 | T | b73 | | | | |
| 154 | Ampli-con179595 | 26717 | 187 | 187 | SNP | C | mo17 | T | b73 | | | | |
| 154 | Ampli-con179595 | 26719 | 194 | 194 | SNP | C | b73 | G | mo17 | | | | |
| 154 | Ampli-con179595 | 26720 | 213 | 213 | SNP | A | b73 | C | mo17 | | | | |

-continued

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 154 | Ampli-con179595 | 26722 | 233 | 233 | SNP | C | b73 | T | mo17 | | | | |
| 154 | Ampli-con179595 | 26723 | 285 | 285 | SNP | C | mo17 | T | b73 | | | | |
| 154 | Ampli-con179595 | 26725 | 395 | 395 | SNP | G | mo17 | T | b73 | | | | |
| 155 | Ampli-con179720 | 27268 | 249 | 249 | SNP | A | b73 | G | mo17 | | | | |
| 155 | Ampli-con179720 | 27272 | 336 | 336 | SNP | A | b73 | T | mo17 | | | | |
| 155 | Ampli-con179720 | 27274 | 355 | 355 | SNP | A | b73 | G | mo17 | | | | |
| 155 | Ampli-con179720 | 27276 | 357 | 357 | IND | * | mo17 | C | b73 | | | | |
| 155 | Ampli-con179720 | 27278 | 368 | 368 | SNP | C | b73 | G | mo17 | | | | |
| 156 | Ampli-con179741 | 28164 | 267 | 267 | SNP | C | mo17 | G | b73 | | | | |
| 156 | Ampli-con179741 | 27359 | 20 | 20 | SNP | A | mo17 | G | b73 | | | | |
| 156 | Ampli-con179741 | 27360 | 218 | 218 | SNP | C | mo17 | G | b73 | | | | |
| 156 | Ampli-con179741 | 27361 | 228 | 228 | SNP | C | mo17 | T | b73 | | | | |
| 156 | Ampli-con179741 | 27363 | 459 | 459 | SNP | A | b73 | G | mo17 | | | | |
| 157 | Ampli-con179806 | 27613 | 32 | 32 | SNP | * | mo17 | T | b73 | | | | |
| 157 | Ampli-con179806 | 27615 | 235 | 235 | IND | C | b73 | T | mo17 | | | | |
| 158 | Ampli-con179806 | 27874 | 345 | 345 | SNP | * | b73 | C | mo17 | | | | |
| 159 | Ampli-con179868 | 28913 | 103 | 103 | IND | * | mo17 | C | b73 | | | | |
| 159 | Ampli-con234986 | 28914 | 149 | 149 | IND | ** | mo17 | C* | b73 | | | | |
| 159 | Ampli-con234986 | 28915 | 149 | 150 | IND | A | b73 | G | mo17 | | | | |
| 159 | Ampli-con234986 | 28916 | 169 | 169 | SNP | A | b73 | C | mo17 | | | | |
| 159 | Ampli-con234986 | 28917 | 256 | 256 | SNP | C | b73 | G | mo17 | | | | |
| 159 | Ampli-con234986 | 28918 | 311 | 311 | SNP | G | b73 | T | mo17 | | | | |
| 159 | Ampli-con234986 | 28919 | 469 | 469 | SNP | A | mo17 | G | b73 | | | | |
| 159 | Ampli-con234986 | 28920 | 501 | 501 | SNP | A | b73 | T | mo17 | | | | |
| 159 | Ampli-con234986 | 28921 | 834 | 834 | SNP | A | mo17 | T | b73 | | | | |
| 159 | Ampli-con234986 | 28922 | 911 | 911 | SNP | A | b73 | G | mo17 | | | | |
| 159 | Ampli-con234986 | 28923 | 1056 | 1056 | SNP | C | b73 | G | mo17 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 160 | Ampli-con234993 | 28931 | 175 | 175 | IND | * | mo17 | A | b73 | | | | |
| 160 | Ampli-con234993 | 28932 | 1103 | 1103 | SNP | A | mo17 | G | b73 | | | | |
| 161 | Ampli-con234996 | 28933 | 354 | 354 | SNP | A | mo17 | C | b73 | | | | |
| 161 | Ampli-con234996 | 28934 | 555 | 555 | SNP | C | mo17 | T | b73 | | | | |
| 161 | Ampli-con234996 | 28935 | 593 | 593 | SNP | A | mo17 | G | b73 | | | | |
| 162 | Ampli-con235018 | 29005 | 243 | 243 | SNP | A | b73 | G | mo17 | | | | |
| 163 | Ampli-con235123 | 29193 | 287 | 287 | IND | * | mo17 | C | b73 | | | | |
| 163 | Ampli-con235123 | 29194 | 291 | 291 | SNP | A | b73 | G | mo17 | | | | |
| 163 | Ampli-con235123 | 29195 | 673 | 678 | IND | ****** | mo17 | GCATTA | b73 | | | | |
| 163 | Ampli-con235123 | 29196 | 757 | 757 | SNP | A | b73 | G | mo17 | | | | |
| 164 | Ampli-con235210 | 29362 | 105 | 105 | SNP | C | b73 | T | mo17 | | | | |
| 164 | Ampli-con235210 | 29363 | 135 | 135 | SNP | A | b73 | G | mo17 | | | | |
| 164 | Ampli-con235210 | 29364 | 145 | 145 | SNP | C | b73 | G | mo17 | | | | |
| 164 | Ampli-con235210 | 29365 | 168 | 168 | SNP | A | mo17 | G | b73 | | | | |
| 164 | Ampli-con235210 | 29366 | 207 | 207 | IND | * | mo17 | C | b73 | | | | |
| 164 | Ampli-con235210 | 29367 | 218 | 218 | SNP | A | b73 | G | mo17 | | | | |
| 164 | Ampli-con235210 | 29368 | 225 | 225 | SNP | C | b73 | T | mo17 | | | | |
| 164 | Ampli-con235210 | 29369 | 275 | 275 | SNP | C | mo17 | T | b73 | | | | |
| 164 | Ampli-con235210 | 29370 | 283 | 283 | SNP | A | b73 | C | mo17 | | | | |
| 164 | Ampli-con235210 | 29371 | 392 | 392 | SNP | G | mo17 | T | b73 | | | | |
| 164 | Ampli-con235210 | 29372 | 406 | 406 | SNP | A | mo17 | G | b73 | | | | |
| 164 | Ampli-con235210 | 29373 | 418 | 418 | SNP | A | b73 | G | mo17 | | | | |
| 164 | Ampli-con235210 | 29374 | 422 | 422 | IND | * | mo17 | A | b73 | | | | |
| 164 | Ampli-con235210 | 29375 | 433 | 433 | SNP | A | b73 | G | mo17 | | | | |
| 164 | Ampli-con235210 | 29376 | 434 | 434 | SNP | A | b73 | G | mo17 | | | | |
| 164 | Ampli-con235210 | 29377 | 441 | 441 | IND | * | mo17 | A | b73 | | | | |
| 165 | Ampli-con235220 | 29390 | 302 | 302 | SNP | C | b73 | T | mo17 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 166 | Ampli-con235234 | 29435 | 555 | 555 | SNP | A | b73 | G | mo17 | | | | |
| 167 | Ampli-con235395 | 29745 | 1024 | 1024 | SNP | C | b73 | G | mo17 | | | | |
| 167 | Ampli-con235395 | 29746 | 1061 | 1061 | SNP | C | mo17 | T | b73 | | | | |
| 167 | Ampli-con235395 | 29747 | 1143 | 1143 | SNP | A | mo17 | G | b73 | | | | |
| 167 | Ampli-con235395 | 29748 | 1166 | 1166 | IND | * | b73 | A | mo17 | | | | |
| 168 | Ampli-con235410 | 29779 | 83 | 83 | SNP | A | b73 | T | mo17 | | | | |
| 168 | Ampli-con235410 | 29780 | 140 | 140 | SNP | C | mo17 | T | b73 | | | | |
| 168 | Ampli-con235410 | 29781 | 211 | 213 | IND | *** | mo17 | GCT | b73 | | | | |
| 168 | Ampli-con235410 | 29782 | 313 | 313 | SNP | A | b73 | G | mo17 | | | | |
| 168 | Ampli-con235410 | 29783 | 315 | 315 | SNP | C | mo17 | T | b73 | | | | |
| 169 | Ampli-con235434 | 29819 | 64 | 64 | SNP | A | b73 | T | mo17 | | | | |
| 169 | Ampli-con235434 | 29820 | 108 | 108 | SNP | A | mo17 | G | b73 | | | | |
| 169 | Ampli-con235434 | 29821 | 120 | 120 | SNP | A | b73 | G | mo17 | | | | |
| 169 | Ampli-con235434 | 29822 | 121 | 121 | SNP | C | mo17 | T | b73 | | | | |
| 169 | Ampli-con235434 | 29823 | 180 | 180 | SNP | A | b73 | G | mo17 | | | | |
| 169 | Ampli-con235434 | 29824 | 186 | 186 | SNP | A | mo17 | C | b73 | | | | |
| 169 | Ampli-con235434 | 29825 | 202 | 202 | SNP | A | b73 | G | mo17 | | | | |
| 169 | Ampli-con235434 | 29826 | 210 | 210 | SNP | C | b73 | T | mo17 | | | | |
| 169 | Ampli-con235434 | 29827 | 215 | 215 | SNP | A | mo17 | G | b73 | | | | |
| 170 | Ampli-con235438 | 29829 | 161 | 161 | SNP | C | b73 | T | mo17 | | | | |
| 171 | Ampli-con235446 | 29832 | 136 | 136 | SNP | C | mo17 | G | b73 | | | | |
| 171 | Ampli-con235446 | 29833 | 247 | 247 | SNP | A | b73 | G | mo17 | | | | |
| 171 | Ampli-con235446 | 29834 | 255 | 255 | SNP | A | b73 | G | mo17 | | | | |
| 171 | Ampli-con235446 | 29835 | 303 | 303 | SNP | C | mo17 | T | b73 | | | | |
| 171 | Ampli-con235446 | 29836 | 304 | 304 | SNP | A | b73 | G | mo17 | | | | |
| 171 | Ampli-con235446 | 29837 | 435 | 435 | SNP | C | mo17 | T | b73 | | | | |
| 171 | Ampli-con235446 | 29838 | 501 | 511 | IND | ********** | mo17 | GTATATATATT | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 172 | Ampli-con235447 | 29839 | 101 | 101 | SNP | C | mo17 | G | b73 | | | | |
| 172 | Ampli-con235447 | 29840 | 106 | 106 | SNP | C | b73 | T | mo17 | | | | |
| 172 | Ampli-con235447 | 29841 | 107 | 107 | SNP | A | mo17 | T | b73 | | | | |
| 172 | Ampli-con235447 | 29842 | 260 | 260 | SNP | A | b73 | G | mo17 | | | | |
| 172 | Ampli-con235447 | 29843 | 285 | 285 | SNP | A | b73 | G | mo17 | | | | |
| 172 | Ampli-con235447 | 29844 | 286 | 286 | IND | * | mo17 | A | b73 | | | | |
| 172 | Ampli-con235447 | 29845 | 313 | 313 | SNP | G | b73 | T | mo17 | | | | |
| 172 | Ampli-con235447 | 29846 | 321 | 321 | SNP | C | b73 | T | mo17 | | | | |
| 172 | Ampli-con235447 | 29847 | 329 | 329 | SNP | C | mo17 | T | b73 | | | | |
| 172 | Ampli-con235447 | 29848 | 441 | 441 | SNP | A | mo17 | T | b73 | | | | |
| 172 | Ampli-con235447 | 29849 | 488 | 488 | SNP | C | mo17 | T | b73 | | | | |
| 173 | Ampli-con235447 | 29867 | 80 | 83 | IND | **** | mo17 | TGAG | b73 | | | | |
| 173 | Ampli-con235455 | 29868 | 194 | 195 | IND | ** | mo17 | AA | b73 | | | | |
| 173 | Ampli-con235455 | 29869 | 362 | 362 | SNP | A | b73 | G | mo17 | | | | |
| 173 | Ampli-con235455 | 29870 | 364 | 364 | SNP | C | mo17 | G | b73 | | | | |
| 173 | Ampli-con235455 | 29871 | 374 | 374 | SNP | A | b73 | C | mo17 | | | | |
| 174 | Ampli-con235516 | 30000 | 152 | 152 | SNP | A | b73 | C | mo17 | | | | |
| 175 | Ampli-con235541 | 30025 | 170 | 170 | SNP | C | b73 | T | mo17 | | | | |
| 175 | Ampli-con235541 | 30026 | 196 | 196 | SNP | C | b73 | T | mo17 | | | | |
| 175 | Ampli-con235541 | 30027 | 265 | 265 | SNP | C | b73 | T | mo17 | | | | |
| 175 | Ampli-con235541 | 30028 | 283 | 283 | SNP | C | mo17 | G | b73 | | | | |
| 175 | Ampli-con235541 | 30029 | 316 | 316 | SNP | C | mo17 | T | b73 | | | | |
| 176 | Ampli-con235586 | 30174 | 674 | 674 | SNP | C | mo17 | T | b73 | | | | |
| 176 | Ampli-con235586 | 30175 | 699 | 699 | IND | * | b73 | C | mo17 | | | | |
| 176 | Ampli-con235586 | 30176 | 733 | 733 | SNP | A | mo17 | T | b73 | | | | |
| 177 | Ampli-con235641 | 30270 | 1134 | 1134 | SNP | C | mo17 | T | b73 | | | | |
| 178 | Ampli-con235855 | 30673 | 56 | 56 | SNP | C | mo17 | G | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 178 | Ampli-con235855 | 30674 | 136 | 136 | SNP | C | mo17 | T | b73 | | | | |
| 178 | Ampli-con235855 | 30675 | 182 | 182 | SNP | A | b73 | G | mo17 | | | | |
| 178 | Ampli-con235855 | 30676 | 188 | 188 | SNP | C | mo17 | T | b73 | | | | |
| 178 | Ampli-con235855 | 30677 | 194 | 194 | SNP | C | b73 | T | mo17 | | | | |
| 178 | Ampli-con235855 | 30678 | 236 | 236 | SNP | A | b73 | C | mo17 | | | | |
| 178 | Ampli-con235855 | 30679 | 305 | 305 | SNP | C | b73 | T | mo17 | | | | |
| 178 | Ampli-con235855 | 30745 | 1028 | 1028 | SNP | C | mo17 | T | b73 | | | | |
| 179 | Ampli-con235879 | 30771 | 165 | 165 | SNP | C | mo17 | T | b73 | | | | |
| 180 | Ampli-con235892 | 30835 | 131 | 131 | SNP | A | mo17 | G | b73 | | | | |
| 181 | Ampli-con235914 | 30836 | 168 | 168 | SNP | G | b73 | T | mo17 | | | | |
| 181 | Ampli-con235914 | 30837 | 201 | 201 | SNP | A | mo17 | G | b73 | | | | |
| 181 | Ampli-con235914 | 30838 | 213 | 213 | SNP | C | b73 | T | mo17 | | | | |
| 181 | Ampli-con235914 | 30839 | 269 | 269 | SNP | A | mo17 | G | b73 | | | | |
| 181 | Ampli-con235914 | 30840 | 412 | 412 | SNP | A | b73 | G | mo17 | | | | |
| 182 | Ampli-con235959 | 30871 | 294 | 294 | SNP | A | b73 | G | mo17 | | | | |
| 182 | Ampli-con235959 | 30872 | 811 | 811 | SNP | C | b73 | T | b73 | | | | |
| 183 | Ampli-con236049 | 31050 | 33 | 33 | SNP | A | b73 | C | mo17 | | | | |
| 183 | Ampli-con236049 | 31051 | 35 | 35 | SNP | A | b73 | C | mo17 | | | | |
| 183 | Ampli-con236049 | 31052 | 37 | 37 | SNP | A | b73 | G | mo17 | | | | |
| 183 | Ampli-con236049 | 31053 | 46 | 46 | SNP | A | mo17 | T | b73 | | | | |
| 183 | Ampli-con236049 | 31054 | 47 | 47 | SNP | A | mo17 | G | b73 | | | | |
| 183 | Ampli-con236049 | 31055 | 48 | 48 | SNP | C | b73 | G | mo17 | | | | |
| 183 | Ampli-con236049 | 31056 | 51 | 51 | SNP | A | b73 | T | mo17 | | | | |
| 183 | Ampli-con236049 | 31057 | 53 | 53 | SNP | C | b73 | T | mo17 | | | | |
| 183 | Ampli-con236049 | 31058 | 54 | 54 | SNP | A | b73 | C | mo17 | | | | |
| 183 | Ampli-con236049 | 31059 | 55 | 55 | SNP | A | b73 | C | mo17 | | | | |
| 183 | Ampli-con236049 | 31060 | 56 | 56 | SNP | G | b73 | T | mo17 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 183 | Ampli-con236049 | 31061 | 58 | 58 | SNP | C | b73 | G | mo17 | | | | |
| 183 | Ampli-con236049 | 31062 | 62 | 62 | SNP | C | b73 | T | mo17 | | | | |
| 183 | Ampli-con236049 | 31063 | 64 | 65 | IND | ** | mo17 | TC | b73 | | | | |
| 183 | Ampli-con236049 | 31064 | 125 | 125 | SNP | A | b73 | C | mo17 | | | | |
| 183 | Ampli-con236049 | 31065 | 179 | 179 | SNP | C | mo17 | G | b73 | | | | |
| 183 | Ampli-con236049 | 31066 | 539 | 539 | SNP | G | mo17 | T | b73 | | | | |
| 184 | Ampli-con236057 | 31084 | 52 | 52 | SNP | C | b73 | G | mo17 | | | | |
| 184 | Ampli-con236057 | 31085 | 297 | 297 | SNP | A | mo17 | G | b73 | | | | |
| 185 | Ampli-con236120 | 31233 | 1066 | 1066 | SNP | A | mo17 | C | b73 | | | | |
| 186 | Ampli-con236181 | 31370 | 432 | 432 | SNP | G | mo17 | T | b73 | | | | |
| 187 | Ampli-con236216 | 31473 | 760 | 760 | SNP | A | b73 | G | mo17 | | | | |
| 187 | Ampli-con236216 | 31474 | 843 | 843 | SNP | A | mo17 | T | b73 | | | | |
| 187 | Ampli-con236216 | 31475 | 938 | 938 | SNP | C | mo17 | G | b73 | | | | |
| 187 | Ampli-con236216 | 31476 | 1016 | 1016 | IND | * | mo17 | T | b73 | | | | |
| 188 | Ampli-con236259 | 31477 | 1058 | 1058 | SNP | A | mo17 | G | b73 | | | | |
| 188 | Ampli-con236259 | 31546 | 306 | 306 | SNP | A | mo17 | C | b73 | | | | |
| 188 | Ampli-con236259 | 31547 | 473 | 473 | SNP | C | mo17 | T | b73 | | | | |
| 188 | Ampli-con236259 | 31548 | 482 | 482 | SNP | A | b73 | G | mo17 | | | | |
| 189 | Ampli-con236326 | 31684 | 259 | 259 | SNP | A | b73 | T | b73 | | | | |
| 190 | Ampli-con236386 | 31790 | 510 | 510 | SNP | A | mo17 | T | b73 | | | | |
| 191 | Ampli-con236471 | 31993 | 365 | 365 | SNP | A | mo17 | G | b73 | | | | |
| 191 | Ampli-con236471 | 31994 | 367 | 367 | IND | * | mo17 | C | b73 | | | | |
| 192 | Ampli-con236482 | 32014 | 68 | 68 | SNP | A | mo17 | G | mo17 | | | | |
| 192 | Ampli-con236482 | 32015 | 93 | 93 | SNP | C | b73 | G | b73 | | | | |
| 192 | Ampli-con236482 | 32016 | 196 | 196 | SNP | A | b73 | G | mo17 | | | | |
| 192 | Ampli-con236482 | 32017 | 674 | 674 | SNP | G | b73 | T | mo17 | | | | |
| 193 | Ampli-con236492 | 32028 | 81 | 81 | SNP | C | mo17 | T | b73 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 193 | Ampli-con236492 | 32029 | 102 | 102 | SNP | C | mo17 | G | b73 | | | | |
| 193 | Ampli-con236492 | 32030 | 162 | 164 | IND | *** | b73 | TGG | mo17 | | | | |
| 193 | Ampli-con236492 | 32031 | 192 | 197 | IND | ****** | b73 | TGCCGG | mo17 | | | | |
| 193 | Ampli-con236492 | 32032 | 310 | 310 | SNP | A | mo17 | C | b73 | | | | |
| 193 | Ampli-con236492 | 32033 | 435 | 435 | SNP | C | b73 | T | mo17 | | | | |
| 194 | Ampli-con236492 | 32034 | 497 | 497 | SNP | A | mo17 | G | b73 | | | | |
| 195 | Ampli-con236499 | 32049 | 182 | 182 | SNP | C | mo17 | T | b73 | | | | |
| 195 | Ampli-con236499 | 32050 | 401 | 401 | SNP | C | b73 | T | mo17 | | | | |
| 195 | Ampli-con236499 | 32051 | 402 | 402 | SNP | A | b73 | G | mo17 | | | | |
| 196 | Ampli-con236499 | 32137 | 257 | 257 | IND | * | b73 | A | mo17 | | | | |
| 196 | Ampli-con236541 | 32138 | 419 | 429 | IND | *********** | mo17 | CCGATCCATCT | b73 | | | | |
| 197 | Ampli-con236541 | 32244 | 26 | 26 | SNP | C | b73 | T | mo17 | | | | |
| 197 | Ampli-con236590 | 32245 | 81 | 81 | SNP | A | b73 | G | mo17 | | | | |
| 197 | Ampli-con236590 | 32246 | 91 | 97 | IND | ******* | mo17 | AGTGCTG | b73 | | | | |
| 197 | Ampli-con236590 | 32247 | 161 | 161 | SNP | C | b73 | T | mo17 | | | | |
| 198 | Ampli-con236590 | 32248 | 274 | 274 | SNP | C | b73 | T | mo17 | | | | |
| 198 | Ampli-con236597 | 32252 | 36 | 36 | SNP | C | b73 | G | mo17 | | | | |
| 198 | Ampli-con236597 | 32253 | 43 | 43 | SNP | A | mo17 | C | b73 | | | | |
| 198 | Ampli-con236597 | 32254 | 117 | 117 | SNP | C | mo17 | T | b73 | | | | |
| 198 | Ampli-con236597 | 32255 | 288 | 288 | SNP | C | mo17 | G | b73 | | | | |
| 198 | Ampli-con236597 | 32256 | 318 | 318 | SNP | A | mo17 | G | b73 | | | | |
| 198 | Ampli-con236597 | 32257 | 345 | 345 | SNP | A | b73 | G | mo17 | | | | |
| 198 | Ampli-con236597 | 32258 | 351 | 351 | SNP | G | b73 | T | mo17 | | | | |
| 198 | Ampli-con236597 | 32259 | 364 | 364 | SNP | C | mo17 | T | b73 | | | | |
| 198 | Ampli-con236597 | 32260 | 407 | 407 | SNP | C | mo17 | G | b73 | | | | |
| 198 | Ampli-con236597 | 32261 | 450 | 450 | SNP | C | b73 | T | mo17 | | | | |
| 198 | Ampli-con236597 | 32262 | 458 | 458 | SNP | A | mo17 | G | b73 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 198 | Ampli-con236597 | 32263 | 582 | 582 | SNP | A | b73 | G | mo17 | | | | |
| 198 | Ampli-con236597 | 32264 | 589 | 589 | SNP | A | b73 | G | mo17 | | | | |
| 198 | Ampli-con236597 | 32265 | 604 | 604 | SNP | C | mo17 | T | b73 | | | | |
| 198 | Ampli-con236597 | 32266 | 848 | 848 | SNP | A | b73 | G | mo17 | | | | |
| 198 | Ampli-con236597 | 32267 | 865 | 865 | SNP | C | mo17 | T | b73 | | | | |
| 199 | Ampli-con236600 | 32272 | 260 | 260 | SNP | C | mo17 | T | b73 | | | | |
| 200 | Ampli-con236692 | 32428 | 101 | 101 | SNP | C | mo17 | G | b73 | | | | |
| 200 | Ampli-con236692 | 32429 | 112 | 112 | SNP | A | b73 | G | mo17 | | | | |
| 200 | Ampli-con236692 | 32430 | 202 | 202 | SNP | A | b73 | G | mo17 | | | | |
| 200 | Ampli-con236692 | 32431 | 250 | 250 | SNP | C | mo17 | T | b73 | | | | |
| 201 | Ampli-con276424 | 33246 | 113 | 113 | SNP | G | mo17 | T | b73 | | | | |
| 201 | Ampli-con276424 | 33247 | 120 | 120 | SNP | A | mo17 | G | b73 | | | | |
| 201 | Ampli-con276424 | 33248 | 140 | 140 | SNP | A | b73 | G | mo17 | | | | |
| 201 | Ampli-con276424 | 33249 | 190 | 190 | SNP | C | mo17 | T | b73 | | | | |
| 201 | Ampli-con276424 | 33250 | 231 | 231 | IND | * | b73 | A | mo17 | | | | |
| 201 | Ampli-con276424 | 33251 | 231 | 232 | IND | ** | b73 | AT | mo17 | | | | |
| 201 | Ampli-con276424 | 33252 | 243 | 243 | SNP | G | b73 | T | mo17 | | | | |
| 201 | Ampli-con276424 | 33253 | 296 | 296 | SNP | G | b73 | T | mo17 | | | | |
| 201 | Ampli-con276424 | 33254 | 340 | 340 | IND | * | b73 | G | mo17 | | | | |
| 201 | Ampli-con276424 | 33255 | 341 | 342 | IND | ** | b73 | CC | mo17 | | | | |
| 202 | Ampli-con276456 | 33315 | 93 | 93 | SNP | A | b73 | G | mo17 | | | | |
| 202 | Ampli-con276456 | 33316 | 111 | 111 | SNP | C | b73 | T | mo17 | | | | |
| 202 | Ampli-con276456 | 33317 | 118 | 118 | SNP | A | b73 | T | mo17 | | | | |
| 202 | Ampli-con276456 | 33318 | 151 | 153 | IND | *** | mo17 | TGT | b73 | | | | |
| 202 | Ampli-con276456 | 33319 | 154 | 157 | IND | **** | mo17 | TCTG | b73 | | | | |
| 202 | Ampli-con276456 | 33320 | 208 | 208 | SNP | C | b73 | G | mo17 | | | | |
| 202 | Ampli-con276456 | 33321 | 241 | 241 | SNP | A | mo17 | G | b73 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 202 | Ampli-con276456 | 33322 | 396 | 396 | SNP | C | b73 | T | mo17 | | | | |
| 203 | Ampli-con276493 | 33371 | 163 | 163 | IND | * | mo17 | G | b73 | | | | |
| 203 | Ampli-con276493 | 33372 | 238 | 238 | SNP | A | b73 | C | mo17 | | | | |
| 204 | Ampli-con276497 | 33373 | 95 | 95 | SNP | C | mo17 | T | b73 | | | | |
| 204 | Ampli-con276497 | 33374 | 127 | 127 | SNP | C | mo17 | T | b73 | | | | |
| 204 | Ampli-con276497 | 33375 | 130 | 130 | SNP | C | b73 | T | mo17 | | | | |
| 204 | Ampli-con276497 | 33376 | 362 | 362 | SNP | G | b73 | T | mo17 | | | | |
| 204 | Ampli-con276497 | 33377 | 370 | 370 | SNP | A | mo17 | G | b73 | | | | |
| 205 | Ampli-con276744 | 33764 | 728 | 728 | SNP | C | b73 | T | mo17 | | | | |
| 205 | Ampli-con276744 | 33765 | 835 | 835 | SNP | A | mo17 | T | b73 | | | | |
| 205 | Ampli-con276744 | 33766 | 874 | 874 | SNP | C | b73 | T | mo17 | | | | |
| 205 | Ampli-con276744 | 33767 | 919 | 919 | SNP | A | mo17 | T | b73 | | | | |
| 205 | Ampli-con276744 | 33768 | 1014 | 1014 | SNP | A | b73 | T | mo17 | | | | |
| 205 | Ampli-con276744 | 33769 | 1078 | 1081 | IND | **** | mo17 | TAGC | b73 | | | | |
| 206 | Ampli-con276782 | 33816 | 252 | 252 | SNP | C | mo17 | T | b73 | | | | |
| 206 | Ampli-con276782 | 33819 | 319 | 319 | SNP | A | mo17 | G | b73 | | | | |
| 207 | Ampli-con277037 | 34205 | 117 | 117 | SNP | C | mo17 | T | b73 | | | | |
| 207 | Ampli-con277037 | 34206 | 248 | 248 | SNP | A | b73 | T | mo17 | | | | |
| 208 | Ampli-con277306 | 34556 | 519 | 519 | SNP | A | b73 | G | mo17 | | | | |
| 208 | Ampli-con277306 | 34557 | 558 | 558 | SNP | A | mo17 | G | b73 | | | | |
| 208 | Ampli-con277306 | 34558 | 576 | 576 | SNP | A | b73 | G | mo17 | | | | |
| 208 | Ampli-con277306 | 34559 | 625 | 625 | SNP | C | mo17 | T | b73 | | | | |
| 208 | Ampli-con277306 | 34560 | 681 | 681 | SNP | A | b73 | G | mo17 | | | | |
| 208 | Ampli-con277306 | 34561 | 770 | 770 | SNP | C | mo17 | T | b73 | | | | |
| 208 | Ampli-con277306 | 34562 | 771 | 771 | IND | * | b73 | A | mo17 | | | | |
| 208 | Ampli-con277306 | 34563 | 788 | 788 | SNP | C | b73 | T | mo17 | | | | |
| 208 | Ampli-con277306 | 34564 | 852 | 852 | SNP | A | b73 | G | mo17 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 209 | Amplicon277511 | 34895 | 47 | 47 | SNP | C | b73 | G | mo17 | | | | |
| 209 | Amplicon277511 | 34896 | 48 | 48 | SNP | C | b73 | T | mo17 | | | | |
| 209 | Amplicon277511 | 34897 | 52 | 52 | IND | * | b73 | C | mo17 | | | | |
| 209 | Amplicon277511 | 34898 | 52 | 53 | IND | ** | b73 | C* | mo17 | | | | |
| 209 | Amplicon277511 | 34899 | 75 | 75 | SNP | C | b73 | T | mo17 | | | | |
| 209 | Amplicon277511 | 34900 | 307 | 307 | SNP | A | mo17 | C | b73 | | | | |
| 209 | Amplicon277511 | 34901 | 344 | 344 | SNP | A | mo17 | G | b73 | | | | |
| 209 | Amplicon277511 | 34902 | 347 | 347 | SNP | C | b73 | T | mo17 | | | | |
| 209 | Amplicon277511 | 34903 | 408 | 408 | SNP | C | mo17 | T | b73 | | | | |
| 209 | Amplicon277511 | 35173 | 659 | 659 | IND | * | mo17 | G | b73 | | | | |
| 210 | Amplicon277716 | 35174 | 767 | 767 | SNP | C | b73 | T | mo17 | | | | |
| 210 | Amplicon277716 | 35175 | 770 | 770 | SNP | A | mo17 | G | b73 | | | | |
| 211 | Amplicon277824 | 35294 | 186 | 186 | SNP | A | mo17 | G | mo17 | | | | |
| 212 | Amplicon277832 | 35295 | 102 | 102 | SNP | C | b73 | T | mo17 | | | | |
| 212 | Amplicon277832 | 35296 | 193 | 193 | SNP | A | mo17 | G | b73 | | | | |
| 212 | Amplicon277832 | 35297 | 206 | 206 | SNP | A | b73 | G | mo17 | | | | |
| 212 | Amplicon277832 | 35298 | 218 | 218 | IND | * | b73 | C | mo17 | | | | |
| 212 | Amplicon277832 | 35299 | 220 | 222 | IND | *** | b73 | GCT | mo17 | | | | |
| 212 | Amplicon277832 | 35300 | 265 | 265 | SNP | C | mo17 | T | b73 | | | | |
| 212 | Amplicon277832 | 35301 | 277 | 279 | IND | *** | mo17 | ATG | b73 | | | | |
| 212 | Amplicon277832 | 35302 | 449 | 449 | SNP | C | b73 | T | mo17 | | | | |
| 213 | Amplicon277876 | 35338 | 104 | 104 | SNP | C | mo17 | G | b73 | | | | |
| 213 | Amplicon277876 | 35339 | 329 | 333 | IND | ***** | b73 | CAAAG | mo17 | | | | |
| 213 | Amplicon277876 | 35340 | 367 | 367 | SNP | A | b73 | G | mo17 | | | | |
| 214 | Amplicon277914 | 35377 | 66 | 66 | SNP | C | b73 | G | mo17 | | | | |
| 215 | Amplicon277962 | 35407 | 31 | 31 | SNP | A | mo17 | G | b73 | | | | |
| 215 | Amplicon277962 | 35408 | 220 | 220 | SNP | A | mo17 | C | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 215 | Amplicon277962 | 35409 | 292 | 292 | SNP | A | b73 | C | mo17 | | | | |
| 215 | Amplicon277962 | 35410 | 339 | 339 | SNP | A | mo17 | G | b73 | | | | |
| 216 | Amplicon277971 | 35413 | 48 | 48 | SNP | A | b73 | C | mo17 | | | | |
| 216 | Amplicon277971 | 35414 | 58 | 58 | SNP | A | mo17 | G | b73 | | | | |
| 216 | Amplicon277971 | 35415 | 160 | 161 | IND | ** | mo17 | TA | b73 | | | | |
| 216 | Amplicon277971 | 35416 | 163 | 163 | SNP | G | b73 | T | mo17 | | | | |
| 216 | Amplicon277971 | 35417 | 175 | 175 | SNP | A | b73 | G | mo17 | | | | |
| 216 | Amplicon277971 | 35418 | 254 | 254 | IND | * | mo17 | T | b73 | | | | |
| 217 | Amplicon278078 | 35567 | 278 | 278 | SNP | G | b73 | T | mo17 | | | | |
| 217 | Amplicon278078 | 35568 | 297 | 297 | SNP | A | mo17 | G | b73 | | | | |
| 217 | Amplicon278078 | 35569 | 331 | 331 | IND | * | b73 | G | mo17 | | | | |
| 218 | Amplicon278078 | 35574 | 384 | 384 | SNP | C | mo17 | T | b73 | | | | |
| 219 | Amplicon278086 | 35631 | 115 | 115 | SNP | C | mo17 | T | b73 | | | | |
| 219 | Amplicon278122 | 35632 | 267 | 267 | SNP | A | b73 | G | mo17 | | | | |
| 219 | Amplicon278122 | 35633 | 318 | 318 | SNP | A | b73 | C | mo17 | | | | |
| 220 | Amplicon278122 | 36022 | 77 | 77 | SNP | C | b73 | G | mo17 | | | | |
| 220 | Amplicon310557 | 36023 | 80 | 80 | SNP | G | b73 | T | mo17 | | | | |
| 220 | Amplicon310557 | 36024 | 269 | 269 | SNP | A | mo17 | G | b73 | | | | |
| 220 | Amplicon310557 | 36025 | 283 | 283 | SNP | G | mo17 | T | b73 | | | | |
| 220 | Amplicon310557 | 36026 | 353 | 353 | IND | * | mo17 | A | b73 | | | | |
| 220 | Amplicon310557 | 36027 | 353 | 354 | IND | ** | mo17 | AT | b73 | | | | |
| 221 | Amplicon310599 | 36062 | 94 | 94 | SNP | A | mo17 | C | b73 | | | | |
| 221 | Amplicon310599 | 36063 | 95 | 95 | SNP | A | mo17 | C | b73 | | | | |
| 221 | Amplicon310599 | 36064 | 128 | 128 | SNP | C | mo17 | G | b73 | | | | |
| 221 | Amplicon310599 | 36065 | 129 | 129 | SNP | A | mo17 | G | b73 | | | | |
| 221 | Amplicon310599 | 36066 | 135 | 135 | SNP | G | mo17 | T | b73 | | | | |
| 221 | Amplicon310599 | 36067 | 144 | 144 | SNP | C | b73 | T | mo17 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 221 | Ampli-con310599 | 36068 | 279 | 279 | SNP | G | b73 | T | mo17 | | | | |
| 221 | Ampli-con310599 | 36069 | 280 | 280 | SNP | C | mo17 | T | b73 | | | | |
| 221 | Ampli-con310599 | 36070 | 300 | 300 | IND | * | b73 | A | mo17 | | | | |
| 221 | Ampli-con310599 | 36071 | 324 | 324 | SNP | A | b73 | T | mo17 | | | | |
| 221 | Ampli-con310599 | 36072 | 367 | 367 | SNP | A | mo17 | G | b73 | | | | |
| 221 | Ampli-con310599 | 36073 | 403 | 403 | SNP | A | mo17 | G | b73 | | | | |
| 221 | Ampli-con310599 | 36074 | 422 | 422 | SNP | C | mo17 | T | b73 | | | | |
| 221 | Ampli-con310599 | 36075 | 426 | 426 | SNP | C | mo17 | T | b73 | | | | |
| 221 | Ampli-con310599 | 36076 | 465 | 465 | SNP | C | mo17 | T | b73 | | | | |
| 222 | Ampli-con310656 | 36195 | 119 | 119 | SNP | A | mo17 | C | b73 | | | | |
| 222 | Ampli-con310656 | 36196 | 122 | 122 | SNP | C | b73 | T | mo17 | | | | |
| 222 | Ampli-con310656 | 36197 | 134 | 134 | SNP | A | b73 | C | mo17 | | | | |
| 222 | Ampli-con310656 | 36198 | 146 | 146 | SNP | A | mo17 | C | b73 | | | | |
| 222 | Ampli-con310656 | 36199 | 182 | 182 | SNP | A | mo17 | C | b73 | | | | |
| 222 | Ampli-con310656 | 36200 | 213 | 218 | IND | ******* | mo17 | AGCGAC | b73 | | | | |
| 222 | Ampli-con310656 | 36201 | 239 | 239 | SNP | A | b73 | G | mo17 | | | | |
| 222 | Ampli-con310656 | 36202 | 317 | 317 | SNP | C | b73 | G | mo17 | | | | |
| 223 | Ampli-con310739 | 36286 | 335 | 336 | IND | ** | mo17 | AT | b73 | | | | |
| 223 | Ampli-con310739 | 36287 | 435 | 436 | IND | ** | b73 | CT | mo17 | | | | |
| 223 | Ampli-con310739 | 36288 | 455 | 455 | SNP | A | b73 | G | mo17 | | | | |
| 224 | Ampli-con310739 | 36323 | 240 | 240 | SNP | G | mo17 | T | b73 | | | | |
| 225 | Ampli-con310755 | 36448 | 201 | 201 | SNP | C | mo17 | T | b73 | | | | |
| 225 | Ampli-con310817 | 36449 | 252 | 254 | IND | *** | mo17 | AGC | b73 | | | | |
| 226 | Ampli-con310817 | 36487 | 201 | 203 | IND | *** | b73 | TGG | mo17 | | | | |
| 226 | Ampli-con310854 | 36488 | 227 | 228 | IND | ** | b73 | AT | mo17 | | | | |
| 226 | Ampli-con310854 | 36489 | 235 | 235 | IND | * | mo17 | T | b73 | | | | |
| 226 | Ampli-con310854 | 36490 | 243 | 243 | SNP | G | b73 | T | mo17 | | | | |

-continued

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 226 | Amplicon310854 | 36491 | 272 | 274 | IND | *** | b73 | TAG | mo17 | | | | |
| 226 | Amplicon310854 | 36492 | 272 | 275 | IND | **** | b73 | TAGC | mo17 | | | | |
| 226 | Amplicon310854 | 36493 | 315 | 316 | IND | ** | mo17 | GA | b73 | | | | |
| 226 | Amplicon310854 | 36494 | 319 | 319 | SNP | C | b73 | T | mo17 | | | | |
| 227 | Amplicon311004 | 36636 | 637 | 637 | SNP | A | mo17 | G | b73 | | | | |
| 227 | Amplicon311004 | 36637 | 698 | 698 | SNP | C | mo17 | T | b73 | | | | |
| 227 | Amplicon311004 | 36638 | 957 | 957 | SNP | G | mo17 | T | b73 | | | | |
| 227 | Amplicon311004 | 36639 | 958 | 958 | SNP | G | b73 | G | mo17 | | | | |
| 227 | Amplicon311004 | 36640 | 968 | 968 | SNP | A | mo17 | C | b73 | | | | |
| 227 | Amplicon311004 | 36641 | 1085 | 1085 | SNP | A | mo17 | G | b73 | | | | |
| 227 | Amplicon311004 | 36642 | 1086 | 1086 | SNP | A | b73 | G | mo17 | | | | |
| 227 | Amplicon311004 | 36643 | 1127 | 1127 | SNP | A | b73 | G | mo17 | | | | |
| 228 | Amplicon311038 | 36685 | 202 | 202 | SNP | A | mo17 | T | b73 | | | | |
| 228 | Amplicon311038 | 36686 | 444 | 444 | SNP | A | mo17 | T | b73 | | | | |
| 229 | Amplicon311045 | 36694 | 179 | 179 | SNP | C | b73 | T | mo17 | | | | |
| 229 | Amplicon311045 | 36695 | 242 | 242 | SNP | C | b73 | T | mo17 | | | | |
| 230 | Amplicon311184 | 36862 | 296 | 296 | SNP | A | mo17 | G | b73 | | | | |
| 230 | Amplicon311184 | 36863 | 326 | 326 | SNP | C | b73 | T | mo17 | | | | |
| 230 | Amplicon311184 | 36864 | 374 | 374 | SNP | C | b73 | T | mo17 | | | | |
| 230 | Amplicon311184 | 36865 | 507 | 507 | SNP | A | mo17 | C | b73 | | | | |
| 230 | Amplicon311184 | 36866 | 547 | 547 | SNP | C | b73 | T | mo17 | | | | |
| 231 | Amplicon311375 | 37066 | 105 | 105 | SNP | C | b73 | T | mo17 | | | | |
| 231 | Amplicon311375 | 37067 | 127 | 127 | SNP | A | b73 | G | mo17 | | | | |
| 231 | Amplicon311375 | 37068 | 163 | 171 | IND | ********* | mo17 | GATACGGCG | b73 | | | | |
| 232 | Amplicon311650 | 37492 | 125 | 125 | IND | * | mo17 | G | b73 | | | | |
| 232 | Amplicon311650 | 37493 | 130 | 130 | SNP | A | mo17 | G | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 232 | Ampli-con311650 | 37494 | 204 | 204 | SNP | A | mo17 | G | b73 | | | | |
| 232 | Ampli-con311650 | 37495 | 211 | 211 | SNP | A | b73 | G | mo17 | | | | |
| 232 | Ampli-con311650 | 37496 | 212 | 212 | SNP | A | b73 | G | mo17 | | | | |
| 232 | Ampli-con311650 | 37497 | 221 | 221 | IND | * | mo17 | G | b73 | | | | |
| 232 | Ampli-con311650 | 37498 | 236 | 236 | SNP | G | mo17 | T | b73 | | | | |
| 232 | Ampli-con311650 | 37499 | 239 | 242 | IND | **** | mo17 | CTTG | b73 | | | | |
| 232 | Ampli-con311650 | 37500 | 359 | 362 | IND | **** | mo17 | TGCC | b73 | | | | |
| 232 | Ampli-con311650 | 37501 | 410 | 410 | SNP | A | mo17 | C | b73 | | | | |
| 232 | Ampli-con311650 | 37502 | 411 | 411 | SNP | A | b73 | C | mo17 | | | | |
| 232 | Ampli-con311650 | 37503 | 426 | 426 | SNP | G | mo17 | T | b73 | | | | |
| 232 | Ampli-con311650 | 37504 | 465 | 471 | IND | ******* | mo17 | AGTGCTG | b73 | | | | |
| 232 | Ampli-con311650 | 37505 | 535 | 536 | IND | ** | mo17 | CT | b73 | | | | |
| 232 | Ampli-con311650 | 37506 | 541 | 541 | SNP | C | b73 | T | mo17 | | | | |
| 232 | Ampli-con311650 | 37507 | 610 | 610 | IND | * | mo17 | C | b73 | | | | |
| 233 | Ampli-con311695 | 37555 | 394 | 394 | SNP | C | b73 | T | mo17 | | | | |
| 233 | Ampli-con311695 | 37556 | 505 | 505 | SNP | A | mo17 | G | b73 | | | | |
| 234 | Ampli-con311695 | 37631 | 271 | 271 | SNP | C | mo17 | G | b73 | | | | |
| 234 | Ampli-con311738 | 37632 | 333 | 340 | IND | ********* | mo17 | CGTTCTAA | b73 | | | | |
| 234 | Ampli-con311738 | 37633 | 389 | 397 | IND | ********** | b73 | CGTTGGGGG | mo17 | | | | |
| 234 | Ampli-con311738 | 37634 | 542 | 542 | SNP | G | mo17 | T | b73 | | | | |
| 235 | Ampli-con311738 | 37684 | 397 | 397 | SNP | C | b73 | T | mo17 | | | | |
| 235 | Ampli-con346446 | 37685 | 407 | 407 | SNP | A | mo17 | C | b73 | | | | |
| 235 | Ampli-con346446 | 37686 | 417 | 417 | SNP | A | mo17 | T | b73 | | | | |
| 235 | Ampli-con346446 | 37687 | 483 | 483 | IND | * | b73 | G | mo17 | | | | |
| 235 | Ampli-con346446 | 37688 | 562 | 562 | SNP | C | mo17 | T | b73 | | | | |
| 235 | Ampli-con346446 | 37689 | 685 | 691 | IND | ******** | mo17 | ATTATAA | b73 | | | | |
| 236 | Ampli-con346472 | 37715 | 392 | 392 | SNP | A | b73 | G | mo17 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 236 | Amplicon346472 | 37716 | 512 | 512 | SNP | C | b73 | T | mo17 | | | | |
| 236 | Amplicon346472 | 37717 | 522 | 522 | IND | * | mo17 | A | b73 | | | | |
| 236 | Amplicon346472 | 37718 | 563 | 563 | SNP | G | mo17 | T | b73 | | | | |
| 236 | Amplicon346472 | 37719 | 573 | 576 | IND | **** | b73 | ACGA | mo17 | | | | |
| 237 | Amplicon346640 | 37946 | 41 | 41 | SNP | A | mo17 | G | b73 | | | | |
| 237 | Amplicon346640 | 37947 | 86 | 86 | SNP | A | b73 | G | mo17 | | | | |
| 237 | Amplicon346640 | 37948 | 134 | 134 | SNP | G | b73 | T | mo17 | | | | |
| 237 | Amplicon346640 | 37949 | 191 | 191 | SNP | A | mo17 | G | b73 | | | | |
| 237 | Amplicon346640 | 37950 | 194 | 194 | SNP | C | b73 | T | mo17 | | | | |
| 237 | Amplicon346640 | 37951 | 197 | 197 | SNP | C | b73 | T | mo17 | | | | |
| 237 | Amplicon346640 | 37952 | 199 | 199 | SNP | A | mo17 | G | b73 | | | | |
| 237 | Amplicon346640 | 37953 | 229 | 232 | IND | **** | mo17 | TATA | b73 | | | | |
| 237 | Amplicon346640 | 37954 | 284 | 284 | IND | * | b73 | C | mo17 | | | | |
| 237 | Amplicon346640 | 37955 | 286 | 286 | IND | * | b73 | A | mo17 | | | | |
| 237 | Amplicon346640 | 37956 | 288 | 288 | SNP | A | b73 | C | mo17 | | | | |
| 237 | Amplicon346640 | 37957 | 343 | 343 | SNP | A | mo17 | G | b73 | | | | |
| 237 | Amplicon346640 | 37958 | 368 | 368 | IND | * | mo17 | C | b73 | | | | |
| 237 | Amplicon346640 | 37959 | 392 | 392 | SNP | G | mo17 | T | b73 | | | | |
| 237 | Amplicon346640 | 37960 | 393 | 394 | IND | ** | mo17 | TT | b73 | | | | |
| 237 | Amplicon346640 | 37961 | 397 | 397 | SNP | A | b73 | G | mo17 | | | | |
| 237 | Amplicon346640 | 37962 | 410 | 410 | SNP | A | mo17 | C | b73 | | | | |
| 237 | Amplicon346640 | 37963 | 411 | 411 | SNP | A | mo17 | G | b73 | | | | |
| 237 | Amplicon346640 | 37964 | 450 | 450 | SNP | G | mo17 | T | b73 | | | | |
| 237 | Amplicon346640 | 37965 | 514 | 514 | SNP | A | mo17 | G | b73 | | | | |
| 237 | Amplicon346640 | 37966 | 552 | 552 | SNP | C | b73 | G | mo17 | | | | |
| 237 | Amplicon346640 | 37967 | 773 | 773 | SNP | A | mo17 | C | b73 | | | | |
| 238 | Amplicon346980 | 38478 | 262 | 262 | SNP | C | mo17 | T | b73 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 238 | Ampli-con346980 | 38479 | 400 | 400 | SNP | A | b73 | C | mo17 | | | | |
| 238 | Ampli-con346980 | 38480 | 549 | 554 | IND | ****** | b73 | TCGCTC | mo17 | | | | |
| 239 | Ampli-con347076 | 38604 | 172 | 172 | SNP | A | mo17 | G | b73 | | | | |
| 239 | Ampli-con347076 | 38605 | 207 | 207 | SNP | C | mo17 | T | b73 | | | | |
| 239 | Ampli-con347076 | 38606 | 224 | 224 | SNP | A | mo17 | A | b73 | | | | |
| 239 | Ampli-con347076 | 38607 | 252 | 253 | IND | ** | b73 | GG | mo17 | | | | |
| 239 | Ampli-con347076 | 38608 | 380 | 380 | SNP | A | mo17 | G | b73 | | | | |
| 239 | Ampli-con347076 | 38609 | 387 | 387 | SNP | A | b73 | G | mo17 | | | | |
| 239 | Ampli-con347076 | 38610 | 432 | 432 | SNP | G | b73 | T | mo17 | | | | |
| 239 | Ampli-con347076 | 38611 | 505 | 505 | SNP | A | mo17 | G | b73 | | | | |
| 239 | Ampli-con347076 | 38612 | 506 | 506 | SNP | A | mo17 | G | b73 | | | | |
| 239 | Ampli-con347076 | 38613 | 515 | 515 | IND | * | b73 | T | mo17 | | | | |
| 239 | Ampli-con347076 | 38614 | 521 | 521 | IND | * | b73 | T | mo17 | | | | |
| 239 | Ampli-con347076 | 38615 | 587 | 592 | IND | ****** | b73 | CCCCCA | mo17 | | | | |
| 239 | Ampli-con347076 | 38616 | 599 | 599 | SNP | A | mo17 | G | b73 | | | | |
| 239 | Ampli-con347076 | 38617 | 611 | 611 | SNP | A | mo17 | G | b73 | | | | |
| 239 | Ampli-con347076 | 38618 | 614 | 614 | SNP | G | b73 | T | mo17 | | | | |
| 240 | Ampli-con347095 | 38652 | 23 | 23 | IND | * | b73 | A | mo17 | | | | |
| 240 | Ampli-con347095 | 38653 | 200 | 200 | SNP | A | mo17 | T | b73 | | | | |
| 240 | Ampli-con347095 | 38654 | 414 | 414 | SNP | A | mo17 | G | b73 | | | | |
| 240 | Ampli-con347095 | 38655 | 599 | 599 | SNP | C | mo17 | T | b73 | | | | |
| 240 | Ampli-con347095 | 38656 | 682 | 682 | SNP | A | b73 | T | mo17 | | | | |
| 241 | Ampli-con347114 | 38700 | 228 | 228 | SNP | C | b73 | T | mo17 | | | | |
| 241 | Ampli-con347114 | 38701 | 303 | 308 | IND | ****** | b73 | AATCAT | mo17 | | | | |
| 242 | Ampli-con347251 | 38848 | 39 | 39 | SNP | G | b73 | T | mo17 | | | | |
| 242 | Ampli-con347251 | 38849 | 83 | 83 | SNP | A | mo17 | T | b73 | | | | |
| 242 | Ampli-con347251 | 38850 | 262 | 262 | SNP | G | b73 | T | mo17 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 242 | Ampli-con347251 | 38851 | 263 | 264 | IND | ** | b73 | TT | mo17 | | | | |
| 242 | Ampli-con347251 | 38852 | 550 | 550 | SNP | C | b73 | G | mo17 | | | | |
| 243 | Ampli-con347285 | 38909 | 41 | 41 | SNP | A | b73 | T | mo17 | | | | |
| 243 | Ampli-con347285 | 38910 | 93 | 96 | IND | **** | mo17 | TGCA | b73 | | | | |
| 243 | Ampli-con347285 | 38911 | 99 | 99 | SNP | A | b73 | G | mo17 | | | | |
| 243 | Ampli-con347285 | 38912 | 100 | 100 | SNP | C | b73 | T | mo17 | | | | |
| 243 | Ampli-con347285 | 38913 | 105 | 105 | SNP | A | mo17 | C | b73 | | | | |
| 243 | Ampli-con347285 | 38914 | 128 | 131 | IND | **** | mo17 | ATTA | b73 | | | | |
| 243 | Ampli-con347285 | 38915 | 148 | 148 | SNP | A | mo17 | G | b73 | | | | |
| 243 | Ampli-con347285 | 38916 | 152 | 152 | SNP | A | mo17 | C | b73 | | | | |
| 243 | Ampli-con347285 | 38917 | 158 | 158 | SNP | C | b73 | T | mo17 | | | | |
| 243 | Ampli-con347285 | 38918 | 175 | 175 | SNP | A | mo17 | G | b73 | | | | |
| 243 | Ampli-con347285 | 38919 | 180 | 180 | IND | * | mo17 | G | b73 | | | | |
| 243 | Ampli-con347285 | 38920 | 280 | 280 | SNP | C | b73 | T | mo17 | | | | |
| 243 | Ampli-con347285 | 38921 | 375 | 375 | SNP | C | mo17 | G | b73 | | | | |
| 243 | Ampli-con347285 | 38922 | 511 | 511 | SNP | G | mo17 | T | b73 | | | | |
| 243 | Ampli-con347285 | 38923 | 517 | 517 | SNP | C | mo17 | T | b73 | | | | |
| 244 | Ampli-con347285 | 39063 | 80 | 80 | SNP | A | mo17 | G | b73 | | | | |
| 244 | Ampli-con347403 | 39064 | 316 | 316 | SNP | C | mo17 | T | b73 | | | | |
| 245 | Ampli-con347403 | 39266 | 89 | 93 | IND | ****** | b73 | CTCCC | mo17 | | | | |
| 245 | Ampli-con347507 | 39267 | 118 | 118 | SNP | A | mo17 | G | b73 | | | | |
| 245 | Ampli-con347507 | 39268 | 126 | 126 | SNP | C | b73 | T | mo17 | | | | |
| 245 | Ampli-con347507 | 39269 | 165 | 165 | SNP | C | mo17 | T | b73 | | | | |
| 245 | Ampli-con347507 | 39270 | 174 | 174 | SNP | C | b73 | G | mo17 | | | | |
| 245 | Ampli-con347507 | 39271 | 251 | 251 | SNP | G | b73 | T | mo17 | | | | |
| 245 | Ampli-con347507 | 39272 | 306 | 319 | IND | ************** | mo17 | ACCTGACCCGCGGC | b73 | | | | |
| 245 | Ampli-con347507 | 39273 | 306 | 320 | IND | *************** | mo17 | ACCTGACCCGGGCG | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 245 | Ampli-con347507 | 39274 | 361 | 361 | SNP | C | mo17 | G | b73 | | | | |
| 245 | Ampli-con347507 | 39275 | 396 | 396 | SNP | C | b73 | T | mo17 | | | | |
| 245 | Ampli-con347507 | 39276 | 505 | 505 | SNP | C | b73 | G | mo17 | | | | |
| 245 | Ampli-con347507 | 39277 | 507 | 507 | SNP | C | b73 | G | mo17 | | | | |
| 245 | Ampli-con347507 | 39278 | 508 | 508 | SNP | A | b73 | C | mo17 | | | | |
| 245 | Ampli-con347507 | 39279 | 509 | 509 | SNP | A | b73 | G | mo17 | | | | |
| 245 | Ampli-con347507 | 39280 | 510 | 510 | SNP | C | mo17 | G | b73 | | | | |
| 245 | Ampli-con347507 | 39281 | 511 | 511 | SNP | A | mo17 | C | b73 | | | | |
| 245 | Ampli-con347507 | 39282 | 512 | 512 | SNP | G | mo17 | T | b73 | | | | |
| 245 | Ampli-con347507 | 39283 | 516 | 516 | SNP | A | mo17 | T | b73 | | | | |
| 246 | Ampli-con347517 | 39286 | 405 | 405 | SNP | C | b73 | T | mo17 | | | | |
| 246 | Ampli-con347517 | 39287 | 424 | 424 | SNP | A | mo17 | G | b73 | | | | |
| 246 | Ampli-con347517 | 39288 | 436 | 436 | SNP | A | mo17 | G | b73 | | | | |
| 246 | Ampli-con347517 | 39289 | 500 | 500 | SNP | C | b73 | T | mo17 | | | | |
| 247 | Ampli-con347532 | 39348 | 485 | 485 | SNP | A | mo17 | T | b73 | | | | |
| 247 | Ampli-con347532 | 39349 | 488 | 488 | SNP | A | b73 | G | mo17 | | | | |
| 247 | Ampli-con347532 | 39350 | 594 | 594 | SNP | C | mo17 | T | b73 | | | | |
| 247 | Ampli-con347532 | 39351 | 680 | 680 | SNP | A | b73 | G | mo17 | | | | |
| 247 | Ampli-con347532 | 39352 | 700 | 700 | IND | * | mo17 | T | b73 | | | | |
| 247 | Ampli-con347532 | 39353 | 714 | 714 | SNP | G | mo17 | T | b73 | | | | |
| 247 | Ampli-con347532 | 39354 | 729 | 729 | SNP | C | b73 | G | mo17 | | | | |
| 248 | Ampli-con347593 | 39502 | 51 | 51 | SNP | A | b73 | G | mo17 | | | | |
| 249 | Ampli-con347598 | 39507 | 137 | 137 | SNP | C | mo17 | T | b73 | | | | |
| 249 | Ampli-con347598 | 39508 | 433 | 434 | IND | ** | mo17 | CC | b73 | | | | |
| 249 | Ampli-con347598 | 39509 | 477 | 479 | IND | *** | b73 | GCT | mo17 | | | | |
| 249 | Ampli-con347598 | 39510 | 500 | 508 | IND | ********* | b73 | ATGGCAGGC | mo17 | | | | |
| 249 | Ampli-con347598 | 39511 | 559 | 559 | SNP | C | mo17 | G | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 250 | Ampli-con347833 | 39773 | 47 | 47 | SNP | C | b73 | T | mo17 | | | | |
| 250 | Ampli-con347833 | 39774 | 91 | 91 | IND | * | mo17 | G | b73 | | | | |
| 250 | Ampli-con347833 | 39775 | 117 | 117 | SNP | A | b73 | T | mo17 | | | | |
| 250 | Ampli-con347833 | 39776 | 153 | 153 | SNP | A | b73 | C | mo17 | | | | |
| 250 | Ampli-con347833 | 39777 | 164 | 164 | SNP | A | b73 | G | mo17 | | | | |
| 250 | Ampli-con347833 | 39778 | 545 | 546 | IND | ** | b73 | TT | mo17 | | | | |
| 250 | Ampli-con347833 | 39779 | 568 | 568 | SNP | C | mo17 | T | b73 | | | | |
| 250 | Ampli-con347833 | 39780 | 579 | 579 | SNP | G | mo17 | T | b73 | | | | |
| 250 | Ampli-con347833 | 39781 | 580 | 580 | SNP | A | b73 | C | mo17 | | | | |
| 250 | Ampli-con347833 | 39782 | 322 | 322 | SNP | C | mo17 | G | b73 | | | | |
| 251 | Ampli-con347845 | 39783 | 359 | 359 | SNP | C | mo17 | T | b73 | | | | |
| 251 | Ampli-con347845 | 39784 | 385 | 385 | SNP | C | mo17 | T | b73 | | | | |
| 251 | Ampli-con347845 | 39785 | 515 | 515 | SNP | G | b73 | T | mo17 | | | | |
| 251 | Ampli-con347845 | 39786 | 569 | 569 | SNP | A | mo17 | C | b73 | | | | |
| 251 | Ampli-con347845 | 39787 | 719 | 719 | IND | * | mo17 | G | b73 | | | | |
| 251 | Ampli-con347845 | 39788 | 724 | 724 | IND | * | mo17 | T | b73 | | | | |
| 252 | Ampli-con347958 | 39886 | 118 | 118 | IND | * | b73 | G | mo17 | | | | |
| 252 | Ampli-con347958 | 39887 | 220 | 220 | SNP | A | b73 | C | mo17 | | | | |
| 252 | Ampli-con347958 | 39888 | 275 | 275 | SNP | C | mo17 | G | b73 | | | | |
| 252 | Ampli-con347958 | 39889 | 290 | 290 | SNP | G | mo17 | T | b73 | | | | |
| 252 | Ampli-con347958 | 39890 | 308 | 308 | SNP | C | mo17 | T | b73 | | | | |
| 252 | Ampli-con347958 | 39891 | 335 | 335 | SNP | C | b73 | G | mo17 | | | | |
| 252 | Ampli-con347958 | 39892 | 379 | 379 | IND | * | mo17 | C | b73 | | | | |
| 252 | Ampli-con347958 | 39893 | 402 | 402 | SNP | A | mo17 | G | b73 | | | | |
| 252 | Ampli-con347958 | 39894 | 435 | 435 | SNP | A | mo17 | C | b73 | | | | |
| 252 | Ampli-con347958 | 39895 | 483 | 483 | SNP | G | mo17 | T | b73 | | | | |
| 252 | Ampli-con347958 | 39896 | 651 | 651 | SNP | A | mo17 | C | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 253 | Amplicon348012 | 39978 | 226 | 226 | SNP | C | b73 | T | mo17 | | | | |
| 254 | Amplicon389945 | 40124 | 212 | 212 | SNP | A | b73 | G | mo17 | | | | |
| 255 | Amplicon390056 | 40189 | 324 | 324 | SNP | C | mo17 | T | b73 | | | | |
| 256 | Amplicon390137 | 40320 | 319 | 319 | SNP | C | b73 | T | mo17 | | | | |
| 257 | Amplicon390154 | 40337 | 106 | 106 | SNP | C | mo17 | G | b73 | | | | |
| 257 | Amplicon390154 | 40338 | 457 | 457 | SNP | G | mo17 | T | b73 | | | | |
| 258 | Amplicon390253 | 40431 | 243 | 243 | SNP | C | b73 | T | mo17 | | | | |
| 258 | Amplicon390253 | 40432 | 245 | 245 | SNP | C | b73 | T | mo17 | | | | |
| 258 | Amplicon390253 | 40433 | 246 | 246 | IND | * | b73 | T | mo17 | | | | |
| 259 | Amplicon390282 | 40451 | 23 | 24 | IND | ** | mo17 | CA | b73 | | | | |
| 259 | Amplicon390282 | 40452 | 28 | 28 | SNP | C | mo17 | G | b73 | | | | |
| 259 | Amplicon390282 | 40453 | 146 | 149 | IND | **** | b73 | CTAG | mo17 | | | | |
| 259 | Amplicon390282 | 40454 | 201 | 204 | IND | **** | b73 | TATA | mo17 | | | | |
| 259 | Amplicon390282 | 40455 | 222 | 222 | SNP | A | b73 | G | mo17 | | | | |
| 259 | Amplicon390282 | 40456 | 242 | 242 | SNP | A | mo17 | T | b73 | | | | |
| 259 | Amplicon390282 | 40457 | 266 | 266 | SNP | C | mo17 | T | b73 | | | | |
| 259 | Amplicon390282 | 40458 | 270 | 270 | SNP | C | mo17 | T | b73 | | | | |
| 259 | Amplicon390282 | 40459 | 296 | 296 | SNP | A | mo17 | C | b73 | | | | |
| 259 | Amplicon390282 | 40460 | 309 | 311 | IND | *** | mo17 | TTT | b73 | | | | |
| 259 | Amplicon390282 | 40461 | 365 | 365 | SNP | A | mo17 | T | b73 | | | | |
| 259 | Amplicon390282 | 40462 | 395 | 395 | SNP | A | mo17 | G | b73 | | | | |
| 259 | Amplicon390282 | 40463 | 399 | 399 | SNP | * | b73 | A | mo17 | | | | |
| 259 | Amplicon390282 | 40464 | 399 | 400 | IND | ** | b73 | AT | mo17 | | | | |
| 260 | Amplicon390291 | 40473 | 281 | 281 | SNP | A | mo17 | C | b73 | | | | |
| 260 | Amplicon390291 | 40474 | 397 | 397 | IND | * | mo17 | C | b73 | | | | |
| 260 | Amplicon390291 | 40475 | 407 | 407 | SNP | C | mo17 | T | b73 | | | | |
| 260 | Amplicon390291 | 40476 | 408 | 408 | SNP | A | b73 | C | mo17 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 260 | Ampli-con390291 | 40477 | 409 | 409 | IND | * | mo17 | T | b73 | | | | |
| 260 | Ampli-con390291 | 40478 | 417 | 418 | IND | ** | mo17 | CA | b73 | | | | |
| 261 | Ampli-con390465 | 40655 | 58 | 58 | SNP | A | b73 | G | mo17 | | | | |
| 262 | Ampli-con390649 | 40931 | 355 | 357 | IND | *** | b73 | CTT | mo17 | | | | |
| 263 | Ampli-con390853 | 41280 | 224 | 224 | SNP | C | mo17 | T | b73 | | | | |
| 263 | Ampli-con390853 | 41281 | 283 | 283 | SNP | C | mo17 | G | b73 | | | | |
| 264 | Ampli-con391267 | 41850 | 54 | 54 | SNP | C | b73 | T | mo17 | | | | |
| 264 | Ampli-con391267 | 41851 | 111 | 111 | SNP | A | mo17 | G | b73 | | | | |
| 264 | Ampli-con391267 | 41852 | 119 | 119 | SNP | A | mo17 | T | b73 | | | | |
| 265 | Ampli-con391526 | 42161 | 133 | 133 | SNP | G | b73 | T | mo17 | | | | |
| 265 | Ampli-con391526 | 42162 | 193 | 193 | SNP | A | mo17 | G | b73 | | | | |
| 265 | Ampli-con391526 | 42163 | 253 | 253 | SNP | A | b73 | G | mo17 | | | | |
| 265 | Ampli-con391526 | 42164 | 319 | 319 | SNP | A | mo17 | G | b73 | | | | |
| 265 | Ampli-con391526 | 42165 | 349 | 349 | SNP | C | mo17 | T | b73 | | | | |
| 265 | Ampli-con391526 | 42166 | 373 | 373 | SNP | A | b73 | G | mo17 | | | | |
| 266 | Ampli-con391532 | 42173 | 90 | 91 | IND | ** | mo17 | TA | b73 | | | | |
| 266 | Ampli-con391532 | 42174 | 122 | 122 | IND | * | b73 | G | mo17 | | | | |
| 266 | Ampli-con391532 | 42175 | 128 | 129 | IND | ** | b73 | AA | mo17 | | | | |
| 266 | Ampli-con391532 | 42176 | 237 | 238 | IND | ** | mo17 | GC | b73 | | | | |
| 266 | Ampli-con391532 | 42177 | 278 | 286 | IND | ********** | mo17 | GCCTTGTTG | b73 | | | | |
| 266 | Ampli-con391532 | 42178 | 317 | 318 | IND | ** | b73 | CT | mo17 | | | | |
| 266 | Ampli-con391532 | 42179 | 320 | 323 | IND | **** | b73 | CGAC | mo17 | | | | |
| 266 | Ampli-con391532 | 42180 | 334 | 334 | SNP | C | mo17 | G | b73 | | | | |
| 266 | Ampli-con391532 | 42181 | 345 | 347 | IND | *** | b73 | CTA | mo17 | | | | |
| 266 | Ampli-con391532 | 42182 | 360 | 360 | SNP | A | mo17 | G | b73 | | | | |
| 266 | Ampli-con391532 | 42183 | 371 | 371 | IND | * | b73 | G | mo17 | | | | |
| 266 | Ampli-con391532 | 42184 | 375 | 375 | IND | * | b73 | A | mo17 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 266 | Ampli-con391532 | 42185 | 383 | 383 | SNP | G | b73 | T | mo17 | | | | |
| 266 | Ampli-con391532 | 42186 | 400 | 400 | SNP | A | mo17 | T | b73 | | | | |
| 266 | Ampli-con391532 | 42187 | 405 | 405 | IND | * | b73 | A | mo17 | | | | |
| 266 | Ampli-con391532 | 42188 | 414 | 416 | IND | *** | b73 | ATA | mo17 | | | | |
| 266 | Ampli-con391532 | 42189 | 433 | 433 | SNP | A | b73 | T | mo17 | | | | |
| 266 | Ampli-con391532 | 42190 | 443 | 446 | IND | **** | b73 | TGTA | mo17 | | | | |
| 266 | Ampli-con391532 | 42191 | 448 | 448 | IND | * | b73 | C | mo17 | | | | |
| 267 | Ampli-con437734 | 42930 | 136 | 136 | SNP | A | mo17 | C | b73 | | | | |
| 267 | Ampli-con437734 | 42931 | 195 | 195 | SNP | C | b73 | T | mo17 | | | | |
| 267 | Ampli-con437734 | 42932 | 297 | 297 | SNP | A | b73 | G | mo17 | | | | |
| 267 | Ampli-con437734 | 42933 | 338 | 338 | SNP | A | b73 | G | mo17 | | | | |
| 267 | Ampli-con437734 | 42934 | 421 | 421 | SNP | A | b73 | T | mo17 | | | | |
| 267 | Ampli-con437734 | 42935 | 427 | 427 | SNP | C | b73 | G | mo17 | | | | |
| 268 | Ampli-con437882 | 43119 | 80 | 80 | SNP | C | b73 | T | mo17 | | | | |
| 268 | Ampli-con437882 | 43120 | 141 | 141 | SNP | C | b73 | G | mo17 | | | | |
| 268 | Ampli-con437882 | 43121 | 310 | 310 | SNP | A | b73 | G | mo17 | | | | |
| 268 | Ampli-con437882 | 43122 | 354 | 354 | SNP | C | b73 | G | b73 | | | | |
| 268 | Ampli-con437882 | 43123 | 410 | 410 | SNP | A | mo17 | G | b73 | | | | |
| 269 | Ampli-con437962 | 43220 | 44 | 44 | SNP | G | mo17 | T | b73 | | | | |
| 269 | Ampli-con437962 | 43221 | 73 | 76 | IND | **** | mo17 | CTAG | b73 | | | | |
| 269 | Ampli-con437962 | 43222 | 114 | 114 | SNP | C | mo17 | T | mo17 | | | | |
| 269 | Ampli-con437962 | 43223 | 119 | 119 | IND | * | b73 | C | mo17 | | | | |
| 269 | Ampli-con437962 | 43224 | 206 | 206 | IND | * | b73 | G | mo17 | | | | |
| 269 | Ampli-con437962 | 43225 | 208 | 208 | SNP | A | b73 | C | mo17 | | | | |
| 269 | Ampli-con437962 | 43226 | 209 | 209 | SNP | C | mo17 | G | b73 | | | | |
| 269 | Ampli-con437962 | 43227 | 220 | 220 | SNP | A | mo17 | G | b73 | | | | |
| 269 | Ampli-con437962 | 43228 | 452 | 455 | IND | **** | mo17 | ATAC | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 269 | Ampli-con437962 | 43229 | 533 | 533 | SNP | C | b73 | T | mo17 | | | | |
| 269 | Ampli-con437962 | 43230 | 649 | 649 | SNP | C | b73 | G | mo17 | | | | |
| 270 | Ampli-con438229 | 43576 | 47 | 47 | SNP | A | b73 | T | mo17 | | | | |
| 270 | Ampli-con438229 | 43577 | 48 | 48 | SNP | A | b73 | T | mo17 | | | | |
| 270 | Ampli-con438229 | 43578 | 71 | 71 | SNP | A | mo17 | T | b73 | | | | |
| 270 | Ampli-con438229 | 43579 | 153 | 153 | SNP | C | b73 | T | mo17 | | | | |
| 270 | Ampli-con438229 | 43580 | 217 | 217 | SNP | C | b73 | T | mo17 | | | | |
| 270 | Ampli-con438229 | 43581 | 274 | 274 | SNP | A | mo17 | C | b73 | | | | |
| 271 | Ampli-con438421 | 43789 | 109 | 109 | SNP | C | b73 | T | mo17 | | | | |
| 272 | Ampli-con557338 | 48404 | 106 | 106 | SNP | C | mo17 | G | b73 | | | | |
| 272 | Ampli-con557338 | 48405 | 137 | 137 | SNP | A | b73 | C | mo17 | | | | |
| 272 | Ampli-con557338 | 48406 | 142 | 142 | SNP | G | b73 | T | mo17 | | | | |
| 272 | Ampli-con557338 | 48407 | 175 | 175 | SNP | C | b73 | C | mo17 | | | | |
| 272 | Ampli-con557338 | 48408 | 192 | 192 | SNP | C | mo17 | T | b73 | | | | |
| 272 | Ampli-con557338 | 48409 | 193 | 193 | SNP | C | mo17 | T | b73 | | | | |
| 272 | Ampli-con557338 | 48410 | 203 | 207 | IND | ****** | mo17 | TGAAT | b73 | | | | |
| 272 | Ampli-con557338 | 48412 | 215 | 215 | SNP | A | b73 | C | mo17 | | | | |
| 272 | Ampli-con557338 | 48413 | 223 | 228 | IND | ****** | mo17 | TATCCA | b73 | | | | |
| 272 | Ampli-con557338 | 48414 | 256 | 256 | SNP | A | mo17 | T | b73 | | | | |
| 272 | Ampli-con557338 | 48415 | 266 | 266 | SNP | C | mo17 | T | b73 | | | | |
| 272 | Ampli-con557338 | 48416 | 317 | 317 | SNP | A | mo17 | C | b73 | | | | |
| 272 | Ampli-con557338 | 48417 | 356 | 356 | SNP | A | mo17 | T | b73 | | | | |
| 272 | Ampli-con557338 | 48418 | 365 | 365 | SNP | A | b73 | C | mo17 | | | | |
| 272 | Ampli-con557338 | 48419 | 366 | 366 | IND | * | b73 | G | mo17 | | | | |
| 272 | Ampli-con557338 | 48420 | 370 | 370 | SNP | C | b73 | T | mo17 | | | | |
| 272 | Ampli-con557338 | 48421 | 401 | 401 | SNP | G | mo17 | T | b73 | | | | |
| 272 | Ampli-con557338 | 48423 | 407 | 408 | IND | ** | mo17 | TT | b73 | | | | |

-continued

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 272 | Ampli-con557338 | 48424 | 417 | 417 | SNP | C | mo17 | G | b73 | | | | |
| 272 | Ampli-con557338 | 48425 | 487 | 487 | SNP | C | mo17 | T | b73 | | | | |
| 272 | Ampli-con557338 | 48426 | 491 | 491 | IND | * | mo17 | C | b73 | | | | |
| 272 | Ampli-con557338 | 48427 | 528 | 531 | IND | **** | mo17 | CAGC | b73 | | | | |
| 273 | Ampli-con557363 | 48561 | 27 | 27 | SNP | C | b73 | T | mo17 | | | | |
| 273 | Ampli-con557363 | 48562 | 216 | 216 | SNP | G | mo17 | T | b73 | | | | |
| 274 | Ampli-con557374 | 48615 | 33 | 33 | SNP | C | mo17 | T | b73 | | | | |
| 274 | Ampli-con557374 | 48616 | 87 | 87 | SNP | C | mo17 | T | b73 | | | | |
| 275 | Ampli-con557514 | 49292 | 161 | 161 | SNP | C | mo17 | T | b73 | | | | |
| 275 | Ampli-con557514 | 49293 | 182 | 182 | SNP | A | mo17 | C | b73 | | | | |
| 275 | Ampli-con557514 | 49294 | 185 | 185 | SNP | A | b73 | G | mo17 | | | | |
| 275 | Ampli-con557514 | 49295 | 222 | 222 | SNP | A | b73 | G | mo17 | | | | |
| 275 | Ampli-con557514 | 49296 | 223 | 223 | SNP | A | b73 | G | mo17 | | | | |
| 275 | Ampli-con557514 | 49297 | 242 | 242 | SNP | G | b73 | T | mo17 | | | | |
| 275 | Ampli-con557514 | 49298 | 295 | 295 | SNP | C | mo17 | T | b73 | | | | |
| 275 | Ampli-con557514 | 49299 | 371 | 371 | SNP | C | b73 | G | mo17 | | | | |
| 275 | Ampli-con557514 | 49301 | 448 | 448 | SNP | C | mo17 | T | b73 | | | | |
| 276 | Ampli-con557514 | 49557 | 463 | 463 | SNP | A | mo17 | G | b73 | | | | |
| 277 | Ampli-con557572 | 50315 | 255 | 255 | SNP | A | mo17 | G | b73 | | | | |
| 277 | Ampli-con557793 | 50316 | 355 | 355 | SNP | A | mo17 | G | b73 | | | | |
| 278 | Ampli-con557793 | 51399 | 37 | 43 | IND | ******* | mo17 | TCAGTGG | b73 | | | | |
| 278 | Ampli-con558092 | 51400 | 178 | 178 | SNP | A | mo17 | T | b73 | | | | |
| 278 | Ampli-con558092 | 51401 | 179 | 179 | SNP | A | mo17 | C | b73 | | | | |
| 278 | Ampli-con558092 | 51402 | 234 | 234 | SNP | A | mo17 | C | b73 | | | | |
| 278 | Ampli-con558092 | 51403 | 278 | 278 | SNP | A | mo17 | C | b73 | | | | |
| 278 | Ampli-con558092 | 51404 | 284 | 284 | SNP | C | mo17 | T | b73 | | | | |
| 278 | Ampli-con558092 | 51405 | 327 | 327 | SNP | C | mo17 | T | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 279 | Ampli-con558095 | 51419 | 251 | 251 | SNP | C | b73 | T | mo17 | | | | |
| 280 | Ampli-con558139 | 51609 | 45 | 45 | SNP | A | b73 | T | mo17 | | | | |
| 280 | Ampli-con558139 | 51610 | 196 | 196 | SNP | C | b73 | G | mo17 | | | | |
| 280 | Ampli-con558139 | 51611 | 200 | 200 | SNP | C | mo17 | T | b73 | | | | |
| 280 | Ampli-con558139 | 51613 | 270 | 270 | SNP | A | mo17 | G | b73 | | | | |
| 280 | Ampli-con558139 | 51614 | 319 | 319 | SNP | C | b73 | T | mo17 | | | | |
| 281 | Ampli-con558289 | 52078 | 104 | 104 | IND | * | mo17 | G | b73 | | | | |
| 281 | Ampli-con558289 | 52080 | 106 | 106 | IND | * | mo17 | C | b73 | | | | |
| 281 | Ampli-con558289 | 52081 | 350 | 350 | SNP | C | b73 | T | mo17 | | | | |
| 282 | Ampli-con558289 | 53097 | 334 | 334 | SNP | A | mo17 | T | b73 | | | | |
| 283 | Ampli-con558536 | 53899 | 472 | 473 | IND | ** | mo17 | TA | b73 | | | | |
| 284 | Ampli-con558731 | 54409 | 76 | 76 | SNP | C | mo17 | T | b73 | | | | |
| 284 | Ampli-con558865 | 54410 | 100 | 100 | SNP | C | mo17 | T | b73 | | | | |
| 284 | Ampli-con558865 | 54411 | 110 | 110 | SNP | A | mo17 | G | b73 | | | | |
| 284 | Ampli-con558865 | 54412 | 444 | 444 | SNP | A | b73 | T | mo17 | | | | |
| 284 | Ampli-con558865 | 54413 | 478 | 478 | SNP | A | b73 | G | mo17 | | | | |
| 285 | Ampli-con558865 | 54460 | 410 | 410 | SNP | A | mo17 | T | b73 | | | | |
| 286 | Ampli-con558883 | 55370 | 254 | 254 | SNP | C | b73 | T | mo17 | | | | |
| 286 | Ampli-con559082 | 55371 | 354 | 354 | SNP | C | b73 | T | mo17 | | | | |
| 286 | Ampli-con559082 | 55372 | 355 | 355 | SNP | G | mo17 | T | b73 | | | | |
| 286 | Ampli-con559082 | 55373 | 418 | 418 | IND | * | mo17 | C | b73 | | | | |
| 286 | Ampli-con559082 | 55374 | 490 | 490 | SNP | A | mo17 | T | b73 | | | | |
| 287 | Ampli-con559082 | 56934 | 179 | 179 | SNP | G | mo17 | T | b73 | | | | |
| 287 | Ampli-con559441 | 56935 | 212 | 212 | SNP | C | mo17 | T | b73 | | | | |
| 287 | Ampli-con559441 | 56936 | 240 | 240 | SNP | C | mo17 | T | b73 | | | | |
| 287 | Ampli-con559441 | 56937 | 258 | 258 | SNP | G | mo17 | T | b73 | | | | |
| 287 | Ampli-con559441 | 56938 | 383 | 383 | SNP | C | b73 | T | mo17 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 287 | Ampli-con559441 | 56939 | 425 | 425 | SNP | A | b73 | C | mo17 | | | | |
| 288 | Ampli-con559491 | 57136 | 129 | 129 | SNP | G | b73 | T | mo17 | | | | |
| 288 | Ampli-con559491 | 57137 | 540 | 540 | SNP | A | b73 | G | mo17 | | | | |
| 289 | Ampli-con559625 | 57758 | 45 | 45 | SNP | A | b73 | G | mo17 | | | | |
| 290 | Ampli-con559759 | 58375 | 493 | 493 | SNP | C | mo17 | T | b73 | | | | |
| 291 | Ampli-con559897 | 58904 | 119 | 119 | SNP | C | b73 | G | mo17 | | | | |
| 291 | Ampli-con559897 | 58905 | 215 | 215 | SNP | A | mo17 | T | b73 | | | | |
| 291 | Ampli-con559897 | 58906 | 313 | 313 | SNP | A | b73 | T | mo17 | | | | |
| 292 | Ampli-con559922 | 59006 | 21 | 21 | SNP | A | b73 | T | mo17 | | | | |
| 292 | Ampli-con559922 | 59007 | 33 | 33 | SNP | C | b73 | G | mo17 | | | | |
| 292 | Ampli-con559922 | 59008 | 82 | 82 | SNP | C | mo17 | T | b73 | | | | |
| 292 | Ampli-con559922 | 59009 | 183 | 183 | SNP | A | b73 | C | mo17 | | | | |
| 292 | Ampli-con559922 | 59010 | 233 | 233 | SNP | G | b73 | T | mo17 | | | | |
| 292 | Ampli-con559922 | 59011 | 260 | 260 | SNP | C | mo17 | T | b73 | | | | |
| 293 | Ampli-con560273 | 60430 | 62 | 62 | SNP | A | mo17 | G | b73 | | | | |
| 293 | Ampli-con560273 | 60431 | 81 | 81 | IND | * | mo17 | T | b73 | | | | |
| 293 | Ampli-con560273 | 60433 | 143 | 143 | SNP | A | b73 | C | mo17 | | | | |
| 293 | Ampli-con560273 | 60434 | 165 | 165 | IND | * | mo17 | T | b73 | | | | |
| 294 | Ampli-con560371 | 60751 | 298 | 298 | SNP | A | mo17 | G | b73 | | | | |
| 294 | Ampli-con560371 | 60753 | 370 | 370 | SNP | A | mo17 | T | b73 | | | | |
| 294 | Ampli-con560371 | 60754 | 375 | 375 | SNP | A | b73 | C | mo17 | | | | |
| 294 | Ampli-con560371 | 60755 | 444 | 444 | SNP | A | mo17 | T | b73 | | | | |
| 295 | Ampli-con617328 | 68149 | 297 | 297 | SNP | C | b73 | T | mo17 | | | | |
| 295 | Ampli-con617328 | 68150 | 598 | 598 | SNP | C | mo17 | G | b73 | | | | |
| 296 | Ampli-con617436 | 68421 | 153 | 153 | SNP | C | b73 | T | mo17 | | | | |
| 296 | Ampli-con617436 | 68422 | 180 | 180 | SNP | C | b73 | T | mo17 | | | | |
| 296 | Ampli-con617436 | 68423 | 252 | 252 | SNP | A | b73 | G | mo17 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 296 | Ampli-con617436 | 68424 | 304 | 304 | SNP | C | b73 | T | mo17 | | | | |
| 296 | Ampli-con617436 | 68425 | 363 | 363 | SNP | A | mo17 | G | b73 | | | | |
| 296 | Ampli-con617436 | 68426 | 434 | 434 | SNP | C | mo17 | T | b73 | | | | |
| 296 | Ampli-con617436 | 68427 | 459 | 459 | SNP | C | mo17 | T | b73 | | | | |
| 297 | Ampli-con617439 | 68435 | 54 | 54 | SNP | A | mo17 | G | b73 | | | | |
| 297 | Ampli-con617439 | 68436 | 80 | 80 | SNP | A | mo17 | C | b73 | | | | |
| 297 | Ampli-con617439 | 68437 | 93 | 93 | SNP | A | mo17 | G | b73 | | | | |
| 297 | Ampli-con617439 | 68438 | 123 | 123 | SNP | C | b73 | T | mo17 | | | | |
| 297 | Ampli-con617439 | 68439 | 161 | 161 | SNP | C | b73 | T | mo17 | | | | |
| 297 | Ampli-con617439 | 68440 | 536 | 536 | SNP | C | b73 | G | mo17 | | | | |
| 298 | Ampli-con617662 | 68940 | 113 | 113 | SNP | C | b73 | T | mo17 | | | | |
| 298 | Ampli-con617662 | 68941 | 277 | 277 | SNP | C | mo17 | G | b73 | | | | |
| 298 | Ampli-con617662 | 68942 | 393 | 397 | IND | ***** | b73 | ACGCT | mo17 | | | | |
| 298 | Ampli-con617662 | 68943 | 435 | 435 | IND | * | mo17 | C | b73 | | | | |
| 298 | Ampli-con617662 | 68944 | 436 | 445 | IND | ********** | mo17 | CTTCTAAGAC | b73 | | | | |
| 299 | Ampli-con617671 | 68950 | 126 | 126 | SNP | G | b73 | T | mo17 | | | | |
| 299 | Ampli-con617671 | 68952 | 172 | 172 | SNP | A | b73 | G | mo17 | | | | |
| 299 | Ampli-con617671 | 68953 | 182 | 182 | SNP | C | b73 | T | mo17 | | | | |
| 299 | Ampli-con617671 | 68954 | 214 | 214 | SNP | G | mo17 | T | b73 | | | | |
| 299 | Ampli-con617671 | 68955 | 260 | 260 | SNP | C | b73 | T | mo17 | | | | |
| 299 | Ampli-con617671 | 68956 | 282 | 282 | SNP | C | b73 | T | mo17 | | | | |
| 299 | Ampli-con617671 | 68957 | 285 | 285 | SNP | C | b73 | T | mo17 | | | | |
| 299 | Ampli-con617671 | 68958 | 287 | 287 | SNP | C | mo17 | G | b73 | | | | |
| 299 | Ampli-con617671 | 68959 | 300 | 300 | SNP | C | b73 | T | mo17 | | | | |
| 299 | Ampli-con617671 | 68960 | 327 | 327 | SNP | C | mo17 | T | b73 | | | | |
| 299 | Ampli-con617671 | 68961 | 414 | 414 | SNP | C | mo17 | G | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 299 | Ampli-con617671 | 68962 | 435 | 435 | SNP | A | b73 | G | mo17 | | | | |
| 300 | Ampli-con617706 | 69119 | 200 | 200 | SNP | C | mo17 | T | b73 | | | | |
| 300 | Ampli-con617706 | 69120 | 471 | 471 | SNP | C | mo17 | G | b73 | | | | |
| 300 | Ampli-con617706 | 69121 | 684 | 684 | SNP | A | mo17 | G | b73 | | | | |
| 300 | Ampli-con617706 | 69122 | 743 | 743 | SNP | C | mo17 | T | b73 | | | | |
| 300 | Ampli-con617706 | 69123 | 749 | 749 | IND | * | mo17 | G | b73 | | | | |
| 300 | Ampli-con617706 | 69125 | 754 | 754 | IND | * | mo17 | A | b73 | | | | |
| 301 | Ampli-con617780 | 69188 | 171 | 171 | SNP | A | b73 | G | mo17 | | | | |
| 302 | Ampli-con617951 | 69556 | 98 | 98 | IND | * | mo17 | T | b73 | | | | |
| 302 | Ampli-con617951 | 69557 | 100 | 100 | SNP | A | mo17 | G | b73 | | | | |
| 302 | Ampli-con617951 | 69558 | 179 | 179 | SNP | G | b73 | T | mo17 | | | | |
| 302 | Ampli-con617951 | 69559 | 202 | 202 | SNP | C | mo17 | T | b73 | | | | |
| 302 | Ampli-con617951 | 69562 | 240 | 240 | SNP | C | b73 | G | mo17 | | | | |
| 302 | Ampli-con617951 | 69563 | 261 | 261 | SNP | A | mo17 | G | b73 | | | | |
| 302 | Ampli-con617951 | 69565 | 590 | 590 | SNP | A | mo17 | G | b73 | | | | |
| 303 | Ampli-con617978 | 69588 | 244 | 244 | SNP | C | b73 | T | mo17 | | | | |
| 303 | Ampli-con617978 | 69589 | 264 | 264 | SNP | G | b73 | T | mo17 | | | | |
| 303 | Ampli-con617978 | 69590 | 282 | 282 | SNP | C | b73 | T | mo17 | | | | |
| 303 | Ampli-con617978 | 69591 | 349 | 349 | SNP | C | mo17 | T | b73 | | | | |
| 303 | Ampli-con617978 | 69592 | 438 | 439 | IND | ** | b73 | AT | mo17 | | | | |
| 303 | Ampli-con617978 | 69593 | 540 | 540 | SNP | A | mo17 | C | b73 | | | | |
| 303 | Ampli-con617978 | 69594 | 541 | 541 | SNP | A | mo17 | T | b73 | | | | |
| 303 | Ampli-con617978 | 69595 | 585 | 585 | SNP | A | b73 | G | mo17 | | | | |
| 304 | Ampli-con617990 | 69630 | 598 | 598 | SNP | A | b73 | G | mo17 | | | | |
| 305 | Ampli-con645093 | 70727 | 140 | 140 | SNP | C | b73 | T | mo17 | | | | |
| 305 | Ampli-con645093 | 70728 | 178 | 178 | SNP | C | b73 | T | mo17 | | | | |
| 305 | Ampli-con645093 | 70730 | 330 | 330 | SNP | C | mo17 | G | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 305 | Ampli-con645093 | 70731 | 944 | 944 | SNP | A | mo17 | C | b73 | | | | |
| 305 | Ampli-con645093 | 70732 | 979 | 979 | SNP | A | b73 | G | mo17 | | | | |
| 305 | Ampli-con645093 | 70733 | 1060 | 1060 | SNP | A | b73 | T | mo17 | | | | |
| 305 | Ampli-con645093 | 70734 | 1095 | 1095 | SNP | C | b73 | G | mo17 | | | | |
| 306 | Ampli-con645093 | 71154 | 300 | 302 | IND | *** | b73 | TGA | mo17 | | | | |
| 306 | Ampli-con645262 | 71156 | 400 | 400 | SNP | A | mo17 | C | b73 | | | | |
| 306 | Ampli-con645262 | 71157 | 621 | 626 | IND | ****** | b73 | ATACTT | mo17 | | | | |
| 306 | Ampli-con645262 | 71158 | 779 | 779 | SNP | G | mo17 | T | b73 | | | | |
| 306 | Ampli-con645262 | 71159 | 902 | 903 | IND | ** | mo17 | TG | b73 | | | | |
| 307 | Ampli-con645495 | 71622 | 51 | 51 | SNP | A | mo17 | G | b73 | | | | |
| 307 | Ampli-con645495 | 71623 | 52 | 52 | SNP | A | mo17 | G | b73 | | | | |
| 307 | Ampli-con645495 | 71624 | 105 | 105 | SNP | A | b73 | G | mo17 | | | | |
| 307 | Ampli-con645495 | 71625 | 127 | 127 | SNP | A | b73 | C | mo17 | | | | |
| 307 | Ampli-con645495 | 71627 | 138 | 140 | IND | *** | mo17 | AAA | b73 | | | | |
| 307 | Ampli-con645495 | 71628 | 219 | 219 | SNP | C | b73 | T | mo17 | | | | |
| 307 | Ampli-con645495 | 71629 | 348 | 348 | SNP | A | mo17 | G | b73 | | | | |
| 307 | Ampli-con645495 | 71630 | 551 | 551 | SNP | A | mo17 | T | b73 | | | | |
| 307 | Ampli-con645495 | 71633 | 784 | 784 | SNP | G | b73 | T | mo17 | | | | |
| 307 | Ampli-con645495 | 71634 | 794 | 794 | SNP | A | mo17 | G | b73 | | | | |
| 307 | Ampli-con645495 | 71635 | 824 | 824 | SNP | C | b73 | T | mo17 | | | | |
| 307 | Ampli-con645495 | 71639 | 931 | 931 | SNP | C | b73 | T | mo17 | | | | |
| 307 | Ampli-con645495 | 71640 | 975 | 975 | SNP | A | mo17 | C | b73 | | | | |
| 308 | Ampli-con645495 | 76792 | 194 | 194 | SNP | A | b73 | G | mo17 | | | | |
| 308 | Ampli-con670815 | 76793 | 291 | 291 | SNP | C | b73 | T | mo17 | | | | |
| 309 | Ampli-con670815 | 77118 | 187 | 187 | SNP | A | mo17 | G | b73 | | | | |
| 310 | Ampli-con670910 | 77412 | 88 | 88 | SNP | G | mo17 | T | b73 | | | | |
| 310 | Ampli-con670989 | 77413 | 118 | 118 | SNP | G | mo17 | T | b73 | | | | |

-continued

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 310 | Amplicon670989 | 77414 | 245 | 245 | SNP | C | b73 | T | mo17 | | | | |
| 311 | Amplicon671032 | 77545 | 66 | 66 | SNP | A | b73 | G | mo17 | | | | |
| 312 | Amplicon671043 | 77568 | 249 | 249 | SNP | A | mo17 | G | b73 | | | | |
| 313 | Amplicon671315 | 78437 | 94 | 94 | SNP | C | mo17 | G | b73 | | | | |
| 313 | Amplicon671315 | 78438 | 137 | 137 | SNP | C | b73 | T | mo17 | | | | |
| 314 | Amplicon700255 | 78827 | 122 | 122 | SNP | A | b73 | G | mo17 | | | | |
| 314 | Amplicon700255 | 78828 | 209 | 209 | SNP | C | b73 | T | mo17 | | | | |
| 314 | Amplicon700255 | 78829 | 262 | 266 | IND | ***** | b73 | GTGTG | mo17 | | | | |
| 314 | Amplicon700255 | 78830 | 292 | 292 | IND | * | b73 | T | mo17 | | | | |
| 315 | Amplicon700287 | 79073 | 97 | 97 | SNP | A | mo17 | G | b73 | | | | |
| 316 | Amplicon700291 | 79081 | 79 | 79 | SNP | A | mo17 | C | b73 | | | | |
| 316 | Amplicon700291 | 79082 | 164 | 164 | SNP | A | b73 | G | mo17 | | | | |
| 317 | Amplicon700342 | 79300 | 202 | 202 | SNP | C | b73 | T | mo17 | | | | |
| 317 | Amplicon700342 | 79301 | 223 | 223 | SNP | C | b73 | T | mo17 | | | | |
| 317 | Amplicon700342 | 79303 | 250 | 250 | SNP | A | b73 | T | mo17 | | | | |
| 317 | Amplicon700342 | 79304 | 252 | 252 | SNP | C | mo17 | G | b73 | | | | |
| 317 | Amplicon700342 | 79305 | 297 | 297 | SNP | A | b73 | T | mo17 | | | | |
| 317 | Amplicon700342 | 79306 | 321 | 321 | SNP | A | mo17 | G | b73 | | | | |
| 317 | Amplicon700342 | 79307 | 373 | 373 | IND | * | b73 | T | mo17 | | | | |
| 318 | Amplicon700384 | 79514 | 80 | 80 | SNP | A | b73 | G | mo17 | | | | |
| 318 | Amplicon700384 | 79515 | 255 | 255 | IND | * | b73 | T | mo17 | | | | |
| 318 | Amplicon700384 | 79516 | 307 | 307 | SNP | A | b73 | G | mo17 | | | | |
| 318 | Amplicon700384 | 79517 | 321 | 321 | SNP | A | b73 | G | mo17 | | | | |
| 318 | Amplicon700384 | 79518 | 448 | 448 | SNP | A | mo17 | G | b73 | | | | |
| 318 | Amplicon700384 | 79519 | 480 | 480 | SNP | C | b73 | T | mo17 | | | | |
| 319 | Amplicon700387 | 79529 | 130 | 130 | SNP | A | mo17 | T | b73 | | | | |
| 320 | Amplicon700428 | 79693 | 127 | 127 | SNP | C | mo17 | T | b73 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 320 | Amplicon700428 | 79694 | 159 | 159 | SNP | C | b73 | T | mo17 | | | | |
| 320 | Amplicon700428 | 79695 | 204 | 204 | SNP | G | b73 | T | mo17 | | | | |
| 320 | Amplicon700428 | 79696 | 220 | 220 | IND | * | b73 | T | mo17 | | | | |
| 320 | Amplicon700428 | 79697 | 253 | 253 | SNP | C | mo17 | T | b73 | | | | |
| 320 | Amplicon700428 | 79698 | 255 | 255 | SNP | A | b73 | C | mo17 | | | | |
| 320 | Amplicon700428 | 79701 | 456 | 456 | SNP | A | mo17 | G | b73 | | | | |
| 320 | Amplicon700428 | 79702 | 464 | 464 | SNP | A | mo17 | T | b73 | | | | |
| 321 | Amplicon700512 | 80029 | 50 | 50 | SNP | C | b73 | T | mo17 | | | | |
| 321 | Amplicon700512 | 80030 | 86 | 86 | SNP | A | b73 | T | mo17 | | | | |
| 321 | Amplicon700512 | 80031 | 163 | 163 | SNP | A | mo17 | G | b73 | | | | |
| 321 | Amplicon700512 | 80032 | 260 | 260 | SNP | A | mo17 | G | b73 | | | | |
| 321 | Amplicon700512 | 80033 | 269 | 269 | SNP | C | b73 | T | mo17 | | | | |
| 321 | Amplicon700512 | 80034 | 419 | 419 | SNP | C | b73 | G | mo17 | | | | |
| 321 | Amplicon700512 | 80035 | 458 | 458 | SNP | A | b73 | G | mo17 | | | | |
| 322 | Amplicon700579 | 80475 | 229 | 229 | SNP | A | mo17 | G | b73 | | | | |
| 323 | Amplicon700609 | 80704 | 102 | 102 | SNP | C | mo17 | T | b73 | | | | |
| 323 | Amplicon700609 | 80705 | 281 | 281 | SNP | C | mo17 | G | b73 | | | | |
| 324 | Amplicon700771 | 81460 | 110 | 115 | IND | ******* | mo17 | GACGTA | b73 | | | | |
| 324 | Amplicon700771 | 81461 | 129 | 129 | SNP | C | b73 | T | mo17 | | | | |
| 324 | Amplicon700771 | 81462 | 157 | 157 | SNP | C | mo17 | G | b73 | | | | |
| 324 | Amplicon700771 | 81463 | 195 | 195 | IND | * | mo17 | G | b73 | | | | |
| 324 | Amplicon700771 | 81464 | 203 | 203 | IND | * | mo17 | T | b73 | | | | |
| 324 | Amplicon700771 | 81466 | 207 | 207 | IND | * | mo17 | A | b73 | | | | |
| 324 | Amplicon700771 | 81467 | 260 | 260 | IND | * | b73 | T | mo17 | | | | |
| 324 | Amplicon700771 | 81469 | 264 | 265 | IND | ** | b73 | GG | mo17 | | | | |
| 324 | Amplicon700771 | 81470 | 266 | 266 | SNP | G | mo17 | T | b73 | | | | |
| 324 | Amplicon700771 | 81471 | 315 | 318 | IND | **** | b73 | GGAG | mo17 | | | | |

-continued

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 325 | Ampli-con724218 | 82235 | 506 | 506 | SNP | A | mo17 | C | b73 | | | | |
| 326 | Ampli-con724245 | 82295 | 252 | 252 | SNP | C | mo17 | T | b73 | | | | |
| 326 | Ampli-con724245 | 82296 | 508 | 508 | SNP | A | b73 | G | mo17 | | | | |
| 327 | Ampli-con724279 | 82454 | 156 | 156 | SNP | A | mo17 | C | b73 | | | | |
| 327 | Ampli-con724279 | 82455 | 203 | 203 | SNP | C | b73 | G | mo17 | | | | |
| 327 | Ampli-con724279 | 82456 | 280 | 280 | SNP | A | mo17 | G | b73 | | | | |
| 327 | Ampli-con724279 | 82457 | 282 | 282 | SNP | C | b73 | T | mo17 | | | | |
| 327 | Ampli-con724279 | 82458 | 384 | 384 | SNP | G | mo17 | G | b73 | | | | |
| 327 | Ampli-con724279 | 82460 | 474 | 474 | SNP | A | b73 | T | mo17 | | | | |
| 327 | Ampli-con724279 | 82461 | 481 | 481 | SNP | G | mo17 | T | b73 | | | | |
| 327 | Ampli-con724279 | 82462 | 525 | 525 | SNP | A | mo17 | T | b73 | | | | |
| 327 | Ampli-con724279 | 82463 | 541 | 541 | SNP | G | b73 | G | mo17 | | | | |
| 328 | Ampli-con724510 | 83776 | 319 | 319 | SNP | A | b73 | T | mo17 | | | | |
| 328 | Ampli-con724510 | 83777 | 336 | 336 | SNP | C | b73 | T | mo17 | | | | |
| 328 | Ampli-con724510 | 83778 | 371 | 371 | SNP | C | mo17 | T | b73 | | | | |
| 328 | Ampli-con724510 | 83779 | 374 | 374 | SNP | G | mo17 | T | b73 | | | | |
| 328 | Ampli-con724510 | 83780 | 398 | 398 | SNP | G | mo17 | T | b73 | | | | |
| 329 | Ampli-con724623 | 84517 | 231 | 231 | SNP | A | mo17 | G | b73 | | | | |
| 329 | Ampli-con724623 | 84521 | 299 | 299 | SNP | G | mo17 | T | b73 | | | | |
| 329 | Ampli-con724623 | 84527 | 546 | 546 | SNP | A | mo17 | C | b73 | | | | |
| 329 | Ampli-con724623 | 84529 | 556 | 556 | SNP | C | mo17 | G | b73 | | | | |
| 329 | Ampli-con724623 | 84530 | 565 | 566 | IND | ** | mo17 | TG | b73 | | | | |
| 330 | Ampli-con740235 | 84829 | 505 | 505 | SNP | A | b73 | C | mo17 | | | | |
| 331 | Ampli-con993221 | 104389 | 210 | 210 | SNP | C | LH82 | T | 5CM1 | | | | |
| 331 | Ampli-con993221 | 104390 | 224 | 224 | SNP | C | LH82 | G | 5CM1 | | | | |
| 331 | Ampli-con993221 | 104391 | 225 | 225 | SNP | A | LH82 | G | 5CM1 | | | | |
| 331 | Ampli-con993221 | 104392 | 226 | 226 | SNP | C | 5CM1 | T | LH82 | | | | |

-continued

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 331 | Amplicon993221 | 104393 | 230 | 230 | SNP | C | 5CM1 | T | LH82 | | | | |
| 331 | Amplicon993221 | 104394 | 232 | 232 | SNP | A | 5CM1 | G | LH82 | | | | |
| 331 | Amplicon993221 | 104395 | 251 | 251 | SNP | C | LH82 | G | 5CM1 | | | | |
| 332 | Amplicon993232 | 104447 | 306 | 306 | SNP | A | LH82 | C | 5CM1 | | | | |
| 333 | Amplicon993240 | 104473 | 221 | 221 | SNP | A | 5CM1 | C | LH82 | | | | |
| 333 | Amplicon993240 | 104474 | 260 | 260 | SNP | C | 5CM1 | T | LH82 | | | | |
| 333 | Amplicon993240 | 104475 | 305 | 305 | SNP | A | 5CM1 | C | LH82 | | | | |
| 333 | Amplicon993240 | 104476 | 316 | 316 | SNP | A | LH82 | G | 5CM1 | | | | |
| 334 | Amplicon993248 | 104509 | 287 | 293 | IND | ******* | LH82 | CCAACAA | 5CM1 | | | | |
| 334 | Amplicon993248 | 104510 | 365 | 365 | SNP | C | LH82 | G | 5CM1 | | | | |
| 335 | Amplicon993299 | 104672 | 124 | 124 | SNP | A | LH82 | C | 5CM1 | | | | |
| 336 | Amplicon993328 | 104809 | 22 | 22 | SNP | C | LH82 | T | 5CM1 | | | | |
| 336 | Amplicon993328 | 104810 | 23 | 23 | SNP | G | 5CM1 | T | LH82 | | | | |
| 336 | Amplicon993328 | 104811 | 24 | 24 | SNP | A | 5CM1 | G | LH82 | | | | |
| 336 | Amplicon993328 | 104812 | 25 | 25 | SNP | C | LH82 | T | 5CM1 | | | | |
| 336 | Amplicon993328 | 104813 | 26 | 26 | SNP | C | LH82 | T | 5CM1 | | | | |
| 336 | Amplicon993328 | 104814 | 27 | 27 | SNP | A | LH82 | C | 5CM1 | | | | |
| 336 | Amplicon993328 | 104815 | 28 | 28 | SNP | C | 5CM1 | G | LH82 | | | | |
| 336 | Amplicon993328 | 104816 | 29 | 29 | SNP | A | LH82 | G | 5CM1 | | | | |
| 336 | Amplicon993328 | 104817 | 30 | 30 | SNP | A | 5CM1 | G | LH82 | | | | |
| 336 | Amplicon993328 | 104818 | 31 | 31 | SNP | A | LH82 | T | 5CM1 | | | | |
| 336 | Amplicon993328 | 104819 | 33 | 33 | SNP | A | 5CM1 | C | LH82 | | | | |
| 336 | Amplicon993328 | 104820 | 34 | 34 | SNP | A | LH82 | C | 5CM1 | | | | |
| 336 | Amplicon993328 | 104821 | 35 | 35 | SNP | A | 5CM1 | T | LH82 | | | | |
| 336 | Amplicon993328 | 104822 | 45 | 45 | SNP | A | 5CM1 | C | LH82 | | | | |
| 336 | Amplicon993328 | 104823 | 96 | 96 | SNP | A | LH82 | C | 5CM1 | | | | |
| 336 | Amplicon993328 | 104824 | 97 | 99 | IND | *** | 5CM1 | AAA | LH82 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 336 | Ampli-con993328 | 104825 | 183 | 183 | SNP | C | LH82 | T | 5CM1 | | | | |
| 336 | Ampli-con993328 | 104826 | 212 | 212 | SNP | C | 5CM1 | T | LH82 | | | | |
| 336 | Ampli-con993328 | 104827 | 275 | 275 | SNP | A | 5CM1 | G | LH82 | | | | |
| 336 | Ampli-con993328 | 104828 | 474 | 474 | SNP | C | 5CM1 | T | LH82 | | | | |
| 337 | Ampli-con993333 | 104845 | 32 | 32 | SNP | A | 5CM1 | G | LH82 | | | | |
| 337 | Ampli-con993333 | 104846 | 40 | 40 | SNP | C | 5CM1 | T | LH82 | | | | |
| 337 | Ampli-con993333 | 104847 | 141 | 141 | SNP | A | 5CM1 | T | 5CM1 | | | | |
| 337 | Ampli-con993333 | 104848 | 323 | 323 | SNP | A | LH82 | C | 5CM1 | | | | |
| 337 | Ampli-con993333 | 104849 | 365 | 365 | SNP | G | LH82 | T | LH82 | | | | |
| 337 | Ampli-con993333 | 104850 | 399 | 399 | SNP | A | 5CM1 | C | LH82 | | | | |
| 337 | Ampli-con993333 | 104851 | 431 | 431 | SNP | G | LH82 | T | 5CM1 | | | | |
| 337 | Ampli-con993333 | 104852 | 434 | 434 | SNP | C | 5CM1 | T | LH82 | | | | |
| 337 | Ampli-con993333 | 104853 | 455 | 455 | SNP | A | LH82 | T | 5CM1 | | | | |
| 337 | Ampli-con993333 | 104854 | 456 | 456 | SNP | A | LH82 | T | 5CM1 | | | | |
| 337 | Ampli-con993333 | 104855 | 460 | 460 | IND | * | LH82 | C | 5CM1 | | | | |
| 338 | Ampli-con993333 | 104857 | 84 | 84 | SNP | C | LH82 | T | 5CM1 | | | | |
| 338 | Ampli-con993334 | 104858 | 172 | 174 | IND | *** | LH82 | GCT | 5CM1 | | | | |
| 338 | Ampli-con993334 | 104859 | 209 | 209 | SNP | C | LH82 | T | 5CM1 | | | | |
| 338 | Ampli-con993334 | 104860 | 417 | 417 | SNP | C | LH82 | G | 5CM1 | | | | |
| 339 | Ampli-con993334 | 104861 | 224 | 224 | SNP | G | 5CM1 | T | LH82 | | | | |
| 339 | Ampli-con993335 | 104862 | 320 | 320 | SNP | C | LH82 | T | 5CM1 | | | | |
| 340 | Ampli-con993348 | 104939 | 36 | 36 | SNP | A | LH82 | G | 5CM1 | | | | |
| 340 | Ampli-con993348 | 104940 | 46 | 46 | SNP | C | 5CM1 | T | LH82 | | | | |
| 340 | Ampli-con993348 | 104941 | 53 | 53 | SNP | C | LH82 | G | 5CM1 | | | | |
| 340 | Ampli-con993348 | 104942 | 60 | 60 | SNP | A | 5CM1 | G | LH82 | | | | |
| 340 | Ampli-con993348 | 104943 | 64 | 64 | SNP | A | 5CM1 | G | LH82 | | | | |
| 340 | Ampli-con993348 | 104944 | 81 | 90 | IND | ********** | 5CM1 | CATTTTCAGT | LH82 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 340 | Ampli-con993348 | 104945 | 111 | 111 | SNP | G | 5CM1 | T | LH82 | | | | |
| 340 | Ampli-con993348 | 104946 | 268 | 268 | SNP | A | 5CM1 | T | LH82 | | | | |
| 340 | Ampli-con993348 | 104947 | 273 | 273 | SNP | A | LH82 | G | 5CM1 | | | | |
| 340 | Ampli-con993348 | 104948 | 295 | 295 | SNP | C | LH82 | T | 5CM1 | | | | |
| 340 | Ampli-con993348 | 104949 | 394 | 394 | SNP | A | LH82 | G | 5CM1 | | | | |
| 341 | Ampli-con993350 | 104950 | 76 | 76 | SNP | A | 5CM1 | G | LH82 | | | | |
| 341 | Ampli-con993350 | 104951 | 126 | 126 | SNP | G | 5CM1 | T | LH82 | | | | |
| 341 | Ampli-con993350 | 104952 | 162 | 162 | SNP | A | LH82 | T | 5CM1 | | | | |
| 341 | Ampli-con993350 | 104953 | 314 | 314 | SNP | A | 5CM1 | G | LH82 | | | | |
| 341 | Ampli-con993350 | 104954 | 375 | 375 | SNP | G | 5CM1 | T | LH82 | | | | |
| 342 | Ampli-con993378 | 105008 | 68 | 71 | IND | **** | LH82 | GTGC | 5CM1 | | | | |
| 342 | Ampli-con993378 | 105009 | 97 | 97 | SNP | A | 5CM1 | G | LH82 | | | | |
| 342 | Ampli-con993378 | 105010 | 113 | 113 | SNP | A | 5CM1 | G | LH82 | | | | |
| 342 | Ampli-con993378 | 105011 | 116 | 116 | SNP | C | LH82 | T | 5CM1 | | | | |
| 342 | Ampli-con993378 | 105012 | 270 | 270 | SNP | A | 5CM1 | G | LH82 | | | | |
| 342 | Ampli-con993378 | 105013 | 273 | 273 | SNP | C | 5CM1 | T | LH82 | | | | |
| 342 | Ampli-con993378 | 105014 | 347 | 347 | SNP | C | 5CM1 | G | LH82 | | | | |
| 342 | Ampli-con993378 | 105015 | 428 | 428 | SNP | C | LH82 | T | 5CM1 | | | | |
| 342 | Ampli-con993378 | 105016 | 430 | 430 | SNP | C | 5CM1 | G | LH82 | | | | |
| 342 | Ampli-con993378 | 105017 | 436 | 436 | SNP | A | 5CM1 | T | LH82 | | | | |
| 342 | Ampli-con993378 | 105018 | 438 | 438 | SNP | C | LH82 | T | 5CM1 | | | | |
| 342 | Ampli-con993378 | 105019 | 439 | 439 | SNP | G | LH82 | T | 5CM1 | | | | |
| 343 | Ampli-con993485 | 105546 | 103 | 105 | IND | *** | 5CM1 | AGC | LH82 | | | | |
| 343 | Ampli-con993485 | 105547 | 163 | 168 | IND | ****** | LH82 | GACTGC | 5CM1 | | | | |
| 343 | Ampli-con993485 | 105548 | 221 | 221 | SNP | A | 5CM1 | C | LH82 | | | | |
| 343 | Ampli-con993485 | 105549 | 229 | 229 | SNP | C | LH82 | G | 5CM1 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 344 | Ampli-con993496 | 105584 | 79 | 80 | IND | ** | 5CM1 | CT | LH82 | | | | |
| 344 | Ampli-con993496 | 105586 | 173 | 173 | SNP | C | 5CM1 | G | LH82 | | | | |
| 344 | Ampli-con993496 | 105587 | 376 | 376 | SNP | A | 5CM1 | G | LH82 | | | | |
| 344 | Ampli-con993496 | 105588 | 382 | 382 | SNP | G | 5CM1 | T | LH82 | | | | |
| 344 | Ampli-con993496 | 105589 | 469 | 469 | SNP | A | 5CM1 | T | LH82 | | | | |
| 344 | Ampli-con993496 | 105590 | 474 | 474 | SNP | C | LH82 | T | 5CM1 | | | | |
| 344 | Ampli-con993496 | 105591 | 477 | 477 | SNP | G | 5CM1 | T | 5CM1 | | | | |
| 344 | Ampli-con993496 | 105592 | 523 | 523 | SNP | C | LH82 | T | 5CM1 | | | | |
| 344 | Ampli-con993496 | 105593 | 536 | 538 | IND | *** | LH82 | CGT | 5CM1 | | | | |
| 345 | Ampli-con993496 | 105613 | 177 | 177 | SNP | C | 5CM1 | G | LH82 | | | | |
| 346 | Ampli-con993505 | 105647 | 198 | 198 | SNP | G | 5CM1 | T | 5CM1 | | | | |
| 346 | Ampli-con993513 | 105648 | 275 | 275 | SNP | C | LH82 | T | 5CM1 | | | | |
| 347 | Ampli-con993513 | 105854 | 346 | 346 | SNP | A | 5CM1 | G | LH82 | | | | |
| 347 | Ampli-con993561 | 105855 | 481 | 481 | SNP | A | 5CM1 | C | LH82 | | | | |
| 348 | Ampli-con993561 | 106239 | 72 | 72 | SNP | C | LH82 | T | 5CM1 | | | | |
| 348 | Ampli-con993642 | 106240 | 117 | 117 | IND | * | 5CM1 | T | LH82 | | | | |
| 348 | Ampli-con993642 | 106241 | 142 | 142 | SNP | A | LH82 | G | 5CM1 | | | | |
| 348 | Ampli-con993642 | 106242 | 153 | 154 | IND | ** | 5CM1 | TT | LH82 | | | | |
| 348 | Ampli-con993642 | 106243 | 206 | 206 | SNP | G | 5CM1 | T | LH82 | | | | |
| 348 | Ampli-con993642 | 106244 | 311 | 311 | SNP | A | 5CM1 | G | LH82 | | | | |
| 348 | Ampli-con993642 | 106245 | 361 | 361 | SNP | C | 5CM1 | T | 5CM1 | | | | |
| 349 | Ampli-con993642 | 106297 | 237 | 238 | IND | ** | LH82 | GT | 5CM1 | | | | |
| 349 | Ampli-con993659 | 106298 | 292 | 296 | IND | ***** | LH82 | ATAAT | 5CM1 | | | | |
| 349 | Ampli-con993659 | 106299 | 310 | 310 | SNP | G | 5CM1 | T | LH82 | | | | |
| 349 | Ampli-con993659 | 106300 | 328 | 329 | IND | ** | 5CM1 | CT | LH82 | | | | |
| 349 | Ampli-con993659 | 106301 | 420 | 420 | SNP | C | LH82 | T | 5CM1 | | | | |
| 349 | Ampli-con993659 | 106302 | 424 | 424 | SNP | A | 5CM1 | G | LH82 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 349 | Ampli-con993659 | 106303 | 432 | 434 | IND | *** | LH82 | CGG | 5CM1 | | | | |
| 349 | Ampli-con993659 | 106304 | 455 | 455 | SNP | G | LH82 | T | 5CM1 | | | | |
| 350 | Ampli-con993704 | 106482 | 38 | 38 | SNP | A | 5CM1 | C | LH82 | | | | |
| 350 | Ampli-con993704 | 106483 | 80 | 80 | IND | * | LH82 | A | 5CM1 | | | | |
| 350 | Ampli-con993704 | 106484 | 89 | 89 | SNP | A | 5CM1 | C | LH82 | | | | |
| 350 | Ampli-con993704 | 106485 | 91 | 91 | SNP | C | LH82 | T | 5CM1 | | | | |
| 350 | Ampli-con993704 | 106486 | 109 | 109 | SNP | A | 5CM1 | G | LH82 | | | | |
| 350 | Ampli-con993704 | 106487 | 126 | 126 | SNP | A | 5CM1 | G | LH82 | | | | |
| 350 | Ampli-con993704 | 106488 | 235 | 235 | SNP | C | 5CM1 | G | LH82 | | | | |
| 350 | Ampli-con993704 | 106489 | 354 | 354 | SNP | A | 5CM1 | G | LH82 | | | | |
| 350 | Ampli-con993704 | 106490 | 387 | 387 | SNP | A | 5CM1 | G | LH82 | | | | |
| 350 | Ampli-con993704 | 106491 | 393 | 393 | SNP | C | LH82 | T | 5CM1 | | | | |
| 351 | Ampli-con993739 | 106669 | 152 | 152 | SNP | C | 5CM1 | T | LH82 | | | | |
| 351 | Ampli-con993739 | 106670 | 172 | 172 | SNP | C | LH82 | G | 5CM1 | | | | |
| 351 | Ampli-con993739 | 106671 | 182 | 182 | SNP | A | 5CM1 | T | LH82 | | | | |
| 351 | Ampli-con993739 | 106672 | 183 | 183 | SNP | A | 5CM1 | C | LH82 | | | | |
| 351 | Ampli-con993739 | 106673 | 216 | 219 | IND | **** | LH82 | TATA | 5CM1 | | | | |
| 351 | Ampli-con993739 | 106674 | 235 | 236 | IND | ** | 5CM1 | CT | LH82 | | | | |
| 351 | Ampli-con993739 | 106675 | 241 | 244 | IND | **** | 5CM1 | CTAT | LH82 | | | | |
| 351 | Ampli-con993739 | 106676 | 247 | 247 | SNP | A | LH82 | G | 5CM1 | | | | |
| 351 | Ampli-con993739 | 106677 | 262 | 263 | IND | ** | LH82 | AC | 5CM1 | | | | |
| 351 | Ampli-con993739 | 106678 | 308 | 308 | SNP | C | LH82 | G | 5CM1 | | | | |
| 351 | Ampli-con993739 | 106679 | 319 | 319 | SNP | C | 5CM1 | T | LH82 | | | | |
| 351 | Ampli-con993739 | 106680 | 325 | 325 | SNP | C | 5CM1 | T | LH82 | | | | |
| 351 | Ampli-con993739 | 106681 | 355 | 355 | SNP | C | 5CM1 | T | LH82 | | | | |
| 352 | Ampli-con993761 | 106742 | 107 | 107 | SNP | A | 5CM1 | G | LH82 | | | | |
| 352 | Ampli-con993761 | 106743 | 234 | 234 | SNP | A | 5CM1 | G | LH82 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 352 | Ampli-con993761 | 106744 | 273 | 273 | SNP | A | 5CM1 | G | LH82 | | | | |
| 352 | Ampli-con993761 | 106745 | 501 | 501 | SNP | C | 5CM1 | T | LH82 | | | | |
| 353 | Ampli-con993787 | 106842 | 388 | 388 | SNP | A | 5CM1 | G | LH82 | | | | |
| 354 | Ampli-con993789 | 106844 | 81 | 81 | SNP | A | 5CM1 | G | LH82 | | | | |
| 354 | Ampli-con993789 | 106845 | 109 | 109 | SNP | A | LH82 | G | 5CM1 | | | | |
| 355 | Ampli-con993806 | 106912 | 182 | 182 | SNP | C | LH82 | G | 5CM1 | | | | |
| 356 | Ampli-con993827 | 107061 | 238 | 244 | IND | ******* | 5CM1 | GTATGAA | LH82 | | | | |
| 357 | Ampli-con993841 | 107074 | 180 | 180 | SNP | C | 5CM1 | T | LH82 | | | | |
| 357 | Ampli-con993841 | 107075 | 194 | 194 | SNP | C | 5CM1 | T | LH82 | | | | |
| 357 | Ampli-con993841 | 107076 | 205 | 205 | SNP | C | LH82 | T | 5CM1 | | | | |
| 357 | Ampli-con993841 | 107077 | 380 | 380 | SNP | A | LH82 | G | 5CM1 | | | | |
| 357 | Ampli-con993841 | 107078 | 431 | 431 | SNP | C | LH82 | T | 5CM1 | | | | |
| 358 | Ampli-con993884 | 107274 | 79 | 79 | SNP | C | 5CM1 | G | LH82 | | | | |
| 358 | Ampli-con993884 | 107275 | 289 | 289 | SNP | C | 5CM1 | T | LH82 | | | | |
| 358 | Ampli-con993884 | 107276 | 401 | 401 | SNP | A | LH82 | G | 5CM1 | | | | |
| 358 | Ampli-con993884 | 107277 | 486 | 486 | IND | * | LH82 | G | 5CM1 | | | | |
| 358 | Ampli-con993884 | 107278 | 487 | 489 | IND | *** | 5CM1 | GTG | LH82 | | | | |
| 359 | Ampli-con993886 | 107279 | 159 | 159 | SNP | A | 5CM1 | G | LH82 | | | | |
| 359 | Ampli-con993886 | 107280 | 165 | 165 | SNP | A | LH82 | G | 5CM1 | | | | |
| 359 | Ampli-con993886 | 107285 | 211 | 211 | SNP | A | LH82 | G | 5CM1 | | | | |
| 359 | Ampli-con993886 | 107286 | 256 | 256 | SNP | C | LH82 | T | 5CM1 | | | | |
| 360 | Ampli-con993907 | 107396 | 74 | 76 | IND | *** | LH82 | AGC | 5CM1 | | | | |
| 360 | Ampli-con993907 | 107397 | 90 | 90 | SNP | C | LH82 | G | 5CM1 | | | | |
| 360 | Ampli-con993907 | 107398 | 213 | 213 | SNP | A | 5CM1 | T | LH82 | | | | |
| 361 | Ampli-con993920 | 107449 | 284 | 284 | SNP | C | LH82 | T | 5CM1 | | | | |
| 362 | Ampli-con993953 | 107617 | 110 | 110 | SNP | C | 5CM1 | T | LH82 | | | | |
| 362 | Ampli-con993953 | 107618 | 125 | 125 | SNP | C | LH82 | T | 5CM1 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 362 | Amplicon993953 | 107619 | 127 | 127 | SNP | G | 5CM1 | T | LH82 | | | | |
| 362 | Amplicon993953 | 107620 | 347 | 347 | SNP | A | 5CM1 | G | LH82 | | | | |
| 362 | Amplicon993953 | 107621 | 365 | 371 | IND | ******** | LH82 | GTTACAA | 5CM1 | | | | |
| 363 | Amplicon993958 | 107639 | 206 | 206 | SNP | A | 5CM1 | T | LH82 | | | | |
| 364 | Amplicon993973 | 107693 | 86 | 86 | SNP | C | LH82 | T | 5CM1 | | | | |
| 364 | Amplicon993973 | 107694 | 155 | 155 | SNP | C | 5CM1 | T | LH82 | | | | |
| 364 | Amplicon993973 | 107695 | 160 | 160 | SNP | A | LH82 | G | 5CM1 | | | | |
| 364 | Amplicon993973 | 107696 | 180 | 188 | IND | ********** | LH82 | AAATTTGGT | 5CM1 | | | | |
| 364 | Amplicon993973 | 107697 | 212 | 212 | SNP | A | 5CM1 | G | LH82 | | | | |
| 364 | Amplicon993973 | 107698 | 293 | 293 | SNP | C | LH82 | T | 5CM1 | | | | |
| 364 | Amplicon993973 | 107699 | 336 | 336 | SNP | A | LH82 | G | 5CM1 | | | | |
| 364 | Amplicon993973 | 107700 | 372 | 372 | SNP | A | LH82 | G | 5CM1 | | | | |
| 364 | Amplicon993973 | 107701 | 376 | 376 | SNP | A | 5CM1 | G | LH82 | | | | |
| 364 | Amplicon993973 | 107702 | 441 | 441 | IND | * | LH82 | A | 5CM1 | | | | |
| 365 | Amplicon994009 | 107784 | 96 | 96 | SNP | G | LH82 | T | 5CM1 | | | | |
| 365 | Amplicon994009 | 107785 | 117 | 117 | SNP | C | 5CM1 | G | LH82 | | | | |
| 365 | Amplicon994009 | 107786 | 166 | 166 | SNP | A | LH82 | G | 5CM1 | | | | |
| 365 | Amplicon994009 | 107787 | 174 | 174 | SNP | A | 5CM1 | C | LH82 | | | | |
| 365 | Amplicon994009 | 107788 | 537 | 537 | SNP | A | LH82 | T | 5CM1 | | | | |
| 366 | Amplicon994012 | 107839 | 34 | 34 | IND | * | LH82 | T | 5CM1 | | | | |
| 366 | Amplicon994012 | 107840 | 153 | 153 | SNP | C | 5CM1 | G | LH82 | | | | |
| 366 | Amplicon994012 | 107841 | 211 | 211 | SNP | A | LH82 | C | 5CM1 | | | | |
| 366 | Amplicon994012 | 107842 | 220 | 220 | SNP | A | 5CM1 | G | LH82 | | | | |
| 366 | Amplicon994012 | 107844 | 423 | 431 | IND | ********** | 5CM1 | TATTTTCGT | LH82 | | | | |
| 366 | Amplicon994012 | 107845 | 447 | 447 | SNP | G | LH82 | T | 5CM1 | | | | |
| 367 | Amplicon994024 | 107857 | 186 | 188 | IND | *** | LH82 | TAA | 5CM1 | | | | |
| 367 | Amplicon994024 | 107858 | 400 | 400 | SNP | C | 5CM1 | T | LH82 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 367 | Ampli-con994024 | 107859 | 448 | 448 | IND | * | LH82 | A | 5CM1 | | | | |
| 367 | Ampli-con994024 | 107860 | 474 | 474 | SNP | C | 5CM1 | T | LH82 | | | | |
| 367 | Ampli-con994024 | 107861 | 478 | 478 | SNP | A | LH82 | G | 5CM1 | | | | |
| 368 | Ampli-con994036 | 107908 | 92 | 92 | SNP | G | 5CM1 | T | LH82 | | | | |
| 368 | Ampli-con994036 | 107909 | 151 | 151 | SNP | A | 5CM1 | G | LH82 | | | | |
| 368 | Ampli-con994036 | 107910 | 319 | 319 | SNP | A | 5CM1 | T | LH82 | | | | |
| 368 | Ampli-con994036 | 107911 | 384 | 384 | SNP | G | LH82 | T | 5CM1 | | | | |
| 368 | Ampli-con994036 | 107912 | 442 | 442 | SNP | C | LH82 | T | 5CM1 | | | | |
| 368 | Ampli-con994036 | 107913 | 473 | 473 | SNP | C | LH82 | T | 5CM1 | | | | |
| 369 | Ampli-con994045 | 107937 | 310 | 310 | SNP | A | 5CM1 | G | LH82 | | | | |
| 369 | Ampli-con994045 | 107938 | 331 | 331 | SNP | A | LH82 | T | 5CM1 | | | | |
| 369 | Ampli-con994045 | 107939 | 339 | 339 | SNP | G | LH82 | T | 5CM1 | | | | |
| 369 | Ampli-con994045 | 107940 | 415 | 415 | SNP | A | 5CM1 | C | LH82 | | | | |
| 370 | Ampli-con994047 | 107941 | 365 | 365 | SNP | A | LH82 | G | 5CM1 | | | | |
| 371 | Ampli-con994062 | 108008 | 100 | 100 | SNP | A | LH82 | G | 5CM1 | | | | |
| 371 | Ampli-con994062 | 108009 | 133 | 133 | SNP | C | LH82 | G | 5CM1 | | | | |
| 371 | Ampli-con994062 | 108010 | 153 | 153 | IND | * | LH82 | T | 5CM1 | | | | |
| 371 | Ampli-con994062 | 108011 | 176 | 176 | SNP | C | 5CM1 | T | LH82 | | | | |
| 372 | Ampli-con994062 | 108012 | 233 | 233 | SNP | C | 5CM1 | T | LH82 | | | | |
| 372 | Ampli-con994062 | 108013 | 339 | 339 | SNP | C | 5CM1 | T | LH82 | | | | |
| 372 | Ampli-con994062 | 108211 | 235 | 235 | SNP | A | 5CM1 | G | LH82 | | | | |
| 372 | Ampli-con994124 | 108212 | 336 | 337 | IND | ** | LH82 | GA | 5CM1 | | | | |
| 373 | Ampli-con994124 | 108432 | 59 | 59 | SNP | C | LH82 | T | 5CM1 | | | | |
| 373 | Ampli-con1017005 | 108433 | 227 | 227 | SNP | C | 5CM1 | T | LH82 | | | | |
| 373 | Ampli-con1017005 | 108434 | 240 | 240 | SNP | A | 5CM1 | G | LH82 | | | | |
| 373 | Ampli-con1017005 | 108435 | 268 | 268 | SNP | G | 5CM1 | T | LH82 | | | | |
| 373 | Ampli-con1017005 | 108436 | 382 | 382 | SNP | C | 5CM1 | T | LH82 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 373 | Ampli-con1017005 | 108437 | 479 | 479 | SNP | A | LH82 | G | 5CM1 | | | | |
| 373 | Ampli-con1017005 | 108438 | 502 | 502 | SNP | A | 5CM1 | G | LH82 | | | | |
| 373 | Ampli-con1017005 | 108439 | 513 | 513 | SNP | A | 5CM1 | T | LH82 | | | | |
| 373 | Ampli-con1017005 | 108440 | 514 | 514 | SNP | A | 5CM1 | G | LH82 | | | | |
| 373 | Ampli-con1017005 | 108441 | 515 | 515 | SNP | A | LH82 | T | 5CM1 | | | | |
| 373 | Ampli-con1017005 | 108442 | 516 | 516 | SNP | G | LH82 | T | 5CM1 | | | | |
| 373 | Ampli-con1017005 | 108443 | 518 | 518 | SNP | A | LH82 | T | 5CM1 | | | | |
| 373 | Ampli-con1017005 | 108444 | 519 | 519 | SNP | C | LH82 | T | 5CM1 | | | | |
| 373 | Ampli-con1017005 | 108445 | 520 | 520 | SNP | A | LH82 | C | 5CM1 | | | | |
| 373 | Ampli-con1017005 | 108446 | 521 | 521 | SNP | C | 5CM1 | G | LH82 | | | | |
| 373 | Ampli-con1017005 | 108447 | 522 | 522 | SNP | C | LH82 | T | 5CM1 | | | | |
| 373 | Ampli-con1017005 | 108448 | 523 | 523 | SNP | A | LH82 | T | 5CM1 | | | | |
| 373 | Ampli-con1017005 | 108449 | 524 | 524 | SNP | C | LH82 | G | 5CM1 | | | | |
| 373 | Ampli-con1017005 | 108450 | 525 | 525 | SNP | C | LH82 | T | 5CM1 | | | | |
| 373 | Ampli-con1017005 | 108451 | 526 | 526 | SNP | A | LH82 | T | 5CM1 | | | | |
| 373 | Ampli-con1017005 | 108452 | 527 | 527 | SNP | A | 5CM1 | C | LH82 | | | | |
| 373 | Ampli-con1017005 | 108453 | 530 | 530 | SNP | C | 5CM1 | T | LH82 | | | | |
| 373 | Ampli-con1017005 | 108454 | 531 | 531 | SNP | A | LH82 | T | 5CM1 | | | | |
| 373 | Ampli-con1017005 | 108455 | 532 | 532 | SNP | A | LH82 | T | 5CM1 | | | | |
| 373 | Ampli-con1017005 | 108456 | 533 | 533 | SNP | A | LH82 | T | 5CM1 | | | | |
| 373 | Ampli-con1017005 | 108457 | 534 | 534 | SNP | G | 5CM1 | G | LH82 | | | | |
| 373 | Ampli-con1017005 | 108458 | 535 | 535 | SNP | G | LH82 | T | 5CM1 | | | | |
| 373 | Ampli-con1017005 | 108459 | 536 | 536 | SNP | G | LH82 | T | 5CM1 | | | | |
| 373 | Ampli-con1017005 | 108460 | 538 | 538 | SNP | A | LH82 | T | 5CM1 | | | | |
| 373 | Ampli-con1017005 | 108461 | 539 | 539 | SNP | C | LH82 | T | 5CM1 | | | | |
| 373 | Ampli-con1017005 | 108462 | 540 | 540 | SNP | G | LH82 | T | 5CM1 | | | | |
| 373 | Ampli-con1017005 | 108463 | 541 | 541 | SNP | A | LH82 | T | 5CM1 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 373 | Ampli-con1017005 | 108464 | 542 | 542 | SNP | A | LH82 | T | 5CM1 | | | | |
| 373 | Ampli-con1017005 | 108465 | 544 | 544 | SNP | G | 5CM1 | T | LH82 | | | | |
| 373 | Ampli-con1017005 | 108466 | 546 | 546 | SNP | A | LH82 | T | 5CM1 | | | | |
| 373 | Ampli-con1017005 | 108467 | 547 | 547 | SNP | A | LH82 | T | 5CM1 | | | | |
| 373 | Ampli-con1017005 | 108468 | 549 | 549 | SNP | A | LH82 | T | 5CM1 | | | | |
| 373 | Ampli-con1017005 | 108469 | 551 | 551 | SNP | A | 5CM1 | C | LH82 | | | | |
| 373 | Ampli-con1017005 | 108470 | 552 | 552 | SNP | A | 5CM1 | C | LH82 | | | | |
| 373 | Ampli-con1017005 | 108471 | 553 | 553 | SNP | A | 5CM1 | C | LH82 | | | | |
| 373 | Ampli-con1017005 | 108472 | 554 | 554 | SNP | G | 5CM1 | T | LH82 | | | | |
| 373 | Ampli-con1017005 | 108473 | 556 | 556 | SNP | A | LH82 | T | 5CM1 | | | | |
| 373 | Ampli-con1017005 | 108474 | 557 | 557 | SNP | A | LH82 | G | 5CM1 | | | | |
| 373 | Ampli-con1017005 | 108475 | 558 | 558 | SNP | A | LH82 | C | 5CM1 | | | | |
| 373 | Ampli-con1017005 | 108476 | 559 | 559 | SNP | A | LH82 | C | 5CM1 | | | | |
| 373 | Ampli-con1017005 | 108477 | 561 | 561 | SNP | A | LH82 | G | 5CM1 | | | | |
| 373 | Ampli-con1017005 | 108478 | 562 | 562 | SNP | A | 5CM1 | T | LH82 | | | | |
| 373 | Ampli-con1017005 | 108479 | 564 | 564 | SNP | A | 5CM1 | C | LH82 | | | | |
| 373 | Ampli-con1017005 | 108480 | 565 | 565 | SNP | A | 5CM1 | T | LH82 | | | | |
| 373 | Ampli-con1017005 | 108481 | 566 | 566 | SNP | A | LH82 | T | 5CM1 | | | | |
| 373 | Ampli-con1017005 | 108482 | 567 | 567 | SNP | A | 5CM1 | T | LH82 | | | | |
| 373 | Ampli-con1017005 | 108483 | 568 | 568 | SNP | A | 5CM1 | T | LH82 | | | | |
| 373 | Ampli-con1017005 | 108484 | 569 | 569 | SNP | C | 5CM1 | T | LH82 | | | | |
| 373 | Ampli-con1017005 | 108486 | 571 | 571 | SNP | C | 5CM1 | T | LH82 | | | | |
| 373 | Ampli-con1017005 | 108489 | 575 | 575 | SNP | C | 5CM1 | T | LH82 | | | | |
| 374 | Ampli-con1017007 | 108492 | 126 | 126 | SNP | A | LH82 | T | 5CM1 | | | | |
| 374 | Ampli-con1017007 | 108493 | 303 | 303 | SNP | G | LH82 | T | 5CM1 | | | | |
| 374 | Ampli-con1017007 | 108494 | 356 | 356 | SNP | C | LH82 | T | 5CM1 | | | | |
| 374 | Ampli-con1017007 | 108495 | 480 | 480 | SNP | C | LH82 | T | 5CM1 | | | | |

-continued

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 375 | Amplicon1017028 | 108630 | 340 | 340 | SNP | A | 5CM1 | G | LH82 | | | | |
| 376 | Amplicon1017085 | 108862 | 48 | 48 | SNP | C | LH82 | T | 5CM1 | | | | |
| 376 | Amplicon1017085 | 108863 | 111 | 111 | SNP | C | 5CM1 | G | LH82 | | | | |
| 376 | Amplicon1017085 | 108864 | 118 | 118 | SNP | A | 5CM1 | T | 5CM1 | | | | |
| 376 | Amplicon1017085 | 108865 | 188 | 188 | SNP | C | LH82 | G | 5CM1 | | | | |
| 376 | Amplicon1017085 | 108866 | 296 | 296 | SNP | A | LH82 | C | 5CM1 | | | | |
| 376 | Amplicon1017085 | 108867 | 298 | 298 | SNP | G | 5CM1 | T | LH82 | | | | |
| 376 | Amplicon1017085 | 108868 | 383 | 384 | IND | ** | LH82 | AC | 5CM1 | | | | |
| 376 | Amplicon1017085 | 108869 | 388 | 388 | SNP | A | 5CM1 | G | LH82 | | | | |
| 376 | Amplicon1017085 | 108870 | 411 | 411 | SNP | A | 5CM1 | G | LH82 | | | | |
| 376 | Amplicon1017085 | 108871 | 435 | 435 | SNP | A | 5CM1 | G | LH82 | | | | |
| 376 | Amplicon1017085 | 108872 | 440 | 440 | SNP | C | 5CM1 | T | LH82 | | | | |
| 376 | Amplicon1017085 | 108873 | 496 | 497 | IND | ** | LH82 | GA | 5CM1 | | | | |
| 376 | Amplicon1017085 | 108874 | 524 | 524 | SNP | C | LH82 | T | 5CM1 | | | | |
| 376 | Amplicon1017085 | 108875 | 582 | 582 | SNP | A | LH82 | T | LH82 | | | | |
| 377 | Amplicon1017165 | 109198 | 89 | 89 | SNP | A | LH82 | C | 5CM1 | | | | |
| 377 | Amplicon1017165 | 109199 | 90 | 90 | IND | * | LH82 | T | 5CM1 | | | | |
| 377 | Amplicon1017165 | 109200 | 94 | 95 | IND | ** | LH82 | CC | 5CM1 | | | | |
| 377 | Amplicon1017165 | 109201 | 97 | 97 | SNP | A | 5CM1 | G | LH82 | | | | |
| 377 | Amplicon1017165 | 109202 | 99 | 99 | SNP | C | LH82 | T | 5CM1 | | | | |
| 377 | Amplicon1017165 | 109203 | 100 | 100 | SNP | A | 5CM1 | C | LH82 | | | | |
| 377 | Amplicon1017165 | 109204 | 102 | 102 | SNP | C | 5CM1 | G | LH82 | | | | |
| 377 | Amplicon1017165 | 109205 | 106 | 106 | SNP | C | 5CM1 | G | LH82 | | | | |
| 377 | Amplicon1017165 | 109206 | 107 | 107 | SNP | A | LH82 | G | 5CM1 | | | | |
| 377 | Amplicon1017165 | 109207 | 150 | 150 | SNP | C | 5CM1 | T | LH82 | | | | |
| 377 | Amplicon1017165 | 109208 | 159 | 159 | SNP | A | 5CM1 | G | LH82 | | | | |
| 377 | Amplicon1017165 | 109209 | 272 | 272 | SNP | G | LH82 | T | 5CM1 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 377 | Ampli-con1017165 | 109210 | 299 | 299 | SNP | G | 5CM1 | T | LH82 | | | | |
| 377 | Ampli-con1017165 | 109211 | 303 | 303 | SNP | A | LH82 | G | 5CM1 | | | | |
| 377 | Ampli-con1017165 | 109212 | 477 | 477 | SNP | A | 5CM1 | C | LH82 | | | | |
| 377 | Ampli-con1017165 | 109213 | 478 | 478 | SNP | A | 5CM1 | G | LH82 | | | | |
| 377 | Ampli-con1017165 | 109214 | 479 | 479 | SNP | A | 5CM1 | G | LH82 | | | | |
| 377 | Ampli-con1017165 | 109215 | 506 | 506 | SNP | A | LH82 | G | 5CM1 | | | | |
| 377 | Ampli-con1017165 | 109216 | 530 | 530 | SNP | G | 5CM1 | T | LH82 | | | | |
| 377 | Ampli-con1017165 | 109217 | 548 | 548 | SNP | C | LH82 | T | 5CM1 | | | | |
| 377 | Ampli-con1017165 | 109218 | 575 | 575 | SNP | C | 5CM1 | G | LH82 | | | | |
| 377 | Ampli-con1017165 | 109219 | 581 | 581 | IND | * | 5CM1 | C | LH82 | | | | |
| 377 | Ampli-con1017165 | 109220 | 585 | 585 | IND | * | 5CM1 | C | LH82 | | | | |
| 377 | Ampli-con1017165 | 109221 | 593 | 593 | SNP | A | LH82 | C | 5CM1 | | | | |
| 377 | Ampli-con1017165 | 109222 | 595 | 595 | SNP | A | LH82 | C | 5CM1 | | | | |
| 378 | Ampli-con1017176 | 109306 | 27 | 27 | SNP | A | LH82 | C | 5CM1 | | | | |
| 378 | Ampli-con1017176 | 109307 | 70 | 70 | SNP | A | LH82 | G | 5CM1 | | | | |
| 378 | Ampli-con1017176 | 109308 | 72 | 72 | IND | * | 5CM1 | G | LH82 | | | | |
| 378 | Ampli-con1017176 | 109309 | 78 | 78 | IND | * | 5CM1 | T | LH82 | | | | |
| 378 | Ampli-con1017176 | 109310 | 80 | 80 | SNP | A | LH82 | G | 5CM1 | | | | |
| 378 | Ampli-con1017176 | 109311 | 127 | 127 | SNP | C | 5CM1 | T | LH82 | | | | |
| 378 | Ampli-con1017176 | 109312 | 145 | 145 | SNP | C | 5CM1 | T | LH82 | | | | |
| 378 | Ampli-con1017176 | 109313 | 175 | 176 | IND | ** | 5CM1 | AT | LH82 | | | | |
| 378 | Ampli-con1017176 | 109314 | 250 | 250 | SNP | G | LH82 | T | 5CM1 | | | | |
| 378 | Ampli-con1017176 | 109315 | 268 | 268 | SNP | C | LH82 | T | 5CM1 | | | | |
| 379 | Ampli-con1017183 | 109328 | 565 | 565 | SNP | A | LH82 | G | 5CM1 | | | | |
| 380 | Ampli-con1017186 | 109342 | 525 | 525 | SNP | A | LH82 | G | 5CM1 | | | | |
| 381 | Ampli-con1017193 | 109396 | 439 | 448 | IND | ********** | LH82 | ACACACAC | 5CM1 | | | | |
| 381 | Ampli-con1017193 | 109397 | 481 | 481 | SNP | C | LH82 | G | 5CM1 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 381 | Ampli-con1017193 | 109398 | 487 | 490 | IND | **** | LH82 | CTCA | 5CM1 | | | | |
| 381 | Ampli-con1017193 | 109399 | 495 | 495 | SNP | C | LH82 | G | 5CM1 | | | | |
| 381 | Ampli-con1017193 | 109400 | 499 | 499 | SNP | C | LH82 | G | 5CM1 | | | | |
| 381 | Ampli-con1017193 | 109401 | 503 | 503 | SNP | C | LH82 | G | 5CM1 | | | | |
| 381 | Ampli-con1017193 | 109402 | 510 | 510 | SNP | A | 5CM1 | G | LH82 | | | | |
| 381 | Ampli-con1017193 | 109403 | 522 | 524 | IND | *** | LH82 | TTC | 5CM1 | | | | |
| 381 | Ampli-con1017193 | 109404 | 539 | 539 | SNP | C | LH82 | G | 5CM1 | | | | |
| 382 | Ampli-con1017219 | 109508 | 47 | 47 | SNP | C | LH82 | T | 5CM1 | | | | |
| 382 | Ampli-con1017219 | 109509 | 53 | 53 | SNP | A | 5CM1 | G | LH82 | | | | |
| 382 | Ampli-con1017219 | 109510 | 155 | 155 | SNP | C | LH82 | T | 5CM1 | | | | |
| 382 | Ampli-con1017219 | 109511 | 179 | 179 | SNP | G | LH82 | T | 5CM1 | | | | |
| 382 | Ampli-con1017219 | 109512 | 187 | 187 | SNP | C | LH82 | G | 5CM1 | | | | |
| 382 | Ampli-con1017219 | 109513 | 204 | 204 | SNP | C | LH82 | G | 5CM1 | | | | |
| 382 | Ampli-con1017219 | 109514 | 206 | 208 | IND | *** | 5CM1 | CAC | LH82 | | | | |
| 382 | Ampli-con1017219 | 109516 | 214 | 218 | IND | ***** | 5CM1 | TTCCT | LH82 | | | | |
| 383 | Ampli-con1017256 | 109666 | 74 | 74 | SNP | C | LH82 | G | 5CM1 | | | | |
| 383 | Ampli-con1017256 | 109667 | 80 | 80 | SNP | A | 5CM1 | G | LH82 | | | | |
| 383 | Ampli-con1017256 | 109668 | 267 | 267 | SNP | A | 5CM1 | C | LH82 | | | | |
| 383 | Ampli-con1017256 | 109669 | 326 | 326 | SNP | A | 5CM1 | G | LH82 | | | | |
| 383 | Ampli-con1017256 | 109670 | 355 | 355 | SNP | C | LH82 | T | 5CM1 | | | | |
| 383 | Ampli-con1017256 | 109672 | 447 | 447 | SNP | C | 5CM1 | T | LH82 | | | | |
| 383 | Ampli-con1017256 | 109673 | 476 | 476 | IND | * | LH82 | A | 5CM1 | | | | |
| 383 | Ampli-con1017256 | 109674 | 477 | 478 | IND | ** | LH82 | GA | 5CM1 | | | | |
| 383 | Ampli-con1017256 | 109675 | 542 | 542 | SNP | A | 5CM1 | G | LH82 | | | | |
| 384 | Ampli-con1017272 | 109720 | 108 | 108 | SNP | A | LH82 | G | 5CM1 | | | | |
| 384 | Ampli-con1017272 | 109721 | 193 | 193 | SNP | A | LH82 | C | 5CM1 | | | | |
| 384 | Ampli-con1017272 | 109722 | 560 | 560 | SNP | A | 5CM1 | G | LH82 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 385 | Ampli-con1017287 | 109797 | 165 | 168 | IND | **** | LH82 | TACG | 5CM1 | | | | |
| 385 | Ampli-con1017287 | 109798 | 212 | 212 | SNP | A | LH82 | G | 5CM1 | | | | |
| 385 | Ampli-con1017287 | 109799 | 215 | 215 | SNP | A | LH82 | G | 5CM1 | | | | |
| 385 | Ampli-con1017287 | 109800 | 222 | 224 | IND | *** | LH82 | TCT | 5CM1 | | | | |
| 385 | Ampli-con1017287 | 109801 | 331 | 331 | SNP | A | 5CM1 | C | LH82 | | | | |
| 385 | Ampli-con1017287 | 109802 | 516 | 516 | SNP | C | 5CM1 | G | LH82 | | | | |
| 385 | Ampli-con1017287 | 109803 | 562 | 562 | SNP | C | 5CM1 | T | LH82 | | | | |
| 385 | Ampli-con1017287 | 109804 | 576 | 577 | IND | ** | LH82 | AG | 5CM1 | | | | |
| 385 | Ampli-con1017287 | 109805 | 642 | 642 | SNP | A | LH82 | G | 5CM1 | | | | |
| 386 | Ampli-con1017331 | 110063 | 16 | 16 | SNP | G | 5CM1 | T | LH82 | | | | |
| 386 | Ampli-con1017331 | 110064 | 20 | 20 | SNP | C | 5CM1 | G | LH82 | | | | |
| 386 | Ampli-con1017331 | 110065 | 122 | 122 | SNP | A | 5CM1 | G | LH82 | | | | |
| 386 | Ampli-con1017331 | 110066 | 244 | 247 | IND | **** | LH82 | TATA | 5CM1 | | | | |
| 386 | Ampli-con1017331 | 110067 | 275 | 275 | SNP | A | 5CM1 | G | LH82 | | | | |
| 386 | Ampli-con1017331 | 110068 | 280 | 280 | SNP | C | 5CM1 | G | LH82 | | | | |
| 386 | Ampli-con1017331 | 110069 | 313 | 313 | SNP | A | 5CM1 | G | LH82 | | | | |
| 386 | Ampli-con1017331 | 110070 | 374 | 374 | SNP | G | 5CM1 | T | LH82 | | | | |
| 387 | Ampli-con1017357 | 110147 | 244 | 244 | SNP | C | 5CM1 | T | LH82 | | | | |
| 387 | Ampli-con1017357 | 110148 | 253 | 253 | SNP | C | 5CM1 | T | LH82 | | | | |
| 387 | Ampli-con1017357 | 110149 | 285 | 285 | SNP | A | 5CM1 | G | LH82 | | | | |
| 387 | Ampli-con1017357 | 110150 | 380 | 386 | IND | ******* | 5CM1 | CAGGAAA | LH82 | | | | |
| 388 | Ampli-con1017357 | 110376 | 262 | 262 | SNP | A | 5CM1 | G | LH82 | | | | |
| 388 | Ampli-con1017409 | 110377 | 550 | 550 | SNP | C | LH82 | T | 5CM1 | | | | |
| 389 | Ampli-con1017409 | 110603 | 268 | 268 | SNP | C | 5CM1 | T | LH82 | | | | |
| 389 | Ampli-con1017456 | 110604 | 276 | 276 | IND | * | LH82 | G | 5CM1 | | | | |
| 389 | Ampli-con1017456 | 110605 | 303 | 303 | SNP | A | LH82 | G | 5CM1 | | | | |
| 389 | Ampli-con1017456 | 110606 | 446 | 446 | SNP | A | LH82 | C | 5CM1 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 389 | Ampli-con1017456 | 110607 | 483 | 483 | SNP | G | LH82 | T | 5CM1 | | | | |
| 389 | Ampli-con1017456 | 110608 | 528 | 528 | SNP | A | LH82 | G | 5CM1 | | | | |
| 390 | Ampli-con1017466 | 110684 | 269 | 269 | SNP | C | LH82 | T | 5CM1 | | | | |
| 390 | Ampli-con1017466 | 110685 | 475 | 475 | SNP | C | 5CM1 | T | LH82 | | | | |
| 391 | Ampli-con1017484 | 110769 | 431 | 433 | IND | *** | LH82 | ACT | 5CM1 | | | | |
| 391 | Ampli-con1017484 | 110770 | 434 | 434 | IND | * | LH82 | T | 5CM1 | | | | |
| 391 | Ampli-con1017484 | 110771 | 489 | 489 | SNP | C | LH82 | C | 5CM1 | | | | |
| 392 | Ampli-con1017493 | 110780 | 359 | 359 | SNP | A | LH82 | G | 5CM1 | | | | |
| 393 | Ampli-con1017498 | 110792 | 17 | 17 | SNP | A | LH82 | C | 5CM1 | | | | |
| 393 | Ampli-con1017498 | 110793 | 23 | 23 | SNP | G | LH82 | T | 5CM1 | | | | |
| 393 | Ampli-con1017498 | 110795 | 47 | 48 | IND | ** | LH82 | TA | 5CM1 | | | | |
| 393 | Ampli-con1017498 | 110796 | 117 | 117 | SNP | C | 5CM1 | T | LH82 | | | | |
| 393 | Ampli-con1017498 | 110797 | 170 | 170 | SNP | G | 5CM1 | T | LH82 | | | | |
| 393 | Ampli-con1017498 | 110798 | 248 | 248 | SNP | C | LH82 | T | 5CM1 | | | | |
| 393 | Ampli-con1017498 | 110799 | 282 | 282 | SNP | C | 5CM1 | G | LH82 | | | | |
| 393 | Ampli-con1017498 | 110800 | 405 | 405 | SNP | A | 5CM1 | G | LH82 | | | | |
| 393 | Ampli-con1017498 | 110801 | 411 | 411 | SNP | C | 5CM1 | T | LH82 | | | | |
| 393 | Ampli-con1017498 | 110802 | 412 | 412 | SNP | A | LH82 | C | 5CM1 | | | | |
| 393 | Ampli-con1017498 | 110803 | 567 | 567 | SNP | A | LH82 | G | 5CM1 | | | | |
| 394 | Ampli-con1017519 | 110886 | 93 | 98 | IND | ****** | LH82 | ATCTGC | 5CM1 | | | | |
| 394 | Ampli-con1017519 | 110887 | 135 | 135 | SNP | C | LH82 | T | 5CM1 | | | | |
| 394 | Ampli-con1017519 | 110888 | 261 | 264 | IND | **** | LH82 | TTAT | 5CM1 | | | | |
| 394 | Ampli-con1017519 | 110889 | 355 | 355 | SNP | G | LH82 | T | 5CM1 | | | | |
| 394 | Ampli-con1017519 | 110890 | 402 | 402 | IND | * | LH82 | T | 5CM1 | | | | |
| 394 | Ampli-con1017519 | 110891 | 404 | 408 | IND | ***** | LH82 | CCTGT | 5CM1 | | | | |
| 394 | Ampli-con1017519 | 110892 | 431 | 431 | SNP | A | 5CM1 | T | LH82 | | | | |
| 394 | Ampli-con1017519 | 110894 | 464 | 470 | IND | ******* | LH82 | GAACCAA | 5CM1 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 394 | Ampli-con1017519 | 110895 | 546 | 546 | SNP | C | 5CM1 | G | LH82 | | | | |
| 394 | Ampli-con1017519 | 110896 | 552 | 552 | IND | * | LH82 | A | 5CM1 | | | | |
| 394 | Ampli-con1017519 | 110897 | 554 | 556 | IND | *** | LH82 | CAT | 5CM1 | | | | |
| 395 | Ampli-con1017554 | 110972 | 53 | 53 | SNP | A | 5CM1 | G | LH82 | | | | |
| 395 | Ampli-con1017554 | 110973 | 390 | 390 | SNP | C | LH82 | T | 5CM1 | | | | |
| 396 | Ampli-con1049957 | 111004 | 181 | 181 | SNP | A | 5CM1 | G | LH82 | | | | |
| 396 | Ampli-con1049957 | 111005 | 246 | 246 | SNP | C | 5CM1 | T | LH82 | | | | |
| 396 | Ampli-con1049957 | 111006 | 268 | 268 | SNP | C | 5CM1 | G | LH82 | | | | |
| 396 | Ampli-con1049957 | 111007 | 284 | 284 | SNP | A | LH82 | T | 5CM1 | | | | |
| 396 | Ampli-con1049957 | 111008 | 349 | 349 | SNP | C | LH82 | G | 5CM1 | | | | |
| 396 | Ampli-con1049957 | 111009 | 559 | 559 | SNP | C | 5CM1 | G | LH82 | | | | |
| 397 | Ampli-con1049995 | 111204 | 254 | 254 | SNP | A | 5CM1 | G | LH82 | | | | |
| 397 | Ampli-con1049995 | 111207 | 509 | 509 | SNP | A | 5CM1 | G | LH82 | | | | |
| 398 | Ampli-con1049999 | 111212 | 165 | 165 | SNP | A | 5CM1 | T | LH82 | | | | |
| 399 | Ampli-con1050057 | 111365 | 76 | 76 | SNP | C | 5CM1 | G | LH82 | | | | |
| 399 | Ampli-con1050057 | 111366 | 139 | 139 | SNP | C | 5CM1 | G | LH82 | | | | |
| 399 | Ampli-con1050057 | 111367 | 258 | 258 | SNP | A | 5CM1 | G | LH82 | | | | |
| 399 | Ampli-con1050057 | 111368 | 600 | 600 | SNP | C | 5CM1 | T | LH82 | | | | |
| 400 | Ampli-con1050089 | 111464 | 114 | 114 | SNP | A | 5CM1 | G | LH82 | | | | |
| 400 | Ampli-con1050089 | 111465 | 183 | 183 | SNP | A | 5CM1 | T | LH82 | | | | |
| 400 | Ampli-con1050089 | 111466 | 410 | 410 | SNP | C | 5CM1 | T | LH82 | | | | |
| 400 | Ampli-con1050089 | 111467 | 468 | 468 | SNP | A | 5CM1 | G | LH82 | | | | |
| 400 | Ampli-con1050089 | 111468 | 485 | 485 | SNP | C | 5CM1 | T | LH82 | | | | |
| 400 | Ampli-con1050089 | 111469 | 489 | 489 | SNP | A | LH82 | G | 5CM1 | | | | |
| 400 | Ampli-con1050089 | 111470 | 518 | 518 | SNP | C | 5CM1 | T | LH82 | | | | |
| 400 | Ampli-con1050089 | 111471 | 527 | 527 | SNP | A | 5CM1 | G | LH82 | | | | |
| 401 | Ampli-con1050090 | 111472 | 221 | 221 | SNP | C | 5CM1 | T | LH82 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 402 | Ampli-con1050093 | 111475 | 297 | 297 | SNP | A | LH82 | G | 5CM1 | | | | |
| 403 | Ampli-con1050119 | 111613 | 56 | 56 | SNP | A | LH82 | G | 5CM1 | | | | |
| 403 | Ampli-con1050119 | 111615 | 113 | 113 | SNP | C | LH82 | T | 5CM1 | | | | |
| 403 | Ampli-con1050119 | 111616 | 115 | 115 | SNP | C | LH82 | T | 5CM1 | | | | |
| 403 | Ampli-con1050119 | 111617 | 160 | 160 | SNP | A | LH82 | T | 5CM1 | | | | |
| 403 | Ampli-con1050119 | 111619 | 275 | 275 | SNP | A | 5CM1 | G | LH82 | | | | |
| 403 | Ampli-con1050119 | 111620 | 551 | 551 | IND | * | LH82 | T | 5CM1 | | | | |
| 404 | Ampli-con1050127 | 111628 | 155 | 155 | SNP | A | LH82 | G | 5CM1 | | | | |
| 404 | Ampli-con1050127 | 111629 | 344 | 344 | SNP | C | 5CM1 | T | LH82 | | | | |
| 404 | Ampli-con1050127 | 111630 | 345 | 345 | SNP | A | 5CM1 | G | LH82 | | | | |
| 404 | Ampli-con1050127 | 111631 | 351 | 351 | SNP | C | LH82 | T | 5CM1 | | | | |
| 404 | Ampli-con1050127 | 111632 | 424 | 424 | SNP | C | 5CM1 | T | LH82 | | | | |
| 405 | Ampli-con1050172 | 111817 | 127 | 127 | SNP | A | 5CM1 | G | LH82 | | | | |
| 405 | Ampli-con1050172 | 111818 | 255 | 255 | SNP | A | 5CM1 | G | LH82 | | | | |
| 405 | Ampli-con1050172 | 111819 | 290 | 290 | SNP | A | LH82 | T | 5CM1 | | | | |
| 405 | Ampli-con1050172 | 111820 | 444 | 444 | SNP | A | 5CM1 | T | LH82 | | | | |
| 405 | Ampli-con1050172 | 111821 | 447 | 447 | SNP | C | LH82 | T | 5CM1 | | | | |
| 405 | Ampli-con1050172 | 111822 | 448 | 448 | SNP | A | LH82 | C | 5CM1 | | | | |
| 405 | Ampli-con1050172 | 111823 | 449 | 449 | IND | * | 5CM1 | T | LH82 | | | | |
| 405 | Ampli-con1050172 | 111824 | 452 | 452 | IND | * | 5CM1 | C | LH82 | | | | |
| 405 | Ampli-con1050172 | 111825 | 454 | 454 | IND | * | 5CM1 | C | LH82 | | | | |
| 405 | Ampli-con1050172 | 111826 | 466 | 466 | SNP | A | 5CM1 | G | LH82 | | | | |
| 405 | Ampli-con1050172 | 111827 | 511 | 511 | SNP | C | 5CM1 | T | LH82 | | | | |
| 405 | Ampli-con1050172 | 111828 | 591 | 591 | SNP | C | LH82 | T | 5CM1 | | | | |
| 406 | Ampli-con1050174 | 111829 | 141 | 141 | SNP | G | 5CM1 | T | LH82 | | | | |
| 407 | Ampli-con1050237 | 112139 | 93 | 93 | SNP | C | 5CM1 | G | LH82 | | | | |
| 408 | Ampli-con1050319 | 112496 | 121 | 121 | SNP | A | LH82 | G | 5CM1 | | | | |

-continued

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 408 | Ampli-con1050319 | 112497 | 194 | 194 | SNP | A | LH82 | T | 5CM1 | | | | |
| 409 | Ampli-con1050498 | 113113 | 282 | 282 | SNP | A | LH82 | G | 5CM1 | | | | |
| 410 | Ampli-con1050539 | 113263 | 215 | 215 | SNP | A | 5CM1 | G | LH82 | | | | |
| 410 | Ampli-con1050539 | 113264 | 238 | 238 | SNP | C | LH82 | T | 5CM1 | | | | |
| 410 | Ampli-con1050539 | 113265 | 240 | 240 | SNP | C | 5CM1 | T | LH82 | | | | |
| 410 | Ampli-con1050539 | 113266 | 395 | 395 | SNP | C | 5CM1 | G | LH82 | | | | |
| 411 | Ampli-con1050570 | 113377 | 112 | 112 | SNP | A | LH82 | G | 5CM1 | | | | |
| 411 | Ampli-con1050570 | 113378 | 137 | 137 | SNP | C | 5CM1 | T | LH82 | | | | |
| 411 | Ampli-con1050570 | 113379 | 167 | 167 | SNP | A | LH82 | T | 5CM1 | | | | |
| 411 | Ampli-con1050570 | 113380 | 203 | 203 | SNP | A | 5CM1 | G | LH82 | | | | |
| 411 | Ampli-con1050570 | 113381 | 302 | 302 | SNP | A | 5CM1 | G | LH82 | | | | |
| 411 | Ampli-con1050570 | 113382 | 412 | 413 | IND | ** | LH82 | TC | 5CM1 | | | | |
| 412 | Ampli-con1050570 | 143100 | 329 | 329 | SNP | C | LH82 | G | 5CM1 | | | | |
| 412 | Ampli-con1459173 | 143101 | 350 | 350 | SNP | C | 5CM1 | G | LH82 | | | | |
| 412 | Ampli-con1459173 | 143102 | 379 | 379 | SNP | A | 5CM1 | G | LH82 | | | | |
| 412 | Ampli-con1459173 | 143103 | 413 | 413 | IND | * | LH82 | C | 5CM1 | | | | |
| 412 | Ampli-con1459173 | 143104 | 414 | 415 | IND | ** | LH82 | TC | 5CM1 | | | | |
| 413 | Ampli-con1459173 | 143216 | 67 | 67 | SNP | A | mo17:LH82 | C | b73 | | | | |
| 413 | Ampli-con1459183 | 143217 | 321 | 321 | SNP | A | b73 | G | mo17:LH82 | | | | |
| 414 | Ampli-con1459183 | 143249 | 88 | 88 | SNP | C | mo17:5CM1 | T | b73:LH82 | | | | |
| 414 | Ampli-con1459189 | 143251 | 221 | 221 | SNP | A | mo17:5CM1 | G | b73:LH82 | | | | |
| 415 | Ampli-con1459189 | 143371 | 84 | 84 | SNP | G | mo17 | T | b73:5CM1:LH82 | | | | |
| 415 | Ampli-con1459200 | 143372 | 99 | 99 | SNP | A | mo17 | G | b73:5CM1:LH82 | | | | |
| 415 | Ampli-con1459200 | 143374 | 128 | 128 | SNP | C | mo17 | T | b73:5CM1:LH82 | | | | |
| 415 | Ampli-con1459200 | 143375 | 132 | 132 | SNP | A | mo17 | G | b73:5CM1:LH82 | | | | |
| 415 | Ampli-con1459200 | 143376 | 164 | 164 | SNP | C | b73:mo17:LH82 5CM1 | G | 5CM1 | | | | |
| 416 | Ampli-con1459201 | 143380 | 329 | 329 | SNP | A | | G | b73:mo17:LH82 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 416 | Ampli-con1459201 | 143382 | 542 | 542 | SNP | A | b73:mo17:LH82 | C | 5CM1 | | | | |
| 416 | Ampli-con1459201 | 143384 | 634 | 634 | SNP | C | 5CM1 | T | b73:mo17:LH82 | | | | |
| 417 | Ampli-con1459202 | 143386 | 95 | 95 | SNP | A | b73:mo17:LH82 | C | 5CM1 | | | | |
| 417 | Ampli-con1459202 | 143388 | 148 | 148 | SNP | C | b73:LH82 | T | mo17:5CM1 | | | | |
| 418 | Ampli-con1459202 | 143390 | 236 | 236 | SNP | A | 5CM1 | C | b73:mo17:LH82 | | | | |
| 418 | Ampli-con1459202 | 143407 | 115 | 115 | SNP | C | LH82 | T | 5CM1 | | | | |
| 418 | Ampli-con1459206 | 143408 | 381 | 381 | SNP | G | 5CM1 | T | LH82 | | | | |
| 418 | Ampli-con1459206 | 143409 | 516 | 516 | SNP | A | LH82 | C | 5CM1 | | | | |
| 419 | Ampli-con1459206 | 143413 | 70 | 70 | SNP | A | 5CM1 | G | LH82 | | | | |
| 419 | Ampli-con1459208 | 143418 | 205 | 205 | SNP | A | 5CM1 | T | LH82 | | | | |
| 420 | Ampli-con1459208 | 143641 | 113 | 113 | SNP | A | b73:LH82 | C | mo17:5CM1 | | | | |
| 420 | Ampli-con1459219 | 143642 | 187 | 187 | SNP | A | LH82 | T | b73:mo17:5CM1 | | | | |
| 420 | Ampli-con1459219 | 143643 | 209 | 209 | SNP | A | LH82 | G | b73:mo17:5CM1 | | | | |
| 420 | Ampli-con1459219 | 143644 | 247 | 247 | SNP | C | mo17:5CM1:LH82 | T | b73 | | | | |
| 420 | Ampli-con1459219 | 143645 | 285 | 285 | SNP | A | b73:mo17:LH82 | G | 5CM1 | | | | |
| 420 | Ampli-con1459219 | 143646 | 289 | 289 | SNP | C | 5CM1 | T | b73:mo17:LH82 | | | | |
| 420 | Ampli-con1459219 | 143653 | 707 | 707 | IND | * | mo17 | T | b73:5CM1:LH82 | | | | |
| 420 | Ampli-con1459219 | 143654 | 708 | 708 | IND | * | b73:LH82 | A | mo17:5CM1 | | | | |
| 420 | Ampli-con1459219 | 143657 | 883 | 883 | SNP | C | mo17:5CM1 | T | b73:LH82 | | | | |
| 420 | Ampli-con1459219 | 143658 | 946 | 946 | SNP | A | mo17 | T | b73:5CM1:LH82 | | | | |
| 420 | Ampli-con1459219 | 143659 | 985 | 985 | SNP | C | mo17:5CM1:LH82 | G | b73 | | | | |
| 420 | Ampli-con1459219 | 143660 | 1020 | 1020 | SNP | C | b73:LH82 | T | mo17:5CM1 | | | | |
| 421 | Ampli-con1459219 | 143661 | 1146 | 1146 | SNP | A | b73:LH82 | G | mo17:5CM1 | | | | |
| 421 | Ampli-con1459223 | 143749 | 65 | 65 | SNP | C | mo17:LH82 | T | b73:5CM1 | | | | |
| 421 | Ampli-con1459223 | 143750 | 68 | 68 | SNP | C | mo17:LH82 | T | b73:5CM1 | | | | |
| 421 | Ampli-con1459223 | 143753 | 104 | 104 | SNP | A | mo17:LH82 | G | b73:5CM1 | | | | |
| 421 | Ampli-con1459223 | 143754 | 176 | 176 | SNP | C | mo17:LH82 | T | b73:5CM1 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 421 | Ampli-con1459223 | 143755 | 195 | 195 | SNP | C | b73:5CM1 | T | mo17:LH82 | | | | |
| 422 | Ampli-con1459242 | 143969 | 99 | 100 | IND | ** | 5CM1:LH82 | TA | b73:mo17 | | | | |
| 422 | Ampli-con1459242 | 143974 | 520 | 520 | IND | * | mo17 | A | b73:5CM1:LH82 | | | | |
| 423 | Ampli-con1459247 | 144090 | 409 | 409 | SNP | A | 5CM1 | G | b73:mo17:LH82 | | | | |
| 424 | Ampli-con1459269 | 144505 | 45 | 45 | SNP | C | b73 | T | mo17:5CM1:LH82 | | | | |
| 424 | Ampli-con1459269 | 144506 | 88 | 91 | IND | **** | b73 | TCTA | mo17:5CM1:LH82 | | | | |
| 425 | Ampli-con1459275 | 144686 | 108 | 108 | SNP | C | 5CM1 | G | b73:mo17:LH82 | | | | |
| 425 | Ampli-con1459275 | 144687 | 260 | 260 | SNP | A | mo17:5CM1 | T | b73:LH82 | | | | |
| 425 | Ampli-con1459275 | 144688 | 362 | 362 | SNP | A | b73:mo17:5CM1 | C | LH82 | | | | |
| 425 | Ampli-con1459275 | 144689 | 399 | 401 | IND | *** | b73:mo17:5CM1 | ACC | LH82 | | | | |
| 426 | Ampli-con1459275 | 144731 | 169 | 169 | SNP | A | b73:mo17:5CM1 | G | LH82 | | | | |
| 426 | Ampli-con1459277 | 144732 | 238 | 238 | SNP | A | b73:mo17:5CM1 | G | LH82 | | | | |
| 427 | Ampli-con1459277 | 145065 | 28 | 28 | SNP | A | b73 | G | mo17:LH82 | | | | |
| 427 | Ampli-con1459294 | 145066 | 38 | 38 | SNP | G | b73 | T | mo17:LH82 | | | | |
| 427 | Ampli-con1459294 | 145069 | 110 | 110 | SNP | C | mo17:LH82 | T | b73 | | | | |
| 427 | Ampli-con1459294 | 145070 | 116 | 116 | SNP | C | mo17:LH82 | T | b73 | | | | |
| 427 | Ampli-con1459294 | 145071 | 119 | 119 | SNP | C | mo17:LH82 | T | b73 | | | | |
| 427 | Ampli-con1459294 | 145072 | 127 | 127 | SNP | C | b73 | T | mo17:LH82 | | | | |
| 428 | Ampli-con1459294 | 145073 | 133 | 133 | SNP | A | mo17:LH82 | C | b73 | | | | |
| 428 | Ampli-con1459300 | 145077 | 468 | 468 | SNP | A | mo17:LH82 | C | b73 | | | | |
| 428 | Ampli-con1459300 | 145200 | 102 | 102 | SNP | C | b73 | G | mo17:5CM1:LH82 | | | | |
| 428 | Ampli-con1459300 | 145202 | 176 | 176 | SNP | A | b73 | G | mo17:5CM1:LH82 | | | | |
| 428 | Ampli-con1459300 | 145203 | 177 | 177 | SNP | A | b73 | C | mo17:5CM1:LH82 | | | | |
| 428 | Ampli-con1459300 | 145204 | 271 | 271 | SNP | C | b73 | G | mo17:5CM1:LH82 | | | | |
| 428 | Ampli-con1459300 | 145205 | 454 | 457 | IND | **** | mo17:LH82 | ACGT | b73:5CM1 | | | | |
| 429 | Ampli-con1459304 | 145260 | 158 | 158 | SNP | A | 5CM1 | C | LH82 | | | | |
| 429 | Ampli-con1459304 | 145261 | 172 | 172 | SNP | C | LH82 | G | 5CM1 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 429 | Ampli-con1459304 | 145263 | 235 | 235 | SNP | C | 5CM1 | T | LH82 | | | | |
| 429 | Ampli-con1459304 | 145264 | 525 | 525 | SNP | C | 5CM1 | T | LH82 | | | | |
| 429 | Ampli-con1459304 | 145266 | 574 | 574 | SNP | C | 5CM1 | T | LH82 | | | | |
| 430 | Ampli-con1459307 | 145298 | 58 | 58 | SNP | G | b73 | T | mo17 | | | | |
| 430 | Ampli-con1459307 | 145299 | 92 | 92 | IND | * | mo17 | C | b73 | | | | |
| 430 | Ampli-con1459307 | 145300 | 377 | 377 | SNP | A | b73 | G | mo17 | | | | |
| 430 | Ampli-con1459307 | 145301 | 380 | 380 | SNP | A | b73 | G | mo17 | | | | |
| 430 | Ampli-con1459307 | 145302 | 393 | 393 | SNP | G | b73 | T | mo17 | | | | |
| 430 | Ampli-con1459307 | 145303 | 399 | 399 | SNP | A | mo17 | G | b73 | | | | |
| 430 | Ampli-con1459307 | 145304 | 407 | 407 | SNP | A | mo17 | G | b73 | | | | |
| 430 | Ampli-con1459307 | 145305 | 410 | 410 | SNP | A | mo17 | G | b73 | | | | |
| 430 | Ampli-con1459307 | 145306 | 416 | 416 | SNP | A | mo17 | G | b73 | | | | |
| 430 | Ampli-con1459307 | 145307 | 432 | 432 | SNP | G | mo17 | T | b73 | | | | |
| 430 | Ampli-con1459307 | 145308 | 434 | 434 | IND | * | mo17 | A | b73 | | | | |
| 430 | Ampli-con1459307 | 145309 | 488 | 488 | SNP | A | mo17 | C | b73 | | | | |
| 430 | Ampli-con1459307 | 145310 | 498 | 498 | SNP | C | b73 | T | mo17 | | | | |
| 430 | Ampli-con1459307 | 145312 | 244 | 244 | SNP | A | b73 | G | mo17 | | | | |
| 431 | Ampli-con1459308 | 145314 | 294 | 294 | IND | * | mo17 | T | b73 | | | | |
| 431 | Ampli-con1459308 | 145315 | 314 | 314 | SNP | G | mo17 | T | b73 | | | | |
| 431 | Ampli-con1459308 | 145316 | 426 | 426 | IND | * | mo17 | A | b73 | | | | |
| 431 | Ampli-con1459308 | 145317 | 429 | 429 | IND | * | mo17 | T | b73 | | | | |
| 431 | Ampli-con1459308 | 145318 | 464 | 464 | SNP | A | mo17 | G | b73 | | | | |
| 431 | Ampli-con1459308 | 145319 | 533 | 533 | SNP | A | mo17 | T | b73 | | | | |
| 432 | Ampli-con1459308 | 145322 | 912 | 912 | SNP | C | mo17 | T | b73 | | | | |
| 433 | Ampli-con1459309 | 145573 | 243 | 243 | SNP | A | b73:mo17:LH82 | G | 5CM1 | | | | |
| 433 | Ampli-con1459322 | 145574 | 312 | 312 | SNP | C | 5CM1:LH82 | T | b73:mo17 | | | | |
| 433 | Ampli-con1459322 | 145575 | 406 | 406 | SNP | A | 5CM1 | G | b73:mo17:LH82 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 433 | Ampli-con1459322 | 145577 | 451 | 451 | SNP | C | 5CM1:LH82 | T | b73:mo17 | | | | |
| 433 | Ampli-con1459322 | 145578 | 519 | 519 | SNP | A | 5CM1 | T | b73:mo17:LH82 | | | | |
| 433 | Ampli-con1459322 | 145579 | 550 | 550 | SNP | G | 5CM1 | T | b73:mo17:LH82 | | | | |
| 433 | Ampli-con1459322 | 145580 | 611 | 611 | SNP | A | b73:mo17:5CM1 | T | LH82 | | | | |
| 433 | Ampli-con1459322 | 145581 | 652 | 652 | SNP | A | b73:mo17:LH82 | C | 5CM1 | | | | |
| 433 | Ampli-con1459322 | 145582 | 656 | 656 | SNP | A | 5CM1 | G | b73:mo17:LH82 | | | | |
| 433 | Ampli-con1459322 | 145583 | 657 | 657 | SNP | C | b73:mo17:LH82 | T | 5CM1 | | | | |
| 433 | Ampli-con1459322 | 145584 | 677 | 677 | SNP | A | b73:mo17:LH82 | G | 5CM1 | | | | |
| 433 | Ampli-con1459322 | 145585 | 685 | 685 | SNP | A | b73:mo17:LH82 | C | 5CM1 | | | | |
| 433 | Ampli-con1459322 | 145586 | 703 | 703 | IND | * | b73:mo17 | A | 5CM1:LH82 | | | | |
| 433 | Ampli-con1459322 | 145587 | 713 | 734 | IND | *********************** | b73:mo17:LH82 | GTTGATGAAGCAGGACATTGGG | 5CM1 | | | | |
| 433 | Ampli-con1459322 | 145588 | 784 | 784 | SNP | A | 5CM1 | G | b73:mo17:LH82 | | | | |
| 433 | Ampli-con1459322 | 145590 | 857 | 857 | SNP | G | b73:mo17:LH82 | T | 5CM1 | | | | |
| 433 | Ampli-con1459322 | 145591 | 864 | 864 | SNP | A | 5CM1 | G | b73:mo17:LH82 | | | | |
| 433 | Ampli-con1459322 | 145592 | 868 | 868 | SNP | A | b73:mo17:LH82 | C | 5CM1 | | | | |
| 433 | Ampli-con1459322 | 145594 | 877 | 877 | IND | * | b73:mo17:LH82 | C | 5CM1 | | | | |
| 433 | Ampli-con1459322 | 145596 | 889 | 892 | IND | **** | b73:mo17:LH82 | CCAA | 5CM1:LH82 | | | | |
| 433 | Ampli-con1459322 | 145597 | 905 | 905 | SNP | A | b73:mo17:LH82 | G | 5CM1 | | | | |
| 434 | Ampli-con1459334 | 145794 | 242 | 242 | SNP | C | mo17:5CM1 | T | b73 | | | | |
| 434 | Ampli-con1459334 | 145796 | 419 | 419 | SNP | C | b73 | T | mo17:5CM1 | | | | |
| 434 | Ampli-con1459334 | 145797 | 428 | 428 | SNP | C | b73 | T | mo17:5CM1 | | | | |
| 434 | Ampli-con1459334 | 145798 | 747 | 747 | SNP | A | b73 | G | mo17:5CM1 | | | | |
| 434 | Ampli-con1459334 | 145800 | 867 | 867 | SNP | C | mo17:5CM1 | T | b73 | | | | |
| 434 | Ampli-con1459334 | 145801 | 930 | 930 | SNP | A | mo17:5CM1 | T | b73 | | | | |
| 434 | Ampli-con1459334 | 145802 | 969 | 969 | SNP | C | mo17:5CM1 | G | b73 | | | | |
| 434 | Ampli-con1459334 | 145803 | 1004 | 1004 | SNP | C | b73 | T | mo17:5CM1 | | | | |
| 435 | Ampli-con1459354 | 146152 | 254 | 254 | SNP | A | 5CM1 | G | b73:mo17:LH82 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 435 | Ampli-con1459354 | 146158 | 821 | 822 | IND | ** | 5CM1 | CA | b73:mo17:LH82 b73 | | | | |
| 436 | Ampli-con1459358 | 146190 | 203 | 203 | SNP | G | mo17:5CM1: LH82 | T | mo17:5CM1: LH82 b73 | | | | |
| 436 | Ampli-con1459358 | 146191 | 272 | 272 | SNP | A | mo17:5CM1: LH82 | G | b73 | | | | |
| 436 | Ampli-con1459358 | 146192 | 286 | 286 | SNP | A | mo17:5CM1: LH82 | C | b73 | | | | |
| 436 | Ampli-con1459358 | 146193 | 301 | 301 | SNP | G | b73 | T | mo17:5CM1: LH82 b73:5CM1 | | | | |
| 436 | Ampli-con1459358 | 146194 | 327 | 327 | SNP | A | mo17:LH82 | G | b73:5CM1 | | | | |
| 436 | Ampli-con1459358 | 146195 | 348 | 348 | SNP | C | mo17:5CM1: LH82 | G | b73 | | | | |
| 436 | Ampli-con1459358 | 146196 | 425 | 425 | SNP | A | mo17:5CM1: LH82 | G | b73 | | | | |
| 436 | Ampli-con1459358 | 146197 | 448 | 448 | SNP | C | b73 | G | mo17:5CM1: LH82 5CM1 | | | | |
| 437 | Ampli-con1459369 | 146410 | 123 | 123 | SNP | G | b73:LH82 | T | b73:mo17: LH82 5CM1 | | | | |
| 437 | Ampli-con1459369 | 146411 | 154 | 159 | IND | ******* | 5CM1 | ATCTTC | b73:mo17: LH82 | | | | |
| 437 | Ampli-con1459369 | 146412 | 280 | 280 | SNP | C | 5CM1 | T | b73:mo17: LH82 | | | | |
| 437 | Ampli-con1459369 | 146413 | 330 | 330 | SNP | A | LH82 | T | b73:mo17: 5CM1 | | | | |
| 437 | Ampli-con1459369 | 146414 | 331 | 331 | SNP | A | LH82 | C | b73:mo17: 5CM1 | | | | |
| 437 | Ampli-con1459369 | 146415 | 345 | 345 | SNP | A | b73:LH82 | T | mo17:5CM1 | | | | |
| 437 | Ampli-con1459369 | 146416 | 552 | 552 | SNP | G | b73:mo17: LH82 | T | 5CM1 | | | | |
| 437 | Ampli-con1459369 | 146417 | 555 | 555 | SNP | C | b73:mo17: LH82 | G | 5CM1 | | | | |
| 437 | Ampli-con1459369 | 146418 | 556 | 556 | SNP | G | 5CM1 | T | b73:mo17: LH82 | | | | |
| 437 | Ampli-con1459369 | 146419 | 558 | 558 | SNP | G | b73:mo17: LH82 | T | 5CM1 | | | | |
| 437 | Ampli-con1459369 | 146420 | 559 | 559 | SNP | A | LH82 | T | b73:mo17: 5CM1 | | | | |
| 437 | Ampli-con1459369 | 146421 | 560 | 560 | SNP | A | 5CM1 | T | b73:mo17: LH82 | | | | |
| 437 | Ampli-con1459369 | 146422 | 561 | 561 | SNP | A | 5CM1 | T | b73:mo17: LH82 | | | | |
| 437 | Ampli-con1459369 | 146423 | 562 | 562 | SNP | G | b73:mo17: LH82 | T | 5CM1 | | | | |
| 437 | Ampli-con1459369 | 146424 | 563 | 563 | SNP | A | 5CM1 | G | b73:mo17: LH82 | | | | |
| 437 | Ampli-con1459369 | 146425 | 564 | 564 | SNP | A | 5CM1 | G | b73:mo17: LH82 | | | | |
| 437 | Ampli-con1459369 | 146426 | 565 | 565 | SNP | A | 5CM1 | T | b73:mo17: LH82 | | | | |
| 437 | Ampli-con1459369 | 146427 | 566 | 566 | SNP | A | b73:mo17: LH82 | C | 5CM1 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 437 | Ampli-con1459369 | 146428 | 568 | 568 | SNP | C | 5CM1 | T | b73:mo17:LH82 | | | | |
| 437 | Ampli-con1459369 | 146429 | 569 | 569 | SNP | C | b73:mo17:LH82 5CM1 | G | | | | | |
| 437 | Ampli-con1459369 | 146430 | 570 | 570 | SNP | A | 5CM1 | T | b73:mo17:LH82 | | | | |
| 437 | Ampli-con1459369 | 146431 | 574 | 574 | SNP | A | b73:mo17:LH82 5CM1 | T | | | | | |
| 437 | Ampli-con1459369 | 146432 | 575 | 575 | SNP | A | 5CM1 | T | b73:mo17:LH82 | | | | |
| 437 | Ampli-con1459369 | 146433 | 576 | 576 | SNP | G | 5CM1 | T | b73:mo17:LH82 | | | | |
| 437 | Ampli-con1459369 | 146434 | 577 | 577 | SNP | A | 5CM1 | G | b73:mo17:LH82 | | | | |
| 437 | Ampli-con1459369 | 146435 | 578 | 578 | SNP | A | b73:mo17:LH82 5CM1 | T | | | | | |
| 437 | Ampli-con1459369 | 146436 | 580 | 580 | SNP | C | 5CM1 | G | b73:mo17:LH82 | | | | |
| 437 | Ampli-con1459369 | 146437 | 581 | 581 | SNP | A | 5CM1 | T | b73:mo17:LH82 | | | | |
| 437 | Ampli-con1459369 | 146438 | 582 | 582 | SNP | A | 5CM1 | G | b73:mo17:LH82 | | | | |
| 437 | Ampli-con1459369 | 146439 | 583 | 583 | SNP | A | 5CM1 | G | b73:mo17:LH82 | | | | |
| 437 | Ampli-con1459369 | 146441 | 587 | 587 | SNP | A | b73:mo17:LH82 | C | 5CM1 | | | | |
| 437 | Ampli-con1459369 | 146442 | 588 | 588 | SNP | A | b73:mo17:LH82 | T | 5CM1 | | | | |
| 437 | Ampli-con1459369 | 146443 | 589 | 589 | SNP | G | b73:mo17:LH82 | T | 5CM1 | | | | |
| 437 | Ampli-con1459369 | 146444 | 590 | 590 | SNP | C | 5CM1 | G | b73:mo17:LH82 | | | | |
| 437 | Ampli-con1459369 | 146445 | 592 | 592 | SNP | C | 5CM1 | G | b73:mo17:LH82 | | | | |
| 437 | Ampli-con1459369 | 146446 | 593 | 593 | SNP | A | 5CM1 | T | b73:mo17:LH82 | | | | |
| 437 | Ampli-con1459369 | 146447 | 594 | 594 | SNP | C | b73:mo17:LH82 | T | 5CM1 | | | | |
| 437 | Ampli-con1459369 | 146448 | 595 | 595 | SNP | A | 5CM1 | G | b73:mo17:LH82 | | | | |
| 437 | Ampli-con1459369 | 146449 | 597 | 597 | SNP | A | b73:mo17:LH82 | C | 5CM1 | | | | |
| 437 | Ampli-con1459369 | 146450 | 598 | 598 | SNP | A | b73:mo17:LH82 | T | 5CM1 | | | | |
| 438 | Ampli-con1459371 | 146458 | 233 | 233 | SNP | G | b73 | T | mo17:5CM1:LH82 | | | | |
| 438 | Ampli-con1459371 | 146459 | 246 | 246 | SNP | A | b73 | T | mo17:5CM1:LH82 | | | | |
| 438 | Ampli-con1459371 | 146460 | 419 | 419 | SNP | C | 5CM1 | G | b73:mo17:LH82 | | | | |
| 439 | Ampli-con1459380 | 146534 | 123 | 123 | SNP | C | b73 | T | mo17:5CM1 | | | | |
| 439 | Ampli-con1459380 | 146535 | 141 | 141 | SNP | C | b73 | T | mo17:5CM1 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 439 | Ampli-con1459380 | 146538 | 1015 | 1015 | SNP | G | b73:5CM1 | T | mo17 | | | | |
| 439 | Ampli-con1459380 | 146539 | 1017 | 1017 | SNP | A | b73:5CM1 | C | mo17 | | | | |
| 440 | Ampli-con1459387 | 146593 | 140 | 140 | SNP | C | b73:mo17:5CM1 | G | LH82 | | | | |
| 441 | Ampli-con1459392 | 147037 | 96 | 96 | SNP | C | mo17 | G | b73:5CM1:LH82 | | | | |
| 441 | Ampli-con1459392 | 147039 | 238 | 241 | IND | **** | b73:5CM1:LH82 | CTAT | mo17 | | | | |
| 441 | Ampli-con1459392 | 147041 | 362 | 362 | SNP | G | 5CM1 | T | b73:mo17:LH82 | | | | |
| 441 | Ampli-con1459392 | 147043 | 415 | 415 | SNP | A | b73:mo17:LH82 | G | 5CM1 | | | | |
| 442 | Ampli-con1459392 | 147044 | 464 | 464 | SNP | C | LH82 | T | 5CM1 | | | | |
| 442 | Ampli-con1459402 | 147181 | 148 | 148 | SNP | C | LH82 | G | 5CM1 | | | | |
| 442 | Ampli-con1459402 | 147182 | 183 | 183 | SNP | A | LH82 | G | 5CM1 | | | | |
| 442 | Ampli-con1459402 | 147183 | 303 | 303 | SNP | C | LH82 | T | 5CM1 | | | | |
| 442 | Ampli-con1459402 | 147184 | 305 | 305 | SNP | G | 5CM1 | T | LH82 | | | | |
| 442 | Ampli-con1459402 | 147186 | 348 | 348 | SNP | G | LH82 | G | 5CM1 | | | | |
| 442 | Ampli-con1459402 | 147187 | 396 | 396 | SNP | C | LH82 | G | 5CM1 | | | | |
| 442 | Ampli-con1459402 | 147188 | 422 | 422 | SNP | C | LH82 | T | 5CM1 | | | | |
| 442 | Ampli-con1459402 | 147189 | 477 | 485 | IND | ********** | 5CM1 | TATTGTTTT | LH82 | | | | |
| 442 | Ampli-con1459402 | 147190 | 488 | 491 | IND | **** | 5CM1 | CCTT | LH82 | | | | |
| 442 | Ampli-con1459402 | 147191 | 496 | 496 | IND | * | 5CM1 | A | LH82 | | | | |
| 442 | Ampli-con1459402 | 147192 | 506 | 506 | SNP | C | LH82 | T | 5CM1 | | | | |
| 443 | Ampli-con1459402 | 147216 | 63 | 63 | SNP | A | b73:LH82 | G | 5CM1 | | | | |
| 443 | Ampli-con1459406 | 147217 | 64 | 64 | SNP | C | LH82 | T | 5CM1 | | | | |
| 443 | Ampli-con1459406 | 147218 | 104 | 104 | SNP | C | LH82 | T | 5CM1 | | | | |
| 443 | Ampli-con1459406 | 147219 | 145 | 145 | SNP | A | LH82 | G | b73:5CM1 | | | | |
| 443 | Ampli-con1459406 | 147220 | 253 | 253 | SNP | A | LH82 | G | b73:5CM1 | | | | |
| 443 | Ampli-con1459406 | 147221 | 324 | 324 | SNP | A | LH82 | G | b73:5CM1 | | | | |
| 443 | Ampli-con1459406 | 147222 | 325 | 325 | IND | * | LH82 | G | b73:5CM1 | | | | |
| 443 | Ampli-con1459406 | 147223 | 409 | 409 | SNP | A | b73:5CM1 | G | LH82 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 444 | Ampli-con1459414 | 147406 | 61 | 61 | SNP | G | b73:mo17:5CM1 | T | LH82 | | | | |
| 444 | Ampli-con1459414 | 147407 | 79 | 79 | SNP | G | LH82 | T | b73:mo17:5CM1 | | | | |
| 444 | Ampli-con1459414 | 147408 | 81 | 81 | SNP | C | mo17:LH82 | T | b73:5CM1 | | | | |
| 444 | Ampli-con1459414 | 147409 | 91 | 91 | SNP | C | LH82 | T | b73:mo17:5CM1 | | | | |
| 444 | Ampli-con1459414 | 147410 | 159 | 159 | IND | * | b73:mo17:5CM1 | C | LH82 | | | | |
| 444 | Ampli-con1459414 | 147411 | 207 | 207 | SNP | C | mo17 | T | b73:5CM1:LH82 | | | | |
| 444 | Ampli-con1459414 | 147412 | 415 | 415 | SNP | C | b73 | T | mo17:5CM1:LH82 | | | | |
| 444 | Ampli-con1459414 | 147414 | 453 | 453 | SNP | G | b73:5CM1:LH82 | T | mo17 | | | | |
| 444 | Ampli-con1459414 | 147416 | 493 | 493 | SNP | C | b73:5CM1 | T | mo17:LH82 | | | | |
| 445 | Ampli-con1459414 | 147417 | 82 | 82 | SNP | C | b73 | G | mo17:5CM1:LH82 | | | | |
| 446 | Ampli-con1459415 | 147478 | 165 | 165 | SNP | C | b73:LH82 | G | mo17:5CM1 | | | | |
| 446 | Ampli-con1459421 | 147480 | 205 | 205 | SNP | A | b73:LH82 | G | mo17:5CM1 | | | | |
| 446 | Ampli-con1459421 | 147481 | 226 | 226 | SNP | A | b73:LH82 | C | mo17:5CM1 | | | | |
| 446 | Ampli-con1459421 | 147482 | 259 | 259 | SNP | A | b73:LH82 | G | mo17:5CM1 | | | | |
| 446 | Ampli-con1459421 | 147484 | 316 | 316 | SNP | C | mo17:5CM1 | T | b73:LH82 | | | | |
| 446 | Ampli-con1459421 | 147485 | 355 | 355 | SNP | A | b73:mo17:5CM1 | T | LH82 | | | | |
| 446 | Ampli-con1459421 | 147487 | 375 | 375 | SNP | A | mo17:5CM1 | G | b73:LH82 | | | | |
| 446 | Ampli-con1459421 | 147488 | 391 | 391 | SNP | A | mo17:5CM1 | T | b73:LH82 | | | | |
| 446 | Ampli-con1459421 | 147489 | 400 | 400 | SNP | A | 5CM1 | G | b73:mo17:LH82 | | | | |
| 446 | Ampli-con1459421 | 147496 | 539 | 539 | SNP | G | b73:LH82 | T | b73:mo17:LH82 | | | | |
| 446 | Ampli-con1459421 | 147498 | 577 | 577 | SNP | A | mo17:5CM1 | G | b73:LH82 | | | | |
| 446 | Ampli-con1459421 | 147499 | 631 | 631 | SNP | C | b73:LH82 | T | mo17:5CM1 | | | | |
| 446 | Ampli-con1459421 | 147500 | 650 | 650 | SNP | A | b73:LH82 | G | mo17:5CM1 | | | | |
| 446 | Ampli-con1459421 | 147501 | 660 | 660 | SNP | C | b73:LH82 | T | mo17:5CM1 | | | | |
| 446 | Ampli-con1459421 | 147502 | 740 | 740 | SNP | A | b73:LH82 | G | mo17:5CM1 | | | | |
| 446 | Ampli-con1459421 | 147504 | 820 | 820 | SNP | C | b73:LH82 | T | mo17:5CM1 | | | | |
| 446 | Ampli-con1459421 | 147505 | 822 | 822 | SNP | C | mo17:5CM1 | T | b73:LH82 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 446 | Ampli-con1459421 | 147506 | 866 | 866 | SNP | A | mo17:5CM1 | T | b73:LH82 | | | | |
| 446 | Ampli-con1459421 | 147507 | 907 | 907 | IND | * | mo17 | C | b73:5CM1:LH82 mo17:5CM1 | | | | |
| 446 | Ampli-con1459421 | 147509 | 912 | 912 | SNP | C | b73:LH82 | G | mo17:5CM1 | | | | |
| 447 | Ampli-con1459422 | 147511 | 144 | 144 | SNP | A | b73 | G | mo17:5CM1:LH82 | | | | |
| 447 | Ampli-con1459422 | 147512 | 174 | 174 | SNP | C | b73:mo17:LH82 5CM1 | T | 5CM1 | | | | |
| 447 | Ampli-con1459422 | 147513 | 177 | 177 | SNP | A | b73:mo17:LH82 5CM1 | G | b73:mo17:LH82 5CM1 | | | | |
| 447 | Ampli-con1459422 | 147514 | 281 | 283 | IND | *** | b73:mo17:LH82 | TAA | b73:mo17:LH82 | | | | |
| 447 | Ampli-con1459422 | 147515 | 334 | 334 | SNP | A | b73:5CM1 | T | mo17:LH82 | | | | |
| 447 | Ampli-con1459422 | 147516 | 416 | 416 | SNP | A | 5CM1 | G | b73:LH82 | | | | |
| 447 | Ampli-con1459422 | 147517 | 508 | 508 | SNP | C | b73 | T | mo17:5CM1:LH82 | | | | |
| 447 | Ampli-con1459422 | 147518 | 581 | 581 | SNP | A | mo17:LH82 | C | b73:5CM1 | | | | |
| 447 | Ampli-con1459422 | 147519 | 621 | 621 | SNP | A | mo17:5CM1:LH82 | C | b73 | | | | |
| 447 | Ampli-con1459422 | 147520 | 630 | 630 | SNP | G | mo17:5CM1:LH82 | T | b73 | | | | |
| 447 | Ampli-con1459422 | 147521 | 641 | 641 | SNP | G | b73:5CM1 | T | mo17:LH82 | | | | |
| 447 | Ampli-con1459422 | 147522 | 648 | 648 | SNP | A | mo17:LH82 | T | b73:5CM1 | | | | |
| 447 | Ampli-con1459422 | 147523 | 656 | 656 | SNP | G | b73:mo17:LH82 | T | 5CM1 | | | | |
| 447 | Ampli-con1459422 | 147525 | 697 | 697 | SNP | C | b73:mo17:LH82 | T | 5CM1 | | | | |
| 447 | Ampli-con1459422 | 147526 | 734 | 734 | SNP | C | mo17:LH82 | G | b73:5CM1 | | | | |
| 447 | Ampli-con1459422 | 147527 | 759 | 759 | SNP | C | 5CM1 | T | b73:mo17:LH82 | | | | |
| 447 | Ampli-con1459422 | 147528 | 788 | 788 | SNP | C | 5CM1 | T | b73:mo17:LH82 | | | | |
| 447 | Ampli-con1459422 | 147529 | 791 | 791 | SNP | C | b73 | G | mo17:5CM1:LH82 | | | | |
| 447 | Ampli-con1459422 | 147530 | 792 | 792 | SNP | A | b73 | G | mo17:5CM1:LH82 | | | | |
| 447 | Ampli-con1459422 | 147531 | 830 | 830 | SNP | C | b73:mo17:LH82 | T | 5CM1 | | | | |
| 447 | Ampli-con1459422 | 147532 | 849 | 849 | SNP | C | b73:mo17:LH82 | T | 5CM1 | | | | |
| 447 | Ampli-con1459422 | 147533 | 868 | 868 | SNP | C | mo17:LH82 | T | b73:5CM1 | | | | |
| 447 | Ampli-con1459422 | 147535 | 908 | 908 | SNP | A | 5CM1 | C | b73:mo17:LH82 | | | | |
| 447 | Ampli-con1459422 | 147536 | 921 | 921 | SNP | A | 5CM1 | G | b73:mo17:LH82 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 447 | Ampli-con1459422 | 147537 | 928 | 928 | SNP | G | b73:mo17:LH82 | T | 5CM1 | | | | |
| 447 | Ampli-con1459422 | 147538 | 943 | 947 | IND | ***** | 5CM1 | CTTGT | b73:mo17:LH82 | | | | |
| 447 | Ampli-con1459422 | 147539 | 961 | 961 | SNP | C | mo17:5CM1:LH82 | T | b73 | | | | |
| 447 | Ampli-con1459422 | 147540 | 966 | 966 | SNP | A | b73:mo17:LH82 | T | 5CM1 | | | | |
| 447 | Ampli-con1459422 | 147541 | 1142 | 1142 | SNP | G | b73:mo17:LH82 | T | 5CM1 | | | | |
| 448 | Ampli-con1459423 | 147542 | 183 | 183 | SNP | C | b73:5CM1:LH82 | T | mo17 | | | | |
| 448 | Ampli-con1459423 | 147543 | 455 | 455 | SNP | C | LH82 | T | b73:5CM1:mo17 | | | | |
| 448 | Ampli-con1459423 | 147544 | 533 | 540 | IND | ********* | b73:5CM1:LH82 | ATTGAAAT | mo17 | | | | |
| 448 | Ampli-con1459423 | 147545 | 650 | 650 | SNP | C | mo17 | T | b73:5CM1:LH82 | | | | |
| 448 | Ampli-con1459423 | 147546 | 851 | 851 | SNP | C | mo17 | T | b73:5CM1:LH82 | | | | |
| 448 | Ampli-con1459423 | 147548 | 1046 | 1046 | SNP | A | mo17 | G | b73:5CM1:LH82 | | | | |
| 449 | Ampli-con1459443 | 147767 | 279 | 279 | SNP | G | b73:mo17:LH82 | T | mo17:5CM1:LH82 | | | | |
| 449 | Ampli-con1459443 | 147768 | 429 | 429 | SNP | C | mo17:5CM1:LH82 | T | b73 | | | | |
| 449 | Ampli-con1459443 | 147771 | 483 | 483 | SNP | C | b73:mo17:LH82 | T | 5CM1 | | | | |
| 449 | Ampli-con1459443 | 147772 | 620 | 620 | SNP | A | b73 | T | mo17:5CM1:LH82 | | | | |
| 449 | Ampli-con1459443 | 147773 | 627 | 627 | SNP | A | mo17:5CM1:LH82 | G | b73 | | | | |
| 450 | Ampli-con1460617 | 148018 | 61 | 61 | SNP | C | mo17 | G | b73:LH82 | | | | |
| 450 | Ampli-con1460617 | 148019 | 112 | 112 | SNP | A | b73:LH82 | C | mo17 | | | | |
| 450 | Ampli-con1460617 | 148020 | 224 | 224 | SNP | G | b73:LH82 | T | mo17 | | | | |
| 450 | Ampli-con1460617 | 148021 | 228 | 228 | SNP | C | b73 | G | mo17:LH82 | | | | |
| 450 | Ampli-con1460617 | 148022 | 235 | 235 | SNP | A | LH82 | C | b73:mo17 | | | | |
| 450 | Ampli-con1460617 | 148023 | 245 | 247 | IND | *** | mo17:LH82 | GTC | b73 | | | | |
| 450 | Ampli-con1460617 | 148024 | 283 | 291 | IND | ********* | mo17 | ACGTACGGT | b73:LH82 | | | | |
| 450 | Ampli-con1460617 | 148026 | 329 | 332 | IND | **** | mo17:LH82 | GTAC | b73 | | | | |
| 450 | Ampli-con1460617 | 148027 | 354 | 357 | IND | **** | b73:mo17 | CATC | LH82 | | | | |
| 450 | Ampli-con1460617 | 148028 | 382 | 383 | IND | ** | mo17:LH82 | CA | b73 | | | | |
| 450 | Ampli-con1460617 | 148029 | 426 | 431 | IND | ******* | b73:LH82 | CTGTGT | mo17 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 450 | Ampli-con1460617 | 148030 | 442 | 442 | SNP | C | b73:LH82 | G | mo17 | | | | |
| 450 | Ampli-con1460617 | 148031 | 454 | 456 | IND | *** | b73:LH82 | TAC | mo17 | | | | |
| 450 | Ampli-con1460617 | 148032 | 462 | 462 | SNP | C | mo17 | G | b73:LH82 | | | | |
| 451 | Ampli-con1460632 | 148155 | 229 | 229 | SNP | A | b73:LH82 | C | mo17:5CM1 | | | | |
| 451 | Ampli-con1460632 | 148156 | 280 | 280 | SNP | A | mo17:5CM1 | C | b73:LH82 | | | | |
| 451 | Ampli-con1460632 | 148157 | 546 | 546 | SNP | A | b73:LH82 | C | mo17:5CM1 | | | | |
| 451 | Ampli-con1460632 | 148158 | 587 | 587 | SNP | A | mo17:5CM1:LH82 | G | b73 | | | | |
| 451 | Ampli-con1460632 | 148159 | 613 | 613 | SNP | C | mo17:5CM1:LH82 | T | b73 | | | | |
| 452 | Ampli-con1460638 | 148194 | 467 | 467 | SNP | A | 5CM1 | G | b73 | | | | |
| 453 | Ampli-con1460644 | 148039 | 94 | 94 | SNP | C | b73:5CM1 | T | mo17:LH82 | | | | |
| 453 | Ampli-con1460644 | 148040 | 115 | 115 | SNP | A | LH82 | C | b73:mo17:5CM1 | | | | |
| 453 | Ampli-con1460644 | 148041 | 125 | 125 | SNP | C | 5CM1 | T | b73:mo17:LH82 | | | | |
| 453 | Ampli-con1460644 | 148042 | 139 | 139 | IND | * | 5CM1 | C | b73:mo17:LH82 | | | | |
| 453 | Ampli-con1460644 | 148043 | 146 | 146 | SNP | A | mo17 | C | b73:5CM1:LH82 | | | | |
| 453 | Ampli-con1460644 | 148044 | 171 | 171 | SNP | A | b73:5CM1 | G | mo17:LH82 | | | | |
| 453 | Ampli-con1460644 | 148045 | 190 | 190 | SNP | C | b73:mo17:5CM1 | G | LH82 | | | | |
| 453 | Ampli-con1460644 | 148046 | 192 | 192 | SNP | A | b73:5CM1 | G | mo17:LH82 | | | | |
| 453 | Ampli-con1460644 | 148047 | 209 | 209 | SNP | A | b73:5CM1 | G | LH82 | | | | |
| 453 | Ampli-con1460644 | 148048 | 217 | 217 | SNP | C | b73:mo17:5CM1:LH82 | T | | | | | |
| 453 | Ampli-con1460644 | 148049 | 222 | 222 | SNP | A | LH82 | G | b73:mo17:5CM1 | | | | |
| 453 | Ampli-con1460644 | 148050 | 252 | 252 | SNP | A | b73:5CM1 | G | mo17:LH82 | | | | |
| 453 | Ampli-con1460644 | 148051 | 258 | 258 | SNP | A | b73:5CM1 | G | mo17:LH82 | | | | |
| 453 | Ampli-con1460644 | 148052 | 273 | 273 | SNP | A | b73:5CM1:LH82 | G | mo17 | | | | |
| 453 | Ampli-con1460644 | 148053 | 290 | 290 | SNP | A | b73 | G | mo17:5CM1:LH82 | | | | |
| 453 | Ampli-con1460644 | 148054 | 295 | 295 | SNP | A | mo17:LH82 | G | b73:5CM | | | | |
| 453 | Ampli-con1460644 | 148055 | 308 | 308 | SNP | C | mo17 | T | b73:5CM1:LH82 | | | | |
| 453 | Ampli-con1460644 | 148056 | 325 | 339 | IND | *************** | b73:5CM1 | CCTTCGATGATAATG | mo17 | TCTTCGATGATAATG | LH82 | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 453 | Ampli-con1460644 | 148057 | 342 | 356 | IND | **************** | mo17 | TTCGACGATGACGCC | b73 | TTCGATGATGACGCC | 5CM1 | TTCGATGATG-ATGCC | LH82 |
| 453 | Ampli-con1460644 | 148058 | 359 | 359 | SNP | C | mo17:LH82 | G | b73:5CM1 | | | | |
| 453 | Ampli-con1460644 | 148059 | 360 | 360 | SNP | C | mo17:LH82 | T | b73:5CM1 | | | | |
| 453 | Ampli-con1460644 | 148060 | 367 | 367 | SNP | C | b73:5CM1 | T | mo17:LH82 | | | | |
| 453 | Ampli-con1460644 | 148061 | 372 | 372 | SNP | A | mo17:LH82 | G | b73:5CM1 | | | | |
| 453 | Ampli-con1460644 | 148062 | 375 | 375 | SNP | A | b73:5CM1 | G | mo17:LH82 | | | | |
| 453 | Ampli-con1460644 | 148063 | 378 | 378 | SNP | G | b73:5CM1:LH82 | T | mo17 | | | | |
| 453 | Ampli-con1460644 | 148064 | 382 | 382 | SNP | A | LH82 | C | b73:mo17:5CM1 | | | | |
| 453 | Ampli-con1460644 | 148065 | 384 | 384 | SNP | A | b73:5CM1 | G | mo17:LH82 | | | | |
| 453 | Ampli-con1460644 | 148066 | 393 | 393 | SNP | A | b73:5CM1:LH82 | G | mo17 | | | | |
| 453 | Ampli-con1460644 | 148067 | 399 | 399 | SNP | A | mo17 | G | b73:5CM1:LH82 | | | | |
| 453 | Ampli-con1460644 | 148068 | 424 | 424 | SNP | C | mo17:LH82 | T | b73:5CM1 | | | | |
| 453 | Ampli-con1460644 | 148069 | 432 | 432 | SNP | A | b73 | G | mo17:5CM1:LH82 | | | | |
| 454 | Ampli-con1460702 | 148621 | 441 | 441 | SNP | A | LH82 | G | b73:mo17:5CM1 | | | | |
| 455 | Ampli-con1460724 | 148362 | 274 | 274 | SNP | A | 5CM1 | G | b73:LH82 | | | | |
| 455 | Ampli-con1460724 | 148364 | 425 | 425 | SNP | A | b73:LH82 | C | 5CM1 | | | | |
| 455 | Ampli-con1460724 | 148367 | 548 | 548 | SNP | G | 5CM1 | T | b73:LH82 | | | | |
| 455 | Ampli-con1460724 | 148380 | 600 | 600 | SNP | C | b73:LH82 | G | 5CM1 | | | | |
| 455 | Ampli-con1460724 | 148381 | 601 | 601 | SNP | A | b73:LH82 | T | 5CM1 | | | | |
| 455 | Ampli-con1460724 | 148382 | 605 | 605 | SNP | A | 5CM1 | T | b73:LH82 | | | | |
| 455 | Ampli-con1460724 | 148384 | 618 | 618 | SNP | G | b73:mo17:5CM1 | T | LH82 | | | | |
| 456 | Ampli-con1461863 | 151469 | 54 | 54 | SNP | C | b73:mo17:5CM1 | T | 5CM1 | | | | |
| 456 | Ampli-con1461863 | 151470 | 63 | 63 | SNP | C | b73:mo17:LH82 | T | 5CM1 | | | | |
| 456 | Ampli-con1461863 | 151471 | 69 | 69 | SNP | C | 5CM1 | G | b73:mo17:LH82 | | | | |
| 456 | Ampli-con1461863 | 151472 | 93 | 93 | SNP | A | LH82 | G | b73:mo17:5CM1 | | | | |
| 456 | Ampli-con1461863 | 151473 | 114 | 114 | SNP | C | LH82 | T | b73:mo17:5CM1 | | | | |
| 456 | Ampli-con1461863 | 151474 | 144 | 144 | SNP | A | 5CM1 | G | b73:mo17:LH82 | | | | |

-continued

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 456 | Ampli-con1461863 | 151475 | 223 | 228 | IND | ****** | LH82 | TTCGGT | b73:mo17:5CM1 | | | | |
| 456 | Ampli-con1461863 | 151476 | 240 | 240 | SNP | C | b73:mo17:LH82 | T | 5CM1 | | | | |
| 456 | Ampli-con1461863 | 151477 | 249 | 249 | SNP | A | b73:mo17:5CM1 | C | LH82 | | | | |
| 456 | Ampli-con1461863 | 151478 | 253 | 253 | SNP | G | 5CM1 | T | b73:mo17:LH82 | | | | |
| 456 | Ampli-con1461863 | 151479 | 258 | 258 | SNP | A | b73:mo17 | G | 5CM1:LH82 | | | | |
| 456 | Ampli-con1461863 | 151480 | 268 | 270 | IND | *** | b73:mo17:LH82 | GAG | 5CM1 | | | | |
| 456 | Ampli-con1461863 | 151481 | 297 | 297 | SNP | C | b73:mo17:LH82 | T | 5CM1 | | | | |
| 456 | Ampli-con1461863 | 151482 | 318 | 318 | SNP | C | b73:mo17:LH82 | T | 5CM1 | | | | |
| 456 | Ampli-con1461863 | 151483 | 408 | 408 | SNP | A | b73:mo17:LH82 | G | 5CM1 | | | | |
| 456 | Ampli-con1461863 | 151484 | 450 | 450 | SNP | A | 5CM1 | G | b73:mo17:LH82 | | | | |
| 456 | Ampli-con1461863 | 151485 | 459 | 459 | SNP | A | b73:mo17:LH82 | G | 5CM1 | | | | |
| 456 | Ampli-con1461863 | 151486 | 524 | 524 | SNP | C | b73:LH82 | G | 5CM1:LH82 | | | | |
| 457 | Ampli-con1461872 | 151382 | 224 | 224 | SNP | A | 5CM1 | C | b73:LH82 | | | | |
| 457 | Ampli-con1461872 | 151384 | 418 | 418 | SNP | C | b73:LH82 | G | 5CM1 | | | | |
| 457 | Ampli-con1461872 | 151385 | 444 | 444 | SNP | C | b73:LH82 | G | 5CM1 | | | | |
| 457 | Ampli-con1461872 | 151386 | 531 | 531 | SNP | A | b73 | T | 5CM1:LH82 | | | | |
| 457 | Ampli-con1461872 | 151388 | 534 | 534 | IND | * | b73:LH82 | G | 5CM1 | | | | |
| 457 | Ampli-con1461872 | 151389 | 534 | 536 | IND | *** | b73:LH82 | GCG | 5CM1 | | | | |
| 457 | Ampli-con1461872 | 151390 | 539 | 543 | IND | ****** | b73:LH82 | TTGCC | 5CM1 | | | | |
| 457 | Ampli-con1461872 | 151391 | 558 | 559 | IND | ** | LH82 | *A | b73 | GA | 5CM1 | |
| 457 | Ampli-con1461872 | 151392 | 562 | 562 | IND | * | b73 | A | 5CM1:LH82 | | | | |
| 457 | Ampli-con1461872 | 151393 | 568 | 568 | SNP | C | 5CM1 | G | b73:LH82 | | | | |
| 457 | Ampli-con1461872 | 151396 | 638 | 640 | IND | *** | 5CM1 | GGC | b73:LH82 | | | | |
| 457 | Ampli-con1461872 | 151397 | 642 | 642 | IND | * | 5CM1 | T | b73:LH82 | | | | |
| 458 | Ampli-con1461878 | 151271 | 267 | 267 | SNP | C | b73 | T | 5CM1 | | | | |
| 458 | Ampli-con1461878 | 151273 | 398 | 398 | SNP | G | 5CM1 | T | b73 | | | | |
| 458 | Ampli-con1461878 | 151274 | 406 | 406 | SNP | C | b73 | T | 5CM1 | | | | |

-continued

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 458 | Ampli-con1461878 | 151276 | 465 | 465 | SNP | C | b73 | T | 5CM1 | | | | |
| 458 | Ampli-con1461878 | 151277 | 468 | 468 | SNP | A | b73 | C | 5CM1 | | | | |
| 458 | Ampli-con1461878 | 151280 | 1079 | 1079 | SNP | A | 5CM1 | G | b73 | | | | |
| 458 | Ampli-con1461878 | 151281 | 1142 | 1144 | IND | *** | 5CM1 | GAG | b73 | | | | |
| 458 | Ampli-con1461878 | 151282 | 1155 | 1155 | SNP | A | b73 | G | 5CM1 | | | | |
| 458 | Ampli-con1461878 | 151283 | 1167 | 1167 | SNP | A | 5CM1 | G | b73 | | | | |
| 458 | Ampli-con1461878 | 151284 | 1180 | 1180 | SNP | A | b73 | G | 5CM1 | | | | |
| 458 | Ampli-con1461878 | 151285 | 1280 | 1280 | SNP | A | 5CM1 | T | b73 | | | | |
| 458 | Ampli-con1461878 | 151287 | 1323 | 1323 | SNP | C | b73 | G | 5CM1 | | | | |
| 458 | Ampli-con1461878 | 151288 | 1419 | 1419 | SNP | A | 5CM1 | T | b73 | | | | |
| 458 | Ampli-con1461878 | 151289 | 1447 | 1447 | SNP | C | 5CM1 | T | b73 | | | | |
| 458 | Ampli-con1461878 | 151290 | 1586 | 1586 | SNP | A | 5CM1 | G | b73 | | | | |
| 459 | Ampli-con1461878 | 151356 | 119 | 119 | SNP | A | LH82 | G | b73:mo17:5CM1 LH82 | | | | |
| 459 | Ampli-con1461887 | 151357 | 200 | 200 | SNP | A | b73:mo17:5CM1 | C | LH82 | | | | |
| 459 | Ampli-con1461887 | 151358 | 201 | 201 | SNP | C | b73:mo17:5CM1 | T | LH82 | | | | |
| 459 | Ampli-con1461887 | 151359 | 420 | 420 | SNP | A | b73:mo17:5CM1 | G | LH82 | | | | |
| 459 | Ampli-con1461887 | 151360 | 621 | 621 | SNP | A | b73 | G | mo17:5CM1:LH82 | | | | |
| 459 | Ampli-con1461887 | 151362 | 642 | 642 | SNP | C | b73:mo17:5CM1 | T | LH82 | | | | |
| 459 | Ampli-con1461887 | 151363 | 644 | 644 | SNP | A | b73:mo17:5CM1 | T | LH82 | | | | |
| 459 | Ampli-con1461887 | 151364 | 645 | 645 | SNP | A | LH82 | C | b73:mo17:5CM1 | | | | |
| 460 | Ampli-con1462250 | 153431 | 205 | 205 | SNP | A | LH82 | G | b73:mo17:5CM1 | | | | |
| 460 | Ampli-con1462250 | 153432 | 325 | 325 | SNP | A | b73:mo17:LH82 | G | 5CM1 | | | | |
| 460 | Ampli-con1462250 | 153433 | 391 | 391 | SNP | A | 5CM1 | G | b73:mo17:LH82 | | | | |
| 460 | Ampli-con1462250 | 153434 | 529 | 529 | SNP | A | 5CM1 | G | b73:LH82 | | | | |
| 461 | Ampli-con1462274 | 153427 | 79 | 79 | SNP | C | mo17:5CM1 | T | LH82 | | | | |
| 462 | Ampli-con1462278 | 153630 | 55 | 55 | SNP | A | b73:5CM1 | T | LH82 | | | | |
| 462 | Ampli-con1462278 | 153631 | 59 | 59 | SNP | C | b73:5CM1 | T | LH82 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 462 | Ampli-con1462278 | 153632 | 103 | 103 | SNP | G | 5CM1:LH82 | T | b73 | | | | |
| 462 | Ampli-con1462278 | 153633 | 141 | 141 | IND | * | b73:LH82 | A | 5CM1 | | | | |
| 462 | Ampli-con1462278 | 153636 | 210 | 210 | SNP | C | b73:5CM1 | T | LH82 | | | | |
| 462 | Ampli-con1462278 | 153637 | 245 | 245 | SNP | G | b73:LH82 | T | 5CM1 | | | | |
| 462 | Ampli-con1462278 | 153638 | 399 | 399 | SNP | C | 5CM1 | T | b73:LH82 | | | | |
| 462 | Ampli-con1462278 | 153639 | 408 | 415 | IND | ******** | 5CM1 | GCCAAGTC | b73:LH82 | | | | |
| 462 | Ampli-con1462278 | 153640 | 418 | 420 | IND | *** | 5CM1 | CAG | b73:LH82 | | | | |
| 462 | Ampli-con1462278 | 153641 | 423 | 427 | IND | ***** | 5CM1 | AGCCA | b73:LH82 | | | | |
| 462 | Ampli-con1462278 | 153642 | 433 | 433 | SNP | A | 5CM1 | C | b73:LH82 | | | | |
| 462 | Ampli-con1462278 | 153643 | 434 | 434 | SNP | C | 5CM1 | G | b73:LH82 | | | | |
| 462 | Ampli-con1462278 | 153644 | 435 | 435 | SNP | A | 5CM1 | T | b73:LH82 | | | | |
| 462 | Ampli-con1462278 | 153645 | 454 | 457 | IND | **** | 5CM1 | ATCA | b73:LH82 | | | | |
| 462 | Ampli-con1462278 | 153646 | 467 | 467 | SNP | A | b73:LH82 | T | 5CM1 | | | | |
| 462 | Ampli-con1462278 | 153647 | 468 | 468 | SNP | C | b73:LH82 | G | 5CM1 | | | | |
| 462 | Ampli-con1462278 | 153648 | 470 | 470 | SNP | C | 5CM1 | G | b73:LH82 | | | | |
| 462 | Ampli-con1462278 | 153649 | 503 | 503 | SNP | A | b73:LH82 | C | 5CM1 | | | | |
| 462 | Ampli-con1462278 | 153650 | 527 | 527 | SNP | A | b73:LH82 | C | 5CM1 | | | | |
| 462 | Ampli-con1462278 | 153651 | 548 | 548 | IND | * | 5CM1 | T | b73:LH82 | | | | |
| 462 | Ampli-con1462278 | 153652 | 672 | 672 | SNP | A | b73:LH82 | G | 5CM1 | | | | |
| 463 | Ampli-con1462297 | 153856 | 137 | 138 | IND | ** | b73:LH82 | AC | 5CM1 | | | | |
| 463 | Ampli-con1462297 | 153857 | 151 | 151 | SNP | A | 5CM1 | T | b73:LH82 | | | | |
| 463 | Ampli-con1462297 | 153858 | 160 | 163 | IND | **** | LH82 | AGCT | b73:5CM1 | | | | |
| 463 | Ampli-con1462297 | 153860 | 197 | 197 | SNP | C | 5CM1:LH82 | T | b73 | | | | |
| 463 | Ampli-con1462297 | 153861 | 201 | 201 | SNP | A | 5CM1:LH82 | G | b73 | | | | |
| 463 | Ampli-con1462297 | 153862 | 207 | 207 | SNP | G | b73:5CM1 | T | LH82 | | | | |
| 463 | Ampli-con1462297 | 153863 | 221 | 221 | SNP | C | b73:LH82 | T | 5CM1 | | | | |
| 463 | Ampli-con1462297 | 153864 | 232 | 232 | SNP | A | 5CM1 | C | b73:LH82 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 463 | Ampli-con1462297 | 153865 | 270 | 276 | IND | ******** | b73:5CM1 | TCTCCCG | LH82 | | | | |
| 463 | Ampli-con1462297 | 153866 | 292 | 292 | SNP | G | 5CM1 | T | b73:LH82 | | | | |
| 463 | Ampli-con1462297 | 153867 | 302 | 303 | IND | ** | b73 | GG | 5CM1:LH82 | | | | |
| 463 | Ampli-con1462297 | 153868 | 303 | 322 | IND | ******************* | 5CM1 | ***CAGAGCATGGTACCGAG | b73 | GGGCAGAGCATGG-TACCGAG | LH82 | | |
| 463 | Ampli-con1462297 | 153869 | 324 | 324 | SNP | C | LH82 | T | b73:5CM1 | | | | |
| 463 | Ampli-con1462297 | 153870 | 334 | 338 | IND | ***** | LH82 | TATGA | b73:5CM1 | | | | |
| 463 | Ampli-con1462297 | 153871 | 374 | 374 | SNP | A | LH82 | G | b73:5CM1 | | | | |
| 463 | Ampli-con1462297 | 153872 | 389 | 389 | SNP | C | b73 | T | 5CM1:LH82 | | | | |
| 463 | Ampli-con1462297 | 153873 | 392 | 392 | SNP | C | 5CM1:LH82 | T | b73:LH82 | | | | |
| 463 | Ampli-con1462297 | 153874 | 411 | 411 | IND | * | b73:LH82 | T | 5CM1 | | | | |
| 463 | Ampli-con1462297 | 153875 | 414 | 414 | IND | * | 5CM1 | C | b73:LH82 | | | | |
| 463 | Ampli-con1462297 | 153876 | 420 | 420 | SNP | A | b73:5CM1 | G | LH82 | | | | |
| 463 | Ampli-con1462297 | 153877 | 443 | 447 | IND | ***** | 5CM1:LH82 | TTAAA | b73 | | | | |
| 463 | Ampli-con1462297 | 153878 | 472 | 472 | SNP | A | 5CM1:LH82 | G | b73 | | | | |
| 463 | Ampli-con1462297 | 153879 | 553 | 553 | SNP | C | 5CM1:LH82 | G | b73 | | | | |
| 463 | Ampli-con1462297 | 153880 | 714 | 714 | SNP | C | 5CM1:LH82 | T | b73 | | | | |
| 463 | Ampli-con1462297 | 153881 | 715 | 715 | SNP | A | 5CM1:LH82 | T | b73 | | | | |
| 464 | Ampli-con1462302 | 153412 | 260 | 260 | SNP | C | 5CM1:LH82 | G | b73 | | | | |
| 464 | Ampli-con1462302 | 153413 | 286 | 286 | SNP | A | 5CM1:LH82 | T | b73 | | | | |
| 464 | Ampli-con1462302 | 153414 | 320 | 320 | SNP | A | b73 | G | 5CM1:LH82 | | | | |
| 464 | Ampli-con1462302 | 153415 | 430 | 430 | SNP | C | b73 | T | 5CM1:LH82 | | | | |
| 464 | Ampli-con1462302 | 153416 | 434 | 434 | SNP | C | b73 | T | 5CM1:LH82 | | | | |
| 464 | Ampli-con1462302 | 153417 | 492 | 492 | SNP | A | b73 | G | 5CM1:LH82 | | | | |
| 464 | Ampli-con1462302 | 153420 | 1001 | 1001 | SNP | A | 5CM1:LH82 | T | b73 | | | | |
| 464 | Ampli-con1462302 | 153423 | 1032 | 1032 | SNP | G | 5CM1:LH82 | T | b73 | | | | |
| 464 | Ampli-con1462302 | 153424 | 1042 | 1042 | SNP | A | b73 | T | 5CM1:LH82 | | | | |
| 464 | Ampli-con1462302 | 153425 | 1493 | 1493 | SNP | A | b73 | T | 5CM1:LH82 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 464 | Ampli-con1462302 | 153426 | 1495 | 1495 | SNP | A | b73 | G | 5CM1:LH82 | | | | |
| 465 | Ampli-con1462306 | 153885 | 53 | 53 | SNP | C | 5CM1:LH82 | T | b73 | | | | |
| 465 | Ampli-con1462306 | 153886 | 86 | 86 | SNP | A | b73 | G | 5CM1:LH82 | | | | |
| 465 | Ampli-con1462306 | 153887 | 311 | 311 | IND | * | b73 | C | 5CM1:LH82 | | | | |
| 465 | Ampli-con1462306 | 153889 | 352 | 352 | SNP | A | b73 | C | 5CM1:LH82 | | | | |
| 465 | Ampli-con1462306 | 153890 | 372 | 372 | IND | * | b73 | T | 5CM1:LH82 | | | | |
| 465 | Ampli-con1462306 | 153891 | 479 | 479 | SNP | A | b73 | G | 5CM1:LH82 | | | | |
| 465 | Ampli-con1462306 | 153892 | 577 | 577 | SNP | C | 5CM1:LH82 | T | b73 | | | | |
| 465 | Ampli-con1462306 | 153893 | 601 | 601 | SNP | G | 5CM1:LH82 | G | b73 | | | | |
| 465 | Ampli-con1462306 | 153894 | 1032 | 1032 | SNP | A | 5CM1:LH82 | T | b73 | | | | |
| 465 | Ampli-con1462306 | 153895 | 1090 | 1090 | SNP | G | b73 | T | 5CM1:LH82 | | | | |
| 465 | Ampli-con1462306 | 153897 | 1166 | 1166 | SNP | C | b73 | G | 5CM1:LH82 | | | | |
| 465 | Ampli-con1462306 | 153898 | 1214 | 1214 | SNP | C | b73 | T | 5CM1:LH82 | | | | |
| 465 | Ampli-con1462306 | 153901 | 1276 | 1276 | SNP | C | b73 | T | 5CM1:LH82 | | | | |
| 465 | Ampli-con1462306 | 153902 | 1297 | 1297 | SNP | G | 5CM1:LH82 | T | b73 | | | | |
| 465 | Ampli-con1462306 | 153903 | 1362 | 1362 | SNP | C | 5CM1:LH82 | T | b73 | | | | |
| 465 | Ampli-con1462306 | 153904 | 1374 | 1374 | SNP | A | 5CM1:LH82 | G | b73 | | | | |
| 465 | Ampli-con1462306 | 153905 | 1380 | 1383 | IND | **** | b73 | ATAT | 5CM1:LH82 | | | | |
| 465 | Ampli-con1462306 | 153906 | 1385 | 1385 | SNP | C | b73 | T | 5CM1:LH82 | | | | |
| 465 | Ampli-con1462306 | 153907 | 1412 | 1412 | SNP | A | 5CM1:LH82 | G | b73 | | | | |
| 465 | Ampli-con1462306 | 153908 | 1414 | 1414 | SNP | A | 5CM1:LH82 | T | b73 | | | | |
| 465 | Ampli-con1462306 | 153909 | 1466 | 1466 | SNP | C | 5CM1:LH82 | T | b73 | | | | |
| 465 | Ampli-con1462306 | 153910 | 1469 | 1469 | SNP | C | b73 | T | 5CM1:LH82 | | | | |
| 465 | Ampli-con1462306 | 153911 | 1516 | 1516 | SNP | C | b73 | G | 5CM1:LH82 | | | | |
| 465 | Ampli-con1462306 | 153912 | 1555 | 1555 | SNP | C | b73 | T | 5CM1:LH82 | | | | |
| 465 | Ampli-con1462306 | 153913 | 1562 | 1562 | SNP | C | 5CM1:LH82 | G | b73 | | | | |
| 465 | Ampli-con1462306 | 153914 | 1567 | 1567 | SNP | C | 5CM1:LH82 | T | b73 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 465 | Ampli-con1462306 | 153915 | 1580 | 1581 | IND | ** | 5CM1:LH82 | AC | b73 | | | | |
| 465 | Ampli-con1462306 | 153916 | 1585 | 1590 | IND | ****** | 5CM1:LH82 | TTATTA | b73 | | | | |
| 465 | Ampli-con1462306 | 153917 | 1597 | 1597 | SNP | A | b73 | C | 5CM1:LH82 | | | | |
| 465 | Ampli-con1462306 | 153918 | 1608 | 1608 | SNP | C | 5CM1:LH82 | T | b73 | | | | |
| 466 | Ampli-con1463332 | 153971 | 33 | 33 | SNP | C | b73:LH82 | T | 5CM1 | | | | |
| 466 | Ampli-con1463332 | 153972 | 108 | 108 | SNP | G | 5CM1 | T | b73:LH82 | | | | |
| 466 | Ampli-con1463332 | 153973 | 110 | 110 | SNP | A | b73:LH82 | C | 5CM1 | | | | |
| 466 | Ampli-con1463332 | 153974 | 116 | 116 | IND | * | b73:LH82 | T | 5CM1 | | | | |
| 466 | Ampli-con1463332 | 153975 | 141 | 141 | SNP | A | b73:LH82 | G | 5CM1 | | | | |
| 466 | Ampli-con1463332 | 153976 | 148 | 148 | IND | * | b73:LH82 | A | 5CM1 | | | | |
| 466 | Ampli-con1463332 | 153977 | 170 | 170 | SNP | C | 5CM1 | G | b73:LH82 | | | | |
| 466 | Ampli-con1463332 | 153978 | 180 | 180 | SNP | A | 5CM1 | G | b73:LH82 | | | | |
| 466 | Ampli-con1463332 | 153979 | 181 | 181 | SNP | C | b73:LH82 | T | 5CM1 | | | | |
| 466 | Ampli-con1463332 | 153980 | 214 | 214 | SNP | C | 5CM1 | T | b73:LH82 | | | | |
| 466 | Ampli-con1463332 | 153981 | 313 | 313 | SNP | A | b73:LH82 | G | 5CM1 | | | | |
| 466 | Ampli-con1463332 | 153982 | 331 | 331 | SNP | C | 5CM1 | G | b73:LH82 | | | | |
| 466 | Ampli-con1463332 | 153985 | 463 | 463 | SNP | A | 5CM1 | C | b73:LH82 | | | | |
| 466 | Ampli-con1463332 | 153987 | 485 | 485 | SNP | C | 5CM1 | T | b73:LH82 | | | | |
| 466 | Ampli-con1463332 | 153993 | 971 | 971 | SNP | C | b73:LH82 | T | 5CM1 | | | | |
| 466 | Ampli-con1463332 | 153994 | 1124 | 1124 | SNP | C | b73:LH82 | T | 5CM1 | | | | |
| 466 | Ampli-con1463332 | 153995 | 1146 | 1146 | SNP | A | 5CM1 | G | b73:LH82 | | | | |
| 466 | Ampli-con1463332 | 153996 | 1178 | 1207 | IND | *********************** | b73:LH82 | GGTCCATGGTGCACTTAGAAA-GAACAGTCT | 5CM1 | | | | |
| 466 | Ampli-con1463332 | 153997 | 1215 | 1215 | SNP | A | b73:LH82 | G | 5CM1 | | | | |
| 466 | Ampli-con1463332 | 153998 | 1289 | 1289 | SNP | A | b73:LH82 | G | 5CM1 | | | | |
| 466 | Ampli-con1463332 | 153999 | 1424 | 1424 | SNP | C | 5CM1 | T | b73:LH82 | | | | |
| 467 | Ampli-con1463341 | 154038 | 65 | 65 | SNP | A | mo17:5CM1: LH82 | G | b73 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 467 | Ampli-con1463341 | 154039 | 76 | 76 | SNP | G | mo17:5CM1:LH82 | T | b73 | | | | |
| 467 | Ampli-con1463341 | 154040 | 78 | 78 | SNP | A | mo17:5CM1:LH82 | G | b73 | | | | |
| 467 | Ampli-con1463341 | 154041 | 98 | 98 | SNP | G | b73:5CM1 | T | mo17:LH82 | | | | |
| 467 | Ampli-con1463341 | 154042 | 163 | 163 | SNP | A | mo17:5CM1:LH82 | T | b73 | | | | |
| 467 | Ampli-con1463341 | 154043 | 168 | 168 | SNP | C | mo17:LH82 | T | b73:5CM1 | | | | |
| 467 | Ampli-con1463341 | 154044 | 177 | 177 | SNP | A | mo17:LH82 | G | b73:5CM1 | | | | |
| 467 | Ampli-con1463341 | 154045 | 179 | 179 | SNP | A | b73:5CM1 | G | mo17:LH82 | | | | |
| 467 | Ampli-con1463341 | 154046 | 184 | 184 | SNP | A | mo17:LH82 | G | b73:5CM1 | | | | |
| 467 | Ampli-con1463341 | 154047 | 187 | 187 | SNP | G | b73:5CM1 | T | mo17:LH82 | | | | |
| 467 | Ampli-con1463341 | 154048 | 192 | 192 | SNP | A | mo17:5CM1:LH82 | G | b73 | | | | |
| 467 | Ampli-con1463341 | 154049 | 236 | 250 | IND | ************ | mo17:LH82 | CCAGAGGCACGCGCC | b73:5CM1 | | | | |
| 467 | Ampli-con1463341 | 154052 | 317 | 318 | IND | ** | 5CM1 | CT | b73:mo17:LH82 | | | | |
| 467 | Ampli-con1463341 | 154053 | 395 | 395 | SNP | A | mo17:LH82 | G | b73:5CM1 | | | | |
| 467 | Ampli-con1463341 | 154054 | 493 | 493 | SNP | A | b73:5CM1 | C | mo17:LH82 | | | | |
| 467 | Ampli-con1463341 | 154055 | 503 | 503 | SNP | A | b73 | C | mo17:5CM1:LH82 | | | | |
| 467 | Ampli-con1463341 | 154056 | 504 | 504 | SNP | C | 5CM1 | G | b73:mo17:LH82 | | | | |
| 467 | Ampli-con1463341 | 154057 | 538 | 538 | SNP | C | mo17:5CM1:LH82 | G | b73 | | | | |
| 467 | Ampli-con1463341 | 154058 | 557 | 557 | SNP | G | mo17:LH82 | T | b73:5CM1 | | | | |
| 467 | Ampli-con1463341 | 154059 | 602 | 602 | SNP | C | b73:mo17:LH82 | T | 5CM1 | | | | |
| 467 | Ampli-con1463341 | 154060 | 606 | 606 | SNP | A | mo17:5CM1:LH82 | G | b73 | | | | |
| 467 | Ampli-con1463341 | 154061 | 679 | 679 | SNP | G | mo17:5CM1:LH82 | T | b73 | | | | |
| 467 | Ampli-con1463341 | 154062 | 681 | 681 | SNP | C | mo17:5CM1:LH82 | T | b73 | | | | |
| 467 | Ampli-con1463341 | 154063 | 682 | 682 | SNP | A | mo17:5CM1:LH82 | G | b73 | | | | |
| 467 | Ampli-con1463341 | 154064 | 683 | 683 | SNP | C | mo17:5CM1:LH82 | G | b73 | | | | |
| 467 | Ampli-con1463341 | 154065 | 684 | 684 | SNP | A | b73 | T | mo17:5CM1:LH82 | | | | |
| 467 | Ampli-con1463341 | 154066 | 687 | 687 | SNP | A | mo17:5CM1:LH82 | G | b73 | | | | |
| 467 | Ampli-con1463341 | 154067 | 688 | 688 | SNP | A | mo17:5CM1:LH82 | C | b73 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 467 | Ampli-con1463341 | 154068 | 690 | 690 | SNP | C | b73 | T | mo17:5CM1: LH82 b73 | | | | |
| 467 | Ampli-con1463341 | 154069 | 691 | 691 | SNP | G | mo17:5CM1: LH82 | T | mo17:5CM1: LH82 b73 | | | | |
| 467 | Ampli-con1463341 | 154070 | 692 | 692 | SNP | A | b73 | T | mo17:5CM1: LH82 b73 | | | | |
| 467 | Ampli-con1463341 | 154071 | 693 | 693 | SNP | C | b73 | G | mo17:5CM1: LH82 b73 | | | | |
| 467 | Ampli-con1463341 | 154072 | 694 | 694 | SNP | G | mo17:5CM1: LH82 | T | mo17:5CM1: LH82 b73 | | | | |
| 467 | Ampli-con1463341 | 154073 | 695 | 695 | SNP | A | b73 | T | mo17:5CM1: LH82 b73 | | | | |
| 467 | Ampli-con1463341 | 154074 | 696 | 696 | SNP | A | mo17:5CM1: LH82 | T | mo17:5CM1: LH82 b73 | | | | |
| 467 | Ampli-con1463341 | 154075 | 697 | 697 | SNP | A | b73 | G | mo17:5CM1: LH82 b73 | | | | |
| 467 | Ampli-con1463341 | 154076 | 698 | 698 | SNP | G | b73 | T | mo17:5CM1: LH82 b73 | | | | |
| 467 | Ampli-con1463341 | 154077 | 699 | 699 | SNP | A | b73 | G | mo17:5CM1: LH82 b73 | | | | |
| 467 | Ampli-con1463341 | 154078 | 700 | 700 | SNP | G | mo17:5CM1: LH82 | T | mo17:5CM1: LH82 b73 | | | | |
| 467 | Ampli-con1463341 | 154079 | 702 | 702 | SNP | A | b73 | G | mo17:5CM1: LH82 b73 | | | | |
| 467 | Ampli-con1463341 | 154080 | 704 | 704 | SNP | G | b73 | T | mo17:5CM1: LH82 b73 | | | | |
| 467 | Ampli-con1463341 | 154081 | 705 | 705 | SNP | A | b73 | T | mo17:5CM1: LH82 b73 | | | | |
| 467 | Ampli-con1463341 | 154082 | 706 | 706 | SNP | G | mo17:5CM1: LH82 | T | mo17:5CM1: LH82 b73 | | | | |
| 467 | Ampli-con1463341 | 154083 | 708 | 708 | SNP | G | mo17:5CM1: LH82 | T | mo17:5CM1: LH82 b73 | | | | |
| 467 | Ampli-con1463341 | 154084 | 709 | 709 | SNP | A | b73 | C | mo17:5CM1: LH82 b73 | | | | |
| 467 | Ampli-con1463341 | 154085 | 711 | 711 | SNP | A | mo17:5CM1: LH82 | G | mo17:5CM1: LH82 b73 | | | | |
| 467 | Ampli-con1463341 | 154086 | 712 | 712 | SNP | A | mo17:5CM1: LH82 | C | b73 | | | | |
| 467 | Ampli-con1463341 | 154087 | 713 | 713 | SNP | A | b73 | C | mo17:5CM1: LH82 b73 | | | | |
| 467 | Ampli-con1463341 | 154088 | 714 | 714 | SNP | A | mo17:5CM1: LH82 | G | mo17:5CM1: LH82 b73 | | | | |
| 467 | Ampli-con1463341 | 154089 | 715 | 715 | SNP | A | mo17:5CM1: LH82 | T | b73 | | | | |
| 467 | Ampli-con1463341 | 154090 | 717 | 717 | SNP | A | b73 | G | mo17:5CM1: LH82 b73 | | | | |
| 467 | Ampli-con1463341 | 154091 | 718 | 718 | SNP | A | b73:mo17: LH82 | G | mo17:5CM1: 5CM1 | | | | |
| 467 | Ampli-con1463341 | 154092 | 719 | 719 | SNP | A | b73 | G | mo17:5CM1: LH82 | | | | |
| 467 | Ampli-con1463341 | 154093 | 720 | 720 | SNP | C | b73 | T | mo17:5CM1: LH82 b73 | | | | |
| 467 | Ampli-con1463341 | 154094 | 721 | 721 | SNP | A | b73 | G | mo17:5CM1: LH82 | | | | |

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 467 | Amplicon1463341 | 154095 | 722 | 722 | SNP | C | mo17:5CM1:LH82 | T | b73 | | | | |
| 467 | Amplicon1463341 | 154096 | 723 | 723 | SNP | A | b73 | T | mo17:5CM1:LH82 | | | | |
| 467 | Amplicon1463341 | 154097 | 724 | 724 | SNP | G | b73 | T | mo17:5CM1:LH82 | | | | |
| 467 | Amplicon1463341 | 154098 | 726 | 726 | SNP | C | b73 | T | mo17:5CM1:LH82 | | | | |
| 467 | Amplicon1463341 | 154099 | 727 | 727 | SNP | A | b73 | T | mo17:5CM1:LH82 | | | | |
| 467 | Amplicon1463341 | 154100 | 728 | 728 | SNP | A | mo17:5CM1:LH82 | C | b73 | | | | |
| 467 | Amplicon1463341 | 154101 | 729 | 729 | SNP | C | mo17:5CM1:LH82 | T | b73 | | | | |
| 468 | Amplicon1463358 | 154007 | 50 | 50 | SNP | A | 5CM1 | G | b73:LH82 | | | | |
| 468 | Amplicon1463358 | 154008 | 73 | 73 | SNP | A | b73:LH82 | G | 5CM1 | | | | |
| 468 | Amplicon1463358 | 154009 | 208 | 208 | SNP | C | 5CM1 | T | b73:LH82 | | | | |
| 468 | Amplicon1463358 | 154010 | 282 | 282 | SNP | C | 5CM1 | T | b73:LH82 | | | | |
| 468 | Amplicon1463358 | 154011 | 292 | 321 | IND | ****************** | b73:LH82 | ACTGTTCTTTCTAAGTGCAC-CATGGACCAG | 5CM1 | | | | |
| 468 | Amplicon1463358 | 154012 | 351 | 351 | SNP | C | b73:LH82 | T | 5CM1 | | | | |
| 468 | Amplicon1463358 | 154013 | 373 | 373 | SNP | A | 5CM1 | G | b73:LH82 | | | | |
| 468 | Amplicon1463358 | 154014 | 526 | 526 | SNP | A | 5CM1 | G | b73:LH82 | | | | |
| 468 | Amplicon1463358 | 154020 | 927 | 927 | SNP | C | b73:LH82 | T | 5CM1 | | | | |
| 468 | Amplicon1463358 | 154021 | 1012 | 1012 | SNP | A | 5CM1 | G | b73:LH82 | | | | |
| 468 | Amplicon1463358 | 154023 | 1034 | 1034 | SNP | G | b73:LH82 | T | 5CM1 | | | | |
| 468 | Amplicon1463358 | 154026 | 1166 | 1166 | SNP | C | 5CM1 | G | b73:LH82 | | | | |
| 468 | Amplicon1463358 | 154027 | 1184 | 1184 | SNP | C | 5CM1 | T | b73:LH82 | | | | |
| 468 | Amplicon1463358 | 154028 | 1283 | 1283 | SNP | A | b73:LH82 | G | 5CM1 | | | | |
| 468 | Amplicon1463358 | 154029 | 1316 | 1316 | SNP | A | 5CM1 | G | b73:LH82 | | | | |
| 468 | Amplicon1463358 | 154030 | 1317 | 1317 | SNP | C | b73:LH82 | T | 5CM1 | | | | |
| 468 | Amplicon1463358 | 154031 | 1327 | 1327 | SNP | C | b73:LH82 | G | 5CM1 | | | | |
| 468 | Amplicon1463358 | 154032 | 1350 | 1350 | IND | * | b73:LH82 | T | 5CM1 | | | | |
| 468 | Amplicon1463358 | 154033 | 1356 | 1356 | SNP | C | 5CM1 | T | b73:LH82 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 468 | Ampli-con1463358 | 154034 | 1383 | 1383 | IND | * | b73:LH82 | A | 5CM1 | | | | |
| 468 | Ampli-con1463358 | 154035 | 1387 | 1387 | SNP | G | 5CM1 | T | b73:LH82 | | | | |
| 468 | Ampli-con1463358 | 154036 | 1389 | 1389 | SNP | A | b73:LH82 | C | 5CM1 | | | | |
| 468 | Ampli-con1463358 | 154037 | 1464 | 1464 | SNP | A | 5CM1 | G | b73:LH82 | | | | |
| 469 | Ampli-con1463815 | 154534 | 64 | 64 | SNP | A | 5CM1 | G | b73:mo17:LH82 5CM1 | | | | |
| 469 | Ampli-con1463815 | 154535 | 100 | 100 | SNP | C | b73:mo17:LH82 | T | 5CM1 | | | | |
| 469 | Ampli-con1463815 | 154536 | 238 | 238 | SNP | C | b73:mo17:LH82 5CM1 | T | 5CM1 | | | | |
| 469 | Ampli-con1463815 | 154537 | 304 | 304 | SNP | C | b73:mo17:LH82 5CM1 | T | b73:mo17:LH82 | | | | |
| 470 | Ampli-con1463828 | 155152 | 30 | 31 | IND | ** | b73:5CM1 | TA | LH82 | | | | |
| 470 | Ampli-con1463828 | 155153 | 83 | 93 | IND | ********** | LH82 | ATATATATACA | b73:5CM1 | | | | |
| 470 | Ampli-con1463828 | 155154 | 158 | 158 | SNP | A | b73:5CM1 | T | LH82 | | | | |
| 470 | Ampli-con1463828 | 155155 | 289 | 289 | SNP | C | LH82 | G | b73:5CM1 | | | | |
| 470 | Ampli-con1463828 | 155156 | 290 | 290 | SNP | A | b73:5CM1 | T | LH82 | | | | |
| 470 | Ampli-con1463828 | 155157 | 338 | 338 | SNP | C | LH82 | T | b73:5CM1 | | | | |
| 470 | Ampli-con1463828 | 155158 | 346 | 346 | SNP | C | LH82 | G | b73:5CM1 | | | | |
| 470 | Ampli-con1463828 | 155159 | 457 | 457 | SNP | A | b73:5CM1 | G | LH82 | | | | |
| 471 | Ampli-con1463835 | 154552 | 194 | 194 | SNP | C | b73:LH82 | C | 5CM1 | | | | |
| 471 | Ampli-con1463835 | 154553 | 271 | 271 | SNP | C | 5CM1 | T | b73:LH82 | | | | |
| 471 | Ampli-con1463835 | 154554 | 276 | 276 | SNP | A | b73:LH82 | G | 5CM1 | | | | |
| 471 | Ampli-con1463835 | 154555 | 330 | 330 | SNP | C | b73:LH82 | T | 5CM1 | | | | |
| 471 | Ampli-con1463835 | 154557 | 388 | 388 | SNP | A | 5CM1 | G | b73:LH82 | | | | |
| 471 | Ampli-con1463835 | 154558 | 395 | 395 | SNP | A | 5CM1 | G | b73:LH82 | | | | |
| 471 | Ampli-con1463835 | 154559 | 433 | 436 | IND | **** | b73:LH82 | AATT | 5CM1 | | | | |
| 471 | Ampli-con1463835 | 154560 | 627 | 627 | IND | * | 5CM1 | G | b73:LH82 | | | | |
| 471 | Ampli-con1463835 | 154561 | 633 | 633 | SNP | C | 5CM1 | T | b73:LH82 | | | | |
| 471 | Ampli-con1463835 | 154562 | 680 | 680 | SNP | C | b73:LH82 | T | 5CM1 | | | | |
| 471 | Ampli-con1463835 | 154563 | 764 | 764 | SNP | A | b73:LH82 | G | 5CM1 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 471 | Ampli-con1463835 | 154564 | 859 | 859 | SNP | A | 5CM1 | T | b73:LH82 | | | | |
| 471 | Ampli-con1463835 | 154565 | 874 | 874 | SNP | C | b73:LH82 | T | 5CM1 | | | | |
| 471 | Ampli-con1463835 | 154567 | 1063 | 1063 | SNP | A | 5CM1 | G | b73:LH82 | | | | |
| 471 | Ampli-con1463835 | 154568 | 1099 | 1099 | SNP | C | b73:LH82 | T | 5CM1 | | | | |
| 471 | Ampli-con1463835 | 154569 | 1237 | 1237 | SNP | C | b73:LH82 | T | 5CM1 | | | | |
| 472 | Ampli-con1463848 | 154530 | 79 | 79 | SNP | A | 5CM1 | G | b73:mo17:LH82 | | | | |
| 472 | Ampli-con1463848 | 154531 | 115 | 115 | SNP | C | b73:mo17:LH82 | T | 5CM1 | | | | |
| 472 | Ampli-con1463848 | 154532 | 253 | 253 | SNP | C | b73:mo17:LH82 | T | 5CM1 | | | | |
| 472 | Ampli-con1463848 | 154533 | 319 | 319 | SNP | C | 5CM1 | T | b73:mo17:LH82 | | | | |
| 473 | Ampli-con1463850 | 154616 | 221 | 221 | SNP | A | b73 | C | 5CM1 | | | | |
| 473 | Ampli-con1463850 | 154617 | 298 | 298 | SNP | C | 5CM1 | T | b73 | | | | |
| 473 | Ampli-con1463850 | 154618 | 303 | 303 | SNP | A | b73 | T | 5CM1 | | | | |
| 473 | Ampli-con1463850 | 154619 | 357 | 357 | SNP | A | b73 | G | 5CM1 | | | | |
| 473 | Ampli-con1463850 | 154621 | 415 | 415 | SNP | A | 5CM1 | G | b73 | | | | |
| 473 | Ampli-con1463850 | 154622 | 422 | 422 | SNP | A | 5CM1 | G | b73 | | | | |
| 473 | Ampli-con1463850 | 154623 | 460 | 461 | IND | ** | b73 | AA | 5CM1 | | | | |
| 473 | Ampli-con1463850 | 154624 | 463 | 463 | IND | * | b73 | T | 5CM1 | | | | |
| 473 | Ampli-con1463850 | 154626 | 609 | 609 | SNP | C | 5CM1 | T | b73 | | | | |
| 473 | Ampli-con1463850 | 154627 | 707 | 707 | SNP | C | 5CM1 | T | b73 | | | | |
| 473 | Ampli-con1463850 | 154628 | 791 | 791 | SNP | A | 5CM1 | G | b73 | | | | |
| 473 | Ampli-con1463850 | 154629 | 886 | 886 | SNP | A | 5CM1 | T | b73 | | | | |
| 473 | Ampli-con1463850 | 154630 | 901 | 901 | SNP | C | 5CM1 | T | b73 | | | | |
| 473 | Ampli-con1463850 | 154632 | 1090 | 1090 | SNP | A | 5CM1 | G | b73 | | | | |
| 473 | Ampli-con1463850 | 154633 | 1126 | 1126 | SNP | C | b73 | T | 5CM1 | | | | |
| 474 | Ampli-con1463853 | 154505 | 131 | 131 | SNP | C | b73:mo17:LH82 | T | 5CM1 | | | | |
| 474 | Ampli-con1463853 | 154506 | 335 | 335 | SNP | C | 5CM1 | T | b73:mo17:LH82 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 475 | Ampli-con1463858 | 154511 | 221 | 221 | SNP | A | b73:LH82 | C | 5CM1 | | | | |
| 475 | Ampli-con1463858 | 154512 | 298 | 298 | SNP | C | 5CM1 | T | b73:LH82 | | | | |
| 475 | Ampli-con1463858 | 154513 | 303 | 303 | SNP | A | Ampli-con1463858 | T | 5CM1 | | | | |
| 475 | Ampli-con1463858 | 154514 | 357 | 357 | SNP | A | b73:LH82 | G | 5CM1 | | | | |
| 475 | Ampli-con1463858 | 154516 | 415 | 415 | SNP | A | 5CM1 | G | b73:LH82 | | | | |
| 475 | Ampli-con1463858 | 154517 | 422 | 422 | SNP | A | 5CM1 | G | b73:LH82 | | | | |
| 475 | Ampli-con1463858 | 154518 | 460 | 464 | IND | **T | LH82 | T** | b73 | AATTT | 5CM1 | | |
| 475 | Ampli-con1463858 | 154519 | 609 | 609 | SNP | C | 5CM1 | T | b73:LH82 | | | | |
| 475 | Ampli-con1463858 | 154520 | 650 | 650 | IND | * | 5CM1 | A | b73:LH82 | | | | |
| 475 | Ampli-con1463858 | 154521 | 654 | 654 | IND | * | 5CM1 | G | b73:LH82 | | | | |
| 475 | Ampli-con1463858 | 154522 | 660 | 660 | SNP | C | 5CM1 | T | b73:LH82 | | | | |
| 475 | Ampli-con1463858 | 154523 | 707 | 707 | SNP | C | b73:LH82 | T | 5CM1 | | | | |
| 475 | Ampli-con1463858 | 154524 | 791 | 791 | SNP | A | b73:LH82 | G | 5CM1 | | | | |
| 475 | Ampli-con1463858 | 154526 | 901 | 901 | SNP | C | b73:LH82 | T | 5CM1 | | | | |
| 475 | Ampli-con1463858 | 154528 | 1090 | 1090 | SNP | A | 5CM1 | G | b73:LH82 | | | | |
| 475 | Ampli-con1463858 | 154529 | 1126 | 1126 | SNP | C | b73:LH82 | T | 5CM1 | | | | |
| 476 | Ampli-con1463864 | 154843 | 93 | 95 | IND | *** | b73:mo17 | CAC | 5CM1 | | | | |
| 476 | Ampli-con1463864 | 154844 | 114 | 114 | IND | * | b73:5CM1 | T | mo17 | | | | |
| 476 | Ampli-con1463864 | 154845 | 169 | 169 | SNP | A | 5CM1 | G | b73:mo17 | | | | |
| 476 | Ampli-con1463864 | 154846 | 251 | 257 | IND | ******** | mo17 | CGGGGCG | b73:5CM1 | | | | |
| 476 | Ampli-con1463864 | 154849 | 289 | 289 | IND | * | mo17:5CM1 | G | b73 | | | | |
| 476 | Ampli-con1463864 | 154853 | 459 | 461 | IND | *** | b73:5CM1 | AAG | mo17 | | | | |
| 476 | Ampli-con1463864 | 154854 | 467 | 467 | SNP | *** | mo17:5CM1 | T | b73 | | | | |
| 476 | Ampli-con1463864 | 154855 | 471 | 471 | SNP | G | 5CM1 | A | b73:mo17 | | | | |
| 476 | Ampli-con1463864 | 154856 | 479 | 479 | SNP | C | b73:5CM1 | T | mo17 | | | | |
| 476 | Ampli-con1463864 | 154857 | 498 | 499 | IND | ** | mo17 | GC | b73:5CM1 | | | | |

-continued

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 476 | Ampli-con1463864 | 154858 | 501 | 501 | IND | * | mo17 | G | b73:5CM1 | | | | |
| 477 | Ampli-con1463878 | 154507 | 62 | 62 | SNP | A | 5CM1 | G | b73:mo17:LH82 | | | | |
| 477 | Ampli-con1463878 | 154508 | 98 | 98 | SNP | C | b73:mo17:LH82 | T | 5CM1 | | | | |
| 477 | Ampli-con1463878 | 154509 | 236 | 236 | SNP | C | b73:mo17:LH82 | T | 5CM1 | | | | |
| 477 | Ampli-con1463878 | 154510 | 302 | 302 | SNP | C | 5CM1 | T | b73:mo17:LH82 | | | | |
| 478 | Ampli-con1464068 | 154475 | 92 | 92 | SNP | A | b73 | T | 5CM1 | | | | |
| 479 | Ampli-con1464087 | 155688 | 97 | 97 | SNP | C | b73:mo17:LH82 | T | 5CM1 | | | | |
| 479 | Ampli-con1464087 | 155689 | 235 | 235 | SNP | C | b73:mo17:LH82 | T | 5CM1 | | | | |
| 479 | Ampli-con1464087 | 155690 | 301 | 301 | SNP | C | 5CM1 | T | b73:LH82 | | | | |
| 480 | Ampli-con1464088 | 155691 | 273 | 273 | SNP | A | 5CM1 | G | b73:mo17:LH82 | | | | |
| 480 | Ampli-con1464088 | 155692 | 309 | 309 | SNP | C | b73:mo17:LH82 | T | 5CM1 | | | | |
| 480 | Ampli-con1464088 | 155696 | 608 | 608 | SNP | C | 5CM1 | T | b73:LH82 | | | | |
| 480 | Ampli-con1464088 | 155697 | 692 | 692 | SNP | A | 5CM1 | G | b73:LH82 | | | | |
| 480 | Ampli-con1464088 | 155702 | 977 | 977 | SNP | C | b73:LH82 | T | 5CM1 | | | | |
| 480 | Ampli-con1464088 | 155703 | 984 | 984 | SNP | C | b73:LH82 | T | 5CM1 | | | | |
| 480 | Ampli-con1464088 | 155705 | 1042 | 1042 | SNP | C | 5CM1 | T | b73:LH82 | | | | |
| 480 | Ampli-con1464088 | 155706 | 1096 | 1096 | SNP | A | 5CM1 | T | b73:LH82 | | | | |
| 480 | Ampli-con1464088 | 155707 | 1101 | 1101 | SNP | A | b73:LH82 | G | 5CM1 | | | | |
| 480 | Ampli-con1464088 | 155708 | 1178 | 1178 | SNP | G | 5CM1 | T | b73:LH82 | | | | |
| 481 | Ampli-con1464097 | 155827 | 341 | 341 | SNP | A | LH82 | T | b73 | | | | |
| 481 | Ampli-con1464097 | 155828 | 347 | 347 | SNP | C | b73 | G | LH82 | | | | |
| 481 | Ampli-con1464097 | 155829 | 417 | 417 | SNP | A | LH82 | G | b73 | | | | |
| 481 | Ampli-con1464097 | 155830 | 484 | 484 | SNP | C | b73 | T | LH82 | | | | |
| 481 | Ampli-con1464097 | 155831 | 510 | 510 | IND | * | b73 | T | LH82 | | | | |
| 481 | Ampli-con1464097 | 155832 | 511 | 511 | IND | * | b73 | A | LH82 | | | | |
| 481 | Ampli-con1464097 | 155833 | 620 | 620 | SNP | C | LH82 | T | b73 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 481 | Ampli-con1464097 | 155835 | 811 | 811 | SNP | C | b73 | T | LH82 | | | | |
| 481 | Ampli-con1464097 | 155836 | 814 | 814 | SNP | C | LH82 | T | b73 | | | | |
| 481 | Ampli-con1464097 | 155837 | 865 | 865 | SNP | A | b73 | G | LH82 | | | | |
| 481 | Ampli-con1464097 | 155838 | 872 | 872 | SNP | A | b73 | G | LH82 | | | | |
| 481 | Ampli-con1464097 | 155839 | 881 | 881 | SNP | C | b73 | T | LH82 | | | | |
| 481 | Ampli-con1464097 | 155840 | 892 | 892 | SNP | A | b73 | C | LH82 | | | | |
| 481 | Ampli-con1464097 | 155841 | 950 | 950 | SNP | A | LH82 | T | b73 | | | | |
| 481 | Ampli-con1464097 | 155842 | 978 | 978 | SNP | G | b73 | T | LH82 | | | | |
| 481 | Ampli-con1464097 | 155843 | 987 | 987 | SNP | A | b73 | G | LH82 | | | | |
| 481 | Ampli-con1464097 | 155844 | 1035 | 1035 | SNP | A | LH82 | G | b73 | | | | |
| 481 | Ampli-con1464097 | 155845 | 1100 | 1100 | SNP | A | b73 | C | LH82 | | | | |
| 481 | Ampli-con1464097 | 155846 | 1133 | 1133 | SNP | C | b73 | T | LH82 | | | | |
| 481 | Ampli-con1464097 | 155848 | 1192 | 1192 | SNP | G | b73 | G | LH82 | | | | |
| 481 | Ampli-con1464097 | 155849 | 1215 | 1215 | SNP | G | b73 | T | LH82 | | | | |
| 481 | Ampli-con1464097 | 155850 | 1239 | 1239 | SNP | A | LH82 | G | b73 | | | | |
| 481 | Ampli-con1464097 | 155851 | 1264 | 1264 | SNP | G | b73 | T | b73 | | | | |
| 481 | Ampli-con1464097 | 155852 | 1265 | 1265 | SNP | C | b73 | G | LH82 | | | | |
| 481 | Ampli-con1464097 | 155853 | 1273 | 1273 | SNP | A | LH82 | T | b73 | | | | |
| 482 | Ampli-con1464098 | 155861 | 117 | 117 | SNP | C | b73:5CM1 | T | mo17:LH82 | | | | |
| 482 | Ampli-con1464098 | 155862 | 138 | 138 | SNP | A | LH82 | C | b73:mo17:5CM1 | | | | |
| 482 | Ampli-con1464098 | 155863 | 148 | 148 | SNP | C | 5CM1 | T | b73:mo17:LH82 | | | | |
| 482 | Ampli-con1464098 | 155864 | 162 | 162 | IND | * | 5CM1 | C | b73:mo17:LH82 | | | | |
| 482 | Ampli-con1464098 | 155865 | 169 | 169 | SNP | A | mo17 | C | b73:5CM1:LH82 | | | | |
| 482 | Ampli-con1464098 | 155866 | 194 | 194 | SNP | A | b73:5CM1 | G | mo17:LH82 | | | | |
| 482 | Ampli-con1464098 | 155867 | 213 | 213 | SNP | A | b73:mo17:5CM1 | C | LH82 | | | | |
| 482 | Ampli-con1464098 | 155868 | 215 | 215 | SNP | A | b73:5CM1 | G | mo17:LH82 | | | | |

-continued

| SEQ_NUM | SEQ_ID | MUTATION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 482 | Ampli-con1464098 | 155869 | 232 | 232 | SNP | A | b73:5CM1 | G | mo17:LH82 | | | | |
| 482 | Ampli-con1464098 | 155870 | 240 | 240 | SNP | C | b73:mo17:5CM1 LH82 | T | LH82 | | | | |
| 482 | Ampli-con1464098 | 155871 | 245 | 245 | SNP | A | LH82 | G | b73:mo17:5CM1 | | | | |
| 482 | Ampli-con1464098 | 155872 | 275 | 275 | SNP | A | b73:5CM1 | G | mo17:LH82 | | | | |
| 482 | Ampli-con1464098 | 155873 | 281 | 281 | SNP | A | b73:5CM1 | G | mo17:LH82 | | | | |
| 482 | Ampli-con1464098 | 155874 | 296 | 296 | SNP | A | b73:5CM1:LH82 | G | mo17 | | | | |
| 482 | Ampli-con1464098 | 155875 | 313 | 313 | SNP | A | b73 | G | mo17:5CM1:LH82 | | | | |
| 482 | Ampli-con1464098 | 155876 | 318 | 318 | SNP | A | mo17:LH82 | G | b73:5CM1 | | | | |
| 482 | Ampli-con1464098 | 155877 | 331 | 331 | SNP | C | mo17 | T | b73:5CM1:LH82 | | | | |
| 482 | Ampli-con1464098 | 155878 | 348 | 362 | IND | ************** | b73:5CM1 | TCTTCGATGATGATAATG | LH82 | | | | |
| 482 | Ampli-con1464098 | 155879 | 370 | 370 | SNP | C | b73 | T | 5CM1:LH82 | | | | |
| 482 | Ampli-con1464098 | 155880 | 376 | 387 | IND | *********** | LH82 | CGCCGAGTATGA | b73:5CM1 | | | | |
| 482 | Ampli-con1464098 | 155881 | 401 | 406 | IND | ****** | b73:5CM1 | GTCACC | mo17:LH82 | | | | |
| 482 | Ampli-con1464098 | 155882 | 414 | 419 | IND | ATGACG | LH82 | ATGCCG | mo17 | | | | |
| 482 | Ampli-con1464098 | 155883 | 428 | 428 | SNP | A | b73:5CM1:LH82 | G | mo17 | | | | |
| 482 | Ampli-con1464098 | 155884 | 434 | 434 | SNP | A | mo17 | G | b73:5CM1:LH82 | | | | |
| 482 | Ampli-con1464098 | 155885 | 534 | 536 | IND | *** | LH82 | CAA | b73:mo17:5CM1 | | | | |
| 482 | Ampli-con1464098 | 155886 | 551 | 551 | SNP | C | b73:mo17 | G | 5CM1:LH82 | C***CA | b73:5CM1 | | |
| 483 | Ampli-con1464112 | 155790 | 40 | 40 | SNP | G | b73:LH82 | T | 5CM1 | | | | |
| 483 | Ampli-con1464112 | 155791 | 72 | 72 | SNP | A | 5CM1 | G | b73:LH82 | | | | |
| 483 | Ampli-con1464112 | 155792 | 78 | 78 | SNP | A | 5CM1 | G | b73:LH82 | | | | |
| 483 | Ampli-con1464112 | 155793 | 132 | 132 | SNP | C | b73:LH82 | T | 5CM1 | | | | |
| 483 | Ampli-con1464112 | 155794 | 151 | 151 | SNP | A | b73:LH82 | G | 5CM1 | | | | |
| 483 | Ampli-con1464112 | 155795 | 161 | 161 | SNP | C | b73:LH82 | T | 5CM1 | | | | |
| 483 | Ampli-con1464112 | 155796 | 241 | 241 | SNP | A | b73:LH82 | G | 5CM1 | | | | |
| 483 | Ampli-con1464112 | 155797 | 252 | 252 | SNP | C | 5CM1 | T | b73:LH82 | | | | |

| SEQ_NUM | SEQ_ID | MUTA-TION_ID | START_POS | END_POS | TYPE | ALLELE1 | STRAINS1 | ALLELE2 | STRAINS2 | ALLELE3 | STRAINS3 | ALLELE4 | STRAINS4 |
|---|---|---|---|---|---|---|---|---|---|---|---|---|---|
| 483 | Ampli-con1464112 | 155798 | 321 | 321 | SNP | C | b73:LH82 | T | 5CM1 | | | | |
| 483 | Ampli-con1464112 | 155799 | 323 | 323 | SNP | C | 5CM1 | T | b73:LH82 | | | | |
| 483 | Ampli-con1464112 | 155800 | 367 | 367 | SNP | A | 5CM1 | T | b73:LH82 | | | | |
| 483 | Ampli-con1464112 | 155801 | 409 | 409 | IND | * | 5CM1 | C | b73:LH82 | | | | |
| 483 | Ampli-con1464112 | 155802 | 413 | 413 | SNP | C | b73:LH82 | G | 5CM1 | | | | |
| 484 | Ampli-con1464142 | 156240 | 92 | 94 | IND | *** | b73 | ATA | 5CM1:LH82 | | | | |
| 484 | Ampli-con1464142 | 156241 | 133 | 133 | SNP | A | LH82 | C | 5CM1 | G | b73 | | |
| 484 | Ampli-con1464142 | 156242 | 214 | 214 | SNP | A | b73 | T | mo17:5CM1:LH82 | | | | |
| 484 | Ampli-con1464142 | 156243 | 247 | 247 | SNP | A | b73 | C | mo17:5CM1:LH82 | | | | |
| 484 | Ampli-con1464142 | 156245 | 286 | 286 | SNP | C | mo17:LH82 | G | 5CM1 | T | b73 | | |
| 484 | Ampli-con1464142 | 156247 | 370 | 370 | SNP | A | mo17:LH82 | G | b73:5CM1 | | | | |
| 484 | Ampli-con1464142 | 156248 | 411 | 411 | SNP | A | b73:LH82 | C | 5CM1 | T | mo17 | | |
| 484 | Ampli-con1464142 | 156249 | 548 | 548 | SNP | A | b73 | C | mo17:LH82 | | | | |
| 484 | Ampli-con1464142 | 156251 | 582 | 582 | SNP | C | mo17:LH82 | T | b73 | | | | |
| 484 | Ampli-con1464142 | 156252 | 593 | 593 | SNP | A | mo17:LH82 | G | b73 | | | | |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07939708B2). An electronic copy of the "Sequence Listing" will also be available from the USPTO upon request and payment of the fee set forth in 37 CFR 1.19(b)(3).

What is claimed is:

1. A method of identifying oil-associated QTLs in maize comprising
   (a) establishing a population of maize plants derived from the Illinois high oil line and/or the Illinois low oil line,
   (b) selecting a set of oil informative allelic polymorphic markers from at least 40 loci from the set of polymorphic markers listed in Table 3,
   (c) using said markers to identify oil-associated QTLs in said maize plants.

* * * * *